US011155596B2

(12) United States Patent
Wahlberg et al.

(10) Patent No.: US 11,155,596 B2
(45) Date of Patent: Oct. 26, 2021

(54) POLYPEPTIDE

(71) Applicant: AFFIBODY AB, Solna (SE)

(72) Inventors: Elisabet Wahlberg, Sigtuna (SE); Elin Gunneriusson, Saltsjöbaden (SE)

(73) Assignee: AFFIBODY AB, Solna (SE)

(*) Notice: Subject to any disclaimer, the term of this patent is extended or adjusted under 35 U.S.C. 154(b) by 787 days.

(21) Appl. No.: 15/770,956

(22) PCT Filed: Oct. 28, 2016

(86) PCT No.: PCT/EP2016/076040
§ 371 (c)(1),
(2) Date: Apr. 25, 2018

(87) PCT Pub. No.: WO2017/072280
PCT Pub. Date: May 4, 2017

(65) Prior Publication Data

US 2018/0312565 A1 Nov. 1, 2018

(30) Foreign Application Priority Data

Feb. 24, 2016 (EP) .................................... 16157154

(51) Int. Cl.

| | |
|---|---|
| ***A61K 38/00*** | (2006.01) |
| ***C07K 14/705*** | (2006.01) |
| ***A61K 38/16*** | (2006.01) |
| ***A61K 38/17*** | (2006.01) |
| ***A61K 38/36*** | (2006.01) |
| ***C07K 14/745*** | (2006.01) |
| ***A61P 35/00*** | (2006.01) |
| ***A61K 47/42*** | (2017.01) |
| ***C07K 14/47*** | (2006.01) |

(52) U.S. Cl.
CPC ........ *C07K 14/70532* (2013.01); *A61K 38/16* (2013.01); *A61K 38/1709* (2013.01); *A61K 38/36* (2013.01); *A61K 47/42* (2013.01); *A61P 35/00* (2018.01); *C07K 14/4747* (2013.01); *C07K 14/745* (2013.01); *A61K 38/00* (2013.01)

(58) Field of Classification Search
CPC ........ A61K 38/00; A61K 47/42; A61K 38/16; A61K 38/1709; A61K 38/36; A61P 35/00; C07K 14/4747; C07K 14/70532; C07K 14/745; C07K 2319/00
See application file for complete search history.

(56) References Cited

U.S. PATENT DOCUMENTS

| | | | |
|---|---|---|---|
| 5,595,756 | A | 1/1997 | Bally et al. |
| 2018/0305437 | A1 | 10/2018 | Wahlberg |

FOREIGN PATENT DOCUMENTS

| | | | |
|---|---|---|---|
| CN | 103304638 | A | 9/2013 |
| CN | 103936835 | A | 7/2014 |
| CN | 104086627 | A | 10/2014 |
| CN | 104761633 | A | 7/2015 |
| WO | 2009089149 | A1 | 7/2009 |
| WO | 2014140366 | A1 | 9/2014 |
| WO | 2015095418 | A1 | 6/2015 |
| WO | 2017/072273 | A1 | 5/2017 |

OTHER PUBLICATIONS

Bharat B. Aggarwal et al., "Models for prevention and treatment of cancer: Problems vs. promises", Biochemical Pharmacology, vol. 78, 2009, 12 pages.
Michael B. Sporn et al., "Chemoprevention of cancer" Carcinogenesis, vol. 21, No. 3, 2000, 6 pages.
Trisha Gura, "Cancer Models: Systems for Identifying New Drugs are Often Faulty", Science Magazine, vol. 278, No. 5340, Nov. 7, 1997, 5 pages.
Arnau, Jose et al., "Current strategies for the use of affinity tags and tag removal for the purification of recombinant proteins", Protein Expression and Purification 48 (2006); pp. 1-13.
БОРИСОВА Е. И. и др., Эволюция иммуноте рапии рака почки, Эффективная фармакотерапия (Borisova, YE. I. et al., "Evolution of Kidney Cancer Immunotherapy", Effective Pharmacotherapy), 2014, N. 47, c.28-31 (English abstract on last page).
Pakula, Andrew A., et al., "Genetic Analysis of Protein Stability and Function", Anna. Rev. Gent. 1989 23; pp. 289-310.
Hao-Nan Chang et al., "Blocking of the PD-1/PD-L1 Interaction by a D-Peptide Antagonist for Cancer Immunotherapy", Angewandte Comminication, Cancer Immunotherapy, International Edition, vol. 54, No. 40, Aug. 10, 2015, pp. 11760-11764.
International Search Report issued in International Application No. PCT/EP2016/076040 dated Jan. 13, 2017; 5 pages.
Written Opinion issued in International Application No. PCT/EP2016/076040 dated Jan. 13, 2017; 5 pages.
Fan Wang et al., "Synthetic small peptides acting on B7H1 enhance apoptosis in pancreatic caner cells", Molecular Medicine Reports, vol. 6, Jun. 27, 2012, pp. 553-557.
Zhou, Binbin, "Design and Synthesis of Functional Peptides and Their Applications", Central South University, China Academic Dissertation Full-text Database, published Feb. 15, 2014; 130 pages; English Abstract pp. 6-8 Part 1—pp. 1-52.

(Continued)

*Primary Examiner* — James H Alstrum-Acevedo
*Assistant Examiner* — Mercy H Sabila
(74) *Attorney, Agent, or Firm* — Cantor Colburn LLP

(57) ABSTRACT

The present disclosure relates to a class of engineered polypeptides having a binding affinity for programmed death-ligand 1 (PD-L1), and provides a PD-L1 binding polypeptide comprising the sequence ERNX$_4$AAX$_7$EIL X$_{11}$LPNLX$_{16}$X$_{17}$X$_{18}$QX$_{20}$ WAFIWX$_{26}$LX$_{28}$D. The present disclosure also relates to the use of such a PD-L1 binding polypeptide as a therapeutic, prognostic and/or diagnostic agent.

34 Claims, 42 Drawing Sheets

Specification includes a Sequence Listing.

(56) References Cited

OTHER PUBLICATIONS

Zhou, Binbin, "Design and Synthesis of Functional Peptides and Their Applications", Central South University, China Academic Dissertation Full-text Database, published Feb. 15, 2014; 130 pages; English Abstract pp. 6-8 Part 2 pp. 53-117.

Zhao J. et al., "Antigen binding allosterically promotes Fc receptor recognition", MAbs, 2019, V. 11, N. 1, p. 58-74.

Kontermann R. E. et al., "Bispecific antibodies", Drug Discovery Today, 2015, V. 7, N. 20, p. 838-847.

Moreira I. S. et al., "Hot spots—A review of the protein-protein interface determinant amino-acid residues", Proteins: Structure, Function, and Bioinformatics, 2007, V. 68, N. 4, p. 803-812.

Ou D. L. et al., "Development of a PD-L1-expressing orthotopic liver cancer model: implications for immunotherapy for hepatocellular carcinoma", Liver cancer, 2019, V. 8, N. 3, p. 155-171.

Reynoso E. D. et al., "Intestinal tolerance is converted to autoimmune enteritis upon PD-1 ligand blockade", The Journal of Immunology, 2009, V. 182, N. 4, p. 2102-2112.

Shen B. Q. et al., "Conjugation site modulates the in vivo stability and therapeutic activity of antibody-drug conjugates", Nature biotechnology, 2012, V. 30, N. 2, p. 184-189.

Tokuriki N. et al., "Stability effects of mutations and protein evolvability", Curr. Opin. Struct. Biol., 2009, v.19, n.5, p. 596-604.

Figure 1A

| Designation | Sequence | SEQ ID NO: |
|---|---|---|
| Z18064 | VDAKYAKERNKAAYEILYLPNLTNAQKWAFIWKLDDDPSQSSELLSEAKKLNDSQAPK | 1 |
| Z17964 | VDAKYAKERNAAAYEILYLPNLTNAQKWAFIWKLDDDPSQSSELLSEAKKLNDSQAPK | 2 |
| Z17911 | VDAKYAKERNNAAYEILYLPNLTNAQKWAFIWKLDDDPSQSSELLSEAKKLNDSQAPK | 3 |
| Z18048 | VDAKYAKERNSAAYEILYLPNLTNAQKWAFIWKLDDDPSQSSELLSEAKKLNDSQAPK | 4 |
| Z17825 | VDAKYAKERNLAAYEILYLPNLTNAQKWAFIWKLDDDPSQSSELLSEAKKLNDSQAPK | 5 |
| Z18074 | VDAKYAKERNQAAFEILYLPNLTNAQKWAFIWKLDDDPSQSSELLSEAKKLNDSQAPK | 6 |
| Z17756 | VDAKYAKERNAAAFEILYLPNLTNAQKWAFIWKLDDDPSQSSELLSEAKKLNDSQAPK | 7 |
| Z17746 | VDAKYAKERNEAAYEILYLPNLTNAQKWAFIWKLDDDPSQSSELLSEAKKLNDSQAPK | 8 |
| Z18022 | VDAKYAKERNSAAYEILYLPNLTNQQKWAFIWKLDDDPSQSSELLSEAKKLNDSQAPK | 9 |
| Z18070 | VDAKYAKERNAAAYEILYLPNLTNHQKWAFIWKLDDDPSQSSELLSEAKKLNDSQAPK | 10 |
| Z17748 | VDAKYAKERNAAAYEILYLPNLTQSQKWAFIWKLDDDPSQSSELLSEAKKLNDSQAPK | 11 |
| Z18066 | VDAKYAKERNEAAYEILYLPNLTNSQKWAFIWKLDDDPSQSSELLSEAKKLNDSQAPK | 12 |
| Z17978 | VDAKYAKERNEAAYEILYLPNLTQSQKWAFIWKLDDDPSQSSELLSEAKKLNDSQAPK | 13 |
| Z18052 | VDAKYAKERNIAAYEILYLPNLTQSQIWAFIWKLDDDPSQSSELLSEAKKLNDSQAPK | 14 |
| Z18353 | VDAKYAKERNEAAYEILYLPNLTQAQKWAFIWKLDDDPSQSSELLSEAKKLNDSQAPK | 15 |
| Z18129 | VDAKYAKERNSAAYEILYLPNLTQAQKWAFIWKLDDDPSQSSELLSEAKKLNDSQAPK | 16 |
| Z18090 | VDAKYAKERNDAAYEILYLPNLTNQQKWAFIWKLADDPSQSSELLSEAKKLNDSQAPK | 17 |
| Z18149 | VDAKYAKERNNAAYEILYLPNLTQAQKWAFIWKLDDDPSQSSELLSEAKKLNDSQAPK | 18 |
| Z17972 | VDAKYAKERNIAAYEILYLPNLTNNQKWAFIWKLDDDPSQSSELLSEAKKLNDSQAPK | 19 |
| Z18039 | VDAKYAKERNEAAYEILYLPNLTQSQIWAFIWKLDDDPSQSSELLSEAKKLNDSQAPK | 20 |
| Z18233 | VDAKYAKERNTAAQEILYLPNLTQGQKWAFIWKLDDDPSQSSELLSEAKKLNDSQAPK | 21 |
| Z18054 | VDAKYAKERNDAAFEILYLPNLTQAQIWAFIWKLDDDPSQSSELLSEAKKLNDSQAPK | 22 |
| Z18101 | VDAKYAKERNSAAYEILYLPNLTNLQKWAFIWKLDDDPSQSSELLSEAKKLNDSQAPK | 23 |
| Z18418 | VDAKYAKERNEAAYEILHLPNLTSYQHWAFIWKLDDDPSQSSELLSEAKKLNDSQAPK | 24 |
| Z17758 | VDAKYAKERNKAAYEILYLPNLTNKQKWAFIWKLDDDPSQSSELLSEAKKLNDSQAPK | 25 |
| Z17772 | VDAKYAKERNKAAHEILYLPNLTNAQKWAFIWKLDDDPSQSSELLSEAKKLNDSQAPK | 26 |
| Z17843 | VDAKYAKERNAAAYEILYLPNLTNKQKWAFIWKLDDDPSQSSELLSEAKKLNDSQAPK | 27 |
| Z17928 | VDAKYAKERNAAAYEILYLPNLTQKQRWAFIWKLDDDPSQSSELLSEAKKLNDSQAPK | 28 |
| Z17950 | VDAKYAKERNAAAQEILYLPNLTSQQRWAFIWKLDDDPSQSSELLSEAKKLNDSQAPK | 29 |

Figure 1B

| Designation | Sequence | SEQ ID NO: |
| --- | --- | --- |
| Z17968 | VDAKYAKERNQAAFEILYLPNLTQQQKWAFIWKLDDDPSQSSELLSEAKKLNDSQAPK | 30 |
| Z17975 | VDAKYAKERNHAAYEILYLPNLTNKQKWAFIWKLDDDPSQSSELLSEAKKLNDSQAPK | 31 |
| Z17990 | VDAKYAKERNEAAYEILYLPNLTNRQKWAFIWKLDDDPSQSSELLSEAKKLNDSQAPK | 32 |
| Z17995 | VDAKYAKERNTAAQEILYLPNLTNYQKWAFIWKLDDDPSQSSELLSEAKKLNDSQAPK | 33 |
| Z17997 | VDAKYAKERNLAAYEILYLPNLTQKQRWAFIWKLDDDPSQSSELLSEAKKLNDSQAPK | 34 |
| Z17999 | VDAKYAKERNDAAYEILYLPNLTQEQRWAFIWKLDDDPSQSSELLSEAKKLNDSQAPK | 35 |
| Z18000 | VDAKYAKERNVAAYEILYLPNLTNQQKWAFIWKLDDDPSQSSELLSEAKKLNDSQAPK | 36 |
| Z18005 | VDAKYAKERNEAAYEILYLPNLTQVQKWAFIWKLDDDPSQSSELLSEAKKLNDSQAPK | 37 |
| Z18008 | VDAKYAKERNTAAYEILYLPNLTQSQRWAFIWKLDDDPSQSSELLSEAKKLNDSQAPK | 38 |
| Z18021 | VDAKYAKERNFAAYEILYLPNLTSQQKWAFIWKLDDDPSQSSELLSEAKKLNDSQAPK | 39 |
| Z18027 | VDAKYAKERNNAAYEILYLPNLTSAQKWAFIWKLDDDPSQSSELLSEAKKLNDSQAPK | 40 |
| Z18036 | VDAKYAKERNQAAYEILYLPNLTNKQKWAFIWKLDDDPSQSSELLSEAKKLNDSQAPK | 41 |
| Z18037 | VDAKYAKERNEAAYEILYLPNLTNEQKWAFIWKLDDDPSQSSELLSEAKKLNDSQAPK | 42 |
| Z18038 | VDAKYAKERNTAAYEILYLPNLTNAQKWAFIWKLDDDPSQSSELLSEAKKLNDSQAPK | 43 |
| Z18060 | VDAKYAKERNSAAYEILYLPNLTKQQKWAFIWKLDDDPSQSSELLSEAKKLNDSQAPK | 44 |
| Z18065 | VDAKYAKERNKAAYEILYLPNLTQAQKWAFIWKLDDDPSQSSELLSEAKKLNDSQAPK | 45 |
| Z18069 | VDAKYAKERNEAAYEILYLPNLTASQRWAFIWKLDDDPSQSSELLSEAKKLNDSQAPK | 46 |
| Z18078 | VDAKYAKERNTAAQEILYLPNLTSGQKWAFIWKLDDDPSQSSELLSEAKKLNDSQAPK | 47 |
| Z18092 | VDAKYAKERNIAAYEILWLPNLTNAQKWAFIWKLDDDPSQSSELLSEAKKLNDSQAPK | 48 |
| Z18095 | VDAKYAKERNAAAFEILYLPNLTQSQKWAFIWKLDDDPSQSSELLSEAKKLNDSQAPK | 49 |
| Z18096 | VDAKYAKERNEAAYEILYLPNLTSSQKWAFIWKLDDDPSQSSELLSEAKKLNDSQAPK | 50 |
| Z18099 | VDAKYAKERNEAAHEILYLPNLTQKQIWAFIWKLDDDPSQSSELLSEAKKLNDSQAPK | 51 |
| Z18104 | VDAKYAKERNFAAYEILYLPNLTNSQKWAFIWKLDDDPSQSSELLSEAKKLNDSQAPK | 52 |
| Z18106 | VDAKYAKERNAAAFEILYLPNLTSAQVWAFIWKLDDDPSQSSELLSEAKKLNDSQAPK | 53 |
| Z18108 | VDAKYAKERNDAAYEILYLPNLTKQQKWAFIWKLDDDPSQSSELLSEAKKLNDSQAPK | 54 |
| Z18110 | VDAKYAKERNKAAYEILYLPNLTQQQIWAFIWKLDDDPSQSSELLSEAKKLNDSQAPK | 55 |
| Z18111 | VDAKYAKERNHAAYEILYLPNLTQQQKWAFIWKLDDDPSQSSELLSEAKKLNDSQAPK | 56 |
| Z18115 | VDAKYAKERNFAAYEILYLPNLTNAQKWAFIWKLDDDPSQSSELLSEAKKLNDSQAPK | 57 |
| Z18116 | VDAKYAKERNAAAYEILYLPNLTQAQKWAFIWKLDDDPSQSSELLSEAKKLNDSQAPK | 58 |

Figure 1C

| Designation | Sequence | SEQ ID NO: |
|---|---|---|
| Z18117 | VDAKYAKERNKAAFEILYLPNLTQEQKWAFIWKLDDDPSQSSELLSEAKKLNDSQAPK | 59 |
| Z18118 | VDAKYAKERNAAAYEILYLPNLTAGQKWAFIWKLDDDPSQSSELLSEAKKLNDSQAPK | 60 |
| Z18119 | VDAKYAKERNQAAYEILYLPNLTNSQIWAFIWKLDDDPSQSSELLSEAKKLNDSQAPK | 61 |
| Z18124 | VDAKYAKERNDAAYEILQLPNLTNQQHWAFIWKLDDDPSQSSELLSEAKKLNDSQAPK | 62 |
| Z18128 | VDAKYAKERNSAAYEILYLPNLTNQQRWAFIWKLDDDPSQSSELLSEAKKLNDSQAPK | 63 |
| Z18130 | VDAKYAKERNSAAQEILYLPNLTNRQKWAFIWKLDDDPSQSSELLSEAKKLNDSQAPK | 64 |
| Z18131 | VDAKYAKERNEAAYEILYLPNLTAAQKWAFIWKLDDDPSQSSELLSEAKKLNDSQAPK | 65 |
| Z18133 | VDAKYAKERNQAAYEILYLPNLTQKQKWAFIWKLDDDPSQSSELLSEAKKLNDSQAPK | 66 |
| Z18135 | VDAKYAKERNTAAYEILYLPNLTKSQQWAFIWKLDDDPSQSSELLSEAKKLNDSQAPK | 67 |
| Z18137 | VDAKYAKERNSAAYEILYLPNLTSQQKWAFIWKLDDDPSQSSELLSEAKKLNDSQAPK | 68 |
| Z18138 | VDAKYAKERNIAAYEILYLPNLTQNQKWAFIWKLDDDPSQSSELLSEAKKLNDSQAPK | 69 |
| Z18140 | VDAKYAKERNIAAQEILYLPNLTNAQKWAFIWKLDDDPSQSSELLSEAKKLNDSQAPK | 70 |
| Z18143 | VDAKYAKERNDAAYEILYLPNLTNSQKWAFIWKLDDDPSQSSELLSEAKKLNDSQAPK | 71 |
| Z18144 | VDAKYAKERNHAAFEILYLPNLTNAQKWAFIWKLDDDPSQSSELLSEAKKLNDSQAPK | 72 |
| Z18148 | VDAKYAKERNEAAYEILYLPNLTQKQKWAFIWKLDDDPSQSSELLSEAKKLNDSQAPK | 73 |
| Z18150 | VDAKYAKERNQAAFEILYLPNLTNSQKWAFIWKLDDDPSQSSELLSEAKKLNDSQAPK | 74 |
| Z18152 | VDAKYAKERNVAAYEILYLPNLTQNQKWAFIWKLDDDPSQSSELLSEAKKLNDSQAPK | 75 |
| Z18153 | VDAKYAKERNIAAYEILYLPNLTNQQKWAFIWKLDDDPSQSSELLSEAKKLNDSQAPK | 76 |
| Z18156 | VDAKYAKERNFAAYEILYLPNLTQRQKWAFIWKLDDDPSQSSELLSEAKKLNDSQAPK | 77 |
| Z18158 | VDAKYAKERNRAAYEILYLPNLTHSQKWAFIWKLDDDPSQSSELLSEAKKLNDSQAPK | 78 |
| Z18164 | VDAKYAKERNTAAYEILYLPNLTQEQKWAFIWKLDDDPSQSSELLSEAKKLNDSQAPK | 79 |
| Z18167 | VDAKYAKERNEAAYEILYLPNLTNNQKWAFIWKLDDDPSQSSELLSEAKKLNDSQAPK | 80 |
| Z18172 | VDAKYAKERNSAAFEILYLPNLTNAQKWAFIWKLDDDPSQSSELLSEAKKLNDSQAPK | 81 |
| Z18174 | VDAKYAKERNQAAYEILYLPNLTQRQKWAFIWKLDDDPSQSSELLSEAKKLNDSQAPK | 82 |
| Z18176 | VDAKYAKERNDAAYEILYLPNLTASQRWAFIWKLDDDPSQSSELLSEAKKLNDSQAPK | 83 |
| Z18179 | VDAKYAKERNLAAQEILYLPNLTQKQRWAFIWKLDDDPSQSSELLSEAKKLNDSQAPK | 84 |
| Z18185 | VDAKYAKERNEAAQEILYLPNLTQKQIWAFIWKLDDDPSQSSELLSEAKKLNDSQAPK | 85 |
| Z18220 | VDAKYAKERNEAAYEILYLPNLTSKQKWAFIWKLDDDPSQSSELLSEAKKLNDSQAPK | 86 |
| Z18228 | VDAKYAKERNKAAQEILYLPNLTQNQIWAFIWKLDDDPSQSSELLSEAKKLNDSQAPK | 87 |

Figure 1D

| Designation | Sequence | SEQ ID NO: |
|---|---|---|
| Z18240 | VDAKYAKERNQAAYEILYLPNLTQAQKWAFIWKLDDDPSQSSELLSEAKKLNDSQAPK | 88 |
| Z18243 | VDAKYAKERNAAAYEILYLPNLTQLQKWAFIWKLDDDPSQSSELLSEAKKLNDSQAPK | 89 |
| Z18252 | VDAKYAKERNEAAFEILYLPNLTNQQKWAFIWKLDDDPSQSSELLSEAKKLNDSQAPK | 90 |
| Z18268 | VDAKYAKERNAAAFEILWLPNLTNAQKWAFIWKLDDDPSQSSELLSEAKKLNDSQAPK | 91 |
| Z18374 | VDAKYAKERNEAAFEILHLPNLTKAQHWAFIWKLADDPSQSSELLSEAKKLNDSQAPK | 92 |
| Z18377 | VDAKYAKERNDAAFEILYLPNLTQTQIWAFIWKLDDDPSQSSELLSEAKKLNDSQAPK | 93 |
| Z17721 | VDAKYAKERNEAAYEILYLPNLTSAQRWAFIWKLDDDPSQSSELLSEAKKLNDSQAPK | 94 |
| Z17723 | VDAKYAKERNTAAHEILYLPNLTQSQIWAFIWKLDDDPSQSSELLSEAKKLNDSQAPK | 95 |
| Z17725 | VDAKYAKERNTAAYEILKLPNLTKYQHWAFIWKLDDDPSQSSELLSEAKKLNDSQAPK | 96 |
| Z17726 | VDAKYAKERNDAAYEILQLPNLTQSQLWAFIWKLDDDPSQSSELLSEAKKLNDSQAPK | 97 |
| Z17727 | VDAKYAKERNIAAYEILKLPNLTENQRWAFIWKLDDDPSQSSELLSEAKKLNDSQAPK | 98 |
| Z17728 | VDAKYAKERNIAASEILKLPNLTKEQHWAFIWKLDDDPSQSSELLSEAKKLNDSQAPK | 99 |
| Z17729 | VDAKYAKERNDAAYEILYLPNLTQYQKWAFIWKLDDDPSQSSELLSEAKKLNDSQAPK | 100 |
| Z17730 | VDAKYAKERNDAAEEILYLPNLTNNQKWAFIWKLDDDPSQSSELLSEAKKLNDSQAPK | 101 |
| Z17731 | VDAKYAKERNAAAYEILYLPNLTWSQQWAFIWKLDDDPSQSSELLSEAKKLNDSQAPK | 102 |
| Z17732 | VDAKYAKERNKAAYEILYLPNLTASQHWAFIWKLDDDPSQSSELLSEAKKLNDSQAPK | 103 |
| Z17733 | VDAKYAKERNNAAYEILYLPNLTQQQKWAFIWKLDDDPSQSSELLSEAKKLNDSQAPK | 104 |
| Z17734 | VDAKYAKERNTAAYEILYLPNLTNKQKWAFIWKLDDDPSQSSELLSEAKKLNDSQAPK | 105 |
| Z17735 | VDAKYAKERNEAAYEILYLPNLTDAQIWAFIWKLDDDPSQSSELLSEAKKLNDSQAPK | 106 |
| Z17736 | VDAKYAKERNTAASEILYLPNLTSQQRWAFIWKLDDDPSQSSELLSEAKKLNDSQAPK | 107 |
| Z17738 | VDAKYAKERNIAAFEILWLPNLTAHQKWAFIWKLDDDPSQSSELLSEAKKLNDSQAPK | 108 |
| Z17739 | VDAKYAKERNDAAFEILYLPNLTSEQIWAFIWKLDDDPSQSSELLSEAKKLNDSQAPK | 109 |
| Z17741 | VDAKYAKERNHAADEILKLPNLTSDQNWAFIWKLDDDPSQSSELLSEAKKLNDSQAPK | 110 |
| Z17743 | VDAKYAKERNDAAYEILYLPNLTNEQKWAFIWKLDDDPSQSSELLSEAKKLNDSQAPK | 111 |
| Z17744 | VDAKYAKERNIAAEEILILPNLTQNQKWAFIWKLDDDPSQSSELLSEAKKLNDSQAPK | 112 |
| Z17745 | VDAKYAKERNEAAQEILYLPNLTQNQIWAFIWKLDDDPSQSSELLSEAKKLNDSQAPK | 113 |
| Z17751 | VDAKYAKERNSAAQEILYLPNLTQNQIWAFIWKLDDDPSQSSELLSEAKKLNDSQAPK | 114 |
| Z17752 | VDAKYAKERNFAAQEILYLPNLTQKQIWAFIWKLDDDPSQSSELLSEAKKLNDSQAPK | 115 |
| Z17753 | VDAKYAKERNNAAYEILYLPNLTQKQKWAFIWKLDDDPSQSSELLSEAKKLNDSQAPK | 116 |

Figure 1E

| Designation | Sequence | SEQ ID NO: |
|---|---|---|
| Z17754 | VDAKYAKERNEAAYEILYLPNLTNGQKWAFIWKLDDDPSQSSELLSEAKKLNDSQAPK | 117 |
| Z17755 | VDAKYAKERNAAAQEILYLPNLTQAQKWAFIWKLDDDPSQSSELLSEAKKLNDSQAPK | 118 |
| Z17757 | VDAKYAKERNAAAYEILYLPNLTKAQKWAFIWKLDDDPSQSSELLSEAKKLNDSQAPK | 119 |
| Z17759 | VDAKYAKERNKAAFEILYLPNLTNNQKWAFIWKLDDDPSQSSELLSEAKKLNDSQAPK | 120 |
| Z17761 | VDAKYAKERNNAAQEILYLPNLTQKQIWAFIWKLDDDPSQSSELLSEAKKLNDSQAPK | 121 |
| Z17762 | VDAKYAKERNEAAHEILTLPNLTAEQYWAFIWKLDDDPSQSSELLSEAKKLNDSQAPK | 122 |
| Z17763 | VDAKYAKERNWAAAEILYLPNLTNAQTWAFIWKLDDDPSQSSELLSEAKKLNDSQAPK | 123 |
| Z17764 | VDAKYAKERNDAAYEILYLPNLTQDQIWAFIWKLDDDPSQSSELLSEAKKLNDSQAPK | 124 |
| Z17765 | VDAKYAKERNEAAHEILYLPNLTNAQKWAFIWKLDDDPSQSSELLSEAKKLNDSQAPK | 125 |
| Z17766 | VDAKYAKERNAAAQEILYLPNLTNHQKWAFIWKLEDDPSQSSELLSEAKKLNDSQAPK | 126 |
| Z17767 | VDAKYAKERNRAAHEILYLPNLTRQQQWAFIWKLDDDPSQSSELLSEAKKLNDSQAPK | 127 |
| Z17768 | VDAKYAKERNEAAYEILYLPNLTNKQRWAFIWKLDDDPSQSSELLSEAKKLNDSQAPK | 128 |
| Z17769 | VDAKYAKERNHAAFEILYLPNLTNEQKWAFIWKLDDDPSQSSELLSEAKKLNDSQAPK | 129 |
| Z17770 | VDAKYAKERNEAAYEILYLPNLTSQQIWAFIWKLDDDPSQSSELLSEAKKLNDSQAPK | 130 |
| Z17771 | VDAKYAKERNTAAYEILQLPNLTKSQKWAFIWKLADDPSQSSELLSEAKKLNDSQAPK | 131 |
| Z17773 | VDAKYAKERNHAAAEILSLPNLTKKQNWAFIWKLDDDPSQSSELLSEAKKLNDSQAPK | 132 |
| Z17774 | VDAKYAKERNEAAYEILYLPNLTHAQKWAFIWKLDDDPSQSSELLSEAKKLNDSQAPK | 133 |
| Z17776 | VDAKYAKERNIAASEILTLPNLTKSQTWAFIWKLDDDPSQSSELLSEAKKLNDSQAPK | 134 |
| Z17777 | VDAKYAKERNKAAYEILNLPNLTQSQLWAFIWKLDDDPSQSSELLSEAKKLNDSQAPK | 135 |
| Z17779 | VDAKYAKERNAAAQEILELPNLTWAQHWAFIWKLDDDPSQSSELLSEAKKLNDSQAPK | 136 |
| Z17782 | VDAKYAKERNSAAYEILYLPNLTQSQIWAFIWKLADDPSQSSELLSEAKKLNDSQAPK | 137 |
| Z17783 | VDAKYAKERNYAAYEILYLPNLTEAQRWAFIWKLDDDPSQSSELLSEAKKLNDSQAPK | 138 |
| Z17785 | VDAKYAKERNNAAYEILLLPNLTQEQKWAFIWKLDDDPSQSSELLSEAKKLNDSQAPK | 139 |
| Z17786 | VDAKYAKERNNAAQEILYLPNLTNYQKWAFIWKLDDDPSQSSELLSEAKKLNDSQAPK | 140 |
| Z17787 | VDAKYAKERNQAAYEILQLPNLTNDQYWAFIWKLDDDPSQSSELLSEAKKLNDSQAPK | 141 |
| Z17788 | VDAKYAKERNTAAYEILYLPNLTNNQKWAFIWKLDDDPSQSSELLSEAKKLNDSQAPK | 142 |
| Z17789 | VDAKYAKERNKAAYEILYLPNLTQKQKWAFIWKLDDDPSQSSELLSEAKKLNDSQAPK | 143 |
| Z17790 | VDAKYAKERNTAAEEILKLPNLTNKQHWAFIWKLDDDPSQSSELLSEAKKLNDSQAPK | 144 |
| Z17791 | VDAKYAKERNRAAYEILYLPNLTNSQKWAFIWKLADDPSQSSELLSEAKKLNDSQAPK | 145 |

Figure 1F

| Designation | Sequence | SEQ ID NO: |
|---|---|---|
| Z17792 | VDAKYAKERNSAAHEILYLPNLTTAQRWAFIWKLDDDPSQSSELLSEAKKLNDSQAPK | 146 |
| Z17794 | VDAKYAKERNSAAYEILYLPNLTANQRWAFIWKLDDDPSQSSELLSEAKKLNDSQAPK | 147 |
| Z17795 | VDAKYAKERNKAAYEILYLPNLTNLQRWAFIWKLADDPSQSSELLSEAKKLNDSQAPK | 148 |
| Z17796 | VDAKYAKERNQAASEILSLPNLTKSQKWAFIWKLDDDPSQSSELLSEAKKLNDSQAPK | 149 |
| Z17797 | VDAKYAKERNHAAWEILKLPNLTKSQEWAFIWKLDDDPSQSSELLSEAKKLNDSQAPK | 150 |
| Z17798 | VDAKYAKERNVAAQEILYLPNLTQKQKWAFIWKLDDDPSQSSELLSEAKKLNDSQAPK | 151 |
| Z17800 | VDAKYAKERNLAAYEILYLPNLTRAQQWAFIWKLDDDPSQSSELLSEAKKLNDSQAPK | 152 |
| Z17801 | VDAKYAKERNVAAYEILYLPNLTANQKWAFIWKLDDDPSQSSELLSEAKKLNDSQAPK | 153 |
| Z17802 | VDAKYAKERNDAAYEILYLPNLTSAQVWAFIWKLDDDPSQSSELLSEAKKLNDSQAPK | 154 |
| Z17803 | VDAKYAKERNQAAEEILRLPNLTWEQNWAFIWKLDDDPSQSSELLSEAKKLNDSQAPK | 155 |
| Z17804 | VDAKYAKERNNAAYEILQLPNLTQLQTWAFIWKLDDDPSQSSELLSEAKKLNDSQAPK | 156 |
| Z17805 | VDAKYAKERNSAAYEILYLPNLTQKQKWAFIWKLDDDPSQSSELLSEAKKLNDSQAPK | 157 |
| Z17806 | VDAKYAKERNFAAQEILYLPNLTKAQTWAFIWKLDDDPSQSSELLSEAKKLNDSQAPK | 158 |
| Z17808 | VDAKYAKERNHAAQEILELPNLTNKQRWAFIWKLDDDPSQSSELLSEAKKLNDSQAPK | 159 |
| Z17809 | VDAKYAKERNIAAQEILFLPNLTQAQKWAFIWKLDDDPSQSSELLSEAKKLNDSQAPK | 160 |
| Z17810 | VDAKYAKERNEAAFEILYLPNLTEKQRWAFIWKLDDDPSQSSELLSEAKKLNDSQAPK | 161 |
| Z17811 | VDAKYAKERNIAANEILKLPNLTANQYWAFIWKLDDDPSQSSELLSEAKKLNDSQAPK | 162 |
| Z17812 | VDAKYAKERNEAAVEILYLPNLTNSQKWAFIWKLDDDPSQSSELLSEAKKLNDSQAPK | 163 |
| Z17813 | VDAKYAKERNEAAQEILNLPNLTQSQEWAFIWKLDDDPSQSSELLSEAKKLNDSQAPK | 164 |
| Z17814 | VDAKYAKERNIAAYEILQLPNLTQRQIWAFIWKLDDDPSQSSELLSEAKKLNDSQAPK | 165 |
| Z17816 | VDAKYAKERNYAAYEILQLPNLTAAQYWAFIWKLDDDPSQSSELLSEAKKLNDSQAPK | 166 |
| Z17817 | VDAKYAKERNEAAHEILYLPNLTQGQIWAFIWKLDDDPSQSSELLSEAKKLNDSQAPK | 167 |
| Z17818 | VDAKYAKERNEAAHEILQLPNLTSLQTWAFIWKLDDDPSQSSELLSEAKKLNDSQAPK | 168 |
| Z17819 | VDAKYAKERNHAAFEILYLPNLTAAQKWAFIWKLDDDPSQSSELLSEAKKLNDSQAPK | 169 |
| Z17820 | VDAKYAKERNYAAEEILKLPNLTNGQQWAFIWKLDDDPSQSSELLSEAKKLNDSQAPK | 170 |
| Z17823 | VDAKYAKERNNAATEILRLPNLTASQYWAFIWKLDDDPSQSSELLSEAKKLNDSQAPK | 171 |
| Z17824 | VDAKYAKERNHAAYEILYLPNLTAEQYWAFIWKLDDDPSQSSELLSEAKKLNDSQAPK | 172 |
| Z17826 | VDAKYAKERNLAAFEILYLPNLTQSQIWAFIWKLDDDPSQSSELLSEAKKLNDSQAPK | 173 |
| Z17828 | VDAKYAKERNYAAYEILYLPNLTQFQKWAFIWKLDDDPSQSSELLSEAKKLNDSQAPK | 174 |

Figure 1G

| Designation | Sequence | SEQ ID NO: |
|---|---|---|
| Z17829 | VDAKYAKERNEAAQEILYLPNLTSSQIWAFIWKLDDDPSQSSELLSEAKKLNDSQAPK | 175 |
| Z17831 | VDAKYAKERNKAAFEILNLPNLTSSQRWAFIWKLDDDPSQSSELLSEAKKLNDSQAPK | 176 |
| Z17832 | VDAKYAKERNTAAHEILYLPNLTQSQIWAFIWKLADDPSQSSELLSEAKKLNDSQAPK | 177 |
| Z17833 | VDAKYAKERNDAAQEILYLPNLTKGQQWAFIWKLDDDPSQSSELLSEAKKLNDSQAPK | 178 |
| Z17834 | VDAKYAKERNFAAHEILYLPNLTQEQKWAFIWKLDDDPSQSSELLSEAKKLNDSQAPK | 179 |
| Z17835 | VDAKYAKERNSAAHEILYLPNLTEKQKWAFIWKLDDDPSQSSELLSEAKKLNDSQAPK | 180 |
| Z17836 | VDAKYAKERNDAAYEILYLPNLTHEQHWAFIWKLDDDPSQSSELLSEAKKLNDSQAPK | 181 |
| Z17837 | VDAKYAKERNIAAHEILYLPNLTNEQKWAFIWKLDDDPSQSSELLSEAKKLNDSQAPK | 182 |
| Z17838 | VDAKYAKERNEAAFEILYLPNLTNKQRWAFIWKLDDDPSQSSELLSEAKKLNDSQAPK | 183 |
| Z17839 | VDAKYAKERNKAAYEILYLPNLTQQQKWAFIWKLDDDPSQSSELLSEAKKLNDSQAPK | 184 |
| Z17840 | VDAKYAKERNKAAQEILYLPNLTQRQKWAFIWKLDDDPSQSSELLSEAKKLNDSQAPK | 185 |
| Z17842 | VDAKYAKERNDAAQEILTLPNLTAKQYWAFIWKLDDDPSQSSELLSEAKKLNDSQAPK | 186 |
| Z17844 | VDAKYAKERNSAAYEILYLPNLTSDQKWAFIWKLDDDPSQSSELLSEAKKLNDSQAPK | 187 |
| Z17846 | VDAKYAKERNKAAFEILYLPNLTNQQKWAFIWKLDDDPSQSSELLSEAKKLNDSQAPK | 188 |
| Z17847 | VDAKYAKERNQAAQEILELPNLTNAQYWAFIWKLDDDPSQSSELLSEAKKLNDSQAPK | 189 |
| Z17851 | VDAKYAKERNEAAYEILKLPNLTSQQYWAFIWKLDDDPSQSSELLSEAKKLNDSQAPK | 190 |
| Z17852 | VDAKYAKERNEAAYEILNLPNLTRHQHWAFIWKLDDDPSQSSELLSEAKKLNDSQAPK | 191 |
| Z17853 | VDAKYAKERNLAAYEILKLPNLTNEQNWAFIWKLDDDPSQSSELLSEAKKLNDSQAPK | 192 |
| Z17854 | VDAKYAKERNKAAYEILYLPNLTQEQIWAFIWKLDDDPSQSSELLSEAKKLNDSQAPK | 193 |
| Z17855 | VDAKYAKERNKAAYEILYLPNLTSQQIWAFIWKLDDDPSQSSELLSEAKKLNDSQAPK | 194 |
| Z17856 | VDAKYAKERNTAAHEILYLPNLTNYQKWAFIWKLDDDPSQSSELLSEAKKLNDSQAPK | 195 |
| Z17857 | VDAKYAKERNHAAFEILKLPNLTNEQHWAFIWKLDDDPSQSSELLSEAKKLNDSQAPK | 196 |
| Z17858 | VDAKYAKERNDAAFEILYLPNLTNAQKWAFIWKLDDDPSQSSELLSEAKKLNDSQAPK | 197 |
| Z17859 | VDAKYAKERNLAAHEILYLPNLTNAQKWAFIWKLDDDPSQSSELLSEAKKLNDSQAPK | 198 |
| Z17860 | VDAKYAKERNHAAYEILQLPNLTKNQKWAFIWKLDDDPSQSSELLSEAKKLNDSQAPK | 199 |
| Z17861 | VDAKYAKERNSAAYEILYLPNLTNSQKWAFIWKLDDDPSQSSELLSEAKKLNDSQAPK | 200 |
| Z17862 | VDAKYAKERNAAAYEILYLPNLTNNQKWAFIWKLDDDPSQSSELLSEAKKLNDSQAPK | 201 |
| Z17863 | VDAKYAKERNDAAYEILQLPNLTNQQLWAFIWKLDDDPSQSSELLSEAKKLNDSQAPK | 202 |
| Z17866 | VDAKYAKERNNAAEEILYLPNLTNSQKWAFIWKLDDDPSQSSELLSEAKKLNDSQAPK | 203 |

Figure 1H

| Designation | Sequence | SEQ ID NO: |
|---|---|---|
| Z17868 | VDAKYAKERNEAAHEILYLPNLTESQRWAFIWKLDDDPSQSSELLSEAKKLNDSQAPK | 204 |
| Z17869 | VDAKYAKERNNAAYEILSLPNLTKSQHWAFIWKLDDDPSQSSELLSEAKKLNDSQAPK | 205 |
| Z17870 | VDAKYAKERNVAAYEILYLPNLTNNQKWAFIWKLDDDPSQSSELLSEAKKLNDSQAPK | 206 |
| Z17871 | VDAKYAKERNEAAYEILQLPNLTNYQYWAFIWKLDDDPSQSSELLSEAKKLNDSQAPK | 207 |
| Z17872 | VDAKYAKERNQAAFEILYLPNLTRFQKWAFIWKLDDDPSQSSELLSEAKKLNDSQAPK | 208 |
| Z17873 | VDAKYAKERNFAAQEILYLPNLTNAQRWAFIWKLDDDPSQSSELLSEAKKLNDSQAPK | 209 |
| Z17874 | VDAKYAKERNSAAYEILYLPNLTNKQKWAFIWKLDDDPSQSSELLSEAKKLNDSQAPK | 210 |
| Z17875 | VDAKYAKERNSAASEILYLPNLTQNQKWAFIWKLDDDPSQSSELLSEAKKLNDSQAPK | 211 |
| Z17876 | VDAKYAKERNYAAWEILQLPNLTKAQHWAFIWKLDDDPSQSSELLSEAKKLNDSQAPK | 212 |
| Z17878 | VDAKYAKERNHAAHEILYLPNLTNEQKWAFIWKLDDDPSQSSELLSEAKKLNDSQAPK | 213 |
| Z17879 | VDAKYAKERNEAAFEILYLPNLTNAQKWAFIWKLDDDPSQSSELLSEAKKLNDSQAPK | 214 |
| Z17880 | VDAKYAKERNEAAYEILYLPNLTSAQLWAFIWKLDDDPSQSSELLSEAKKLNDSQAPK | 215 |
| Z17881 | VDAKYAKERNSAAQEILELPNLTNQQLWAFIWKLDDDPSQSSELLSEAKKLNDSQAPK | 216 |
| Z17882 | VDAKYAKERNSAAHEILKLPNLTQEQYWAFIWKLDDDPSQSSELLSEAKKLNDSQAPK | 217 |
| Z17883 | VDAKYAKERNHAAQEILILPNLTRAQTWAFIWKLDDDPSQSSELLSEAKKLNDSQAPK | 218 |
| Z17884 | VDAKYAKERNTAAFEILYLPNLTAAQKWAFIWKLDDDPSQSSELLSEAKKLNDSQAPK | 219 |
| Z17885 | VDAKYAKERNVAAQEILYLPNLTNNQKWAFIWKLDDDPSQSSELLSEAKKLNDSQAPK | 220 |
| Z17886 | VDAKYAKERNKAAHEILYLPNLTNNQKWAFIWKLDDDPSQSSELLSEAKKLNDSQAPK | 221 |
| Z17887 | VDAKYAKERNQAAFEILYLPNLTQSQKWAFIWKLDDDPSQSSELLSEAKKLNDSQAPK | 222 |
| Z17888 | VDAKYAKERNSAAYEILNLPNLTARQYWAFIWKLDDDPSQSSELLSEAKKLNDSQAPK | 223 |
| Z17889 | VDAKYAKERNQAAQEILALPNLTRQQTWAFIWKLDDDPSQSSELLSEAKKLNDSQAPK | 224 |
| Z17890 | VDAKYAKERNSAAVEILNLPNLTKEQHWAFIWKLDDDPSQSSELLSEAKKLNDSQAPK | 225 |
| Z17891 | VDAKYAKERNEAAYEILFLPNLTQNQIWAFIWKLDDDPSQSSELLSEAKKLNDSQAPK | 226 |
| Z17892 | VDAKYAKERNEAAEEILYLPNLTQHQKWAFIWKLDDDPSQSSELLSEAKKLNDSQAPK | 227 |
| Z17893 | VDAKYAKERNKAAYEILYLPNLTNNQKWAFIWKLDDDPSQSSELLSEAKKLNDSQAPK | 228 |
| Z17894 | VDAKYAKERNNAAHEILYLPNLTSKQKWAFIWKLDDDPSQSSELLSEAKKLNDSQAPK | 229 |
| Z17895 | VDAKYAKERNEAAYEILYLPNLTSNQIWAFIWKLDDDPSQSSELLSEAKKLNDSQAPK | 230 |
| Z17896 | VDAKYAKERNEAAQEILELPNLTREQEWAFIWKLDDDPSQSSELLSEAKKLNDSQAPK | 231 |
| Z17897 | VDAKYAKERNTAAYEILYLPNLTDAQKWAFIWKLDDDPSQSSELLSEAKKLNDSQAPK | 232 |

Figure 1I

| Designation | Sequence | SEQ ID NO: |
|---|---|---|
| Z17898 | VDAKYAKERNYAAYEILYLPNLTQRQKWAFIWKLDDDPSQSSELLSEAKKLNDSQAPK | 233 |
| Z17899 | VDAKYAKERNKAAYEILYLPNLTKIQKWAFIWKLDDDPSQSSELLSEAKKLNDSQAPK | 234 |
| Z17900 | VDAKYAKERNKAAEEILWLPNLTNGQQWAFIWKLDDDPSQSSELLSEAKKLNDSQAPK | 235 |
| Z17901 | VDAKYAKERNFAAYEILYLPNLTRQQKWAFIWKLDDDPSQSSELLSEAKKLNDSQAPK | 236 |
| Z17902 | VDAKYAKERNEAAFEILTLPNLTNAQLWAFIWKLDDDPSQSSELLSEAKKLNDSQAPK | 237 |
| Z17904 | VDAKYAKERNVAAHEILYLPNLTQEQLWAFIWKLDDDPSQSSELLSEAKKLNDSQAPK | 238 |
| Z17905 | VDAKYAKERNEAAHEILYLPNLTAQQRWAFIWKLDDDPSQSSELLSEAKKLNDSQAPK | 239 |
| Z17906 | VDAKYAKERNAAAQEILYLPNLTQHQKWAFIWKLDDDPSQSSELLSEAKKLNDSQAPK | 240 |
| Z17907 | VDAKYAKERNSAAFEILNLPNLTKAQHWAFIWKLDDDPSQSSELLSEAKKLNDSQAPK | 241 |
| Z17908 | VDAKYAKERNHAAEEILYLPNLTNLQRWAFIWKLDDDPSQSSELLSEAKKLNDSQAPK | 242 |
| Z17909 | VDAKYAKERNSAAHEILYLPNLTNEQIWAFIWKLDDDPSQSSELLSEAKKLNDSQAPK | 243 |
| Z17910 | VDAKYAKERNHAAWEILQLPNLTNEQHWAFIWKLDDDPSQSSELLSEAKKLNDSQAPK | 244 |
| Z17912 | VDAKYAKERNNAAFEILQLPNLTWEQYWAFIWKLDDDPSQSSELLSEAKKLNDSQAPK | 245 |
| Z17913 | VDAKYAKERNRAAHEILYLPNLTSQQRWAFIWKLDDDPSQSSELLSEAKKLNDSQAPK | 246 |
| Z17914 | VDAKYAKERNQAAHEILYLPNLTANQKWAFIWKLDDDPSQSSELLSEAKKLNDSQAPK | 247 |
| Z17915 | VDAKYAKERNIAAYEILYLPNLTNAQKWAFIWKLDDDPSQSSELLSEAKKLNDSQAPK | 248 |
| Z17916 | VDAKYAKERNDAAYEILSLPNLTNGQYWAFIWKLDDDPSQSSELLSEAKKLNDSQAPK | 249 |
| Z17917 | VDAKYAKERNAAAQEILELPNLTNRQYWAFIWKLADDPSQSSELLSEAKKLNDSQAPK | 250 |
| Z17918 | VDAKYAKERNEAAYEILYLPNLTRDQRWAFIWKLDDDPSQSSELLSEAKKLNDSQAPK | 251 |
| Z17919 | VDAKYAKERNAAAQEILTLPNLTRKQTWAFIWKLDDDPSQSSELLSEAKKLNDSQAPK | 252 |
| Z17920 | VDAKYAKERNFAAQEILYLPNLTNSQKWAFIWKLDDDPSQSSELLSEAKKLNDSQAPK | 253 |
| Z17921 | VDAKYAKERNTAAYEILYLPNLTDEQVWAFIWKLDDDPSQSSELLSEAKKLNDSQAPK | 254 |
| Z17922 | VDAKYAKERNAAAQEILYLPNLTHAQKWAFIWKLEDDPSQSSELLSEAKKLNDSQAPK | 255 |
| Z17923 | VDAKYAKERNHAAYEILKLPNLTKEQHWAFIWKLDDDPSQSSELLSEAKKLNDSQAPK | 256 |
| Z17924 | VDAKYAKERNEAAYEILYLPNLTNSQRWAFIWKLDDDPSQSSELLSEAKKLNDSQAPK | 257 |
| Z17925 | VDAKYAKERNFAAHEILYLPNLTQQQKWAFIWKLDDDPSQSSELLSEAKKLNDSQAPK | 258 |
| Z17926 | VDAKYAKERNKAAEEILRLPNLTQAQFWAFIWKLDDDPSQSSELLSEAKKLNDSQAPK | 259 |
| Z17927 | VDAKYAKERNFAAHEILYLPNLTSQQKWAFIWKLDDDPSQSSELLSEAKKLNDSQAPK | 260 |
| Z17929 | VDAKYAKERNVAAHEILYLPNLTRSQKWAFIWKLDDDPSQSSELLSEAKKLNDSQAPK | 261 |

Figure 1J

| Designation | Sequence | SEQ ID NO: |
|---|---|---|
| Z17930 | VDAKYAKERNTAAQEILELPNLTNRQHWAFIWKLDDDPSQSSELLSEAKKLNDSQAPK | 262 |
| Z17931 | VDAKYAKERNIAAAEILKLPNLTNSQRWAFIWKLDDDPSQSSELLSEAKKLNDSQAPK | 263 |
| Z17932 | VDAKYAKERNQAAHEILYLPNLTSAQIWAFIWKLDDDPSQSSELLSEAKKLNDSQAPK | 264 |
| Z17933 | VDAKYAKERNSAAHEILYLPNLTQLQKWAFIWKLDDDPSQSSELLSEAKKLNDSQAPK | 265 |
| Z17934 | VDAKYAKERNAAAFEILYLPNLTKSQKWAFIWKLDDDPSQSSELLSEAKKLNDSQAPK | 266 |
| Z17935 | VDAKYAKERNHAAFEILNLPNLTQKQKWAFIWKLDDDPSQSSELLSEAKKLNDSQAPK | 267 |
| Z17936 | VDAKYAKERNHAAEEILYLPNLTKKQQWAFIWKLDDDPSQSSELLSEAKKLNDSQAPK | 268 |
| Z17937 | VDAKYAKERNEAATEILNLPNLTAKQYWAFIWKLDDDPSQSSELLSEAKKLNDSQAPK | 269 |
| Z17938 | VDAKYAKERNAAAFEILYLPNLTNDQIWAFIWKLDDDPSQSSELLSEAKKLNDSQAPK | 270 |
| Z17939 | VDAKYAKERNLAAYEILYLPNLTNKQRWAFIWKLDDDPSQSSELLSEAKKLNDSQAPK | 271 |
| Z17940 | VDAKYAKERNNAAQEILFLPNLTQAQKWAFIWKLDDDPSQSSELLSEAKKLNDSQAPK | 272 |
| Z17941 | VDAKYAKERNRAAQEILELPNLTQYQLWAFIWKLDDDPSQSSELLSEAKKLNDSQAPK | 273 |
| Z17942 | VDAKYAKERNEAAHEILYLPNLTQSQKWAFIWKLDDDPSQSSELLSEAKKLNDSQAPK | 274 |
| Z17943 | VDAKYAKERNLAAQEILTLPNLTKAQIWAFIWKLDDDPSQSSELLSEAKKLNDSQAPK | 275 |
| Z17945 | VDAKYAKERNTAAHEILYLPNLTQKQKWAFIWKLDDDPSQSSELLSEAKKLNDSQAPK | 276 |
| Z17946 | VDAKYAKERNEAAYEILNLPNLTSSQYWAFIWKLDDDPSQSSELLSEAKKLNDSQAPK | 277 |
| Z17947 | VDAKYAKERNEAAYEILQLPNLTTAQYWAFIWKLDDDPSQSSELLSEAKKLNDSQAPK | 278 |
| Z17948 | VDAKYAKERNKAAYEILYLPNLTNLQKWAFIWKLDDDPSQSSELLSEAKKLNDSQAPK | 279 |
| Z17949 | VDAKYAKERNEAAHEILYLPNLTNLQKWAFIWKLDDDPSQSSELLSEAKKLNDSQAPK | 280 |
| Z17951 | VDAKYAKERNEAAEEILYLPNLTQDQVWAFIWKLDDDPSQSSELLSEAKKLNDSQAPK | 281 |
| Z17952 | VDAKYAKERNTAAVEILELPNLTNAQIWAFIWKLDDDPSQSSELLSEAKKLNDSQAPK | 282 |
| Z17953 | VDAKYAKERNYAAEEILYLPNLTQQQRWAFIWKLDDDPSQSSELLSEAKKLNDSQAPK | 283 |
| Z17954 | VDAKYAKERNKAAQEILYLPNLTAKQRWAFIWKLDDDPSQSSELLSEAKKLNDSQAPK | 284 |
| Z17955 | VDAKYAKERNDAAYEILSLPNLTNQQYWAFIWKLDDDPSQSSELLSEAKKLNDSQAPK | 285 |
| Z17956 | VDAKYAKERNDAAYEILKLPNLTNGQHWAFIWKLDDDPSQSSELLSEAKKLNDSQAPK | 286 |
| Z17957 | VDAKYAKERNRAAHEILYLPNLTNAQKWAFIWKLDDDPSQSSELLSEAKKLNDSQAPK | 287 |
| Z17958 | VDAKYAKERNQAANEILYLPNLTQSQIWAFIWKLDDDPSQSSELLSEAKKLNDSQAPK | 288 |
| Z17960 | VDAKYAKERNEAAQEILKLPNLTSDQLWAFIWKLDDDPSQSSELLSEAKKLNDSQAPK | 289 |
| Z17961 | VDAKYAKERNAAAEEILELPNLTNGQKWAFIWKLDDDPSQSSELLSEAKKLNDSQAPK | 290 |

Figure 1K

| Designation | Sequence | SEQ ID NO: |
|---|---|---|
| Z17962 | VDAKYAKERNAAAYEILYLPNLTWDQHWAFIWKLDDDPSQSSELLSEAKKLNDSQAPK | 291 |
| Z17963 | VDAKYAKERNAAAQEILELPNLTASQLWAFIWKLDDDPSQSSELLSEAKKLNDSQAPK | 292 |
| Z17965 | VDAKYAKERNEAAFEILRLPNLTQGQHWAFIWKLDDDPSQSSELLSEAKKLNDSQAPK | 293 |
| Z17966 | VDAKYAKERNKAAQEILYLPNLTSKQYWAFIWKLDDDPSQSSELLSEAKKLNDSQAPK | 294 |
| Z17967 | VDAKYAKERNSAAHEILYLPNLTKNQKWAFIWKLDDDPSQSSELLSEAKKLNDSQAPK | 295 |
| Z17969 | VDAKYAKERNDAAYEILYLPNLTNLQTWAFIWKLDDDPSQSSELLSEAKKLNDSQAPK | 296 |
| Z17970 | VDAKYAKERNKAAYEILQLPNLTQQQTWAFIWKLDDDPSQSSELLSEAKKLNDSQAPK | 297 |
| Z17971 | VDAKYAKERNAAAEEILDLPNLTNAQYWAFIWKLDDDPSQSSELLSEAKKLNDSQAPK | 298 |
| Z17973 | VDAKYAKERNFAAQEILYLPNLTNYQKWAFIWKLDDDPSQSSELLSEAKKLNDSQAPK | 299 |
| Z17974 | VDAKYAKERNFAAQEILYLPNLTNNQRWAFIWKLDDDPSQSSELLSEAKKLNDSQAPK | 300 |
| Z17976 | VDAKYAKERNAAASEILYLPNLTQKQKWAFIWKLDDDPSQSSELLSEAKKLNDSQAPK | 301 |
| Z17977 | VDAKYAKERNYAAYEILKLPNLTNDQHWAFIWKLDDDPSQSSELLSEAKKLNDSQAPK | 302 |
| Z17979 | VDAKYAKERNKAAVEILNLPNLTNEQYWAFIWKLDDDPSQSSELLSEAKKLNDSQAPK | 303 |
| Z17980 | VDAKYAKERNSAAQEILYLPNLTKSQKWAFIWKLDDDPSQSSELLSEAKKLNDSQAPK | 304 |
| Z17981 | VDAKYAKERNIAAHEILSLPNLTKQQHWAFIWKLDDDPSQSSELLSEAKKLNDSQAPK | 305 |
| Z17982 | VDAKYAKERNYAAYEILKLPNLTKSQHWAFIWKLDDDPSQSSELLSEAKKLNDSQAPK | 306 |
| Z17983 | VDAKYAKERNQAAQEILYLPNLTSSQKWAFIWKLDDDPSQSSELLSEAKKLNDSQAPK | 307 |
| Z17984 | VDAKYAKERNQAAQEILILPNLTQKQKWAFIWKLDDDPSQSSELLSEAKKLNDSQAPK | 308 |
| Z17987 | VDAKYAKERNAAAWEILSLPNLTTLQNWAFIWKLDDDPSQSSELLSEAKKLNDSQAPK | 309 |
| Z17988 | VDAKYAKERNYAAYEILYLPNLTDEQKWAFIWKLDDDPSQSSELLSEAKKLNDSQAPK | 310 |
| Z17989 | VDAKYAKERNQAAYEILYLPNLTRRQQWAFIWKLDDDPSQSSELLSEAKKLNDSQAPK | 311 |
| Z17991 | VDAKYAKERNSAAHEILYLPNLTNRQKWAFIWKLDDDPSQSSELLSEAKKLNDSQAPK | 312 |
| Z17992 | VDAKYAKERNTAAYEILYLPNLTNHQKWAFIWKLDDDPSQSSELLSEAKKLNDSQAPK | 313 |
| Z17993 | VDAKYAKERNDAAYEILELPNLTNAQYWAFIWKLDDDPSQSSELLSEAKKLNDSQAPK | 314 |
| Z17994 | VDAKYAKERNLAAHEILYLPNLTQDQKWAFIWKLDDDPSQSSELLSEAKKLNDSQAPK | 315 |
| Z17996 | VDAKYAKERNTAAQEILELPNLTQAQHWAFIWKLDDDPSQSSELLSEAKKLNDSQAPK | 316 |
| Z17998 | VDAKYAKERNDAAQEILELPNLTAAQYWAFIWKLDDDPSQSSELLSEAKKLNDSQAPK | 317 |
| Z18001 | VDAKYAKERNLAAHEILYLPNLTNQQKWAFIWKLDDDPSQSSELLSEAKKLNDSQAPK | 318 |
| Z18002 | VDAKYAKERNKAAYEILYLPNLTQLQKWAFIWKLDDDPSQSSELLSEAKKLNDSQAPK | 319 |

Figure 1L

| Designation | Sequence | SEQ ID NO: |
|---|---|---|
| Z18003 | VDAKYAKERNHAAYEILRLPNLTQDQIWAFIWKLDDDPSQSSELLSEAKKLNDSQAPK | 320 |
| Z18004 | VDAKYAKERNQAAEEILYLPNLTNLQRWAFIWKLDDDPSQSSELLSEAKKLNDSQAPK | 321 |
| Z18006 | VDAKYAKERNDAAQEILYLPNLTSEQYWAFIWKLDDDPSQSSELLSEAKKLNDSQAPK | 322 |
| Z18007 | VDAKYAKERNFAAYEILNLPNLTASQYWAFIWKLDDDPSQSSELLSEAKKLNDSQAPK | 323 |
| Z18009 | VDAKYAKERNDAAHEILYLPNLTQKQRWAFIWKLDDDPSQSSELLSEAKKLNDSQAPK | 324 |
| Z18010 | VDAKYAKERNEAAHEILQLPNLTQNQYWAFIWKLDDDPSQSSELLSEAKKLNDSQAPK | 325 |
| Z18011 | VDAKYAKERNSAAFEILYLPNLTSAQKWAFIWKLDDDPSQSSELLSEAKKLNDSQAPK | 326 |
| Z18012 | VDAKYAKERNAAAYEILYLPNLTNSQKWAFIWKLDDDPSQSSELLSEAKKLNDSQAPK | 327 |
| Z18013 | VDAKYAKERNQAAHEILYLPNLTQSQKWAFIWKLDDDPSQSSELLSEAKKLNDSQAPK | 328 |
| Z18014 | VDAKYAKERNEAAQEILNLPNLTASQYWAFIWKLDDDPSQSSELLSEAKKLNDSQAPK | 329 |
| Z18015 | VDAKYAKERNIAAHEILYLPNLTQNQIWAFIWKLDDDPSQSSELLSEAKKLNDSQAPK | 330 |
| Z18016 | VDAKYAKERNSAAFEILYLPNLTREQKWAFIWKLDDDPSQSSELLSEAKKLNDSQAPK | 331 |
| Z18017 | VDAKYAKERNQAAFEILYLPNLTHAQRWAFIWKLDDDPSQSSELLSEAKKLNDSQAPK | 332 |
| Z18018 | VDAKYAKERNQAAYEILFLPNLTSDQKWAFIWKLDDDPSQSSELLSEAKKLNDSQAPK | 333 |
| Z18019 | VDAKYAKERNAAAYEILYLPNLTREQHWAFIWKLDDDPSQSSELLSEAKKLNDSQAPK | 334 |
| Z18020 | VDAKYAKERNVAAQEILYLPNLTSAQKWAFIWKLDDDPSQSSELLSEAKKLNDSQAPK | 335 |
| Z18023 | VDAKYAKERNIAAHEILYLPNLTQKQKWAFIWKLDDDPSQSSELLSEAKKLNDSQAPK | 336 |
| Z18024 | VDAKYAKERNEAAFEILYLPNLTENQRWAFIWKLDDDPSQSSELLSEAKKLNDSQAPK | 337 |
| Z18025 | VDAKYAKERNEAAYEILYLPNLTDSQIWAFIWKLDDDPSQSSELLSEAKKLNDSQAPK | 338 |
| Z18026 | VDAKYAKERNEAASEILDLPNLTQEQLWAFIWKLDDDPSQSSELLSEAKKLNDSQAPK | 339 |
| Z18028 | VDAKYAKERNFAAHEILYLPNLTQGQKWAFIWKLDDDPSQSSELLSEAKKLNDSQAPK | 340 |
| Z18029 | VDAKYAKERNAAAHEILYLPNLTNKQKWAFIWKLDDDPSQSSELLSEAKKLNDSQAPK | 341 |
| Z18030 | VDAKYAKERNKAAHEILYLPNLTNEQKWAFIWKLDDDPSQSSELLSEAKKLNDSQAPK | 342 |
| Z18031 | VDAKYAKERNEAAFEILYLPNLTQFQKWAFIWKLDDDPSQSSELLSEAKKLNDSQAPK | 343 |
| Z18032 | VDAKYAKERNSAAFEILYLPNLTNFQKWAFIWKLDDDPSQSSELLSEAKKLNDSQAPK | 344 |
| Z18033 | VDAKYAKERNEAAYEILNLPNLTKQQHWAFIWKLDDDPSQSSELLSEAKKLNDSQAPK | 345 |
| Z18034 | VDAKYAKERNIAAHEILYLPNLTKSQKWAFIWKLEDDPSQSSELLSEAKKLNDSQAPK | 346 |
| Z18035 | VDAKYAKERNIAAYEILWLPNLTNAQKWAFIWKLADDPSQSSELLSEAKKLNDSQAPK | 347 |
| Z18040 | VDAKYAKERNIAAHEILYLPNLTQNQRWAFIWKLDDDPSQSSELLSEAKKLNDSQAPK | 348 |

Figure 1M

| Designation | Sequence | SEQ ID NO: |
|---|---|---|
| Z18041 | VDAKYAKERNRAAQEILYLPNLTRRQYWAFIWKLDDDPSQSSELLSEAKKLNDSQAPK | 349 |
| Z18042 | VDAKYAKERNVAAQEILTLPNLTNEQYWAFIWKLDDDPSQSSELLSEAKKLNDSQAPK | 350 |
| Z18043 | VDAKYAKERNVAAHEILYLPNLTASQKWAFIWKLDDDPSQSSELLSEAKKLNDSQAPK | 351 |
| Z18044 | VDAKYAKERNKAAFEILYLPNLTASQKWAFIWKLDDDPSQSSELLSEAKKLNDSQAPK | 352 |
| Z18045 | VDAKYAKERNDAASEILYLPNLTQGQIWAFIWKLDDDPSQSSELLSEAKKLNDSQAPK | 353 |
| Z18046 | VDAKYAKERNAAAQEILYLPNLTRVQKWAFIWKLDDDPSQSSELLSEAKKLNDSQAPK | 354 |
| Z18047 | VDAKYAKERNEAAQEILYLPNLTQKQIWAFIWKLADDPSQSSELLSEAKKLNDSQAPK | 355 |
| Z18049 | VDAKYAKERNQAANEILYLPNLTNKQKWAFIWKLDDDPSQSSELLSEAKKLNDSQAPK | 356 |
| Z18050 | VDAKYAKERNDAAYEILNLPNLTSSQRWAFIWKLDDDPSQSSELLSEAKKLNDSQAPK | 357 |
| Z18051 | VDAKYAKERNEAAYEILYLPNLTSKQRWAFIWKLDDDPSQSSELLSEAKKLNDSQAPK | 358 |
| Z18053 | VDAKYAKERNEAAYEILFLPNLTHNQQWAFIWKLADDPSQSSELLSEAKKLNDSQAPK | 359 |
| Z18055 | VDAKYAKERNDAAYEILYLPNLTNVQKWAFIWKLDDDPSQSSELLSEAKKLNDSQAPK | 360 |
| Z18056 | VDAKYAKERNKAAFEILALPNLTKAQHWAFIWKLDDDPSQSSELLSEAKKLNDSQAPK | 361 |
| Z18057 | VDAKYAKERNHAAFEILQLPNLTSNQYWAFIWKLDDDPSQSSELLSEAKKLNDSQAPK | 362 |
| Z18058 | VDAKYAKERNRAAYEILYLPNLTQSQKWAFIWKLADDPSQSSELLSEAKKLNDSQAPK | 363 |
| Z18059 | VDAKYAKERNAAAQEILQLPNLTHAQYWAFIWKLDDDPSQSSELLSEAKKLNDSQAPK | 364 |
| Z18061 | VDAKYAKERNAAAYEILYLPNLTNAQKWAFIWKLADDPSQSSELLSEAKKLNDSQAPK | 365 |
| Z18062 | VDAKYAKERNEAAQEILELPNLTNVQYWAFIWKLDDDPSQSSELLSEAKKLNDSQAPK | 366 |
| Z18063 | VDAKYAKERNEAAQEILYLPNLTQKQRWAFIWKLDDDPSQSSELLSEAKKLNDSQAPK | 367 |
| Z18067 | VDAKYAKERNLAAHEILYLPNLTSQQKWAFIWKLDDDPSQSSELLSEAKKLNDSQAPK | 368 |
| Z18068 | VDAKYAKERNEAAQEILYLPNLTNAQKWAFIWKLADDPSQSSELLSEAKKLNDSQAPK | 369 |
| Z18071 | VDAKYAKERNTAAFEILYLPNLTNHQKWAFIWKLDDDPSQSSELLSEAKKLNDSQAPK | 370 |
| Z18072 | VDAKYAKERNHAAQEILYLPNLTKKQQWAFIWKLDDDPSQSSELLSEAKKLNDSQAPK | 371 |
| Z18073 | VDAKYAKERNAAANEILYLPNLTHQQIWAFIWKLDDDPSQSSELLSEAKKLNDSQAPK | 372 |
| Z18075 | VDAKYAKERNEAAYEILYLPNLTNSQKWAFIWKLADDPSQSSELLSEAKKLNDSQAPK | 373 |
| Z18077 | VDAKYAKERNFAAQEILYLPNLTNAQKWAFIWKLDDDPSQSSELLSEAKKLNDSQAPK | 374 |
| Z18079 | VDAKYAKERNSAAQEILELPNLTNAQEWAFIWKLDDDPSQSSELLSEAKKLNDSQAPK | 375 |
| Z18080 | VDAKYAKERNNAAHEILYLPNLTQSQRWAFIWKLDDDPSQSSELLSEAKKLNDSQAPK | 376 |
| Z18081 | VDAKYAKERNQAAFEILYLPNLTSAQRWAFIWKLDDDPSQSSELLSEAKKLNDSQAPK | 377 |

Figure 1N

| Designation | Sequence | SEQ ID NO: |
|---|---|---|
| Z18082 | VDAKYAKERNFAAFEILNLPNLTNAQSWAFIWKLDDDPSQSSELLSEAKKLNDSQAPK | 378 |
| Z18083 | VDAKYAKERNEAAQEILYLPNLTNQQKWAFIWKLDDDPSQSSELLSEAKKLNDSQAPK | 379 |
| Z18087 | VDAKYAKERNEAAYEILYLPNLTQSQIWAFIWKLADDPSQSSELLSEAKKLNDSQAPK | 380 |
| Z18091 | VDAKYAKERNKAAFEILYLPNLTHAQIWAFIWKLDDDPSQSSELLSEAKKLNDSQAPK | 381 |
| Z18093 | VDAKYAKERNQAAFEILYLPNLTQGQRWAFIWKLDDDPSQSSELLSEAKKLNDSQAPK | 382 |
| Z18094 | VDAKYAKERNSAAHEILYLPNLTKEQKWAFIWKLDDDPSQSSELLSEAKKLNDSQAPK | 383 |
| Z18097 | VDAKYAKERNYAAQEILYLPNLTNYQKWAFIWKLDDDPSQSSELLSEAKKLNDSQAPK | 384 |
| Z18098 | VDAKYAKERNHAAYEILYLPNLTKDQKWAFIWKLDDDPSQSSELLSEAKKLNDSQAPK | 385 |
| Z18100 | VDAKYAKERNQAAQEILELPNLTNEQYWAFIWKLDDDPSQSSELLSEAKKLNDSQAPK | 386 |
| Z18102 | VDAKYAKERNHAAYEILYLPNLTSSQKWAFIWKLDDDPSQSSELLSEAKKLNDSQAPK | 387 |
| Z18103 | VDAKYAKERNFAAHEILQLPNLTRYQHWAFIWKLDDDPSQSSELLSEAKKLNDSQAPK | 388 |
| Z18105 | VDAKYAKERNEAAYEILYLPNLTNYQKWAFIWKLDDDPSQSSELLSEAKKLNDSQAPK | 389 |
| Z18107 | VDAKYAKERNSAAYEILYLPNLTSNQKWAFIWKLDDDPSQSSELLSEAKKLNDSQAPK | 390 |
| Z18109 | VDAKYAKERNDAAYEILYLPNLTSNQVWAFIWKLDDDPSQSSELLSEAKKLNDSQAPK | 391 |
| Z18112 | VDAKYAKERNEAAYEILNLPNLTKKQHWAFIWKLDDDPSQSSELLSEAKKLNDSQAPK | 392 |
| Z18113 | VDAKYAKERNTAAQEILYLPNLTNEQLWAFIWKLDDDPSQSSELLSEAKKLNDSQAPK | 393 |
| Z18114 | VDAKYAKERNHAAQEILYLPNLTKEQKWAFIWKLDDDPSQSSELLSEAKKLNDSQAPK | 394 |
| Z18120 | VDAKYAKERNVAAAEILKLPNLTQAQHWAFIWKLDDDPSQSSELLSEAKKLNDSQAPK | 395 |
| Z18121 | VDAKYAKERNSAAQEILELPNLTNAQYWAFIWKLDDDPSQSSELLSEAKKLNDSQAPK | 396 |
| Z18122 | VDAKYAKERNTAAEEILYLPNLTHAQQWAFIWKLDDDPSQSSELLSEAKKLNDSQAPK | 397 |
| Z18123 | VDAKYAKERNSAAYEILYLPNLTQKQIWAFIWKLDDDPSQSSELLSEAKKLNDSQAPK | 398 |
| Z18125 | VDAKYAKERNEAANEILYLPNLTRAQQWAFIWKLDDDPSQSSELLSEAKKLNDSQAPK | 399 |
| Z18126 | VDAKYAKERNLAAFEILQLPNLTKDQHWAFIWKLDDDPSQSSELLSEAKKLNDSQAPK | 400 |
| Z18127 | VDAKYAKERNFAAHEILYLPNLTNQQKWAFIWKLDDDPSQSSELLSEAKKLNDSQAPK | 401 |
| Z18132 | VDAKYAKERNEAAHEILYLPNLTNAQRWAFIWKLDDDPSQSSELLSEAKKLNDSQAPK | 402 |
| Z18134 | VDAKYAKERNTAAHEILYLPNLTHAQRWAFIWKLDDDPSQSSELLSEAKKLNDSQAPK | 403 |
| Z18136 | VDAKYAKERNDAAYEILYLPNLTNSQKWAFIWKLADDPSQSSELLSEAKKLNDSQAPK | 404 |
| Z18139 | VDAKYAKERNFAAQEILYLPNLTSAQKWAFIWKLDDDPSQSSELLSEAKKLNDSQAPK | 405 |
| Z18141 | VDAKYAKERNTAAHEILWLPNLTAQQKWAFIWKLDDDPSQSSELLSEAKKLNDSQAPK | 406 |

Figure 1O

| Designation | Sequence | SEQ ID NO: |
|---|---|---|
| Z18142 | VDAKYAKERNVAAYEILYLPNLTQDQIWAFIWKLADDPSQSSELLSEAKKLNDSQAPK | 407 |
| Z18145 | VDAKYAKERNAAAQEILVLPNLTQSQLWAFIWKLDDDPSQSSELLSEAKKLNDSQAPK | 408 |
| Z18146 | VDAKYAKERNSAAFEILQLPNLTRNQHWAFIWKLDDDPSQSSELLSEAKKLNDSQAPK | 409 |
| Z18147 | VDAKYAKERNKAAHEILYLPNLTQHQKWAFIWKLDDDPSQSSELLSEAKKLNDSQAPK | 410 |
| Z18151 | VDAKYAKERNFAANEILYLPNLTASQKWAFIWKLDDDPSQSSELLSEAKKLNDSQAPK | 411 |
| Z18154 | VDAKYAKERNHAAYEILQLPNLTKQQHWAFIWKLDDDPSQSSELLSEAKKLNDSQAPK | 412 |
| Z18155 | VDAKYAKERNTAAYEILYLPNLTSAQTWAFIWKLDDDPSQSSELLSEAKKLNDSQAPK | 413 |
| Z18157 | VDAKYAKERNAAAFEILELPNLTTDQHWAFIWKLDDDPSQSSELLSEAKKLNDSQAPK | 414 |
| Z18159 | VDAKYAKERNDAAYEILYLPNLTSEQRWAFIWKLDDDPSQSSELLSEAKKLNDSQAPK | 415 |
| Z18160 | VDAKYAKERNRAAEEILKLPNLTKEQWWAFIWKLDDDPSQSSELLSEAKKLNDSQAPK | 416 |
| Z18161 | VDAKYAKERNTAAYEILELPNLTKQQKWAFIWKLDDDPSQSSELLSEAKKLNDSQAPK | 417 |
| Z18162 | VDAKYAKERNIAAHEILYLPNLTNQQKWAFIWKLDDDPSQSSELLSEAKKLNDSQAPK | 418 |
| Z18163 | VDAKYAKERNKAASEILYLPNLTKSQVWAFIWKLDDDPSQSSELLSEAKKLNDSQAPK | 419 |
| Z18165 | VDAKYAKERNSAAYEILYLPNLTNYQKWAFIWKLDDDPSQSSELLSEAKKLNDSQAPK | 420 |
| Z18166 | VDAKYAKERNNAAYEILYLPNLTEQQRWAFIWKLDDDPSQSSELLSEAKKLNDSQAPK | 421 |
| Z18168 | VDAKYAKERNIAAQEILYLPNLTQKQKWAFIWKLDDDPSQSSELLSEAKKLNDSQAPK | 422 |
| Z18169 | VDAKYAKERNAAAHEILYLPNLTAEQYWAFIWKLDDDPSQSSELLSEAKKLNDSQAPK | 423 |
| Z18170 | VDAKYAKERNVAASEILNLPNLTQKQKWAFIWKLDDDPSQSSELLSEAKKLNDSQAPK | 424 |
| Z18171 | VDAKYAKERNFAAQEILELPNLTNSQIWAFIWKLDDDPSQSSELLSEAKKLNDSQAPK | 425 |
| Z18173 | VDAKYAKERNKAAHEILYLPNLTQNQIWAFIWKLDDDPSQSSELLSEAKKLNDSQAPK | 426 |
| Z18175 | VDAKYAKERNEAAYEILFLPNLTAAQHWAFIWKLDDDPSQSSELLSEAKKLNDSQAPK | 427 |
| Z18177 | VDAKYAKERNIAAQEILELPNLTSAQRWAFIWKLDDDPSQSSELLSEAKKLNDSQAPK | 428 |
| Z18178 | VDAKYAKERNRAAFEILNLPNLTKQQTWAFIWKLDDDPSQSSELLSEAKKLNDSQAPK | 429 |
| Z18180 | VDAKYAKERNRAAQEILYLPNLTANQRWAFIWKLDDDPSQSSELLSEAKKLNDSQAPK | 430 |
| Z18181 | VDAKYAKERNHAAHEILYLPNLTQNQIWAFIWKLDDDPSQSSELLSEAKKLNDSQAPK | 431 |
| Z18182 | VDAKYAKERNTAAYEILYLPNLTQKQKWAFIWKLDDDPSQSSELLSEAKKLNDSQAPK | 432 |
| Z18183 | VDAKYAKERNRAAYEILYLPNLTQKQKWAFIWKLDDDPSQSSELLSEAKKLNDSQAPK | 433 |
| Z18184 | VDAKYAKERNQAAFEILNLPNLTNEQYWAFIWKLDDDPSQSSELLSEAKKLNDSQAPK | 434 |
| Z18186 | VDAKYAKERNKAAVEILELPNLTNDQYWAFIWKLDDDPSQSSELLSEAKKLNDSQAPK | 435 |

Figure 1P

| Designation | Sequence | SEQ ID NO: |
|---|---|---|
| Z18187 | VDAKYAKERNSAAQEILSLPNLTRSQVWAFIWKLDDDPSQSSELLSEAKKLNDSQAPK | 436 |
| Z18188 | VDAKYAKERNAAAHEILYLPNLTQSQKWAFIWKLDDDPSQSSELLSEAKKLNDSQAPK | 437 |
| Z18189 | VDAKYAKERNYAAYEILQLPNLTNSQYWAFIWKLDDDPSQSSELLSEAKKLNDSQAPK | 438 |
| Z18190 | VDAKYAKERNAAAFEILYLPNLTEEQRWAFIWKLDDDPSQSSELLSEAKKLNDSQAPK | 439 |
| Z18191 | VDAKYAKERNQAAYEILYLPNLTNKQVWAFIWKLDDDPSQSSELLSEAKKLNDSQAPK | 440 |
| Z18192 | VDAKYAKERNEAAYEILYLPNLTKAQKWAFIWKLDDDPSQSSELLSEAKKLNDSQAPK | 441 |
| Z18193 | VDAKYAKERNKAAHEILYLPNLTSSQRWAFIWKLDDDPSQSSELLSEAKKLNDSQAPK | 442 |
| Z18194 | VDAKYAKERNKAAAEILKLPNLTKQQHWAFIWKLDDDPSQSSELLSEAKKLNDSQAPK | 443 |
| Z18195 | VDAKYAKERNQAAYEILQLPNLTREQDWAFIWKLDDDPSQSSELLSEAKKLNDSQAPK | 444 |
| Z18196 | VDAKYAKERNIAAQEILYLPNLTRAQKWAFIWKLDDDPSQSSELLSEAKKLNDSQAPK | 445 |
| Z18197 | VDAKYAKERNDAAQEILYLPNLTKKQQWAFIWKLDDDPSQSSELLSEAKKLNDSQAPK | 446 |
| Z18198 | VDAKYAKERNAAAYEILYLPNLTSDQKWAFIWKLDDDPSQSSELLSEAKKLNDSQAPK | 447 |
| Z18199 | VDAKYAKERNEAAYEILYLPNLTNKQKWAFIWKLDDDPSQSSELLSEAKKLNDSQAPK | 448 |
| Z18200 | VDAKYAKERNDAAYEILYLPNLTNIQKWAFIWKLDDDPSQSSELLSEAKKLNDSQAPK | 449 |
| Z18201 | VDAKYAKERNYAAHEILYLPNLTQNQKWAFIWKLDDDPSQSSELLSEAKKLNDSQAPK | 450 |
| Z18202 | VDAKYAKERNEAAYEILWLPNLTHDQKWAFIWKLDDDPSQSSELLSEAKKLNDSQAPK | 451 |
| Z18203 | VDAKYAKERNNAAQEILELPNLTWGQHWAFIWKLDDDPSQSSELLSEAKKLNDSQAPK | 452 |
| Z18204 | VDAKYAKERNSAAHEILYLPNLTNAQKWAFIWKLDDDPSQSSELLSEAKKLNDSQAPK | 453 |
| Z18205 | VDAKYAKERNDAAQEILDLPNLTNAQYWAFIWKLDDDPSQSSELLSEAKKLNDSQAPK | 454 |
| Z18206 | VDAKYAKERNAAAQEILYLPNLTQIQKWAFIWKLDDDPSQSSELLSEAKKLNDSQAPK | 455 |
| Z18207 | VDAKYAKERNAAAHEILYLPNLTQKQKWAFIWKLDDDPSQSSELLSEAKKLNDSQAPK | 456 |
| Z18208 | VDAKYAKERNKAAHEILYLPNLTASQRWAFIWKLDDDPSQSSELLSEAKKLNDSQAPK | 457 |
| Z18209 | VDAKYAKERNTAAYEILYLPNLTQAQRWAFIWKLDDDPSQSSELLSEAKKLNDSQAPK | 458 |
| Z18210 | VDAKYAKERNIAAQEILYLPNLTQSQIWAFIWKLDDDPSQSSELLSEAKKLNDSQAPK | 459 |
| Z18211 | VDAKYAKERNRAAQEILYLPNLTKEQKWAFIWKLDDDPSQSSELLSEAKKLNDSQAPK | 460 |
| Z18213 | VDAKYAKERNSAAYEILYLPNLTKSQKWAFIWKLDDDPSQSSELLSEAKKLNDSQAPK | 461 |
| Z18214 | VDAKYAKERNAAAFEILYLPNLTNRQKWAFIWKLDDDPSQSSELLSEAKKLNDSQAPK | 462 |
| Z18215 | VDAKYAKERNEAAYEILALPNLTKAQHWAFIWKLDDDPSQSSELLSEAKKLNDSQAPK | 463 |
| Z18216 | VDAKYAKERNTAAFEILYLPNLTNNQKWAFIWKLDDDPSQSSELLSEAKKLNDSQAPK | 464 |

Figure 1Q

| Designation | Sequence | SEQ ID NO: |
|---|---|---|
| Z18217 | VDAKYAKERNIAAYEILYLPNLTQKQKWAFIWKLDDDPSQSSELLSEAKKLNDSQAPK | 465 |
| Z18218 | VDAKYAKERNDAAFEILYLPNLTSRQIWAFIWKLDDDPSQSSELLSEAKKLNDSQAPK | 466 |
| Z18219 | VDAKYAKERNTAAYEILNLPNLTNEQHWAFIWKLDDDPSQSSELLSEAKKLNDSQAPK | 467 |
| Z18221 | VDAKYAKERNDAAYEILNLPNLTQNQTWAFIWKLDDDPSQSSELLSEAKKLNDSQAPK | 468 |
| Z18222 | VDAKYAKERNKAAYEILYLPNLTNHQKWAFIWKLADDPSQSSELLSEAKKLNDSQAPK | 469 |
| Z18223 | VDAKYAKERNTAAAEILKLPNLTNAQLWAFIWKLDDDPSQSSELLSEAKKLNDSQAPK | 470 |
| Z18224 | VDAKYAKERNSAAQEILYLPNLTQIQKWAFIWKLDDDPSQSSELLSEAKKLNDSQAPK | 471 |
| Z18225 | VDAKYAKERNIAAYEILYLPNLTTSQKWAFIWKLDDDPSQSSELLSEAKKLNDSQAPK | 472 |
| Z18226 | VDAKYAKERNTAAYEILYLPNLTNSQKWAFIWKLDDDPSQSSELLSEAKKLNDSQAPK | 473 |
| Z18227 | VDAKYAKERNSAAQEILYLPNLTAAQRWAFIWKLDDDPSQSSELLSEAKKLNDSQAPK | 474 |
| Z18229 | VDAKYAKERNSAAYEILYLPNLTHSQKWAFIWKLDDDPSQSSELLSEAKKLNDSQAPK | 475 |
| Z18230 | VDAKYAKERNDAAYEILNLPNLTSAQYWAFIWKLDDDPSQSSELLSEAKKLNDSQAPK | 476 |
| Z18231 | VDAKYAKERNHAAHEILYLPNLTRRQQWAFIWKLDDDPSQSSELLSEAKKLNDSQAPK | 477 |
| Z18232 | VDAKYAKERNAAAYEILYLPNLTNQQRWAFIWKLDDDPSQSSELLSEAKKLNDSQAPK | 478 |
| Z18234 | VDAKYAKERNQAAFEILYLPNLTNKQKWAFIWKLDDDPSQSSELLSEAKKLNDSQAPK | 479 |
| Z18235 | VDAKYAKERNEAAQEILYLPNLTQAQIWAFIWKLDDDPSQSSELLSEAKKLNDSQAPK | 480 |
| Z18236 | VDAKYAKERNEAAFEILYLPNLTSEQKWAFIWKLDDDPSQSSELLSEAKKLNDSQAPK | 481 |
| Z18237 | VDAKYAKERNRAAYEILYLPNLTNAQKWAFIWKLDDDPSQSSELLSEAKKLNDSQAPK | 482 |
| Z18238 | VDAKYAKERNTAAQEILYLPNLTQKQKWAFIWKLDDDPSQSSELLSEAKKLNDSQAPK | 483 |
| Z18239 | VDAKYAKERNKAAYEILYLPNLTQNQKWAFIWKLDDDPSQSSELLSEAKKLNDSQAPK | 484 |
| Z18241 | VDAKYAKERNLAAFEILNLPNLTRKQHWAFIWKLDDDPSQSSELLSEAKKLNDSQAPK | 485 |
| Z18242 | VDAKYAKERNAAAQEILYLPNLTQKQKWAFIWKLDDDPSQSSELLSEAKKLNDSQAPK | 486 |
| Z18244 | VDAKYAKERNEAAYEILYLPNLTQGQKWAFIWKLDDDPSQSSELLSEAKKLNDSQAPK | 487 |
| Z18245 | VDAKYAKERNAAAYEILYLPNLTQSQKWAFIWKLADDPSQSSELLSEAKKLNDSQAPK | 488 |
| Z18246 | VDAKYAKERNSAAYEILYLPNLTQHQKWAFIWKLDDDPSQSSELLSEAKKLNDSQAPK | 489 |
| Z18247 | VDAKYAKERNDAAFEILYLPNLTKAQKWAFIWKLDDDPSQSSELLSEAKKLNDSQAPK | 490 |
| Z18248 | VDAKYAKERNLAAQEILWLPNLTKEQKWAFIWKLDDDPSQSSELLSEAKKLNDSQAPK | 491 |
| Z18249 | VDAKYAKERNTAAYEILYLPNLTQAQKWAFIWKLADDPSQSSELLSEAKKLNDSQAPK | 492 |
| Z18250 | VDAKYAKERNAAAYEILYLPNLTWGQQWAFIWKLDDDPSQSSELLSEAKKLNDSQAPK | 493 |

Figure 1R

| Designation | Sequence | SEQ ID NO: |
|---|---|---|
| Z18251 | VDAKYAKERNVAAYEILYLPNLTNSQKWAFIWKLADDPSQSSELLSEAKKLNDSQAPK | 494 |
| Z18253 | VDAKYAKERNAAAHEILYLPNLTNAQKWAFIWKLDDDPSQSSELLSEAKKLNDSQAPK | 495 |
| Z18254 | VDAKYAKERNEAAFEILYLPNLTNAQRWAFIWKLDDDPSQSSELLSEAKKLNDSQAPK | 496 |
| Z18255 | VDAKYAKERNVAAHEILYLPNLTSAQKWAFIWKLDDDPSQSSELLSEAKKLNDSQAPK | 497 |
| Z18256 | VDAKYAKERNEAAHEILYLPNLTQGQKWAFIWKLDDDPSQSSELLSEAKKLNDSQAPK | 498 |
| Z18257 | VDAKYAKERNAAAFEILYLPNLTNYQKWAFIWKLDDDPSQSSELLSEAKKLNDSQAPK | 499 |
| Z18258 | VDAKYAKERNKAAFEILNLPNLTNEQKWAFIWKLDDDPSQSSELLSEAKKLNDSQAPK | 500 |
| Z18259 | VDAKYAKERNNAAYEILYLPNLTAQQHWAFIWKLDDDPSQSSELLSEAKKLNDSQAPK | 501 |
| Z18260 | VDAKYAKERNQAAYEILYLPNLTSSQKWAFIWKLDDDPSQSSELLSEAKKLNDSQAPK | 502 |
| Z18261 | VDAKYAKERNNAAQEILELPNLTSSQYWAFIWKLDDDPSQSSELLSEAKKLNDSQAPK | 503 |
| Z18262 | VDAKYAKERNQAAFEILYLPNLTNEQRWAFIWKLDDDPSQSSELLSEAKKLNDSQAPK | 504 |
| Z18263 | VDAKYAKERNSAAYEILYLPNLTWAQHWAFIWKLDDDPSQSSELLSEAKKLNDSQAPK | 505 |
| Z18264 | VDAKYAKERNEAAYEILYLPNLTNAQKWAFIWKLADDPSQSSELLSEAKKLNDSQAPK | 506 |
| Z18265 | VDAKYAKERNIAAYEILYLPNLTNAQKWAFIWKLADDPSQSSELLSEAKKLNDSQAPK | 507 |
| Z18266 | VDAKYAKERNTAAYEILYLPNLTNAQKWAFIWKLADDPSQSSELLSEAKKLNDSQAPK | 508 |
| Z18267 | VDAKYAKERNAAAYEILYLPNLTAAQKWAFIWKLDDDPSQSSELLSEAKKLNDSQAPK | 509 |
| Z18269 | VDAKYAKERNKAAHEILYLPNLTNKQKWAFIWKLDDDPSQSSELLSEAKKLNDSQAPK | 510 |
| Z18270 | VDAKYAKERNAAAFEILYLPNLTNEQKWAFIWKLADDPSQSSELLSEAKKLNDSQAPK | 511 |
| Z18271 | VDAKYAKERNSAAFEILYLPNLTNLQKWAFIWKLDDDPSQSSELLSEAKKLNDSQAPK | 512 |
| Z18272 | VDAKYAKERNEAAFEILYLPNLTSAQIWAFIWKLDDDPSQSSELLSEAKKLNDSQAPK | 513 |
| Z18273 | VDAKYAKERNLAAHEILYLPNLTQKQKWAFIWKLDDDPSQSSELLSEAKKLNDSQAPK | 514 |
| Z18274 | VDAKYAKERNEAAYEILYLPNLTSQQKWAFIWKLDDDPSQSSELLSEAKKLNDSQAPK | 515 |
| Z18275 | VDAKYAKERNNAAYEILYLPNLTEHQRWAFIWKLDDDPSQSSELLSEAKKLNDSQAPK | 516 |
| Z18276 | VDAKYAKERNLAAQEILYLPNLTQSQRWAFIWKLDDDPSQSSELLSEAKKLNDSQAPK | 517 |
| Z18277 | VDAKYAKERNAAAYEILKLPNLTWAQNWAFIWKLDDDPSQSSELLSEAKKLNDSQAPK | 518 |
| Z18278 | VDAKYAKERNSAAQEILYLPNLTQKQKWAFIWKLDDDPSQSSELLSEAKKLNDSQAPK | 519 |
| Z18279 | VDAKYAKERNIAAHEILWLPNLTSSQKWAFIWKLDDDPSQSSELLSEAKKLNDSQAPK | 520 |
| Z18280 | VDAKYAKERNQAAYEILYLPNLTSGQKWAFIWKLDDDPSQSSELLSEAKKLNDSQAPK | 521 |
| Z18281 | VDAKYAKERNEAAYEILYLPNLTNLQKWAFIWKLADDPSQSSELLSEAKKLNDSQAPK | 522 |

Figure 1S

| Designation | Sequence | SEQ ID NO: |
| --- | --- | --- |
| Z18282 | VDAKYAKERNDAAYEILYLPNLTNQQKWAFIWKLDDDPSQSSELLSEAKKLNDSQAPK | 523 |
| Z18284 | VDAKYAKERNAAAYEILYLPNLTQDQKWAFIWKLADDPSQSSELLSEAKKLNDSQAPK | 524 |
| Z18285 | VDAKYAKERNEAAYEILYLPNLTDGQRWAFIWKLDDDPSQSSELLSEAKKLNDSQAPK | 525 |
| Z18286 | VDAKYAKERNTAAYEILYLPNLTNRQKWAFIWKLDDDPSQSSELLSEAKKLNDSQAPK | 526 |
| Z18287 | VDAKYAKERNYAAQEILYLPNLTQAQIWAFIWKLDDDPSQSSELLSEAKKLNDSQAPK | 527 |
| Z18288 | VDAKYAKERNHAAYEILYLPNLTQSQKWAFIWKLDDDPSQSSELLSEAKKLNDSQAPK | 528 |
| Z18289 | VDAKYAKERNEAAYEILWLPNLTNQQKWAFIWKLDDDPSQSSELLSEAKKLNDSQAPK | 529 |
| Z18290 | VDAKYAKERNVAAYEILYLPNLTNQQRWAFIWKLDDDPSQSSELLSEAKKLNDSQAPK | 530 |
| Z18291 | VDAKYAKERNHAAYEILYLPNLTNAQKWAFIWKLDDDPSQSSELLSEAKKLNDSQAPK | 531 |
| Z18292 | VDAKYAKERNLAAHEILYLPNLTQGQIWAFIWKLDDDPSQSSELLSEAKKLNDSQAPK | 532 |
| Z18293 | VDAKYAKERNDAAFEILYLPNLTNSQKWAFIWKLDDDPSQSSELLSEAKKLNDSQAPK | 533 |
| Z18294 | VDAKYAKERNDAAYEILYLPNLTNAQKWAFIWKLDDDPSQSSELLSEAKKLNDSQAPK | 534 |
| Z18295 | VDAKYAKERNHAAQEILYLPNLTQAQKWAFIWKLDDDPSQSSELLSEAKKLNDSQAPK | 535 |
| Z18296 | VDAKYAKERNFAAHEILYLPNLTSKQKWAFIWKLDDDPSQSSELLSEAKKLNDSQAPK | 536 |
| Z18297 | VDAKYAKERNRAAFEILQLPNLTWAQNWAFIWKLDDDPSQSSELLSEAKKLNDSQAPK | 537 |
| Z18298 | VDAKYAKERNIAAQEILYLPNLTQLQIWAFIWKLADDPSQSSELLSEAKKLNDSQAPK | 538 |
| Z18299 | VDAKYAKERNKAAFEILYLPNLTNRQKWAFIWKLDDDPSQSSELLSEAKKLNDSQAPK | 539 |
| Z18300 | VDAKYAKERNLAAFEILYLPNLTNAQKWAFIWKLDDDPSQSSELLSEAKKLNDSQAPK | 540 |
| Z18301 | VDAKYAKERNEAAYEILYLPNLTSEQIWAFIWKLDDDPSQSSELLSEAKKLNDSQAPK | 541 |
| Z18302 | VDAKYAKERNSAAYEILYLPNLTQRQKWAFIWKLDDDPSQSSELLSEAKKLNDSQAPK | 542 |
| Z18303 | VDAKYAKERNIAAQEILYLPNLTQKQIWAFIWKLDDDPSQSSELLSEAKKLNDSQAPK | 543 |
| Z18305 | VDAKYAKERNSAAFEILNLPNLTKDQHWAFIWKLDDDPSQSSELLSEAKKLNDSQAPK | 544 |
| Z18306 | VDAKYAKERNEAAHEILYLPNLTQNQKWAFIWKLDDDPSQSSELLSEAKKLNDSQAPK | 545 |
| Z18307 | VDAKYAKERNDAAFEILQLPNLTKAQHWAFIWKLDDDPSQSSELLSEAKKLNDSQAPK | 546 |
| Z18308 | VDAKYAKERNSAAFEILYLPNLTQNQRWAFIWKLDDDPSQSSELLSEAKKLNDSQAPK | 547 |
| Z18309 | VDAKYAKERNEAAFEILNLPNLTSSQHWAFIWKLDDDPSQSSELLSEAKKLNDSQAPK | 548 |
| Z18310 | VDAKYAKERNVAAQEILYLPNLTNEQRWAFIWKLDDDPSQSSELLSEAKKLNDSQAPK | 549 |
| Z18311 | VDAKYAKERNSAAHEILYLPNLTQAQKWAFIWKLDDDPSQSSELLSEAKKLNDSQAPK | 550 |
| Z18312 | VDAKYAKERNAAAFEILYLPNLTQEQRWAFIWKLDDDPSQSSELLSEAKKLNDSQAPK | 551 |

Figure 1T

| Designation | Sequence | SEQ ID NO: |
|---|---|---|
| Z18313 | VDAKYAKERNRAAHEILYLPNLTQVQKWAFIWKLDDDPSQSSELLSEAKKLNDSQAPK | 552 |
| Z18314 | VDAKYAKERNEAAQEILDLPNLTREQYWAFIWKLDDDPSQSSELLSEAKKLNDSQAPK | 553 |
| Z18315 | VDAKYAKERNHAAQEILYLPNLTRQQKWAFIWKLDDDPSQSSELLSEAKKLNDSQAPK | 554 |
| Z18316 | VDAKYAKERNFAAYEILYLPNLTQQQKWAFIWKLDDDPSQSSELLSEAKKLNDSQAPK | 555 |
| Z18317 | VDAKYAKERNAAAYEILYLPNLTSQQKWAFIWKLDDDPSQSSELLSEAKKLNDSQAPK | 556 |
| Z18318 | VDAKYAKERNQAAQEILTLPNLTAEQYWAFIWKLDDDPSQSSELLSEAKKLNDSQAPK | 557 |
| Z18319 | VDAKYAKERNNAAYEILYLPNLTQKQRWAFIWKLDDDPSQSSELLSEAKKLNDSQAPK | 558 |
| Z18320 | VDAKYAKERNKAAYEILYLPNLTQSQKWAFIWKLDDDPSQSSELLSEAKKLNDSQAPK | 559 |
| Z18321 | VDAKYAKERNQAAAEILKLPNLTKAQHWAFIWKLDDDPSQSSELLSEAKKLNDSQAPK | 560 |
| Z18322 | VDAKYAKERNNAAEEILKLPNLTQGQLWAFIWKLDDDPSQSSELLSEAKKLNDSQAPK | 561 |
| Z18323 | VDAKYAKERNNAAQEILYLPNLTQQQKWAFIWKLDDDPSQSSELLSEAKKLNDSQAPK | 562 |
| Z18324 | VDAKYAKERNAAAHEILYLPNLTHNQIWAFIWKLDDDPSQSSELLSEAKKLNDSQAPK | 563 |
| Z18325 | VDAKYAKERNKAAEEILYLPNLTQGQIWAFIWKLDDDPSQSSELLSEAKKLNDSQAPK | 564 |
| Z18326 | VDAKYAKERNDAAFEILYLPNLTEAQRWAFIWKLDDDPSQSSELLSEAKKLNDSQAPK | 565 |
| Z18327 | VDAKYAKERNDAAYEILYLPNLTQAQRWAFIWKLDDDPSQSSELLSEAKKLNDSQAPK | 566 |
| Z18328 | VDAKYAKERNSAAFEILYLPNLTQEQKWAFIWKLDDDPSQSSELLSEAKKLNDSQAPK | 567 |
| Z18329 | VDAKYAKERNTAAHEILYLPNLTNQQRWAFIWKLDDDPSQSSELLSEAKKLNDSQAPK | 568 |
| Z18330 | VDAKYAKERNAAAFEILYLPNLTQIQKWAFIWKLDDDPSQSSELLSEAKKLNDSQAPK | 569 |
| Z18331 | VDAKYAKERNRAAFEILYLPNLTQAQKWAFIWKLDDDPSQSSELLSEAKKLNDSQAPK | 570 |
| Z18332 | VDAKYAKERNLAAHEILYLPNLTQSQKWAFIWKLDDDPSQSSELLSEAKKLNDSQAPK | 571 |
| Z18333 | VDAKYAKERNKAAHEILYLPNLTAQQKWAFIWKLDDDPSQSSELLSEAKKLNDSQAPK | 572 |
| Z18334 | VDAKYAKERNEAATEILKLPNLTNAQHWAFIWKLDDDPSQSSELLSEAKKLNDSQAPK | 573 |
| Z18335 | VDAKYAKERNLAAHEILYLPNLTNVQKWAFIWKLDDDPSQSSELLSEAKKLNDSQAPK | 574 |
| Z18336 | VDAKYAKERNQAAQEILYLPNLTNHQKWAFIWKLDDDPSQSSELLSEAKKLNDSQAPK | 575 |
| Z18337 | VDAKYAKERNDAAQEILYLPNLTNHQKWAFIWKLDDDPSQSSELLSEAKKLNDSQAPK | 576 |
| Z18338 | VDAKYAKERNAAAYEILYLPNLTNQQKWAFIWKLADDPSQSSELLSEAKKLNDSQAPK | 577 |
| Z18339 | VDAKYAKERNTAAHEILYLPNLTNSQKWAFIWKLDDDPSQSSELLSEAKKLNDSQAPK | 578 |
| Z18340 | VDAKYAKERNHAAQEILYLPNLTQKQIWAFIWKLDDDPSQSSELLSEAKKLNDSQAPK | 579 |
| Z18341 | VDAKYAKERNVAAHEILYLPNLTNEQKWAFIWKLDDDPSQSSELLSEAKKLNDSQAPK | 580 |

Figure 1U

| Designation | Sequence | SEQ ID NO: |
|---|---|---|
| Z18342 | VDAKYAKERNHAAYEILNLPNLTQDQYWAFIWKLDDDPSQSSELLSEAKKLNDSQAPK | 581 |
| Z18343 | VDAKYAKERNDAAYEILYLPNLTSSQIWAFIWKLDDDPSQSSELLSEAKKLNDSQAPK | 582 |
| Z18344 | VDAKYAKERNNAAYEILNLPNLTKAQHWAFIWKLDDDPSQSSELLSEAKKLNDSQAPK | 583 |
| Z18345 | VDAKYAKERNEAAYEILYLPNLTNEQRWAFIWKLDDDPSQSSELLSEAKKLNDSQAPK | 584 |
| Z18346 | VDAKYAKERNTAAYEILYLPNLTQQQKWAFIWKLEDDPSQSSELLSEAKKLNDSQAPK | 585 |
| Z18347 | VDAKYAKERNQAAYEILYLPNLTSHQKWAFIWKLDDDPSQSSELLSEAKKLNDSQAPK | 586 |
| Z18348 | VDAKYAKERNDAAYEILYLPNLTQEQKWAFIWKLDDDPSQSSELLSEAKKLNDSQAPK | 587 |
| Z18349 | VDAKYAKERNIAAHEILYLPNLTQAQKWAFIWKLDDDPSQSSELLSEAKKLNDSQAPK | 588 |
| Z18350 | VDAKYAKERNSAAQEILYLPNLTKQQKWAFIWKLDDDPSQSSELLSEAKKLNDSQAPK | 589 |
| Z18351 | VDAKYAKERNNAAFEILYLPNLTQKQRWAFIWKLDDDPSQSSELLSEAKKLNDSQAPK | 590 |
| Z18352 | VDAKYAKERNSAAHEILYLPNLTQSQKWAFIWKLDDDPSQSSELLSEAKKLNDSQAPK | 591 |
| Z18354 | VDAKYAKERNTAAYEILYLPNLTQEQIWAFIWKLDDDPSQSSELLSEAKKLNDSQAPK | 592 |
| Z18355 | VDAKYAKERNSAAHEILYLPNLTNAQRWAFIWKLDDDPSQSSELLSEAKKLNDSQAPK | 593 |
| Z18357 | VDAKYAKERNFAAYEILYLPNLTSSQKWAFIWKLDDDPSQSSELLSEAKKLNDSQAPK | 594 |
| Z18358 | VDAKYAKERNSAAHEILYLPNLTQKQKWAFIWKLDDDPSQSSELLSEAKKLNDSQAPK | 595 |
| Z18359 | VDAKYAKERNSAAYEILNLPNLTKNQHWAFIWKLDDDPSQSSELLSEAKKLNDSQAPK | 596 |
| Z18360 | VDAKYAKERNDAAFEILNLPNLTQSQTWAFIWKLDDDPSQSSELLSEAKKLNDSQAPK | 597 |
| Z18361 | VDAKYAKERNAAAYEILYLPNLTRSQKWAFIWKLDDDPSQSSELLSEAKKLNDSQAPK | 598 |
| Z18362 | VDAKYAKERNSAAHEILYLPNLTQIQKWAFIWKLDDDPSQSSELLSEAKKLNDSQAPK | 599 |
| Z18363 | VDAKYAKERNDAAHEILYLPNLTQEQKWAFIWKLDDDPSQSSELLSEAKKLNDSQAPK | 600 |
| Z18364 | VDAKYAKERNSAAYEILYLPNLTSQQRWAFIWKLDDDPSQSSELLSEAKKLNDSQAPK | 601 |
| Z18365 | VDAKYAKERNAAAYEILYLPNLTQNQKWAFIWKLDDDPSQSSELLSEAKKLNDSQAPK | 602 |
| Z18366 | VDAKYAKERNHAAYEILKLPNLTREQHWAFIWKLDDDPSQSSELLSEAKKLNDSQAPK | 603 |
| Z18367 | VDAKYAKERNAAAHEILYLPNLTQGQKWAFIWKLDDDPSQSSELLSEAKKLNDSQAPK | 604 |
| Z18369 | VDAKYAKERNKAAQEILELPNLTNEQYWAFIWKLDDDPSQSSELLSEAKKLNDSQAPK | 605 |
| Z18370 | VDAKYAKERNVAAYEILYLPNLTSEQRWAFIWKLDDDPSQSSELLSEAKKLNDSQAPK | 606 |
| Z18371 | VDAKYAKERNKAAYEILNLPNLTSEQVWAFIWKLDDDPSQSSELLSEAKKLNDSQAPK | 607 |
| Z18372 | VDAKYAKERNAAAHEILYLPNLTNVQKWAFIWKLDDDPSQSSELLSEAKKLNDSQAPK | 608 |
| Z18373 | VDAKYAKERNLAAYEILYLPNLTNSQKWAFIWKLDDDPSQSSELLSEAKKLNDSQAPK | 609 |

Figure 1V

| Designation | Sequence | SEQ ID NO: |
|---|---|---|
| Z18375 | VDAKYAKERNDAAHEILYLPNLTNTQKWAFIWKLDDDPSQSSELLSEAKKLNDSQAPK | 610 |
| Z18376 | VDAKYAKERNDAAEEILHLPNLTQGQIWAFIWKLDDDPSQSSELLSEAKKLNDSQAPK | 611 |
| Z18378 | VDAKYAKERNAAAYEILYLPNLTNTQKWAFIWKLADDPSQSSELLSEAKKLNDSQAPK | 612 |
| Z18379 | VDAKYAKERNKAAYEILHLPNLTKGQHWAFIWKLADDPSQSSELLSEAKKLNDSQAPK | 613 |
| Z18380 | VDAKYAKERNAAAFEILHLPNLTQAQQWAFIWKLDDDPSQSSELLSEAKKLNDSQAPK | 614 |
| Z18381 | VDAKYAKERNSAAEEILHLPNLTSNQTWAFIWKLDDDPSQSSELLSEAKKLNDSQAPK | 615 |
| Z18382 | VDAKYAKERNDAAYEILYLPNLTSTQRWAFIWKLDDDPSQSSELLSEAKKLNDSQAPK | 616 |
| Z18383 | VDAKYAKERNFAAQEILHLPNLTAHQYWAFIWKLDDDPSQSSELLSEAKKLNDSQAPK | 617 |
| Z18384 | VDAKYAKERNRAAHEILKLPNLTATQYWAFIWKLDDDPSQSSELLSEAKKLNDSQAPK | 618 |
| Z18385 | VDAKYAKERNAAAHEILYLPNLTNTQKWAFIWKLDDDPSQSSELLSEAKKLNDSQAPK | 619 |
| Z18386 | VDAKYAKERNIAAEEILHLPNLTQDQLWAFIWKLDDDPSQSSELLSEAKKLNDSQAPK | 620 |
| Z18387 | VDAKYAKERNFAANEILWLPNLTNTQKWAFIWKLDDDPSQSSELLSEAKKLNDSQAPK | 621 |
| Z18388 | VDAKYAKERNLAAQEILHLPNLTASQYWAFIWKLDDDPSQSSELLSEAKKLNDSQAPK | 622 |
| Z18389 | VDAKYAKERNNAAFEILHLPNLTNAQRWAFIWKLDDDPSQSSELLSEAKKLNDSQAPK | 623 |
| Z18390 | VDAKYAKERNTAAYEILYLPNLTKTQKWAFIWKLDDDPSQSSELLSEAKKLNDSQAPK | 624 |
| Z18391 | VDAKYAKERNIAAYEILHLPNLTQDQIWAFIWKLDDDPSQSSELLSEAKKLNDSQAPK | 625 |
| Z18392 | VDAKYAKERNVAAEEILHLPNLTNQQLWAFIWKLDDDPSQSSELLSEAKKLNDSQAPK | 626 |
| Z18393 | VDAKYAKERNIAAEEILHLPNLTQAQIWAFIWKLDDDPSQSSELLSEAKKLNDSQAPK | 627 |
| Z18394 | VDAKYAKERNNAAEEILHLPNLTANQLWAFIWKLDDDPSQSSELLSEAKKLNDSQAPK | 628 |
| Z18395 | VDAKYAKERNHAAQEILHLPNLTQAQTWAFIWKLDDDPSQSSELLSEAKKLNDSQAPK | 629 |
| Z18396 | VDAKYAKERNYAAEEILHLPNLTNQQHWAFIWKLDDDPSQSSELLSEAKKLNDSQAPK | 630 |
| Z18397 | VDAKYAKERNAAAQEILYLPNLTQTQKWAFIWKLDDDPSQSSELLSEAKKLNDSQAPK | 631 |
| Z18398 | VDAKYAKERNAAAQEILELPNLTATQYWAFIWKLDDDPSQSSELLSEAKKLNDSQAPK | 632 |
| Z18399 | VDAKYAKERNEAAHEILYLPNLTQTQKWAFIWKLDDDPSQSSELLSEAKKLNDSQAPK | 633 |
| Z18400 | VDAKYAKERNYAAYEILHLPNLTQAQKWAFIWKLDDDPSQSSELLSEAKKLNDSQAPK | 634 |
| Z18401 | VDAKYAKERNSAAYEILYLPNLTQTQKWAFIWKLDDDPSQSSELLSEAKKLNDSQAPK | 635 |
| Z18402 | VDAKYAKERNRAAFEILYLPNLTNTQKWAFIWKLDDDPSQSSELLSEAKKLNDSQAPK | 636 |
| Z18404 | VDAKYAKERNQAAVEILHLPNLTASQYWAFIWKLDDDPSQSSELLSEAKKLNDSQAPK | 637 |
| Z18405 | VDAKYAKERNYAAVEILHLPNLTHQQVWAFIWKLDDDPSQSSELLSEAKKLNDSQAPK | 638 |

Figure 1W

| Designation | Sequence | SEQ ID NO: |
|---|---|---|
| Z18406 | VDAKYAKERNTAAYEILYLPNLTNTQKWAFIWKLDDDPSQSSELLSEAKKLNDSQAPK | 639 |
| Z18407 | VDAKYAKERNDAAEEILHLPNLTQEQLWAFIWKLDDDPSQSSELLSEAKKLNDSQAPK | 640 |
| Z18408 | VDAKYAKERNDAAYEILHLPNLTKAQNWAFIWKLDDDPSQSSELLSEAKKLNDSQAPK | 641 |
| Z18411 | VDAKYAKERNAAAAEILHLPNLTRDQHWAFIWKLDDDPSQSSELLSEAKKLNDSQAPK | 642 |
| Z18412 | VDAKYAKERNEAAEEILHLPNLTWSQHWAFIWKLDDDPSQSSELLSEAKKLNDSQAPK | 643 |
| Z18413 | VDAKYAKERNDAAFEILHLPNLTNAQHWAFIWKLDDDPSQSSELLSEAKKLNDSQAPK | 644 |
| Z18414 | VDAKYAKERNEAAYEILYLPNLTNTQRWAFIWKLDDDPSQSSELLSEAKKLNDSQAPK | 645 |
| Z18415 | VDAKYAKERNKAAEEILHLPNLTSSQYWAFIWKLDDDPSQSSELLSEAKKLNDSQAPK | 646 |
| Z18416 | VDAKYAKERNTAAQEILHLPNLTQGQIWAFIWKLDDDPSQSSELLSEAKKLNDSQAPK | 647 |
| Z18417 | VDAKYAKERNNAAQEILHLPNLTAEQYWAFIWKLDDDPSQSSELLSEAKKLNDSQAPK | 648 |
| Z18419 | VDAKYAKERNDAANEILHLPNLTNEQNWAFIWKLDDDPSQSSELLSEAKKLNDSQAPK | 649 |
| Z18420 | VDAKYAKERNHAAHEILYLPNLTNKQKWAFIWKLDDDPSQSSELLSEAKKLNDSQAPK | 650 |
| Z18421 | VDAKYAKERNQAAYEILQLPNLTKQQHWAFIWKLDDDPSQSSELLSEAKKLNDSQAPK | 651 |
| Z18422 | VDAKYAKERNQAAHEILYLPNLTHKQKWAFIWKLDDDPSQSSELLSEAKKLNDSQAPK | 652 |
| Z18423 | VDAKYAKERNKAAQEILYLPNLTQQQRWAFIWKLDDDPSQSSELLSEAKKLNDSQAPK | 653 |
| Z18424 | VDAKYAKERNIAAHEILYLPNLTSSQKWAFIWKLDDDPSQSSELLSEAKKLNDSQAPK | 654 |
| Z18425 | VDAKYAKERNTAAHEILYLPNLTQQQRWAFIWKLDDDPSQSSELLSEAKKLNDSQAPK | 655 |
| Z18426 | VDAKYAKERNSAAYEILYLPNLTRNQKWAFIWKLDDDPSQSSELLSEAKKLNDSQAPK | 656 |
| Z18427 | VDAKYAKERNDAAFEILYLPNLTQGQIWAFIWKLDDDPSQSSELLSEAKKLNDSQAPK | 657 |
| Z18428 | VDAKYAKERNEAAYEILYLPNLTQNQIWAFIWKLDDDPSQSSELLSEAKKLNDSQAPK | 658 |
| Z18429 | VDAKYAKERNRAAEEILYLPNLTSQQIWAFIWKLDDDPSQSSELLSEAKKLNDSQAPK | 659 |
| Z18430 | VDAKYAKERNYAAFEILNLPNLTNQQHWAFIWKLDDDPSQSSELLSEAKKLNDSQAPK | 660 |
| Z18431 | VDAKYAKERNSAAFEILNLPNLTNEQTWAFIWKLDDDPSQSSELLSEAKKLNDSQAPK | 661 |
| Z18432 | VDAKYAKERNDAAYEILNLPNLTAAQNWAFIWKLDDDPSQSSELLSEAKKLNDSQAPK | 662 |
| Z18433 | VDAKYAKERNAAAQEILDLPNLTQAQYWAFIWKLDDDPSQSSELLSEAKKLNDSQAPK | 663 |
| Z18434 | VDAKYAKERNNAAYEILYLPNLTQQQRWAFIWKLDDDPSQSSELLSEAKKLNDSQAPK | 664 |
| Z18435 | VDAKYAKERNQAAFEILNLPNLTKRQHWAFIWKLDDDPSQSSELLSEAKKLNDSQAPK | 665 |
| Z18437 | VDAKYAKERNAAAHEILYLPNLTNSQKWAFIWKLDDDPSQSSELLSEAKKLNDSQAPK | 666 |
| Z18438 | VDAKYAKERNKAAYEILYLPNLTSKQKWAFIWKLDDDPSQSSELLSEAKKLNDSQAPK | 667 |

Figure 1X

| Designation | Sequence | SEQ ID NO: |
|---|---|---|
| Z18439 | VDAKYAKERNIAAYEILYLPNLTNKQKWAFIWKLDDDPSQSSELLSEAKKLNDSQAPK | 668 |
| Z18440 | VDAKYAKERNLAAQEILYLPNLTQLQKWAFIWKLDDDPSQSSELLSEAKKLNDSQAPK | 669 |
| Z18441 | VDAKYAKERNSAAYEILYLPNLTHSQRWAFIWKLDDDPSQSSELLSEAKKLNDSQAPK | 670 |
| Z18442 | VDAKYAKERNQAAHEILYLPNLTQAQKWAFIWKLDDDPSQSSELLSEAKKLNDSQAPK | 671 |
| Z18443 | VDAKYAKERNQAAYEILYLPNLTQHQKWAFIWKLDDDPSQSSELLSEAKKLNDSQAPK | 672 |
| Z18444 | VDAKYAKERNTAAFEILYLPNLTQGQRWAFIWKLDDDPSQSSELLSEAKKLNDSQAPK | 673 |
| Z18445 | VDAKYAKERNVAAHEILYLPNLTQSQKWAFIWKLDDDPSQSSELLSEAKKLNDSQAPK | 674 |
| Z18446 | VDAKYAKERNLAAQEILELPNLTNEQYWAFIWKLDDDPSQSSELLSEAKKLNDSQAPK | 675 |
| Z18447 | VDAKYAKERNAAAQEILELPNLTNSQLWAFIWKLDDDPSQSSELLSEAKKLNDSQAPK | 676 |
| Z18449 | VDAKYAKERNKAAFEILYLPNLTSAQKWAFIWKLDDDPSQSSELLSEAKKLNDSQAPK | 677 |
| Z18450 | VDAKYAKERNDAAYEILYLPNLTQKQIWAFIWKLDDDPSQSSELLSEAKKLNDSQAPK | 678 |
| Z18451 | VDAKYAKERNLAAQEILYLPNLTQQQKWAFIWKLDDDPSQSSELLSEAKKLNDSQAPK | 679 |
| Z18452 | VDAKYAKERNEAAYEILYLPNLTDRQIWAFIWKLDDDPSQSSELLSEAKKLNDSQAPK | 680 |
| Z18453 | VDAKYAKERNQAAQEILYLPNLTNGQRWAFIWKLDDDPSQSSELLSEAKKLNDSQAPK | 681 |
| Z18454 | VDAKYAKERNHAAQEILYLPNLTSQQRWAFIWKLDDDPSQSSELLSEAKKLNDSQAPK | 682 |
| Z18455 | VDAKYAKERNDAAFEILYLPNLTQEQVWAFIWKLDDDPSQSSELLSEAKKLNDSQAPK | 683 |
| Z18456 | VDAKYAKERNIAAYEILYLPNLTQSQKWAFIWKLDDDPSQSSELLSEAKKLNDSQAPK | 684 |
| Z18457 | VDAKYAKERNYAAHEILYLPNLTNQQKWAFIWKLDDDPSQSSELLSEAKKLNDSQAPK | 685 |
| Z18458 | VDAKYAKERNEAAQEILYLPNLTQAQKWAFIWKLDDDPSQSSELLSEAKKLNDSQAPK | 686 |
| Z18459 | VDAKYAKERNAAAFEILSLPNLTKAQHWAFIWKLDDDPSQSSELLSEAKKLNDSQAPK | 687 |
| Z18461 | VDAKYAKERNTAAFEILYLPNLTQGQKWAFIWKLDDDPSQSSELLSEAKKLNDSQAPK | 688 |
| Z18462 | VDAKYAKERNKAAYEILYLPNLTSNQKWAFIWKLDDDPSQSSELLSEAKKLNDSQAPK | 689 |
| Z18463 | VDAKYAKERNQAAFEILYLPNLTNNQRWAFIWKLDDDPSQSSELLSEAKKLNDSQAPK | 690 |
| Z18465 | VDAKYAKERNDAAYEILYLPNLTSQQIWAFIWKLDDDPSQSSELLSEAKKLNDSQAPK | 691 |
| Z18466 | VDAKYAKERNVAAQEILYLPNLTKAQKWAFIWKLDDDPSQSSELLSEAKKLNDSQAPK | 692 |
| Z18468 | VDAKYAKERNSAAHEILYLPNLTKQQKWAFIWKLDDDPSQSSELLSEAKKLNDSQAPK | 693 |
| Z18469 | VDAKYAKERNTAAYEILYLPNLTQHQKWAFIWKLDDDPSQSSELLSEAKKLNDSQAPK | 694 |
| Z18470 | VDAKYAKERNVAAQEILYLPNLTQYQKWAFIWKLDDDPSQSSELLSEAKKLNDSQAPK | 695 |
| Z18471 | VDAKYAKERNNAAYEILNLPNLTSAQHWAFIWKLDDDPSQSSELLSEAKKLNDSQAPK | 696 |

Figure 1Y

| Designation | Sequence | SEQ ID NO: |
|---|---|---|
| Z18472 | VDAKYAKERNSAAYEILYLPNLTQKQRWAFIWKLDDDPSQSSELLSEAKKLNDSQAPK | 697 |
| Z18473 | VDAKYAKERNEAAYEILYLPNLTSQQRWAFIWKLDDDPSQSSELLSEAKKLNDSQAPK | 698 |
| Z18474 | VDAKYAKERNTAAQEILYLPNLTQSQKWAFIWKLDDDPSQSSELLSEAKKLNDSQAPK | 699 |
| Z18475 | VDAKYAKERNTAAYEILYLPNLTNFQKWAFIWKLDDDPSQSSELLSEAKKLNDSQAPK | 700 |
| Z18476 | VDAKYAKERNSAAQEILYLPNLTSKQKWAFIWKLDDDPSQSSELLSEAKKLNDSQAPK | 701 |
| Z18478 | VDAKYAKERNDAAFEILYLPNLTQSQRWAFIWKLDDDPSQSSELLSEAKKLNDSQAPK | 702 |
| Z18479 | VDAKYAKERNKAAHEILYLPNLTQQQKWAFIWKLDDDPSQSSELLSEAKKLNDSQAPK | 703 |
| Z18480 | VDAKYAKERNTAAYEILYLPNLTQRQKWAFIWKLDDDPSQSSELLSEAKKLNDSQAPK | 704 |
| Z18481 | VDAKYAKERNHAAHEILYLPNLTQSQIWAFIWKLDDDPSQSSELLSEAKKLNDSQAPK | 705 |
| Z18482 | VDAKYAKERNSAAYEILYLPNLTAAQKWAFIWKLDDDPSQSSELLSEAKKLNDSQAPK | 706 |
| Z18484 | VDAKYAKERNSAAYEILYLPNLTNNQKWAFIWKLDDDPSQSSELLSEAKKLNDSQAPK | 707 |
| Z18485 | VDAKYAKERNFAAQEILYLPNLTKGQKWAFIWKLDDDPSQSSELLSEAKKLNDSQAPK | 708 |
| Z18486 | VDAKYAKERNDAAYEILYLPNLTQNQRWAFIWKLDDDPSQSSELLSEAKKLNDSQAPK | 709 |
| Z18487 | VDAKYAKERNTAAYEILYLPNLTQSQKWAFIWKLDDDPSQSSELLSEAKKLNDSQAPK | 710 |
| Z18488 | VDAKYAKERNSAAFEILYLPNLTKDQKWAFIWKLDDDPSQSSELLSEAKKLNDSQAPK | 711 |
| Z18489 | VDAKYAKERNLAAQEILELPNLTSQQYWAFIWKLDDDPSQSSELLSEAKKLNDSQAPK | 712 |
| Z18490 | VDAKYAKERNYAAYEILYLPNLTSKQKWAFIWKLDDDPSQSSELLSEAKKLNDSQAPK | 713 |
| Z18491 | VDAKYAKERNYAAHEILYLPNLTQNQIWAFIWKLDDDPSQSSELLSEAKKLNDSQAPK | 714 |
| Z18492 | VDAKYAKERNQAAYEILYLPNLTQAQIWAFIWKLDDDPSQSSELLSEAKKLNDSQAPK | 715 |
| Z18493 | VDAKYAKERNFAAHEILLLPNLTKQQHWAFIWKLDDDPSQSSELLSEAKKLNDSQAPK | 716 |
| Z18494 | VDAKYAKERNTAAYEILYLPNLTSAQKWAFIWKLDDDPSQSSELLSEAKKLNDSQAPK | 717 |
| Z18495 | VDAKYAKERNIAAYEILYLPNLTNLQKWAFIWKLDDDPSQSSELLSEAKKLNDSQAPK | 718 |
| Z18496 | VDAKYAKERNDAAFEILYLPNLTSEQKWAFIWKLDDDPSQSSELLSEAKKLNDSQAPK | 719 |
| Z18497 | VDAKYAKERNDAAQEILELPNLTWAQHWAFIWKLDDDPSQSSELLSEAKKLNDSQAPK | 720 |
| Z18499 | VDAKYAKERNYAAHEILYLPNLTQKQIWAFIWKLDDDPSQSSELLSEAKKLNDSQAPK | 721 |
| Z18500 | VDAKYAKERNTAAYEILYLPNLTQQQKWAFIWKLDDDPSQSSELLSEAKKLNDSQAPK | 722 |
| Z18501 | VDAKYAKERNSAAEEILYLPNLTQSQIWAFIWKLDDDPSQSSELLSEAKKLNDSQAPK | 723 |
| Z18502 | VDAKYAKERNDAAFEILYLPNLTQYQIWAFIWKLDDDPSQSSELLSEAKKLNDSQAPK | 724 |
| Z18503 | VDAKYAKERNFAAQEILYLPNLTQKQKWAFIWKLDDDPSQSSELLSEAKKLNDSQAPK | 725 |

Figure 1Z

| Designation | Sequence | SEQ ID NO: |
|---|---|---|
| Z18504 | VDAKYAKERNSAAQEILYLPNLTQRQKWAFIWKLDDDPSQSSELLSEAKKLNDSQAPK | 726 |
| Z18505 | VDAKYAKERNAAAFEILYLPNLTQGQKWAFIWKLDDDPSQSSELLSEAKKLNDSQAPK | 727 |
| Z18506 | VDAKYAKERNHAAHEILYLPNLTQAQIWAFIWKLDDDPSQSSELLSEAKKLNDSQAPK | 728 |
| Z18507 | VDAKYAKERNAAAYEILFLPNLTHSQQWAFIWKLDDDPSQSSELLSEAKKLNDSQAPK | 729 |
| Z18508 | VDAKYAKERNIAAQEILHLPNLTAAQYWAFIWKLDDDPSQSSELLSEAKKLNDSQAPK | 730 |
| Z18509 | VDAKYAKERNAAAFEILNLPNLTKSQHWAFIWKLDDDPSQSSELLSEAKKLNDSQAPK | 731 |
| Z18511 | VDAKYAKERNQAAYEILYLPNLTQSQKWAFIWKLDDDPSQSSELLSEAKKLNDSQAPK | 732 |
| Z18512 | VDAKYAKERNTAAYEILYLPNLTQAQKWAFIWKLDDDPSQSSELLSEAKKLNDSQAPK | 733 |
| Z18513 | VDAKYAKERNKAAHEILYLPNLTNLQKWAFIWKLDDDPSQSSELLSEAKKLNDSQAPK | 734 |
| Z18514 | VDAKYAKERNSAAEEILYLPNLTHSQIWAFIWKLDDDPSQSSELLSEAKKLNDSQAPK | 735 |
| Z18515 | VDAKYAKERNLAAYEILYLPNLTQSQKWAFIWKLADDPSQSSELLSEAKKLNDSQAPK | 736 |
| Z18516 | VDAKYAKERNEAAYEILYLPNLTASQIWAFIWKLDDDPSQSSELLSEAKKLNDSQAPK | 737 |
| Z18517 | VDAKYAKERNLAAYEILYLPNLTQSQIWAFIWKLDDDPSQSSELLSEAKKLNDSQAPK | 738 |
| Z18519 | VDAKYAKERNEAAYEILQLPNLTSSQYWAFIWKLDDDPSQSSELLSEAKKLNDSQAPK | 739 |
| Z18520 | VDAKYAKERNEAAYEILYLPNLTQKQRWAFIWKLDDDPSQSSELLSEAKKLNDSQAPK | 740 |
| Z18521 | VDAKYAKERNAAAHEILYLPNLTQGQIWAFIWKLDDDPSQSSELLSEAKKLNDSQAPK | 741 |
| Z18522 | VDAKYAKERNEAAHEILYLPNLTSSQIWAFIWKLDDDPSQSSELLSEAKKLNDSQAPK | 742 |
| Z18523 | VDAKYAKERNVAAFEILYLPNLTNGQKWAFIWKLDDDPSQSSELLSEAKKLNDSQAPK | 743 |
| Z18524 | VDAKYAKERNKAAYEILYLPNLTQQQRWAFIWKLDDDPSQSSELLSEAKKLNDSQAPK | 744 |
| Z18525 | VDAKYAKERNKAAYEILYLPNLTNHQKWAFIWKLDDDPSQSSELLSEAKKLNDSQAPK | 745 |
| Z18526 | VDAKYAKERNEAAQEILYLPNLTSIQRWAFIWKLDDDPSQSSELLSEAKKLNDSQAPK | 746 |
| Z18527 | VDAKYAKERNTAAWEILQLPNLTRAQHWAFIWKLDDDPSQSSELLSEAKKLNDSQAPK | 747 |
| Z18528 | VDAKYAKERNAAAQEILYLPNLTQGQKWAFIWKLDDDPSQSSELLSEAKKLNDSQAPK | 748 |
| Z18529 | VDAKYAKERNTAAYEILYLPNLTAAQKWAFIWKLDDDPSQSSELLSEAKKLNDSQAPK | 749 |
| Z18530 | VDAKYAKERNDAAYEILYLPNLTSKQKWAFIWKLDDDPSQSSELLSEAKKLNDSQAPK | 750 |
| Z18531 | VDAKYAKERNNAAQEILYLPNLTNAQKWAFIWKLDDDPSQSSELLSEAKKLNDSQAPK | 751 |
| Z18532 | VDAKYAKERNVAAYEILYLPNLTSDQKWAFIWKLDDDPSQSSELLSEAKKLNDSQAPK | 752 |
| Z18533 | VDAKYAKERNYAAQEILYLPNLTQTQIWAFIWKLDDDPSQSSELLSEAKKLNDSQAPK | 753 |
| Z18534 | VDAKYAKERNTAAHEILQLPNLTAAQYWAFIWKLDDDPSQSSELLSEAKKLNDSQAPK | 754 |

Figure 1AA

| Designation | Sequence | SEQ ID NO: |
| --- | --- | --- |
| Z18535 | VDAKYAKERNSAAHEILYLPNLTANQKWAFIWKLDDDPSQSSELLSEAKKLNDSQAPK | 755 |
| Z18536 | VDAKYAKERNQAAYEILYLPNLTQGQKWAFIWKLDDDPSQSSELLSEAKKLNDSQAPK | 756 |
| Z18537 | VDAKYAKERNDAAFEILSLPNLTRAQEWAFIWKLDDDPSQSSELLSEAKKLNDSQAPK | 757 |
| Z18538 | VDAKYAKERNNAAQEILYLPNLTQSQKWAFIWKLDDDPSQSSELLSEAKKLNDSQAPK | 758 |
| Z18539 | VDAKYAKERNHAANEILQLPNLTNEQTWAFIWKLDDDPSQSSELLSEAKKLNDSQAPK | 759 |
| Z18540 | VDAKYAKERNSAAHEILYLPNLTNKQKWAFIWKLDDDPSQSSELLSEAKKLNDSQAPK | 760 |
| Z18541 | VDAKYAKERNLAAYEILYLPNLTQAQKWAFIWKLDDDPSQSSELLSEAKKLNDSQAPK | 761 |
| Z18542 | VDAKYAKERNDAAHEILYLPNLTQQQKWAFIWKLDDDPSQSSELLSEAKKLNDSQAPK | 762 |
| Z18543 | VDAKYAKERNDAAYEILYLPNLTAKQRWAFIWKLDDDPSQSSELLSEAKKLNDSQAPK | 763 |
| Z18544 | VDAKYAKERNFAAQEILYLPNLTSYQRWAFIWKLDDDPSQSSELLSEAKKLNDSQAPK | 764 |
| Z18545 | VDAKYAKERNWAAYEILYLPNLTNAQRWAFIWKLDDDPSQSSELLSEAKKLNDSQAPK | 765 |
| Z18546 | VDAKYAKERNKAAYEILKLPNLTRGQHWAFIWKLDDDPSQSSELLSEAKKLNDSQAPK | 766 |
| Z18547 | VDAKYAKERNAAAQEILELPNLTKAQHWAFIWKLDDDPSQSSELLSEAKKLNDSQAPK | 767 |
| Z18548 | VDAKYAKERNLAAYEILYLPNLTQNQKWAFIWKLDDDPSQSSELLSEAKKLNDSQAPK | 768 |
| Z18549 | VDAKYAKERNSAAYEILYLPNLTHAQRWAFIWKLDDDPSQSSELLSEAKKLNDSQAPK | 769 |
| Z18550 | VDAKYAKERNQAAYEILYLPNLTSAQRWAFIWKLDDDPSQSSELLSEAKKLNDSQAPK | 770 |
| Z18551 | VDAKYAKERNQAAHEILYLPNLTQKQKWAFIWKLDDDPSQSSELLSEAKKLNDSQAPK | 771 |
| Z18552 | VDAKYAKERNDAAYEILYLPNLTNHQRWAFIWKLDDDPSQSSELLSEAKKLNDSQAPK | 772 |
| Z18553 | VDAKYAKERNFAAYEILYLPNLTNQQRWAFIWKLDDDPSQSSELLSEAKKLNDSQAPK | 773 |
| Z13080 | VDAKYAKERNSAAEEILHLPNLTMQQLWAFIWKLDDDPSQSSELLSEAKKLNDSQAPK | 774 |
| Z13088 | VDAKYAKERNNAATEILRLPNLTAGQTWAFIWKLDDDPSQSSELLSEAKKLNDSQAPK | 775 |
| Z13091 | VDAKYAKERNNAAFEILRLPNLTNGQHWAFIWKLADDPSQSSELLSEAKKLNDSQAPK | 776 |
| Z13112 | VDAKYAKERNAAAFEILTLPNLTNEQHWAFIWKLDDDPSQSSELLSEAKKLNDSQAPK | 777 |
| Z13120 | VDAKYAKERNRAANEILQLPNLTKGQVWAFIWKLDDDPSQSSELLSEAKKLNDSQAPK | 778 |
| Z13147 | VDAKYAKERNRAAYEILQLPNLTHQQTWAFIWKLDDDPSQSSELLSEAKKLNDSQAPK | 779 |
| Z13154 | VDAKYAKERNDAAYEILQLPNLTKRQVWAFIWKLDDDPSQSSELLSEAKKLNDSQAPK | 780 |
| Z13156 | VDAKYAKERNQAAVEILQLPNLTAAQYWAFIWKLDDDPSQSSELLSEAKKLNDSQAPK | 781 |
| Z13158 | VDAKYAKERNDAAFEILQLPNLTNSQHWAFIWKLEDDPSQSSELLSEAKKLNDSQAPK | 782 |
| Z13164 | VDAKYAKERNNAAQEILQLPNLTQLQRWAFIWKLDDDPSQSSELLSEAKKLNDSQAPK | 783 |

Figure 1BB

| Designation | Sequence | SEQ ID NO: |
|---|---|---|
| Z13165 | VDAKYAKERNYAAWEILRLPNLTASQYWAFIWKLDDDPSQSSELLSEAKKLNDSQAPK | 784 |
| Z13169 | VDAKYAKERNRAAQEILVLPNLTRKQQWAFIWKLDDDPSQSSELLSEAKKLNDSQAPK | 785 |
| Z13198 | VDAKYAKERNAAAYEILTLPNLTNKQRWAFIWKLDDDPSQSSELLSEAKKLNDSQAPK | 786 |
| Z13304 | VDAKYAKERNNAASEILALPNLTQLQYWAFIWKLADDPSQSSELLSEAKKLNDSQAPK | 787 |
| Z13104 | VDAKYAKERNRAAYEILQLPNLTNQQHWAFIWKLMDDPSQSSELLSEAKKLNDSQAPK | 788 |
| Z13115 | VDAKYAKERNRAASEILLLPNLTRMQHWAFIWKLADDPSQSSELLSEAKKLNDSQAPK | 789 |
| Z13117 | VDAKYAKERNLAAWEILQLPNLTNYQHWAFIWKLDDDPSQSSELLSEAKKLNDSQAPK | 790 |
| Z13134 | VDAKYAKERNQAATEILVLPNLTHQQHWAFIWKLDDDPSQSSELLSEAKKLNDSQAPK | 791 |
| Z13186 | VDAKYAKERNTAALEILYLPNLTKDQVWAFIWKLDDDPSQSSELLSEAKKLNDSQAPK | 792 |
| Z13190 | VDAKYAKERNAAAEEILDLPNLTAGQMWAFIWKLDDDPSQSSELLSEAKKLNDSQAPK | 793 |
| Z13210 | VDAKYAKERNRAAWEILQLPNLTRTQWWAFIWKLDDDPSQSSELLSEAKKLNDSQAPK | 794 |
| Z13368 | VDAKYAKERNAAAWEILRLPNLTRHQQWAFIWKLADDPSQSSELLSEAKKLNDSQAPK | 795 |
| Z13447 | VDAKYAKERNQAAYEIVQLPNLTKGQTWAFIWKLDDDPSQSSELLSEAKKLNDSQAPK | 796 |
| Z13087 | VDAKYAKERNLAAAEIIALPNLTRGQHWAFIWKLDDDPSQSSELLSEAKKLNDSQAPK | 797 |
| Z13105 | VDAKYAKERNYAAAEILQLPNLTGLQTWAFIWKLADDPSQSSELLSEAKKLNDSQAPK | 798 |
| Z13130 | VDAKYAKERNRAAQEIVKLPNLTHQQQWAFIWKLDDDPSQSSELLSEAKKLNDSQAPK | 799 |
| Z13163 | VDAKYAKERNAAAHEILQLPNLTNTQRWAFIWKLDDDPSQSSELLSEAKKLNDSQAPK | 800 |
| Z13168 | VDAKYAKERNAAAHEILQLPNLTTRQHWAFIWKLDDDPSQSSELLSEAKKLNDSQAPK | 801 |
| Z13172 | VDAKYAKERNDAAVEILRLPNLTSTQYWAFIWKLDDDPSQSSELLSEAKKLNDSQAPK | 802 |
| Z13195 | VDAKYAKERNQAAAEILSLPNLTGEQHWAFIWKLDDDPSQSSELLSEAKKLNDSQAPK | 803 |
| Z13361 | VDAKYAKERNMAAEEILGLPNLTSHQHWAFIWKLDDDPSQSSELLSEAKKLNDSQAPK | 804 |
| Z13364 | VDAKYAKERNHAAHEILGLPNLTAHQHWAFIWKLADDPSQSSELLSEAKKLNDSQAPK | 805 |
| Z13397 | VDAKYAKERNAAAFEILRLPNLTSSQFWAFIWKLDDDPSQSSELLSEAKKLNDSQAPK | 806 |
| Z13409 | VDAKYAKERNSAAHEILYLPNLTTDQQWAFIWKLDDDPSQSSELLSEAKKLNDSQAPK | 807 |
| Z13419 | VDAKYAKERNAAAGEILRLPNLTANQHWAFIWKLADDPSQSSELLSEAKKLNDSQAPK | 808 |
| Z15168-Cys | AEAKYAKERNNAAFEILRLPNLTNGQHWAFIWKLADDPSQSSELLSEAKKLNDSQAPKVDC | 809 |
| Z15169-Cys | AEAKYAKERNQAAVEILQLPNLTAAQYWAFIWKLDDDPSQSSELLSEAKKLNDSQAPKVDC | 810 |
| Z18608-Cys | AEAKYAKERNKAAYEILYLPNLTNAQKWAFIWKLDDDPSQSSELLSEAKKLNDSQAPKVDC | 811 |
| Z18609-Cys | AEAKYAKERNAAAYEILYLPNLTNAQKWAFIWKLDDDPSQSSELLSEAKKLNDSQAPKVDC | 812 |

Figure 1CC

| Designation | Sequence | SEQ ID NO: |
| --- | --- | --- |
| Z18610-Cys | AEAKYAKERNDAAYEILYLPNLTNQQKWAFIWKLADDPSQSSELLSEAKKLNDSQAPKVDC | 813 |
| Z15170 | AEAKYAKERNYAAWEILRLPNLTASQYWAFIWKLDDDPSQSSELLSEAKKLNDSQAPK | 814 |
| $HC_{Lam}$ | QVQLVQSGVEVKKPGASVKVSCKASGYTFTNYYMYWVRQAPGQGLEWMGGINPSNGGTNFNEKFKNRVT<br>LTTDSSTTTAYMELKSLQFDDTAVYYCARRDYRFDMGFDYWGQGTTVTVSSASTKGPSVFPLAPCSRST<br>SESTAALGCLVKDYFPEPVTVSWNSGALTSGVHTFPAVLQSSGLYSLSSVVTVPSSSLGTKTYTCNVDH<br>KPSNTKVDKRVESKYGPPCPPCPAPEFLGGPSVFLFPPKPKDTLMISRTPEVTCVVVDVSQEDPEVQFN<br>WYVDGVEVHNAKTKPREEQFNSTYRVVSVLTVLHQDWLNGKEYKCKVSNKGLPSSIEKTISKAKGQPRE<br>PQVYTLPPSQEEMTKNQVSLTCLVKGFYPSDIAVEWESNGQPENNYKTTPPVLDSDGSFFLYSRLTVDK<br>SRWQEGNVFSCSVMHEALHNHYTQKSLSLSLGK | 815 |
| $LC_{Lam}$ | EIVLTQSPATLSLSPGERATLSCRASKGVSTSGYSYLHWYQQKPGQAPRLLIYLASYLESGVPARFSGS<br>GSGTDFTLTISSLEPEDFAVYYCQHSRDLPLTFGGGTKVEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTHQGLSS<br>PVTKSFNRGEC | 816 |
| $HC_{Ipi}$ | QVQLVESGGGVVQPGRSLRLSCAASGFTFSSYTMHWVRQAPGKGLEWVTFISYDGNNKYYADSVKGRFT<br>ISRDNSKNTLYLQMNSLRAEDTAIYYCARTGWLGPFDYWGQGTLVTVSSASTKGPSVFPLAPSSKSTSG<br>GTAALGCLVKDYFPEPVTVSWNSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTPPVLDSDGSFFLYSKLTVD<br>KSRWQQGNVFSCSVMHEALHNHYTQKSLSLSPGK | 817 |
| $LC_{Ipi}$ | EIVLTQSPGTLSLSPGERATLSCRASQSVGSSYLAWYQQKPGQAPRLLIYGAFSRATGIPDRFSGSGSG<br>TDFTLTISRLEPEDFAVYYCQQYGSSPWTFGQGTKVEIKRTVAAPSVFIFPPSDEQLKSGTASVVCLLN<br>NFYPREAKVQWKVDNALQSGNSQESVTEQDSKDSTYSLSSTLTLSKADYEKHKVYACEVTHQGLSSPVT<br>KSFNRGEC | 818 |

Figure 8A-B
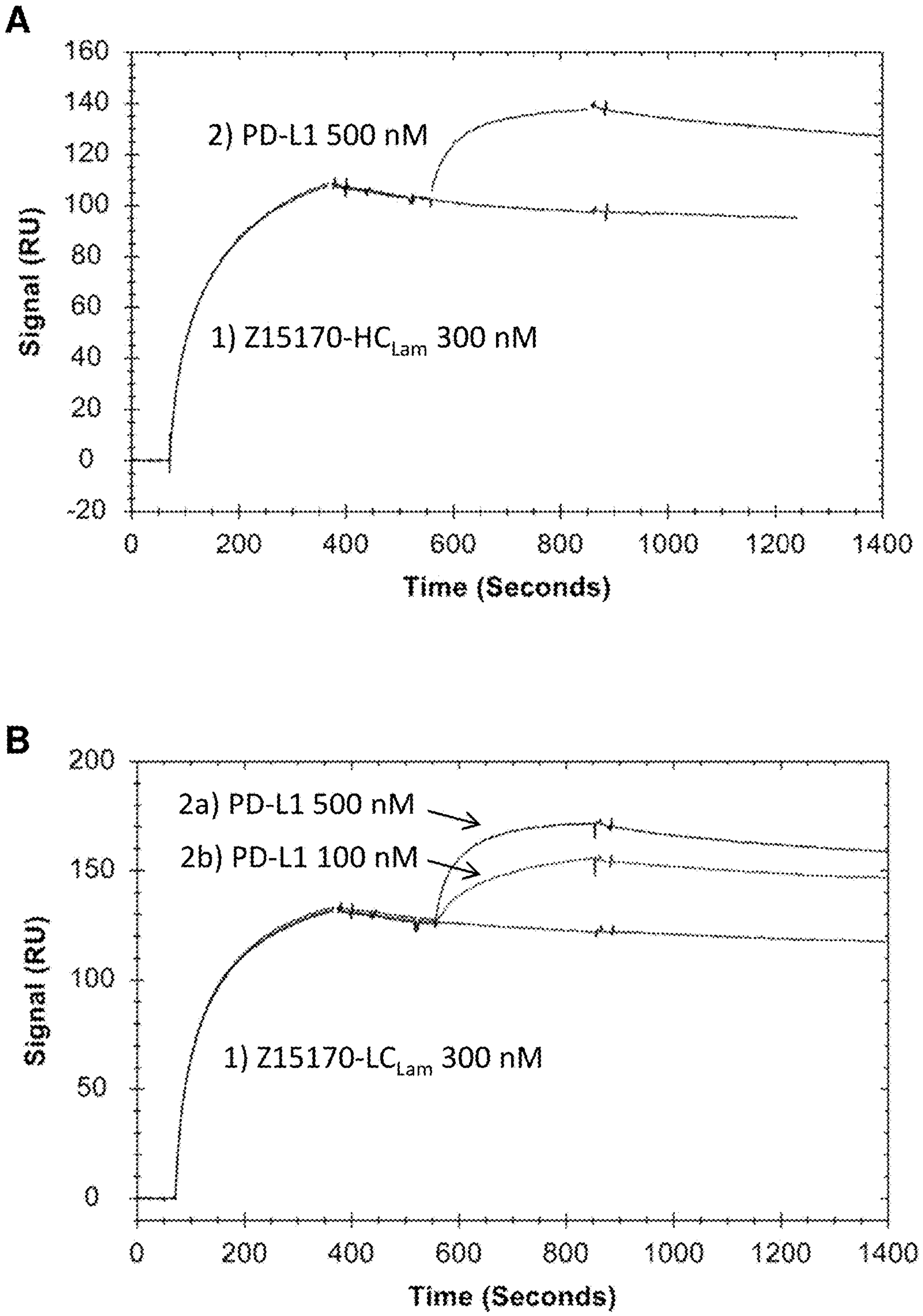

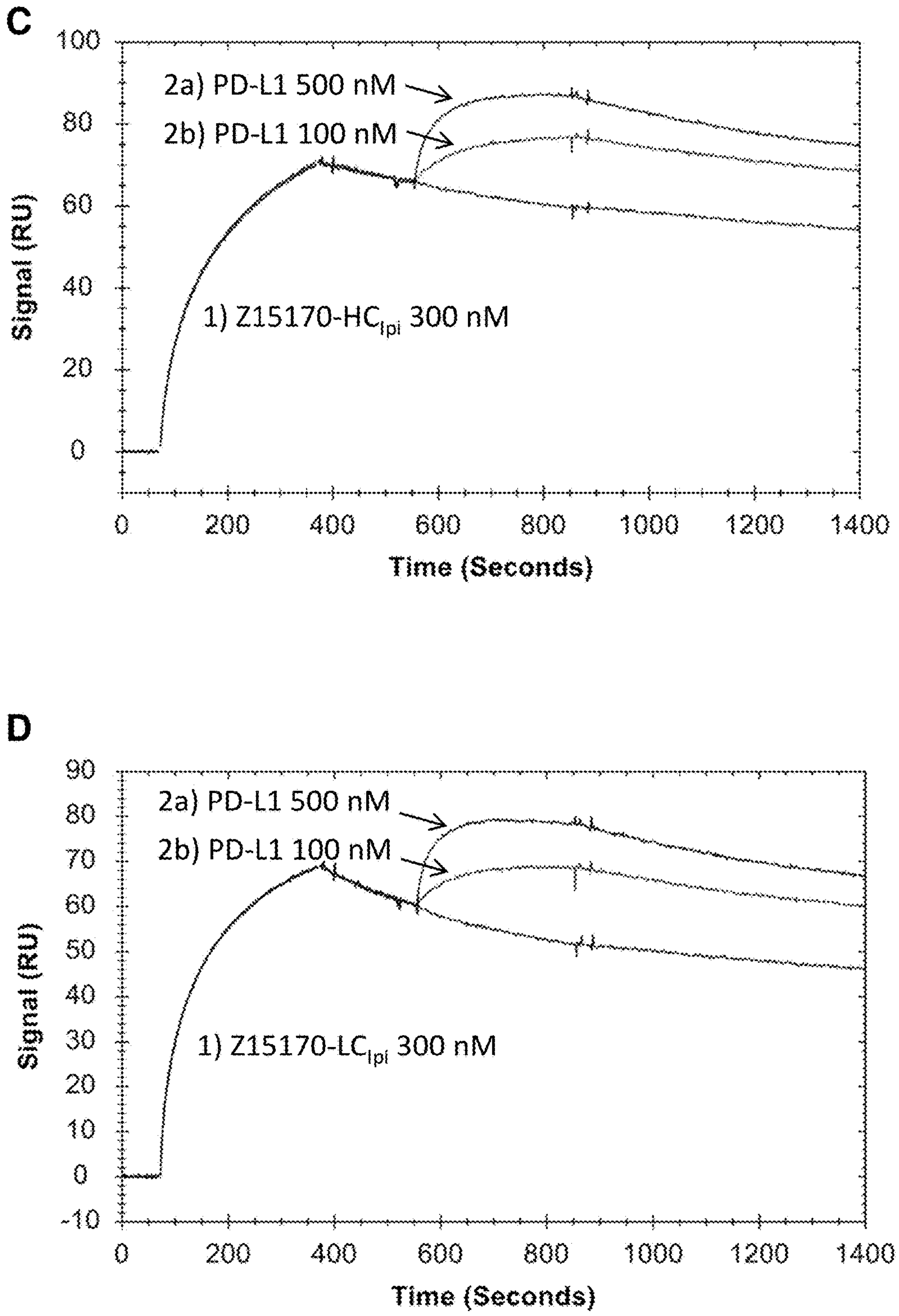
Figure 8C-D

Figure 9A-B
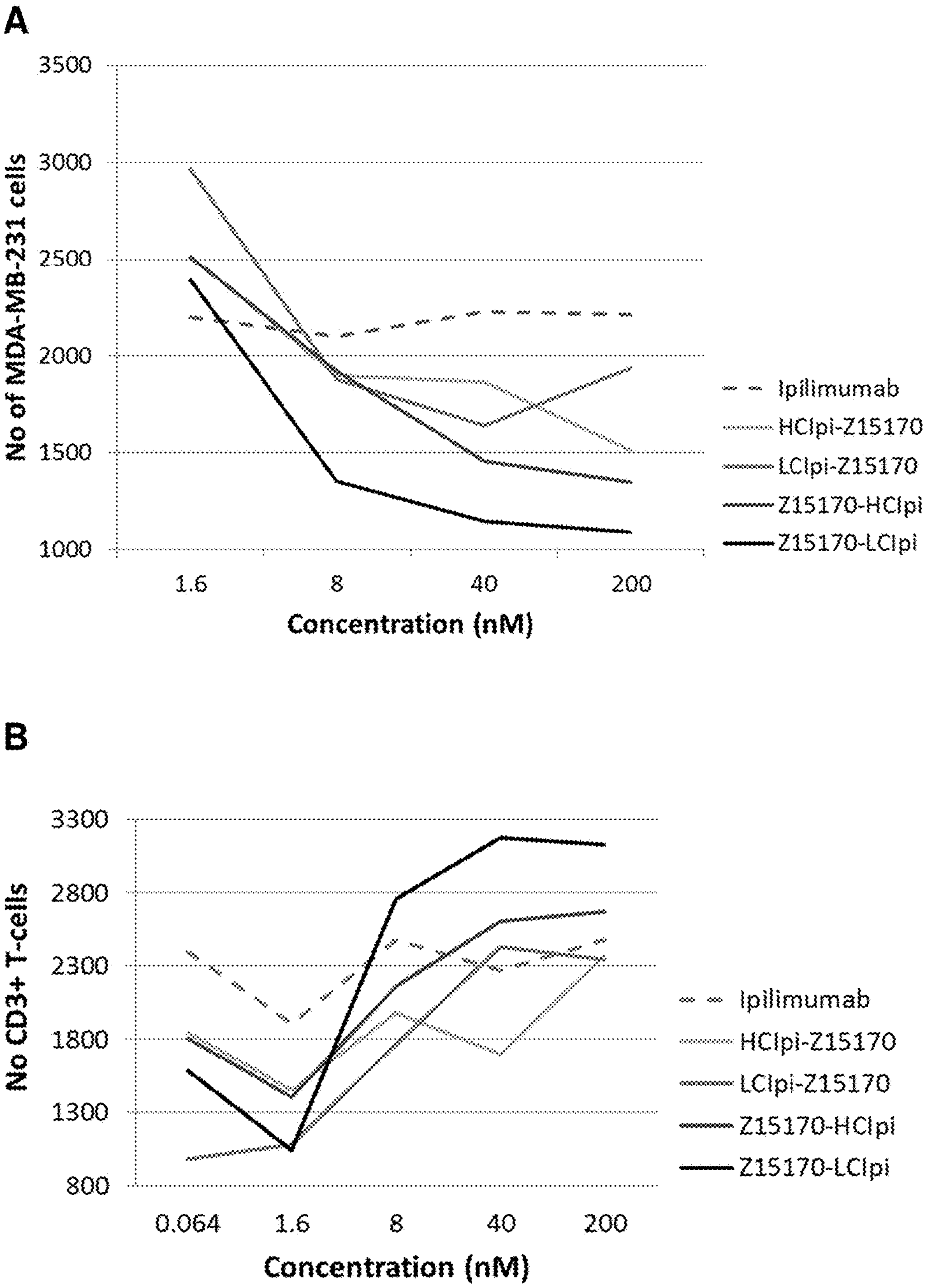

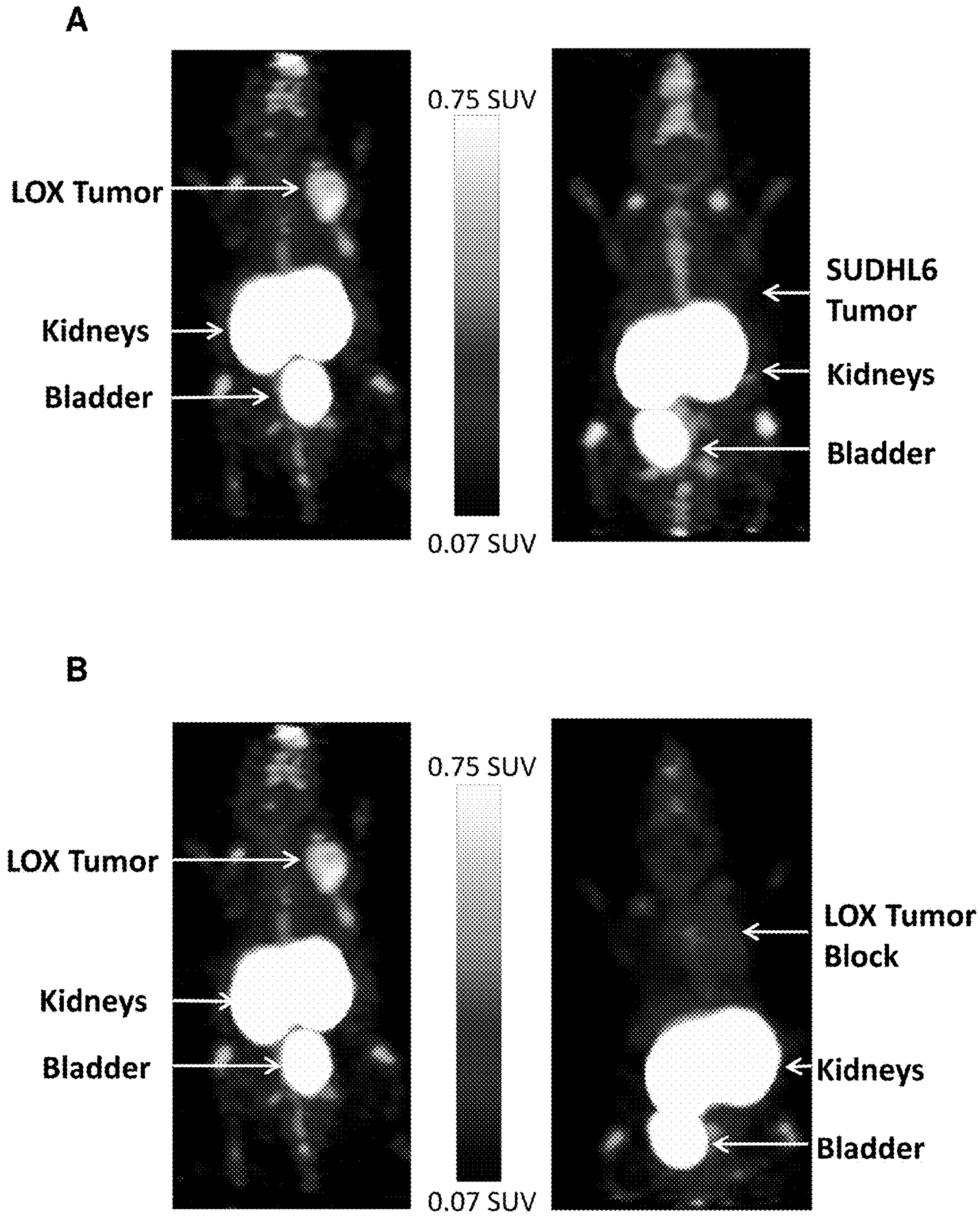
Figure 10A-B

Figure 11A-B
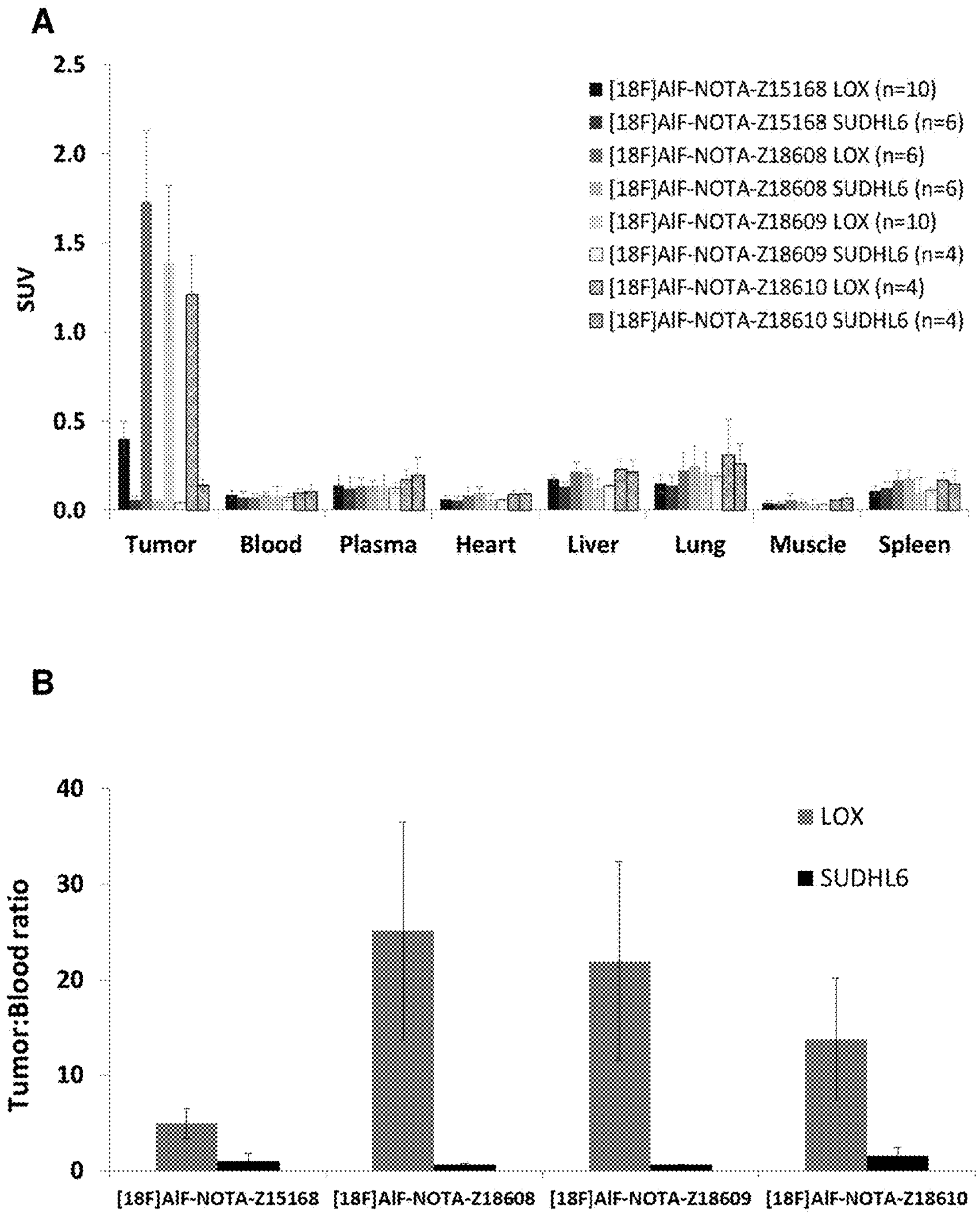

Figure 12A-C
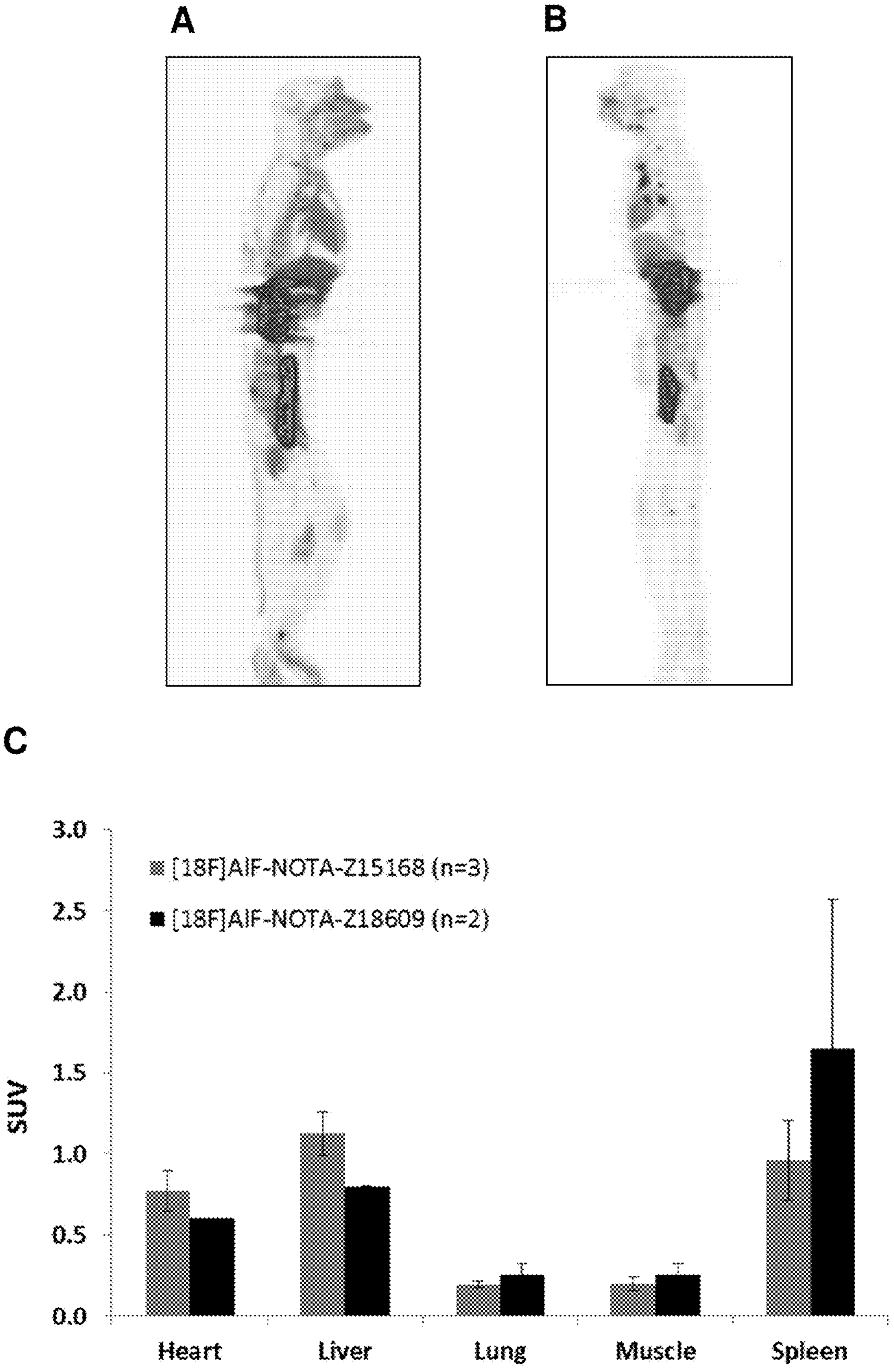

SEQUENCE LISTING

```
<160> NUMBER OF SEQ ID NOS: 897

<210> SEQ ID NO 1
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 1

Val Asp Ala Lys Tyr Ala Lys Glu Arg Asn Lys Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 2
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 2

Val Asp Ala Lys Tyr Ala Lys Glu Arg Asn Ala Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 3
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 3

```
Val Asp Ala Lys Tyr Ala Lys Glu Arg Asn Asn Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 4
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 4

```
Val Asp Ala Lys Tyr Ala Lys Glu Arg Asn Ser Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 5
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 5

```
Val Asp Ala Lys Tyr Ala Lys Glu Arg Asn Leu Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 6
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 6

```
Val Asp Ala Lys Tyr Ala Lys Glu Arg Asn Gln Ala Ala Phe Glu Ile
1               5                   10                  15

Leu Tyr Leu Pro Asn Leu Thr Asn Ala Gln Lys Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 7
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 7

Val Asp Ala Lys Tyr Ala Lys Glu Arg Asn Ala Ala Ala Phe Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 8
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 8

Val Asp Ala Lys Tyr Ala Lys Glu Arg Asn Glu Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 9
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 9

Val Asp Ala Lys Tyr Ala Lys Glu Arg Asn Ser Ala Ala Tyr Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 10
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 10

```
Val Asp Ala Lys Tyr Ala Lys Glu Arg Asn Ala Ala Ala Tyr Glu Ile
1               5                   10                  15

Leu Tyr Leu Pro Asn Leu Thr Asn His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 11
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 11

```
Val Asp Ala Lys Tyr Ala Lys Glu Arg Asn Ala Ala Ala Tyr Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 12
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 12

```
Val Asp Ala Lys Tyr Ala Lys Glu Arg Asn Glu Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 13
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 13

```
Val Asp Ala Lys Tyr Ala Lys Glu Arg Asn Glu Ala Ala Tyr Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45
```

```
Lys Lys Leu Asn Asp Ser Gln Ala Pro Lys
    50                  55


<210> SEQ ID NO 14
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 14

Val Asp Ala Lys Tyr Ala Lys Glu Arg Asn Ile Ala Ala Tyr Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 15
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 15

Val Asp Ala Lys Tyr Ala Lys Glu Arg Asn Glu Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 16
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 16

Val Asp Ala Lys Tyr Ala Lys Glu Arg Asn Ser Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 17
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 17
```

-continued

```
Val Asp Ala Lys Tyr Ala Lys Glu Arg Asn Asp Ala Ala Tyr Glu Ile
1               5                   10                  15

Leu Tyr Leu Pro Asn Leu Thr Asn Gln Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 18
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 18

Val Asp Ala Lys Tyr Ala Lys Glu Arg Asn Asn Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 19
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 19

Val Asp Ala Lys Tyr Ala Lys Glu Arg Asn Ile Ala Ala Tyr Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 20
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 20

Val Asp Ala Lys Tyr Ala Lys Glu Arg Asn Glu Ala Ala Tyr Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 21
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 21

Val Asp Ala Lys Tyr Ala Lys Glu Arg Asn Thr Ala Ala Gln Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 22
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 22

Val Asp Ala Lys Tyr Ala Lys Glu Arg Asn Asp Ala Ala Phe Glu Ile
1               5                   10                  15

Leu Tyr Leu Pro Asn Leu Thr Gln Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 23
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 23

Val Asp Ala Lys Tyr Ala Lys Glu Arg Asn Ser Ala Ala Tyr Glu Ile
1               5                   10                  15

Leu Tyr Leu Pro Asn Leu Thr Asn Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 24
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 24

Val Asp Ala Lys Tyr Ala Lys Glu Arg Asn Glu Ala Ala Tyr Glu Ile
1               5                   10                  15

Leu His Leu Pro Asn Leu Thr Ser Tyr Gln His Trp Ala Phe Ile Trp
```

20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 25
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 25

Val Asp Ala Lys Tyr Ala Lys Glu Arg Asn Lys Ala Ala Tyr Glu Ile
1 5 10 15

Leu Tyr Leu Pro Asn Leu Thr Asn Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 26
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 26

Val Asp Ala Lys Tyr Ala Lys Glu Arg Asn Lys Ala Ala His Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 27
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 27

Val Asp Ala Lys Tyr Ala Lys Glu Arg Asn Ala Ala Ala Tyr Glu Ile
1 5 10 15

Leu Tyr Leu Pro Asn Leu Thr Asn Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 28
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 28

Val Asp Ala Lys Tyr Ala Lys Glu Arg Asn Ala Ala Ala Tyr Glu Ile
1 5 10 15

Leu Tyr Leu Pro Asn Leu Thr Gln Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 29
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 29

Val Asp Ala Lys Tyr Ala Lys Glu Arg Asn Ala Ala Ala Gln Glu Ile
1 5 10 15

Leu Tyr Leu Pro Asn Leu Thr Ser Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 30
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 30

Val Asp Ala Lys Tyr Ala Lys Glu Arg Asn Gln Ala Ala Phe Glu Ile
1 5 10 15

Leu Tyr Leu Pro Asn Leu Thr Gln Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 31
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 31

Val Asp Ala Lys Tyr Ala Lys Glu Arg Asn His Ala Ala Tyr Glu Ile
1 5 10 15

Leu Tyr Leu Pro Asn Leu Thr Asn Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 32
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 32

Val Asp Ala Lys Tyr Ala Lys Glu Arg Asn Glu Ala Ala Tyr Glu Ile
1 5 10 15

Leu Tyr Leu Pro Asn Leu Thr Asn Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 33
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 33

Val Asp Ala Lys Tyr Ala Lys Glu Arg Asn Thr Ala Ala Gln Glu Ile
1 5 10 15

Leu Tyr Leu Pro Asn Leu Thr Asn Tyr Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 34
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 34

Val Asp Ala Lys Tyr Ala Lys Glu Arg Asn Leu Ala Ala Tyr Glu Ile
1 5 10 15

Leu Tyr Leu Pro Asn Leu Thr Gln Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 35
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 35

```
Val Asp Ala Lys Tyr Ala Lys Glu Arg Asn Asp Ala Ala Tyr Glu Ile
1               5                   10                  15

Leu Tyr Leu Pro Asn Leu Thr Gln Glu Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 36
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 36

Val Asp Ala Lys Tyr Ala Lys Glu Arg Asn Val Ala Ala Tyr Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 37
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 37

Val Asp Ala Lys Tyr Ala Lys Glu Arg Asn Glu Ala Ala Tyr Glu Ile
1               5                   10                  15

Leu Tyr Leu Pro Asn Leu Thr Gln Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 38
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 38

Val Asp Ala Lys Tyr Ala Lys Glu Arg Asn Thr Ala Ala Tyr Glu Ile
1               5                   10                  15

Leu Tyr Leu Pro Asn Leu Thr Gln Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 39
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 39

```
Val Asp Ala Lys Tyr Ala Lys Glu Arg Asn Phe Ala Ala Tyr Glu Ile
1               5                   10                  15

Leu Tyr Leu Pro Asn Leu Thr Ser Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 40
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 40

```
Val Asp Ala Lys Tyr Ala Lys Glu Arg Asn Asn Ala Ala Tyr Glu Ile
1               5                   10                  15

Leu Tyr Leu Pro Asn Leu Thr Ser Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 41
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 41

```
Val Asp Ala Lys Tyr Ala Lys Glu Arg Asn Gln Ala Ala Tyr Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 42
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 42

```
Val Asp Ala Lys Tyr Ala Lys Glu Arg Asn Glu Ala Ala Tyr Glu Ile
1               5                   10                  15
```

-continued

```
Leu Tyr Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 43
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 43

Val Asp Ala Lys Tyr Ala Lys Glu Arg Asn Thr Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 44
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 44

Val Asp Ala Lys Tyr Ala Lys Glu Arg Asn Ser Ala Ala Tyr Glu Ile
1               5                   10                  15

Leu Tyr Leu Pro Asn Leu Thr Lys Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 45
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 45

Val Asp Ala Lys Tyr Ala Lys Glu Arg Asn Lys Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 46
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 46

```
Val Asp Ala Lys Tyr Ala Lys Glu Arg Asn Glu Ala Ala Tyr Glu Ile
1               5                   10                  15

Leu Tyr Leu Pro Asn Leu Thr Ala Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 47
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 47

```
Val Asp Ala Lys Tyr Ala Lys Glu Arg Asn Thr Ala Ala Gln Glu Ile
1               5                   10                  15

Leu Tyr Leu Pro Asn Leu Thr Ser Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 48
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 48

```
Val Asp Ala Lys Tyr Ala Lys Glu Arg Asn Ile Ala Ala Tyr Glu Ile
1               5                   10                  15

Leu Trp Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 49
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 49

```
Val Asp Ala Lys Tyr Ala Lys Glu Arg Asn Ala Ala Ala Phe Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
```

35 40 45

Lys Lys Leu Asn Asp Ser Gln Ala Pro Lys
50 55

<210> SEQ ID NO 50
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 50

Val Asp Ala Lys Tyr Ala Lys Glu Arg Asn Glu Ala Ala Tyr Glu Ile
1 5 10 15

Leu Tyr Leu Pro Asn Leu Thr Ser Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 51
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 51

Val Asp Ala Lys Tyr Ala Lys Glu Arg Asn Glu Ala Ala His Glu Ile
1 5 10 15

Leu Tyr Leu Pro Asn Leu Thr Gln Lys Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 52
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 52

Val Asp Ala Lys Tyr Ala Lys Glu Arg Asn Phe Ala Ala Tyr Glu Ile
1 5 10 15

Leu Tyr Leu Pro Asn Leu Thr Asn Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 53
<211> LENGTH: 58
<212> TYPE: PRT
<213> ORGANISM: Artificial Sequence
<220> FEATURE:
<223> OTHER INFORMATION: Engineered PD-L1 binding polypeptide

```
<400> SEQUENCE: 53

Val Asp Ala Lys Tyr Ala Lys Glu Arg Asn Ala Ala Ala Phe Glu Ile
1               5                   10                  15

Leu Tyr Leu Pro Asn Leu Thr Ser Ala Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 54
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 54

Val Asp Ala Lys Tyr Ala Lys Glu Arg Asn Asp Ala Ala Tyr Glu Ile
1               5                   10                  15

Leu Tyr Leu Pro Asn Leu Thr Lys Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 55
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 55

Val Asp Ala Lys Tyr Ala Lys Glu Arg Asn Lys Ala Ala Tyr Glu Ile
1               5                   10                  15

Leu Tyr Leu Pro Asn Leu Thr Gln Gln Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 56
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 56

Val Asp Ala Lys Tyr Ala Lys Glu Arg Asn His Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 57
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 57

```
Val Asp Ala Lys Tyr Ala Lys Glu Arg Asn Phe Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 58
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 58

```
Val Asp Ala Lys Tyr Ala Lys Glu Arg Asn Ala Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 59
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 59

```
Val Asp Ala Lys Tyr Ala Lys Glu Arg Asn Lys Ala Ala Phe Glu Ile
1               5                   10                  15

Leu Tyr Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 60
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 60

```
Val Asp Ala Lys Tyr Ala Lys Glu Arg Asn Ala Ala Ala Tyr Glu Ile
1               5                   10                  15
```

```
Leu Tyr Leu Pro Asn Leu Thr Ala Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 61
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 61

Val Asp Ala Lys Tyr Ala Lys Glu Arg Asn Gln Ala Ala Tyr Glu Ile
1               5                   10                  15

Leu Tyr Leu Pro Asn Leu Thr Asn Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 62
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 62

Val Asp Ala Lys Tyr Ala Lys Glu Arg Asn Asp Ala Ala Tyr Glu Ile
1               5                   10                  15

Leu Gln Leu Pro Asn Leu Thr Asn Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 63
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 63

Val Asp Ala Lys Tyr Ala Lys Glu Arg Asn Ser Ala Ala Tyr Glu Ile
1               5                   10                  15

Leu Tyr Leu Pro Asn Leu Thr Asn Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 64
<211> LENGTH: 58
```

<212> TYPE: PRT
<213> ORGANISM: Artificial Sequence
<220> FEATURE:
<223> OTHER INFORMATION: Engineered PD-L1 binding polypeptide

<400> SEQUENCE: 64

Val Asp Ala Lys Tyr Ala Lys Glu Arg Asn Ser Ala Ala Gln Glu Ile
1 5 10 15

Leu Tyr Leu Pro Asn Leu Thr Asn Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 65
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 65

Val Asp Ala Lys Tyr Ala Lys Glu Arg Asn Glu Ala Ala Tyr Glu Ile
1 5 10 15

Leu Tyr Leu Pro Asn Leu Thr Ala Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 66
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 66

Val Asp Ala Lys Tyr Ala Lys Glu Arg Asn Gln Ala Ala Tyr Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 67
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 67

Val Asp Ala Lys Tyr Ala Lys Glu Arg Asn Thr Ala Ala Tyr Glu Ile
1 5 10 15

Leu Tyr Leu Pro Asn Leu Thr Lys Ser Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 68
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 68

Val Asp Ala Lys Tyr Ala Lys Glu Arg Asn Ser Ala Ala Tyr Glu Ile
1 5 10 15

Leu Tyr Leu Pro Asn Leu Thr Ser Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 69
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 69

Val Asp Ala Lys Tyr Ala Lys Glu Arg Asn Ile Ala Ala Tyr Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 70
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 70

Val Asp Ala Lys Tyr Ala Lys Glu Arg Asn Ile Ala Ala Gln Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 71
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 71

Val Asp Ala Lys Tyr Ala Lys Glu Arg Asn Asp Ala Ala Tyr Glu Ile
1 5 10 15

Leu Tyr Leu Pro Asn Leu Thr Asn Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 72
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 72

Val Asp Ala Lys Tyr Ala Lys Glu Arg Asn His Ala Ala Phe Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 73
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 73

Val Asp Ala Lys Tyr Ala Lys Glu Arg Asn Glu Ala Ala Tyr Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 74
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 74

Val Asp Ala Lys Tyr Ala Lys Glu Arg Asn Gln Ala Ala Phe Glu Ile
1 5 10 15

Leu Tyr Leu Pro Asn Leu Thr Asn Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys 50 55

<210> SEQ ID NO 75
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 75

Val Asp Ala Lys Tyr Ala Lys Glu Arg Asn Val Ala Ala Tyr Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 76
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 76

Val Asp Ala Lys Tyr Ala Lys Glu Arg Asn Ile Ala Ala Tyr Glu Ile
1 5 10 15

Leu Tyr Leu Pro Asn Leu Thr Asn Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 77
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 77

Val Asp Ala Lys Tyr Ala Lys Glu Arg Asn Phe Ala Ala Tyr Glu Ile
1 5 10 15

Leu Tyr Leu Pro Asn Leu Thr Gln Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 78
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 78

Val Asp Ala Lys Tyr Ala Lys Glu Arg Asn Arg Ala Ala Tyr Glu Ile

```
1               5                   10                  15

Leu Tyr Leu Pro Asn Leu Thr His Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 79
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 79

Val Asp Ala Lys Tyr Ala Lys Glu Arg Asn Thr Ala Ala Tyr Glu Ile
1               5                   10                  15

Leu Tyr Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 80
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 80

Val Asp Ala Lys Tyr Ala Lys Glu Arg Asn Glu Ala Ala Tyr Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 81
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 81

Val Asp Ala Lys Tyr Ala Lys Glu Arg Asn Ser Ala Ala Phe Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 82
```

```
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 82

Val Asp Ala Lys Tyr Ala Lys Glu Arg Asn Gln Ala Ala Tyr Glu Ile
1               5                   10                  15

Leu Tyr Leu Pro Asn Leu Thr Gln Arg Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 83
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 83

Val Asp Ala Lys Tyr Ala Lys Glu Arg Asn Asp Ala Ala Tyr Glu Ile
1               5                   10                  15

Leu Tyr Leu Pro Asn Leu Thr Ala Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 84
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 84

Val Asp Ala Lys Tyr Ala Lys Glu Arg Asn Leu Ala Ala Gln Glu Ile
1               5                   10                  15

Leu Tyr Leu Pro Asn Leu Thr Gln Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 85
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 85

Val Asp Ala Lys Tyr Ala Lys Glu Arg Asn Glu Ala Ala Gln Glu Ile
1               5                   10                  15

Leu Tyr Leu Pro Asn Leu Thr Gln Lys Gln Ile Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 86
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 86

Val Asp Ala Lys Tyr Ala Lys Glu Arg Asn Glu Ala Ala Tyr Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 87
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 87

Val Asp Ala Lys Tyr Ala Lys Glu Arg Asn Lys Ala Ala Gln Glu Ile
1               5                   10                  15

Leu Tyr Leu Pro Asn Leu Thr Gln Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 88
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 88

Val Asp Ala Lys Tyr Ala Lys Glu Arg Asn Gln Ala Ala Tyr Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 89
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 89

Val Asp Ala Lys Tyr Ala Lys Glu Arg Asn Ala Ala Ala Tyr Glu Ile
1 5 10 15

Leu Tyr Leu Pro Asn Leu Thr Gln Leu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 90
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 90

Val Asp Ala Lys Tyr Ala Lys Glu Arg Asn Glu Ala Ala Phe Glu Ile
1 5 10 15

Leu Tyr Leu Pro Asn Leu Thr Asn Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 91
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 91

Val Asp Ala Lys Tyr Ala Lys Glu Arg Asn Ala Ala Ala Phe Glu Ile
1 5 10 15

Leu Trp Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 92
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 92

Val Asp Ala Lys Tyr Ala Lys Glu Arg Asn Glu Ala Ala Phe Glu Ile
1 5 10 15

Leu His Leu Pro Asn Leu Thr Lys Ala Gln His Trp Ala Phe Ile Trp
20 25 30

Lys Leu Ala Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 93
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 93

Val Asp Ala Lys Tyr Ala Lys Glu Arg Asn Asp Ala Ala Phe Glu Ile
1               5                   10                  15

Leu Tyr Leu Pro Asn Leu Thr Gln Thr Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 94
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 94

Val Asp Ala Lys Tyr Ala Lys Glu Arg Asn Glu Ala Ala Tyr Glu Ile
1               5                   10                  15

Leu Tyr Leu Pro Asn Leu Thr Ser Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 95
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 95

Val Asp Ala Lys Tyr Ala Lys Glu Arg Asn Thr Ala Ala His Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 96
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 96
```

-continued

```
Val Asp Ala Lys Tyr Ala Lys Glu Arg Asn Thr Ala Ala Tyr Glu Ile
1               5                   10                  15

Leu Lys Leu Pro Asn Leu Thr Lys Tyr Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 97
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 97

Val Asp Ala Lys Tyr Ala Lys Glu Arg Asn Asp Ala Ala Tyr Glu Ile
1               5                   10                  15

Leu Gln Leu Pro Asn Leu Thr Gln Ser Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 98
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 98

Val Asp Ala Lys Tyr Ala Lys Glu Arg Asn Ile Ala Ala Tyr Glu Ile
1               5                   10                  15

Leu Lys Leu Pro Asn Leu Thr Glu Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 99
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 99

Val Asp Ala Lys Tyr Ala Lys Glu Arg Asn Ile Ala Ala Ser Glu Ile
1               5                   10                  15

Leu Lys Leu Pro Asn Leu Thr Lys Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 100
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 100

Val Asp Ala Lys Tyr Ala Lys Glu Arg Asn Asp Ala Ala Tyr Glu Ile
1 5 10 15

Leu Tyr Leu Pro Asn Leu Thr Gln Tyr Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 101
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 101

Val Asp Ala Lys Tyr Ala Lys Glu Arg Asn Asp Ala Ala Glu Glu Ile
1 5 10 15

Leu Tyr Leu Pro Asn Leu Thr Asn Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 102
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 102

Val Asp Ala Lys Tyr Ala Lys Glu Arg Asn Ala Ala Ala Tyr Glu Ile
1 5 10 15

Leu Tyr Leu Pro Asn Leu Thr Trp Ser Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 103
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 103

Val Asp Ala Lys Tyr Ala Lys Glu Arg Asn Lys Ala Ala Tyr Glu Ile
1 5 10 15

Leu Tyr Leu Pro Asn Leu Thr Ala Ser Gln His Trp Ala Phe Ile Trp

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 104
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 104

Val Asp Ala Lys Tyr Ala Lys Glu Arg Asn Asn Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 105
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 105

Val Asp Ala Lys Tyr Ala Lys Glu Arg Asn Thr Ala Ala Tyr Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 106
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 106

Val Asp Ala Lys Tyr Ala Lys Glu Arg Asn Glu Ala Ala Tyr Glu Ile
1               5                   10                  15

Leu Tyr Leu Pro Asn Leu Thr Asp Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 107
<211> LENGTH: 58
<212> TYPE: PRT
<213> ORGANISM: Artificial Sequence
```

```
<220> FEATURE:
<223> OTHER INFORMATION: Engineered PD-L1 binding polypeptide

<400> SEQUENCE: 107

Val Asp Ala Lys Tyr Ala Lys Glu Arg Asn Thr Ala Ala Ser Glu Ile
1               5                   10                  15

Leu Tyr Leu Pro Asn Leu Thr Ser Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 108
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 108

Val Asp Ala Lys Tyr Ala Lys Glu Arg Asn Ile Ala Ala Phe Glu Ile
1               5                   10                  15

Leu Trp Leu Pro Asn Leu Thr Ala His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 109
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 109

Val Asp Ala Lys Tyr Ala Lys Glu Arg Asn Asp Ala Ala Phe Glu Ile
1               5                   10                  15

Leu Tyr Leu Pro Asn Leu Thr Ser Glu Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 110
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 110

Val Asp Ala Lys Tyr Ala Lys Glu Arg Asn His Ala Ala Asp Glu Ile
1               5                   10                  15

Leu Lys Leu Pro Asn Leu Thr Ser Asp Gln Asn Trp Ala Phe Ile Trp
            20                  25                  30

Lys Leu Asp Asp Asp Pro Ser Gln Ser Ser Glu Leu Leu Ser Glu Ala
        35                  40                  45
```

-continued

Lys Lys Leu Asn Asp Ser Gln Ala Pro Lys
50 55

<210> SEQ ID NO 111
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 111

Val Asp Ala Lys Tyr Ala Lys Glu Arg Asn Asp Ala Ala Tyr Glu Ile
1 5 10 15

Leu Tyr Leu Pro Asn Leu Thr Asn Glu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 112
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 112

Val Asp Ala Lys Tyr Ala Lys Glu Arg Asn Ile Ala Ala Glu Glu Ile
1 5 10 15

Leu Ile Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 113
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 113

Val Asp Ala Lys Tyr Ala Lys Glu Arg Asn Glu Ala Ala Gln Glu Ile
1 5 10 15

Leu Tyr Leu Pro Asn Leu Thr Gln Asn Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 114
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 114

```
Val Asp Ala Lys Tyr Ala Lys Glu Arg Asn Ser Ala Ala Gln Glu Ile
1               5                   10                  15

Leu Tyr Leu Pro Asn Leu Thr Gln Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 115
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 115

Val Asp Ala Lys Tyr Ala Lys Glu Arg Asn Phe Ala Ala Gln Glu Ile
1               5                   10                  15

Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 116
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 116

Val Asp Ala Lys Tyr Ala Lys Glu Arg Asn Asn Ala Ala Tyr Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 117
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 117

Val Asp Ala Lys Tyr Ala Lys Glu Arg Asn Glu Ala Ala Tyr Glu Ile
1               5                   10                  15

Leu Tyr Leu Pro Asn Leu Thr Asn Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 118
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 118

```
Val Asp Ala Lys Tyr Ala Lys Glu Arg Asn Ala Ala Ala Gln Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 119
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 119

```
Val Asp Ala Lys Tyr Ala Lys Glu Arg Asn Ala Ala Ala Tyr Glu Ile
1               5                   10                  15

Leu Tyr Leu Pro Asn Leu Thr Lys Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 120
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 120

```
Val Asp Ala Lys Tyr Ala Lys Glu Arg Asn Lys Ala Ala Phe Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 121
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 121

```
Val Asp Ala Lys Tyr Ala Lys Glu Arg Asn Asn Ala Ala Gln Glu Ile
1               5                   10                  15
```

-continued

```
Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 122
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 122

Val Asp Ala Lys Tyr Ala Lys Glu Arg Asn Glu Ala Ala His Glu Ile
1               5                   10                  15

Leu Thr Leu Pro Asn Leu Thr Ala Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 123
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 123

Val Asp Ala Lys Tyr Ala Lys Glu Arg Asn Trp Ala Ala Ala Glu Ile
1               5                   10                  15

Leu Tyr Leu Pro Asn Leu Thr Asn Ala Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 124
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 124

Val Asp Ala Lys Tyr Ala Lys Glu Arg Asn Asp Ala Ala Tyr Glu Ile
1               5                   10                  15

Leu Tyr Leu Pro Asn Leu Thr Gln Asp Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 125
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 125

Val Asp Ala Lys Tyr Ala Lys Glu Arg Asn Glu Ala Ala His Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 126
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 126

Val Asp Ala Lys Tyr Ala Lys Glu Arg Asn Ala Ala Ala Gln Glu Ile
1 5 10 15

Leu Tyr Leu Pro Asn Leu Thr Asn His Gln Lys Trp Ala Phe Ile Trp
20 25 30

Lys Leu Glu Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 127
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 127

Val Asp Ala Lys Tyr Ala Lys Glu Arg Asn Arg Ala Ala His Glu Ile
1 5 10 15

Leu Tyr Leu Pro Asn Leu Thr Arg Gln Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 128
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 128

Val Asp Ala Lys Tyr Ala Lys Glu Arg Asn Glu Ala Ala Tyr Glu Ile
1 5 10 15

Leu Tyr Leu Pro Asn Leu Thr Asn Lys Gln Arg Trp Ala Phe Ile Trp
20 25 30

Lys Leu Asp Asp Asp Pro Ser Gln Ser Ser Glu Leu Leu Ser Glu Ala

```
        35                  40                  45

Lys Lys Leu Asn Asp Ser Gln Ala Pro Lys
    50                  55


<210> SEQ ID NO 129
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 129

Val Asp Ala Lys Tyr Ala Lys Glu Arg Asn His Ala Ala Phe Glu Ile
1               5                   10                  15

Leu Tyr Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 130
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 130

Val Asp Ala Lys Tyr Ala Lys Glu Arg Asn Glu Ala Ala Tyr Glu Ile
1               5                   10                  15

Leu Tyr Leu Pro Asn Leu Thr Ser Gln Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 131
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 131

Val Asp Ala Lys Tyr Ala Lys Glu Arg Asn Thr Ala Ala Tyr Glu Ile
1               5                   10                  15

Leu Gln Leu Pro Asn Leu Thr Lys Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 132
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 132

Val Asp Ala Lys Tyr Ala Lys Glu Arg Asn His Ala Ala Ala Glu Ile
1 5 10 15

Leu Ser Leu Pro Asn Leu Thr Lys Lys Gln Asn Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 133
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 133

Val Asp Ala Lys Tyr Ala Lys Glu Arg Asn Glu Ala Ala Tyr Glu Ile
1 5 10 15

Leu Tyr Leu Pro Asn Leu Thr His Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 134
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 134

Val Asp Ala Lys Tyr Ala Lys Glu Arg Asn Ile Ala Ala Ser Glu Ile
1 5 10 15

Leu Thr Leu Pro Asn Leu Thr Lys Ser Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 135
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 135

Val Asp Ala Lys Tyr Ala Lys Glu Arg Asn Lys Ala Ala Tyr Glu Ile
1 5 10 15

Leu Asn Leu Pro Asn Leu Thr Gln Ser Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 136
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 136

```
Val Asp Ala Lys Tyr Ala Lys Glu Arg Asn Ala Ala Ala Gln Glu Ile
1               5                   10                  15

Leu Glu Leu Pro Asn Leu Thr Trp Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 137
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 137

```
Val Asp Ala Lys Tyr Ala Lys Glu Arg Asn Ser Ala Ala Tyr Glu Ile
1               5                   10                  15

Leu Tyr Leu Pro Asn Leu Thr Gln Ser Gln Ile Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 138
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 138

```
Val Asp Ala Lys Tyr Ala Lys Glu Arg Asn Tyr Ala Ala Tyr Glu Ile
1               5                   10                  15

Leu Tyr Leu Pro Asn Leu Thr Glu Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 139
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 139

```
Val Asp Ala Lys Tyr Ala Lys Glu Arg Asn Asn Ala Ala Tyr Glu Ile
1               5                   10                  15
```

```
Leu Leu Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 140
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 140

Val Asp Ala Lys Tyr Ala Lys Glu Arg Asn Asn Ala Ala Gln Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 141
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 141

Val Asp Ala Lys Tyr Ala Lys Glu Arg Asn Gln Ala Ala Tyr Glu Ile
1               5                   10                  15

Leu Gln Leu Pro Asn Leu Thr Asn Asp Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 142
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 142

Val Asp Ala Lys Tyr Ala Lys Glu Arg Asn Thr Ala Ala Tyr Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 143
<211> LENGTH: 58
```

```
<212> TYPE: PRT
<213> ORGANISM: Artificial Sequence
<220> FEATURE:
<223> OTHER INFORMATION: Engineered PD-L1 binding polypeptide

<400> SEQUENCE: 143

Val Asp Ala Lys Tyr Ala Lys Glu Arg Asn Lys Ala Ala Tyr Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 144
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 144

Val Asp Ala Lys Tyr Ala Lys Glu Arg Asn Thr Ala Ala Glu Glu Ile
1               5                   10                  15

Leu Lys Leu Pro Asn Leu Thr Asn Lys Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 145
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 145

Val Asp Ala Lys Tyr Ala Lys Glu Arg Asn Arg Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 146
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 146

Val Asp Ala Lys Tyr Ala Lys Glu Arg Asn Ser Ala Ala His Glu Ile
1               5                   10                  15

Leu Tyr Leu Pro Asn Leu Thr Thr Ala Gln Arg Trp Ala Phe Ile Trp
            20                  25                  30
```

-continued

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 147
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 147

Val Asp Ala Lys Tyr Ala Lys Glu Arg Asn Ser Ala Ala Tyr Glu Ile
1               5                   10                  15

Leu Tyr Leu Pro Asn Leu Thr Ala Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 148
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 148

Val Asp Ala Lys Tyr Ala Lys Glu Arg Asn Lys Ala Ala Tyr Glu Ile
1               5                   10                  15

Leu Tyr Leu Pro Asn Leu Thr Asn Leu Gln Arg Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 149
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 149

Val Asp Ala Lys Tyr Ala Lys Glu Arg Asn Gln Ala Ala Ser Glu Ile
1               5                   10                  15

Leu Ser Leu Pro Asn Leu Thr Lys Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 150
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 150

```
Val Asp Ala Lys Tyr Ala Lys Glu Arg Asn His Ala Ala Trp Glu Ile
1               5                   10                  15

Leu Lys Leu Pro Asn Leu Thr Lys Ser Gln Glu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 151
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 151

```
Val Asp Ala Lys Tyr Ala Lys Glu Arg Asn Val Ala Ala Gln Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 152
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 152

```
Val Asp Ala Lys Tyr Ala Lys Glu Arg Asn Leu Ala Ala Tyr Glu Ile
1               5                   10                  15

Leu Tyr Leu Pro Asn Leu Thr Arg Ala Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 153
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 153

```
Val Asp Ala Lys Tyr Ala Lys Glu Arg Asn Val Ala Ala Tyr Glu Ile
1               5                   10                  15

Leu Tyr Leu Pro Asn Leu Thr Ala Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
```

50 55

<210> SEQ ID NO 154
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 154

Val Asp Ala Lys Tyr Ala Lys Glu Arg Asn Asp Ala Ala Tyr Glu Ile
1 5 10 15

Leu Tyr Leu Pro Asn Leu Thr Ser Ala Gln Val Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 155
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 155

Val Asp Ala Lys Tyr Ala Lys Glu Arg Asn Gln Ala Ala Glu Glu Ile
1 5 10 15

Leu Arg Leu Pro Asn Leu Thr Trp Glu Gln Asn Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 156
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 156

Val Asp Ala Lys Tyr Ala Lys Glu Arg Asn Asn Ala Ala Tyr Glu Ile
1 5 10 15

Leu Gln Leu Pro Asn Leu Thr Gln Leu Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 157
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 157

Val Asp Ala Lys Tyr Ala Lys Glu Arg Asn Ser Ala Ala Tyr Glu Ile

```
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 158
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 158

Val Asp Ala Lys Tyr Ala Lys Glu Arg Asn Phe Ala Ala Gln Glu Ile
1               5                   10                  15

Leu Tyr Leu Pro Asn Leu Thr Lys Ala Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 159
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 159

Val Asp Ala Lys Tyr Ala Lys Glu Arg Asn His Ala Ala Gln Glu Ile
1               5                   10                  15

Leu Glu Leu Pro Asn Leu Thr Asn Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 160
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 160

Val Asp Ala Lys Tyr Ala Lys Glu Arg Asn Ile Ala Ala Gln Glu Ile
1               5                   10                  15

Leu Phe Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 161
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 161

Val Asp Ala Lys Tyr Ala Lys Glu Arg Asn Glu Ala Ala Phe Glu Ile
1 5 10 15

Leu Tyr Leu Pro Asn Leu Thr Glu Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 162
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 162

Val Asp Ala Lys Tyr Ala Lys Glu Arg Asn Ile Ala Ala Asn Glu Ile
1 5 10 15

Leu Lys Leu Pro Asn Leu Thr Ala Asn Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 163
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 163

Val Asp Ala Lys Tyr Ala Lys Glu Arg Asn Glu Ala Ala Val Glu Ile
1 5 10 15

Leu Tyr Leu Pro Asn Leu Thr Asn Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 164
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 164

Val Asp Ala Lys Tyr Ala Lys Glu Arg Asn Glu Ala Ala Gln Glu Ile
1 5 10 15

Leu Asn Leu Pro Asn Leu Thr Gln Ser Gln Glu Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 165
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 165

Val Asp Ala Lys Tyr Ala Lys Glu Arg Asn Ile Ala Ala Tyr Glu Ile
1               5                   10                  15

Leu Gln Leu Pro Asn Leu Thr Gln Arg Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 166
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 166

Val Asp Ala Lys Tyr Ala Lys Glu Arg Asn Tyr Ala Ala Tyr Glu Ile
1               5                   10                  15

Leu Gln Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 167
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 167

Val Asp Ala Lys Tyr Ala Lys Glu Arg Asn Glu Ala Ala His Glu Ile
1               5                   10                  15

Leu Tyr Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 168
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 168

Val Asp Ala Lys Tyr Ala Lys Glu Arg Asn Glu Ala Ala His Glu Ile
1 5 10 15

Leu Gln Leu Pro Asn Leu Thr Ser Leu Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 169
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 169

Val Asp Ala Lys Tyr Ala Lys Glu Arg Asn His Ala Ala Phe Glu Ile
1 5 10 15

Leu Tyr Leu Pro Asn Leu Thr Ala Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 170
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 170

Val Asp Ala Lys Tyr Ala Lys Glu Arg Asn Tyr Ala Ala Glu Glu Ile
1 5 10 15

Leu Lys Leu Pro Asn Leu Thr Asn Gly Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 171
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 171

Val Asp Ala Lys Tyr Ala Lys Glu Arg Asn Asn Ala Ala Thr Glu Ile
1 5 10 15

Leu Arg Leu Pro Asn Leu Thr Ala Ser Gln Tyr Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 172
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 172

Val Asp Ala Lys Tyr Ala Lys Glu Arg Asn His Ala Ala Tyr Glu Ile
1               5                   10                  15

Leu Tyr Leu Pro Asn Leu Thr Ala Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 173
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 173

Val Asp Ala Lys Tyr Ala Lys Glu Arg Asn Leu Ala Ala Phe Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 174
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 174

Val Asp Ala Lys Tyr Ala Lys Glu Arg Asn Tyr Ala Ala Tyr Glu Ile
1               5                   10                  15

Leu Tyr Leu Pro Asn Leu Thr Gln Phe Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 175
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 175
```

```
Val Asp Ala Lys Tyr Ala Lys Glu Arg Asn Glu Ala Ala Gln Glu Ile
1               5                   10                  15

Leu Tyr Leu Pro Asn Leu Thr Ser Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 176
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 176

Val Asp Ala Lys Tyr Ala Lys Glu Arg Asn Lys Ala Ala Phe Glu Ile
1               5                   10                  15

Leu Asn Leu Pro Asn Leu Thr Ser Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 177
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 177

Val Asp Ala Lys Tyr Ala Lys Glu Arg Asn Thr Ala Ala His Glu Ile
1               5                   10                  15

Leu Tyr Leu Pro Asn Leu Thr Gln Ser Gln Ile Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 178
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 178

Val Asp Ala Lys Tyr Ala Lys Glu Arg Asn Asp Ala Ala Gln Glu Ile
1               5                   10                  15

Leu Tyr Leu Pro Asn Leu Thr Lys Gly Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 179
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 179

```
Val Asp Ala Lys Tyr Ala Lys Glu Arg Asn Phe Ala Ala His Glu Ile
1               5                   10                  15

Leu Tyr Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 180
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 180

```
Val Asp Ala Lys Tyr Ala Lys Glu Arg Asn Ser Ala Ala His Glu Ile
1               5                   10                  15

Leu Tyr Leu Pro Asn Leu Thr Glu Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 181
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 181

```
Val Asp Ala Lys Tyr Ala Lys Glu Arg Asn Asp Ala Ala Tyr Glu Ile
1               5                   10                  15

Leu Tyr Leu Pro Asn Leu Thr His Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 182
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 182

```
Val Asp Ala Lys Tyr Ala Lys Glu Arg Asn Ile Ala Ala His Glu Ile
1               5                   10                  15

Leu Tyr Leu Pro Asn Leu Thr Asn Glu Gln Lys Trp Ala Phe Ile Trp
```

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 183
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 183

Val Asp Ala Lys Tyr Ala Lys Glu Arg Asn Glu Ala Ala Phe Glu Ile
1               5                   10                  15

Leu Tyr Leu Pro Asn Leu Thr Asn Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 184
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 184

Val Asp Ala Lys Tyr Ala Lys Glu Arg Asn Lys Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 185
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 185

Val Asp Ala Lys Tyr Ala Lys Glu Arg Asn Lys Ala Ala Gln Glu Ile
1               5                   10                  15

Leu Tyr Leu Pro Asn Leu Thr Gln Arg Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 186
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 186

Val Asp Ala Lys Tyr Ala Lys Glu Arg Asn Asp Ala Ala Gln Glu Ile
1 5 10 15

Leu Thr Leu Pro Asn Leu Thr Ala Lys Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 187
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 187

Val Asp Ala Lys Tyr Ala Lys Glu Arg Asn Ser Ala Ala Tyr Glu Ile
1 5 10 15

Leu Tyr Leu Pro Asn Leu Thr Ser Asp Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 188
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 188

Val Asp Ala Lys Tyr Ala Lys Glu Arg Asn Lys Ala Ala Phe Glu Ile
1 5 10 15

Leu Tyr Leu Pro Asn Leu Thr Asn Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 189
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 189

Val Asp Ala Lys Tyr Ala Lys Glu Arg Asn Gln Ala Ala Gln Glu Ile
1 5 10 15

Leu Glu Leu Pro Asn Leu Thr Asn Ala Gln Tyr Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 190
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 190

Val Asp Ala Lys Tyr Ala Lys Glu Arg Asn Glu Ala Ala Tyr Glu Ile
1               5                   10                  15

Leu Lys Leu Pro Asn Leu Thr Ser Gln Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 191
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 191

Val Asp Ala Lys Tyr Ala Lys Glu Arg Asn Glu Ala Ala Tyr Glu Ile
1               5                   10                  15

Leu Asn Leu Pro Asn Leu Thr Arg His Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 192
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 192

Val Asp Ala Lys Tyr Ala Lys Glu Arg Asn Leu Ala Ala Tyr Glu Ile
1               5                   10                  15

Leu Lys Leu Pro Asn Leu Thr Asn Glu Gln Asn Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 193
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 193
```

```
Val Asp Ala Lys Tyr Ala Lys Glu Arg Asn Lys Ala Ala Tyr Glu Ile
1               5                   10                  15

Leu Tyr Leu Pro Asn Leu Thr Gln Glu Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 194
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 194

Val Asp Ala Lys Tyr Ala Lys Glu Arg Asn Lys Ala Ala Tyr Glu Ile
1               5                   10                  15

Leu Tyr Leu Pro Asn Leu Thr Ser Gln Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 195
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 195

Val Asp Ala Lys Tyr Ala Lys Glu Arg Asn Thr Ala Ala His Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 196
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 196

Val Asp Ala Lys Tyr Ala Lys Glu Arg Asn His Ala Ala Phe Glu Ile
1               5                   10                  15

Leu Lys Leu Pro Asn Leu Thr Asn Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 197
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 197

```
Val Asp Ala Lys Tyr Ala Lys Glu Arg Asn Asp Ala Ala Phe Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 198
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 198

```
Val Asp Ala Lys Tyr Ala Lys Glu Arg Asn Leu Ala Ala His Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 199
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 199

```
Val Asp Ala Lys Tyr Ala Lys Glu Arg Asn His Ala Ala Tyr Glu Ile
1               5                   10                  15

Leu Gln Leu Pro Asn Leu Thr Lys Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 200
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 200

```
Val Asp Ala Lys Tyr Ala Lys Glu Arg Asn Ser Ala Ala Tyr Glu Ile
1               5                   10                  15
```

```
Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 201
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 201

Val Asp Ala Lys Tyr Ala Lys Glu Arg Asn Ala Ala Ala Tyr Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 202
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 202

Val Asp Ala Lys Tyr Ala Lys Glu Arg Asn Asp Ala Ala Tyr Glu Ile
1               5                   10                  15

Leu Gln Leu Pro Asn Leu Thr Asn Gln Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 203
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 203

Val Asp Ala Lys Tyr Ala Lys Glu Arg Asn Asn Ala Ala Glu Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 204
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 204

Val Asp Ala Lys Tyr Ala Lys Glu Arg Asn Glu Ala Ala His Glu Ile
1 5 10 15

Leu Tyr Leu Pro Asn Leu Thr Glu Ser Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 205
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 205

Val Asp Ala Lys Tyr Ala Lys Glu Arg Asn Asn Ala Ala Tyr Glu Ile
1 5 10 15

Leu Ser Leu Pro Asn Leu Thr Lys Ser Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 206
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 206

Val Asp Ala Lys Tyr Ala Lys Glu Arg Asn Val Ala Ala Tyr Glu Ile
1 5 10 15

Leu Tyr Leu Pro Asn Leu Thr Asn Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 207
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 207

Val Asp Ala Lys Tyr Ala Lys Glu Arg Asn Glu Ala Ala Tyr Glu Ile
1 5 10 15

Leu Gln Leu Pro Asn Leu Thr Asn Tyr Gln Tyr Trp Ala Phe Ile Trp
20 25 30

Lys Leu Asp Asp Asp Pro Ser Gln Ser Ser Glu Leu Leu Ser Glu Ala

```
        35                  40                  45

Lys Lys Leu Asn Asp Ser Gln Ala Pro Lys
    50                  55


<210> SEQ ID NO 208
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 208

Val Asp Ala Lys Tyr Ala Lys Glu Arg Asn Gln Ala Ala Phe Glu Ile
1               5                   10                  15

Leu Tyr Leu Pro Asn Leu Thr Arg Phe Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 209
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 209

Val Asp Ala Lys Tyr Ala Lys Glu Arg Asn Phe Ala Ala Gln Glu Ile
1               5                   10                  15

Leu Tyr Leu Pro Asn Leu Thr Asn Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 210
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 210

Val Asp Ala Lys Tyr Ala Lys Glu Arg Asn Ser Ala Ala Tyr Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 211
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 211

Val Asp Ala Lys Tyr Ala Lys Glu Arg Asn Ser Ala Ala Ser Glu Ile
1               5                   10                  15

Leu Tyr Leu Pro Asn Leu Thr Gln Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 212
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 212

Val Asp Ala Lys Tyr Ala Lys Glu Arg Asn Tyr Ala Ala Trp Glu Ile
1               5                   10                  15

Leu Gln Leu Pro Asn Leu Thr Lys Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 213
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 213

Val Asp Ala Lys Tyr Ala Lys Glu Arg Asn His Ala Ala His Glu Ile
1               5                   10                  15

Leu Tyr Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 214
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 214

Val Asp Ala Lys Tyr Ala Lys Glu Arg Asn Glu Ala Ala Phe Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 215
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 215

Val Asp Ala Lys Tyr Ala Lys Glu Arg Asn Glu Ala Ala Tyr Glu Ile
1               5                   10                  15

Leu Tyr Leu Pro Asn Leu Thr Ser Ala Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 216
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 216

Val Asp Ala Lys Tyr Ala Lys Glu Arg Asn Ser Ala Ala Gln Glu Ile
1               5                   10                  15

Leu Glu Leu Pro Asn Leu Thr Asn Gln Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 217
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 217

Val Asp Ala Lys Tyr Ala Lys Glu Arg Asn Ser Ala Ala His Glu Ile
1               5                   10                  15

Leu Lys Leu Pro Asn Leu Thr Gln Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 218
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 218

Val Asp Ala Lys Tyr Ala Lys Glu Arg Asn His Ala Ala Gln Glu Ile
1               5                   10                  15
```

```
Leu Ile Leu Pro Asn Leu Thr Arg Ala Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 219
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 219

Val Asp Ala Lys Tyr Ala Lys Glu Arg Asn Thr Ala Ala Phe Glu Ile
1               5                   10                  15

Leu Tyr Leu Pro Asn Leu Thr Ala Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 220
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 220

Val Asp Ala Lys Tyr Ala Lys Glu Arg Asn Val Ala Ala Gln Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 221
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 221

Val Asp Ala Lys Tyr Ala Lys Glu Arg Asn Lys Ala Ala His Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 222
<211> LENGTH: 58
```

<212> TYPE: PRT
<213> ORGANISM: Artificial Sequence
<220> FEATURE:
<223> OTHER INFORMATION: Engineered PD-L1 binding polypeptide

<400> SEQUENCE: 222

Val Asp Ala Lys Tyr Ala Lys Glu Arg Asn Gln Ala Ala Phe Glu Ile
1 5 10 15

Leu Tyr Leu Pro Asn Leu Thr Gln Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 223
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 223

Val Asp Ala Lys Tyr Ala Lys Glu Arg Asn Ser Ala Ala Tyr Glu Ile
1 5 10 15

Leu Asn Leu Pro Asn Leu Thr Ala Arg Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 224
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 224

Val Asp Ala Lys Tyr Ala Lys Glu Arg Asn Gln Ala Ala Gln Glu Ile
1 5 10 15

Leu Ala Leu Pro Asn Leu Thr Arg Gln Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 225
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 225

Val Asp Ala Lys Tyr Ala Lys Glu Arg Asn Ser Ala Ala Val Glu Ile
1 5 10 15

Leu Asn Leu Pro Asn Leu Thr Lys Glu Gln His Trp Ala Phe Ile Trp
20 25 30

-continued

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 226
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 226

Val Asp Ala Lys Tyr Ala Lys Glu Arg Asn Glu Ala Ala Tyr Glu Ile
1               5                   10                  15

Leu Phe Leu Pro Asn Leu Thr Gln Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 227
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 227

Val Asp Ala Lys Tyr Ala Lys Glu Arg Asn Glu Ala Ala Glu Glu Ile
1               5                   10                  15

Leu Tyr Leu Pro Asn Leu Thr Gln His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 228
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 228

Val Asp Ala Lys Tyr Ala Lys Glu Arg Asn Lys Ala Ala Tyr Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 229
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 229

Val Asp Ala Lys Tyr Ala Lys Glu Arg Asn Asn Ala Ala His Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 230
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 230

Val Asp Ala Lys Tyr Ala Lys Glu Arg Asn Glu Ala Ala Tyr Glu Ile
1               5                   10                  15

Leu Tyr Leu Pro Asn Leu Thr Ser Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 231
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 231

Val Asp Ala Lys Tyr Ala Lys Glu Arg Asn Glu Ala Ala Gln Glu Ile
1               5                   10                  15

Leu Glu Leu Pro Asn Leu Thr Arg Glu Gln Glu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 232
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 232

Val Asp Ala Lys Tyr Ala Lys Glu Arg Asn Thr Ala Ala Tyr Glu Ile
1               5                   10                  15

Leu Tyr Leu Pro Asn Leu Thr Asp Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys 50 55

<210> SEQ ID NO 233
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 233

Val Asp Ala Lys Tyr Ala Lys Glu Arg Asn Tyr Ala Ala Tyr Glu Ile
1 5 10 15

Leu Tyr Leu Pro Asn Leu Thr Gln Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 234
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 234

Val Asp Ala Lys Tyr Ala Lys Glu Arg Asn Lys Ala Ala Tyr Glu Ile
1 5 10 15

Leu Tyr Leu Pro Asn Leu Thr Lys Ile Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 235
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 235

Val Asp Ala Lys Tyr Ala Lys Glu Arg Asn Lys Ala Ala Glu Glu Ile
1 5 10 15

Leu Trp Leu Pro Asn Leu Thr Asn Gly Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 236
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 236

Val Asp Ala Lys Tyr Ala Lys Glu Arg Asn Phe Ala Ala Tyr Glu Ile

```
1               5                   10                  15

Leu Tyr Leu Pro Asn Leu Thr Arg Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 237
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 237

```
Val Asp Ala Lys Tyr Ala Lys Glu Arg Asn Glu Ala Ala Phe Glu Ile
1               5                   10                  15

Leu Thr Leu Pro Asn Leu Thr Asn Ala Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 238
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 238

```
Val Asp Ala Lys Tyr Ala Lys Glu Arg Asn Val Ala Ala His Glu Ile
1               5                   10                  15

Leu Tyr Leu Pro Asn Leu Thr Gln Glu Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 239
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 239

```
Val Asp Ala Lys Tyr Ala Lys Glu Arg Asn Glu Ala Ala His Glu Ile
1               5                   10                  15

Leu Tyr Leu Pro Asn Leu Thr Ala Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 240

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 240

Val Asp Ala Lys Tyr Ala Lys Glu Arg Asn Ala Ala Ala Gln Glu Ile
1 5 10 15

Leu Tyr Leu Pro Asn Leu Thr Gln His Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 241
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 241

Val Asp Ala Lys Tyr Ala Lys Glu Arg Asn Ser Ala Ala Phe Glu Ile
1 5 10 15

Leu Asn Leu Pro Asn Leu Thr Lys Ala Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 242
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 242

Val Asp Ala Lys Tyr Ala Lys Glu Arg Asn His Ala Ala Glu Glu Ile
1 5 10 15

Leu Tyr Leu Pro Asn Leu Thr Asn Leu Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 243
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 243

Val Asp Ala Lys Tyr Ala Lys Glu Arg Asn Ser Ala Ala His Glu Ile
1 5 10 15

Leu Tyr Leu Pro Asn Leu Thr Asn Glu Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 244
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 244

Val Asp Ala Lys Tyr Ala Lys Glu Arg Asn His Ala Ala Trp Glu Ile
1 5 10 15

Leu Gln Leu Pro Asn Leu Thr Asn Glu Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 245
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 245

Val Asp Ala Lys Tyr Ala Lys Glu Arg Asn Asn Ala Ala Phe Glu Ile
1 5 10 15

Leu Gln Leu Pro Asn Leu Thr Trp Glu Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 246
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 246

Val Asp Ala Lys Tyr Ala Lys Glu Arg Asn Arg Ala Ala His Glu Ile
1 5 10 15

Leu Tyr Leu Pro Asn Leu Thr Ser Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 247
<211> LENGTH: 58
<212> TYPE: PRT
<213> ORGANISM: Artificial Sequence
<220> FEATURE:

<223> OTHER INFORMATION: Engineered PD-L1 binding polypeptide

<400> SEQUENCE: 247

```
Val Asp Ala Lys Tyr Ala Lys Glu Arg Asn Gln Ala Ala His Glu Ile
1               5                   10                  15

Leu Tyr Leu Pro Asn Leu Thr Ala Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 248
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 248

```
Val Asp Ala Lys Tyr Ala Lys Glu Arg Asn Ile Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 249
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 249

```
Val Asp Ala Lys Tyr Ala Lys Glu Arg Asn Asp Ala Ala Tyr Glu Ile
1               5                   10                  15

Leu Ser Leu Pro Asn Leu Thr Asn Gly Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 250
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 250

```
Val Asp Ala Lys Tyr Ala Lys Glu Arg Asn Ala Ala Ala Gln Glu Ile
1               5                   10                  15

Leu Glu Leu Pro Asn Leu Thr Asn Arg Gln Tyr Trp Ala Phe Ile Trp
            20                  25                  30

Lys Leu Ala Asp Asp Pro Ser Gln Ser Ser Glu Leu Leu Ser Glu Ala
        35                  40                  45
```

```
Lys Lys Leu Asn Asp Ser Gln Ala Pro Lys
    50                  55


<210> SEQ ID NO 251
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 251

Val Asp Ala Lys Tyr Ala Lys Glu Arg Asn Glu Ala Ala Tyr Glu Ile
1               5                   10                  15

Leu Tyr Leu Pro Asn Leu Thr Arg Asp Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 252
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 252

Val Asp Ala Lys Tyr Ala Lys Glu Arg Asn Ala Ala Ala Gln Glu Ile
1               5                   10                  15

Leu Thr Leu Pro Asn Leu Thr Arg Lys Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 253
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 253

Val Asp Ala Lys Tyr Ala Lys Glu Arg Asn Phe Ala Ala Gln Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 254
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 254
```

```
Val Asp Ala Lys Tyr Ala Lys Glu Arg Asn Thr Ala Ala Tyr Glu Ile
1               5                   10                  15

Leu Tyr Leu Pro Asn Leu Thr Asp Glu Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 255
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 255

Val Asp Ala Lys Tyr Ala Lys Glu Arg Asn Ala Ala Ala Gln Glu Ile
1               5                   10                  15

Leu Tyr Leu Pro Asn Leu Thr His Ala Gln Lys Trp Ala Phe Ile Trp
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 256
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 256

Val Asp Ala Lys Tyr Ala Lys Glu Arg Asn His Ala Ala Tyr Glu Ile
1               5                   10                  15

Leu Lys Leu Pro Asn Leu Thr Lys Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 257
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 257

Val Asp Ala Lys Tyr Ala Lys Glu Arg Asn Glu Ala Ala Tyr Glu Ile
1               5                   10                  15

Leu Tyr Leu Pro Asn Leu Thr Asn Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 258
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 258

Val Asp Ala Lys Tyr Ala Lys Glu Arg Asn Phe Ala Ala His Glu Ile
1 5 10 15

Leu Tyr Leu Pro Asn Leu Thr Gln Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 259
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 259

Val Asp Ala Lys Tyr Ala Lys Glu Arg Asn Lys Ala Ala Glu Glu Ile
1 5 10 15

Leu Arg Leu Pro Asn Leu Thr Gln Ala Gln Phe Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 260
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 260

Val Asp Ala Lys Tyr Ala Lys Glu Arg Asn Phe Ala Ala His Glu Ile
1 5 10 15

Leu Tyr Leu Pro Asn Leu Thr Ser Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 261
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 261

Val Asp Ala Lys Tyr Ala Lys Glu Arg Asn Val Ala Ala His Glu Ile
1 5 10 15

Leu Tyr Leu Pro Asn Leu Thr Arg Ser Gln Lys Trp Ala Phe Ile Trp

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 262
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 262

Val Asp Ala Lys Tyr Ala Lys Glu Arg Asn Thr Ala Ala Gln Glu Ile
1               5                   10                  15

Leu Glu Leu Pro Asn Leu Thr Asn Arg Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 263
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 263

Val Asp Ala Lys Tyr Ala Lys Glu Arg Asn Ile Ala Ala Ala Glu Ile
1               5                   10                  15

Leu Lys Leu Pro Asn Leu Thr Asn Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 264
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 264

Val Asp Ala Lys Tyr Ala Lys Glu Arg Asn Gln Ala Ala His Glu Ile
1               5                   10                  15

Leu Tyr Leu Pro Asn Leu Thr Ser Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 265
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 265

Val Asp Ala Lys Tyr Ala Lys Glu Arg Asn Ser Ala Ala His Glu Ile
1 5 10 15

Leu Tyr Leu Pro Asn Leu Thr Gln Leu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 266
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 266

Val Asp Ala Lys Tyr Ala Lys Glu Arg Asn Ala Ala Ala Phe Glu Ile
1 5 10 15

Leu Tyr Leu Pro Asn Leu Thr Lys Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 267
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 267

Val Asp Ala Lys Tyr Ala Lys Glu Arg Asn His Ala Ala Phe Glu Ile
1 5 10 15

Leu Asn Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 268
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 268

Val Asp Ala Lys Tyr Ala Lys Glu Arg Asn His Ala Ala Glu Glu Ile
1 5 10 15

Leu Tyr Leu Pro Asn Leu Thr Lys Lys Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
    50                  55

<210> SEQ ID NO 269
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 269

Val Asp Ala Lys Tyr Ala Lys Glu Arg Asn Glu Ala Ala Thr Glu Ile
1               5                   10                  15

Leu Asn Leu Pro Asn Leu Thr Ala Lys Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 270
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 270

Val Asp Ala Lys Tyr Ala Lys Glu Arg Asn Ala Ala Ala Phe Glu Ile
1               5                   10                  15

Leu Tyr Leu Pro Asn Leu Thr Asn Asp Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 271
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 271

Val Asp Ala Lys Tyr Ala Lys Glu Arg Asn Leu Ala Ala Tyr Glu Ile
1               5                   10                  15

Leu Tyr Leu Pro Asn Leu Thr Asn Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 272
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 272

```
Val Asp Ala Lys Tyr Ala Lys Glu Arg Asn Asn Ala Ala Gln Glu Ile
1               5                   10                  15

Leu Phe Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 273
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 273

Val Asp Ala Lys Tyr Ala Lys Glu Arg Asn Arg Ala Ala Gln Glu Ile
1               5                   10                  15

Leu Glu Leu Pro Asn Leu Thr Gln Tyr Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 274
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 274

Val Asp Ala Lys Tyr Ala Lys Glu Arg Asn Glu Ala Ala His Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 275
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 275

Val Asp Ala Lys Tyr Ala Lys Glu Arg Asn Leu Ala Ala Gln Glu Ile
1               5                   10                  15

Leu Thr Leu Pro Asn Leu Thr Lys Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 276
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 276

Val Asp Ala Lys Tyr Ala Lys Glu Arg Asn Thr Ala Ala His Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 277
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 277

Val Asp Ala Lys Tyr Ala Lys Glu Arg Asn Glu Ala Ala Tyr Glu Ile
1               5                   10                  15

Leu Asn Leu Pro Asn Leu Thr Ser Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 278
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 278

Val Asp Ala Lys Tyr Ala Lys Glu Arg Asn Glu Ala Ala Tyr Glu Ile
1               5                   10                  15

Leu Gln Leu Pro Asn Leu Thr Thr Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 279
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 279

Val Asp Ala Lys Tyr Ala Lys Glu Arg Asn Lys Ala Ala Tyr Glu Ile
1               5                   10                  15
```

```
Leu Tyr Leu Pro Asn Leu Thr Asn Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 280
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 280

Val Asp Ala Lys Tyr Ala Lys Glu Arg Asn Glu Ala Ala His Glu Ile
1               5                   10                  15

Leu Tyr Leu Pro Asn Leu Thr Asn Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 281
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 281

Val Asp Ala Lys Tyr Ala Lys Glu Arg Asn Glu Ala Ala Glu Glu Ile
1               5                   10                  15

Leu Tyr Leu Pro Asn Leu Thr Gln Asp Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 282
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 282

Val Asp Ala Lys Tyr Ala Lys Glu Arg Asn Thr Ala Ala Val Glu Ile
1               5                   10                  15

Leu Glu Leu Pro Asn Leu Thr Asn Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 283
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 283

Val Asp Ala Lys Tyr Ala Lys Glu Arg Asn Tyr Ala Ala Glu Glu Ile
1 5 10 15

Leu Tyr Leu Pro Asn Leu Thr Gln Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 284
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 284

Val Asp Ala Lys Tyr Ala Lys Glu Arg Asn Lys Ala Ala Gln Glu Ile
1 5 10 15

Leu Tyr Leu Pro Asn Leu Thr Ala Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 285
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 285

Val Asp Ala Lys Tyr Ala Lys Glu Arg Asn Asp Ala Ala Tyr Glu Ile
1 5 10 15

Leu Ser Leu Pro Asn Leu Thr Asn Gln Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 286
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 286

Val Asp Ala Lys Tyr Ala Lys Glu Arg Asn Asp Ala Ala Tyr Glu Ile
1 5 10 15

Leu Lys Leu Pro Asn Leu Thr Asn Gly Gln His Trp Ala Phe Ile Trp
20 25 30

Lys Leu Asp Asp Asp Pro Ser Gln Ser Ser Glu Leu Leu Ser Glu Ala 35 40 45

Lys Lys Leu Asn Asp Ser Gln Ala Pro Lys
50 55

<210> SEQ ID NO 287
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 287

Val Asp Ala Lys Tyr Ala Lys Glu Arg Asn Arg Ala Ala His Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 288
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 288

Val Asp Ala Lys Tyr Ala Lys Glu Arg Asn Gln Ala Ala Asn Glu Ile
1 5 10 15

Leu Tyr Leu Pro Asn Leu Thr Gln Ser Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 289
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 289

Val Asp Ala Lys Tyr Ala Lys Glu Arg Asn Glu Ala Ala Gln Glu Ile
1 5 10 15

Leu Lys Leu Pro Asn Leu Thr Ser Asp Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 290
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 290

Val Asp Ala Lys Tyr Ala Lys Glu Arg Asn Ala Ala Ala Glu Glu Ile
1               5                   10                  15

Leu Glu Leu Pro Asn Leu Thr Asn Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 291
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 291

Val Asp Ala Lys Tyr Ala Lys Glu Arg Asn Ala Ala Ala Tyr Glu Ile
1               5                   10                  15

Leu Tyr Leu Pro Asn Leu Thr Trp Asp Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 292
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 292

Val Asp Ala Lys Tyr Ala Lys Glu Arg Asn Ala Ala Ala Gln Glu Ile
1               5                   10                  15

Leu Glu Leu Pro Asn Leu Thr Ala Ser Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 293
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 293

Val Asp Ala Lys Tyr Ala Lys Glu Arg Asn Glu Ala Ala Phe Glu Ile
1               5                   10                  15

Leu Arg Leu Pro Asn Leu Thr Gln Gly Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 294
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 294

```
Val Asp Ala Lys Tyr Ala Lys Glu Arg Asn Lys Ala Ala Gln Glu Ile
1               5                   10                  15

Leu Tyr Leu Pro Asn Leu Thr Ser Lys Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 295
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 295

```
Val Asp Ala Lys Tyr Ala Lys Glu Arg Asn Ser Ala Ala His Glu Ile
1               5                   10                  15

Leu Tyr Leu Pro Asn Leu Thr Lys Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 296
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 296

```
Val Asp Ala Lys Tyr Ala Lys Glu Arg Asn Asp Ala Ala Tyr Glu Ile
1               5                   10                  15

Leu Tyr Leu Pro Asn Leu Thr Asn Leu Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 297
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 297

```
Val Asp Ala Lys Tyr Ala Lys Glu Arg Asn Lys Ala Ala Tyr Glu Ile
1               5                   10                  15
```

```
Leu Gln Leu Pro Asn Leu Thr Gln Gln Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 298
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 298

Val Asp Ala Lys Tyr Ala Lys Glu Arg Asn Ala Ala Ala Glu Glu Ile
1               5                   10                  15

Leu Asp Leu Pro Asn Leu Thr Asn Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 299
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 299

Val Asp Ala Lys Tyr Ala Lys Glu Arg Asn Phe Ala Ala Gln Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 300
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 300

Val Asp Ala Lys Tyr Ala Lys Glu Arg Asn Phe Ala Ala Gln Glu Ile
1               5                   10                  15

Leu Tyr Leu Pro Asn Leu Thr Asn Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 301
<211> LENGTH: 58
```

<212> TYPE: PRT
<213> ORGANISM: Artificial Sequence
<220> FEATURE:
<223> OTHER INFORMATION: Engineered PD-L1 binding polypeptide

<400> SEQUENCE: 301

Val Asp Ala Lys Tyr Ala Lys Glu Arg Asn Ala Ala Ala Ser Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 302
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 302

Val Asp Ala Lys Tyr Ala Lys Glu Arg Asn Tyr Ala Ala Tyr Glu Ile
1               5                   10                  15

Leu Lys Leu Pro Asn Leu Thr Asn Asp Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 303
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 303

Val Asp Ala Lys Tyr Ala Lys Glu Arg Asn Lys Ala Ala Val Glu Ile
1               5                   10                  15

Leu Asn Leu Pro Asn Leu Thr Asn Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 304
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 304

Val Asp Ala Lys Tyr Ala Lys Glu Arg Asn Ser Ala Ala Gln Glu Ile
1               5                   10                  15

Leu Tyr Leu Pro Asn Leu Thr Lys Ser Gln Lys Trp Ala Phe Ile Trp
            20                  25                  30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 305
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 305

Val Asp Ala Lys Tyr Ala Lys Glu Arg Asn Ile Ala Ala His Glu Ile
1               5                   10                  15

Leu Ser Leu Pro Asn Leu Thr Lys Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 306
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 306

Val Asp Ala Lys Tyr Ala Lys Glu Arg Asn Tyr Ala Ala Tyr Glu Ile
1               5                   10                  15

Leu Lys Leu Pro Asn Leu Thr Lys Ser Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 307
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 307

Val Asp Ala Lys Tyr Ala Lys Glu Arg Asn Gln Ala Ala Gln Glu Ile
1               5                   10                  15

Leu Tyr Leu Pro Asn Leu Thr Ser Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 308
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 308

Val Asp Ala Lys Tyr Ala Lys Glu Arg Asn Gln Ala Ala Gln Glu Ile
1 5 10 15

Leu Ile Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 309
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 309

Val Asp Ala Lys Tyr Ala Lys Glu Arg Asn Ala Ala Ala Trp Glu Ile
1 5 10 15

Leu Ser Leu Pro Asn Leu Thr Thr Leu Gln Asn Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 310
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 310

Val Asp Ala Lys Tyr Ala Lys Glu Arg Asn Tyr Ala Ala Tyr Glu Ile
1 5 10 15

Leu Tyr Leu Pro Asn Leu Thr Asp Glu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 311
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 311

Val Asp Ala Lys Tyr Ala Lys Glu Arg Asn Gln Ala Ala Tyr Glu Ile
1 5 10 15

Leu Tyr Leu Pro Asn Leu Thr Arg Arg Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys 50 55

<210> SEQ ID NO 312
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 312

Val Asp Ala Lys Tyr Ala Lys Glu Arg Asn Ser Ala Ala His Glu Ile
1 5 10 15

Leu Tyr Leu Pro Asn Leu Thr Asn Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 313
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 313

Val Asp Ala Lys Tyr Ala Lys Glu Arg Asn Thr Ala Ala Tyr Glu Ile
1 5 10 15

Leu Tyr Leu Pro Asn Leu Thr Asn His Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 314
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 314

Val Asp Ala Lys Tyr Ala Lys Glu Arg Asn Asp Ala Ala Tyr Glu Ile
1 5 10 15

Leu Glu Leu Pro Asn Leu Thr Asn Ala Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 315
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 315

Val Asp Ala Lys Tyr Ala Lys Glu Arg Asn Leu Ala Ala His Glu Ile

```
1               5                   10                  15

Leu Tyr Leu Pro Asn Leu Thr Gln Asp Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 316
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 316

Val Asp Ala Lys Tyr Ala Lys Glu Arg Asn Thr Ala Ala Gln Glu Ile
1               5                   10                  15

Leu Glu Leu Pro Asn Leu Thr Gln Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 317
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 317

Val Asp Ala Lys Tyr Ala Lys Glu Arg Asn Asp Ala Ala Gln Glu Ile
1               5                   10                  15

Leu Glu Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 318
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 318

Val Asp Ala Lys Tyr Ala Lys Glu Arg Asn Leu Ala Ala His Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 319
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 319

Val Asp Ala Lys Tyr Ala Lys Glu Arg Asn Lys Ala Ala Tyr Glu Ile
1 5 10 15

Leu Tyr Leu Pro Asn Leu Thr Gln Leu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 320
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 320

Val Asp Ala Lys Tyr Ala Lys Glu Arg Asn His Ala Ala Tyr Glu Ile
1 5 10 15

Leu Arg Leu Pro Asn Leu Thr Gln Asp Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 321
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 321

Val Asp Ala Lys Tyr Ala Lys Glu Arg Asn Gln Ala Ala Glu Glu Ile
1 5 10 15

Leu Tyr Leu Pro Asn Leu Thr Asn Leu Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 322
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 322

Val Asp Ala Lys Tyr Ala Lys Glu Arg Asn Asp Ala Ala Gln Glu Ile
1 5 10 15

Leu Tyr Leu Pro Asn Leu Thr Ser Glu Gln Tyr Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 323
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 323

Val Asp Ala Lys Tyr Ala Lys Glu Arg Asn Phe Ala Ala Tyr Glu Ile
1               5                   10                  15

Leu Asn Leu Pro Asn Leu Thr Ala Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 324
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 324

Val Asp Ala Lys Tyr Ala Lys Glu Arg Asn Asp Ala Ala His Glu Ile
1               5                   10                  15

Leu Tyr Leu Pro Asn Leu Thr Gln Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 325
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 325

Val Asp Ala Lys Tyr Ala Lys Glu Arg Asn Glu Ala Ala His Glu Ile
1               5                   10                  15

Leu Gln Leu Pro Asn Leu Thr Gln Asn Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 326
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 326

Val Asp Ala Lys Tyr Ala Lys Glu Arg Asn Ser Ala Ala Phe Glu Ile
1               5                   10                  15

Leu Tyr Leu Pro Asn Leu Thr Ser Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 327
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 327

Val Asp Ala Lys Tyr Ala Lys Glu Arg Asn Ala Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 328
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 328

Val Asp Ala Lys Tyr Ala Lys Glu Arg Asn Gln Ala Ala His Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 329
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 329

Val Asp Ala Lys Tyr Ala Lys Glu Arg Asn Glu Ala Ala Gln Glu Ile
1               5                   10                  15

Leu Asn Leu Pro Asn Leu Thr Ala Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

```
Lys Lys Leu Asn Asp Ser Gln Ala Pro Lys
    50                  55


<210> SEQ ID NO 330
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 330

Val Asp Ala Lys Tyr Ala Lys Glu Arg Asn Ile Ala Ala His Glu Ile
1               5                   10                  15

Leu Tyr Leu Pro Asn Leu Thr Gln Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 331
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 331

Val Asp Ala Lys Tyr Ala Lys Glu Arg Asn Ser Ala Ala Phe Glu Ile
1               5                   10                  15

Leu Tyr Leu Pro Asn Leu Thr Arg Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 332
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 332

Val Asp Ala Lys Tyr Ala Lys Glu Arg Asn Gln Ala Ala Phe Glu Ile
1               5                   10                  15

Leu Tyr Leu Pro Asn Leu Thr His Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 333
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 333
```

-continued

```
Val Asp Ala Lys Tyr Ala Lys Glu Arg Asn Gln Ala Ala Tyr Glu Ile
1               5                   10                  15

Leu Phe Leu Pro Asn Leu Thr Ser Asp Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 334
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 334

Val Asp Ala Lys Tyr Ala Lys Glu Arg Asn Ala Ala Ala Tyr Glu Ile
1               5                   10                  15

Leu Tyr Leu Pro Asn Leu Thr Arg Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 335
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 335

Val Asp Ala Lys Tyr Ala Lys Glu Arg Asn Val Ala Ala Gln Glu Ile
1               5                   10                  15

Leu Tyr Leu Pro Asn Leu Thr Ser Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 336
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 336

Val Asp Ala Lys Tyr Ala Lys Glu Arg Asn Ile Ala Ala His Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 337
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 337

```
Val Asp Ala Lys Tyr Ala Lys Glu Arg Asn Glu Ala Ala Phe Glu Ile
1               5                   10                  15

Leu Tyr Leu Pro Asn Leu Thr Glu Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 338
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 338

```
Val Asp Ala Lys Tyr Ala Lys Glu Arg Asn Glu Ala Ala Tyr Glu Ile
1               5                   10                  15

Leu Tyr Leu Pro Asn Leu Thr Asp Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 339
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 339

```
Val Asp Ala Lys Tyr Ala Lys Glu Arg Asn Glu Ala Ala Ser Glu Ile
1               5                   10                  15

Leu Asp Leu Pro Asn Leu Thr Gln Glu Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 340
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 340

```
Val Asp Ala Lys Tyr Ala Lys Glu Arg Asn Phe Ala Ala His Glu Ile
1               5                   10                  15

Leu Tyr Leu Pro Asn Leu Thr Gln Gly Gln Lys Trp Ala Phe Ile Trp
```

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 341
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 341

Val Asp Ala Lys Tyr Ala Lys Glu Arg Asn Ala Ala Ala His Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 342
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 342

Val Asp Ala Lys Tyr Ala Lys Glu Arg Asn Lys Ala Ala His Glu Ile
1               5                   10                  15

Leu Tyr Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 343
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 343

Val Asp Ala Lys Tyr Ala Lys Glu Arg Asn Glu Ala Ala Phe Glu Ile
1               5                   10                  15

Leu Tyr Leu Pro Asn Leu Thr Gln Phe Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 344
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 344

Val Asp Ala Lys Tyr Ala Lys Glu Arg Asn Ser Ala Ala Phe Glu Ile
1 5 10 15

Leu Tyr Leu Pro Asn Leu Thr Asn Phe Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 345
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 345

Val Asp Ala Lys Tyr Ala Lys Glu Arg Asn Glu Ala Ala Tyr Glu Ile
1 5 10 15

Leu Asn Leu Pro Asn Leu Thr Lys Gln Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 346
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 346

Val Asp Ala Lys Tyr Ala Lys Glu Arg Asn Ile Ala Ala His Glu Ile
1 5 10 15

Leu Tyr Leu Pro Asn Leu Thr Lys Ser Gln Lys Trp Ala Phe Ile Trp
20 25 30

Lys Leu Glu Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 347
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 347

Val Asp Ala Lys Tyr Ala Lys Glu Arg Asn Ile Ala Ala Tyr Glu Ile
1 5 10 15

Leu Trp Leu Pro Asn Leu Thr Asn Ala Gln Lys Trp Ala Phe Ile Trp
20 25 30

Lys Leu Ala Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 348
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 348

Val Asp Ala Lys Tyr Ala Lys Glu Arg Asn Ile Ala Ala His Glu Ile
1               5                   10                  15

Leu Tyr Leu Pro Asn Leu Thr Gln Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 349
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 349

Val Asp Ala Lys Tyr Ala Lys Glu Arg Asn Arg Ala Ala Gln Glu Ile
1               5                   10                  15

Leu Tyr Leu Pro Asn Leu Thr Arg Arg Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 350
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 350

Val Asp Ala Lys Tyr Ala Lys Glu Arg Asn Val Ala Ala Gln Glu Ile
1               5                   10                  15

Leu Thr Leu Pro Asn Leu Thr Asn Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 351
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 351
```

```
Val Asp Ala Lys Tyr Ala Lys Glu Arg Asn Val Ala Ala His Glu Ile
1               5                   10                  15

Leu Tyr Leu Pro Asn Leu Thr Ala Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 352
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 352

Val Asp Ala Lys Tyr Ala Lys Glu Arg Asn Lys Ala Ala Phe Glu Ile
1               5                   10                  15

Leu Tyr Leu Pro Asn Leu Thr Ala Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 353
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 353

Val Asp Ala Lys Tyr Ala Lys Glu Arg Asn Asp Ala Ala Ser Glu Ile
1               5                   10                  15

Leu Tyr Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 354
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 354

Val Asp Ala Lys Tyr Ala Lys Glu Arg Asn Ala Ala Ala Gln Glu Ile
1               5                   10                  15

Leu Tyr Leu Pro Asn Leu Thr Arg Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 355
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 355

Val Asp Ala Lys Tyr Ala Lys Glu Arg Asn Glu Ala Ala Gln Glu Ile
1 5 10 15

Leu Tyr Leu Pro Asn Leu Thr Gln Lys Gln Ile Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 356
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 356

Val Asp Ala Lys Tyr Ala Lys Glu Arg Asn Gln Ala Ala Asn Glu Ile
1 5 10 15

Leu Tyr Leu Pro Asn Leu Thr Asn Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 357
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 357

Val Asp Ala Lys Tyr Ala Lys Glu Arg Asn Asp Ala Ala Tyr Glu Ile
1 5 10 15

Leu Asn Leu Pro Asn Leu Thr Ser Ser Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 358
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 358

Val Asp Ala Lys Tyr Ala Lys Glu Arg Asn Glu Ala Ala Tyr Glu Ile
1 5 10 15

-continued

```
Leu Tyr Leu Pro Asn Leu Thr Ser Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 359
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 359

Val Asp Ala Lys Tyr Ala Lys Glu Arg Asn Glu Ala Ala Tyr Glu Ile
1               5                   10                  15

Leu Phe Leu Pro Asn Leu Thr His Asn Gln Gln Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 360
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 360

Val Asp Ala Lys Tyr Ala Lys Glu Arg Asn Asp Ala Ala Tyr Glu Ile
1               5                   10                  15

Leu Tyr Leu Pro Asn Leu Thr Asn Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 361
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 361

Val Asp Ala Lys Tyr Ala Lys Glu Arg Asn Lys Ala Ala Phe Glu Ile
1               5                   10                  15

Leu Ala Leu Pro Asn Leu Thr Lys Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 362
<211> LENGTH: 58
<212> TYPE: PRT
```

-continued

<213> ORGANISM: Artificial Sequence
<220> FEATURE:
<223> OTHER INFORMATION: Engineered PD-L1 binding polypeptide

<400> SEQUENCE: 362

```
Val Asp Ala Lys Tyr Ala Lys Glu Arg Asn His Ala Ala Phe Glu Ile
1               5                   10                  15

Leu Gln Leu Pro Asn Leu Thr Ser Asn Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 363
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 363

```
Val Asp Ala Lys Tyr Ala Lys Glu Arg Asn Arg Ala Ala Tyr Glu Ile
1               5                   10                  15

Leu Tyr Leu Pro Asn Leu Thr Gln Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 364
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 364

```
Val Asp Ala Lys Tyr Ala Lys Glu Arg Asn Ala Ala Ala Gln Glu Ile
1               5                   10                  15

Leu Gln Leu Pro Asn Leu Thr His Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 365
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 365

```
Val Asp Ala Lys Tyr Ala Lys Glu Arg Asn Ala Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Ala Asp Asp Pro Ser Gln Ser Ser Glu Leu Leu Ser Glu Ala
```

```
        35                  40                  45

Lys Lys Leu Asn Asp Ser Gln Ala Pro Lys
    50                  55


<210> SEQ ID NO 366
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 366

Val Asp Ala Lys Tyr Ala Lys Glu Arg Asn Glu Ala Ala Gln Glu Ile
1               5                   10                  15

Leu Glu Leu Pro Asn Leu Thr Asn Val Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 367
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 367

Val Asp Ala Lys Tyr Ala Lys Glu Arg Asn Glu Ala Ala Gln Glu Ile
1               5                   10                  15

Leu Tyr Leu Pro Asn Leu Thr Gln Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 368
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 368

Val Asp Ala Lys Tyr Ala Lys Glu Arg Asn Leu Ala Ala His Glu Ile
1               5                   10                  15

Leu Tyr Leu Pro Asn Leu Thr Ser Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 369
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 369

Val Asp Ala Lys Tyr Ala Lys Glu Arg Asn Glu Ala Ala Gln Glu Ile
1 5 10 15

Leu Tyr Leu Pro Asn Leu Thr Asn Ala Gln Lys Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 370
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 370

Val Asp Ala Lys Tyr Ala Lys Glu Arg Asn Thr Ala Ala Phe Glu Ile
1 5 10 15

Leu Tyr Leu Pro Asn Leu Thr Asn His Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 371
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 371

Val Asp Ala Lys Tyr Ala Lys Glu Arg Asn His Ala Ala Gln Glu Ile
1 5 10 15

Leu Tyr Leu Pro Asn Leu Thr Lys Lys Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 372
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 372

Val Asp Ala Lys Tyr Ala Lys Glu Arg Asn Ala Ala Ala Asn Glu Ile
1 5 10 15

Leu Tyr Leu Pro Asn Leu Thr His Gln Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

```
<210> SEQ ID NO 373
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 373

Val Asp Ala Lys Tyr Ala Lys Glu Arg Asn Glu Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 374
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 374

Val Asp Ala Lys Tyr Ala Lys Glu Arg Asn Phe Ala Ala Gln Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 375
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 375

Val Asp Ala Lys Tyr Ala Lys Glu Arg Asn Ser Ala Ala Gln Glu Ile
1               5                   10                  15

Leu Glu Leu Pro Asn Leu Thr Asn Ala Gln Glu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 376
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 376

Val Asp Ala Lys Tyr Ala Lys Glu Arg Asn Asn Ala Ala His Glu Ile
1               5                   10                  15
```

Leu Tyr Leu Pro Asn Leu Thr Gln Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 377
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 377

Val Asp Ala Lys Tyr Ala Lys Glu Arg Asn Gln Ala Ala Phe Glu Ile
1               5                   10                  15

Leu Tyr Leu Pro Asn Leu Thr Ser Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 378
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 378

Val Asp Ala Lys Tyr Ala Lys Glu Arg Asn Phe Ala Ala Phe Glu Ile
1               5                   10                  15

Leu Asn Leu Pro Asn Leu Thr Asn Ala Gln Ser Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 379
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 379

Val Asp Ala Lys Tyr Ala Lys Glu Arg Asn Glu Ala Ala Gln Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 380
<211> LENGTH: 58

<212> TYPE: PRT
<213> ORGANISM: Artificial Sequence
<220> FEATURE:
<223> OTHER INFORMATION: Engineered PD-L1 binding polypeptide

<400> SEQUENCE: 380

Val Asp Ala Lys Tyr Ala Lys Glu Arg Asn Glu Ala Ala Tyr Glu Ile
1               5                   10                  15

Leu Tyr Leu Pro Asn Leu Thr Gln Ser Gln Ile Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 381
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 381

Val Asp Ala Lys Tyr Ala Lys Glu Arg Asn Lys Ala Ala Phe Glu Ile
1               5                   10                  15

Leu Tyr Leu Pro Asn Leu Thr His Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 382
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 382

Val Asp Ala Lys Tyr Ala Lys Glu Arg Asn Gln Ala Ala Phe Glu Ile
1               5                   10                  15

Leu Tyr Leu Pro Asn Leu Thr Gln Gly Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 383
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 383

Val Asp Ala Lys Tyr Ala Lys Glu Arg Asn Ser Ala Ala His Glu Ile
1               5                   10                  15

Leu Tyr Leu Pro Asn Leu Thr Lys Glu Gln Lys Trp Ala Phe Ile Trp
            20                  25                  30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 384
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 384

Val Asp Ala Lys Tyr Ala Lys Glu Arg Asn Tyr Ala Ala Gln Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 385
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 385

Val Asp Ala Lys Tyr Ala Lys Glu Arg Asn His Ala Ala Tyr Glu Ile
1               5                   10                  15

Leu Tyr Leu Pro Asn Leu Thr Lys Asp Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 386
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 386

Val Asp Ala Lys Tyr Ala Lys Glu Arg Asn Gln Ala Ala Gln Glu Ile
1               5                   10                  15

Leu Glu Leu Pro Asn Leu Thr Asn Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 387
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 387

Val Asp Ala Lys Tyr Ala Lys Glu Arg Asn His Ala Ala Tyr Glu Ile
1 5 10 15

Leu Tyr Leu Pro Asn Leu Thr Ser Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 388
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 388

Val Asp Ala Lys Tyr Ala Lys Glu Arg Asn Phe Ala Ala His Glu Ile
1 5 10 15

Leu Gln Leu Pro Asn Leu Thr Arg Tyr Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 389
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 389

Val Asp Ala Lys Tyr Ala Lys Glu Arg Asn Glu Ala Ala Tyr Glu Ile
1 5 10 15

Leu Tyr Leu Pro Asn Leu Thr Asn Tyr Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 390
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 390

Val Asp Ala Lys Tyr Ala Lys Glu Arg Asn Ser Ala Ala Tyr Glu Ile
1 5 10 15

Leu Tyr Leu Pro Asn Leu Thr Ser Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys

```
    50                  55


<210> SEQ ID NO 391
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 391

Val Asp Ala Lys Tyr Ala Lys Glu Arg Asn Asp Ala Ala Tyr Glu Ile
1               5                   10                  15

Leu Tyr Leu Pro Asn Leu Thr Ser Asn Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 392
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 392

Val Asp Ala Lys Tyr Ala Lys Glu Arg Asn Glu Ala Ala Tyr Glu Ile
1               5                   10                  15

Leu Asn Leu Pro Asn Leu Thr Lys Lys Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 393
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 393

Val Asp Ala Lys Tyr Ala Lys Glu Arg Asn Thr Ala Ala Gln Glu Ile
1               5                   10                  15

Leu Tyr Leu Pro Asn Leu Thr Asn Glu Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 394
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 394

Val Asp Ala Lys Tyr Ala Lys Glu Arg Asn His Ala Ala Gln Glu Ile
```

```
1               5                   10                  15

Leu Tyr Leu Pro Asn Leu Thr Lys Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 395
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 395

Val Asp Ala Lys Tyr Ala Lys Glu Arg Asn Val Ala Ala Ala Glu Ile
1               5                   10                  15

Leu Lys Leu Pro Asn Leu Thr Gln Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 396
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 396

Val Asp Ala Lys Tyr Ala Lys Glu Arg Asn Ser Ala Ala Gln Glu Ile
1               5                   10                  15

Leu Glu Leu Pro Asn Leu Thr Asn Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 397
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 397

Val Asp Ala Lys Tyr Ala Lys Glu Arg Asn Thr Ala Ala Glu Glu Ile
1               5                   10                  15

Leu Tyr Leu Pro Asn Leu Thr His Ala Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 398
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 398

```
Val Asp Ala Lys Tyr Ala Lys Glu Arg Asn Ser Ala Ala Tyr Glu Ile
1               5                   10                  15

Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 399
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 399

```
Val Asp Ala Lys Tyr Ala Lys Glu Arg Asn Glu Ala Ala Asn Glu Ile
1               5                   10                  15

Leu Tyr Leu Pro Asn Leu Thr Arg Ala Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 400
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 400

```
Val Asp Ala Lys Tyr Ala Lys Glu Arg Asn Leu Ala Ala Phe Glu Ile
1               5                   10                  15

Leu Gln Leu Pro Asn Leu Thr Lys Asp Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 401
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 401

```
Val Asp Ala Lys Tyr Ala Lys Glu Arg Asn Phe Ala Ala His Glu Ile
1               5                   10                  15

Leu Tyr Leu Pro Asn Leu Thr Asn Gln Gln Lys Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 402
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 402

Val Asp Ala Lys Tyr Ala Lys Glu Arg Asn Glu Ala Ala His Glu Ile
1               5                   10                  15

Leu Tyr Leu Pro Asn Leu Thr Asn Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 403
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 403

Val Asp Ala Lys Tyr Ala Lys Glu Arg Asn Thr Ala Ala His Glu Ile
1               5                   10                  15

Leu Tyr Leu Pro Asn Leu Thr His Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 404
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 404

Val Asp Ala Lys Tyr Ala Lys Glu Arg Asn Asp Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 405
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 405

Val Asp Ala Lys Tyr Ala Lys Glu Arg Asn Phe Ala Ala Gln Glu Ile
1 5 10 15

Leu Tyr Leu Pro Asn Leu Thr Ser Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 406
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 406

Val Asp Ala Lys Tyr Ala Lys Glu Arg Asn Thr Ala Ala His Glu Ile
1 5 10 15

Leu Trp Leu Pro Asn Leu Thr Ala Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 407
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 407

Val Asp Ala Lys Tyr Ala Lys Glu Arg Asn Val Ala Ala Tyr Glu Ile
1 5 10 15

Leu Tyr Leu Pro Asn Leu Thr Gln Asp Gln Ile Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 408
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 408

Val Asp Ala Lys Tyr Ala Lys Glu Arg Asn Ala Ala Ala Gln Glu Ile
1 5 10 15

Leu Val Leu Pro Asn Leu Thr Gln Ser Gln Leu Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 409
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 409

Val Asp Ala Lys Tyr Ala Lys Glu Arg Asn Ser Ala Ala Phe Glu Ile
1               5                   10                  15

Leu Gln Leu Pro Asn Leu Thr Arg Asn Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 410
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 410

Val Asp Ala Lys Tyr Ala Lys Glu Arg Asn Lys Ala Ala His Glu Ile
1               5                   10                  15

Leu Tyr Leu Pro Asn Leu Thr Gln His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 411
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 411

Val Asp Ala Lys Tyr Ala Lys Glu Arg Asn Phe Ala Ala Asn Glu Ile
1               5                   10                  15

Leu Tyr Leu Pro Asn Leu Thr Ala Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 412
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 412
```

Val Asp Ala Lys Tyr Ala Lys Glu Arg Asn His Ala Ala Tyr Glu Ile
1 5 10 15

Leu Gln Leu Pro Asn Leu Thr Lys Gln Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 413
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 413

Val Asp Ala Lys Tyr Ala Lys Glu Arg Asn Thr Ala Ala Tyr Glu Ile
1 5 10 15

Leu Tyr Leu Pro Asn Leu Thr Ser Ala Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 414
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 414

Val Asp Ala Lys Tyr Ala Lys Glu Arg Asn Ala Ala Ala Phe Glu Ile
1 5 10 15

Leu Glu Leu Pro Asn Leu Thr Thr Asp Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 415
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 415

Val Asp Ala Lys Tyr Ala Lys Glu Arg Asn Asp Ala Ala Tyr Glu Ile
1 5 10 15

Leu Tyr Leu Pro Asn Leu Thr Ser Glu Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 416
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 416

```
Val Asp Ala Lys Tyr Ala Lys Glu Arg Asn Arg Ala Ala Glu Glu Ile
1               5                   10                  15

Leu Lys Leu Pro Asn Leu Thr Lys Glu Gln Trp Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 417
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 417

```
Val Asp Ala Lys Tyr Ala Lys Glu Arg Asn Thr Ala Ala Tyr Glu Ile
1               5                   10                  15

Leu Glu Leu Pro Asn Leu Thr Lys Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 418
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 418

```
Val Asp Ala Lys Tyr Ala Lys Glu Arg Asn Ile Ala Ala His Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 419
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 419

```
Val Asp Ala Lys Tyr Ala Lys Glu Arg Asn Lys Ala Ala Ser Glu Ile
1               5                   10                  15

Leu Tyr Leu Pro Asn Leu Thr Lys Ser Gln Val Trp Ala Phe Ile Trp
```

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 420
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 420

Val Asp Ala Lys Tyr Ala Lys Glu Arg Asn Ser Ala Ala Tyr Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 421
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 421

Val Asp Ala Lys Tyr Ala Lys Glu Arg Asn Asn Ala Ala Tyr Glu Ile
1               5                   10                  15

Leu Tyr Leu Pro Asn Leu Thr Glu Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 422
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 422

Val Asp Ala Lys Tyr Ala Lys Glu Arg Asn Ile Ala Ala Gln Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 423
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 423

Val Asp Ala Lys Tyr Ala Lys Glu Arg Asn Ala Ala Ala His Glu Ile
1 5 10 15

Leu Tyr Leu Pro Asn Leu Thr Ala Glu Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 424
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 424

Val Asp Ala Lys Tyr Ala Lys Glu Arg Asn Val Ala Ala Ser Glu Ile
1 5 10 15

Leu Asn Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 425
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 425

Val Asp Ala Lys Tyr Ala Lys Glu Arg Asn Phe Ala Ala Gln Glu Ile
1 5 10 15

Leu Glu Leu Pro Asn Leu Thr Asn Ser Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 426
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 426

Val Asp Ala Lys Tyr Ala Lys Glu Arg Asn Lys Ala Ala His Glu Ile
1 5 10 15

Leu Tyr Leu Pro Asn Leu Thr Gln Asn Gln Ile Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 427
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 427

Val Asp Ala Lys Tyr Ala Lys Glu Arg Asn Glu Ala Ala Tyr Glu Ile
1               5                   10                  15

Leu Phe Leu Pro Asn Leu Thr Ala Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 428
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 428

Val Asp Ala Lys Tyr Ala Lys Glu Arg Asn Ile Ala Ala Gln Glu Ile
1               5                   10                  15

Leu Glu Leu Pro Asn Leu Thr Ser Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 429
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 429

Val Asp Ala Lys Tyr Ala Lys Glu Arg Asn Arg Ala Ala Phe Glu Ile
1               5                   10                  15

Leu Asn Leu Pro Asn Leu Thr Lys Gln Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 430
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 430
```

Val Asp Ala Lys Tyr Ala Lys Glu Arg Asn Arg Ala Ala Gln Glu Ile
1 5 10 15

Leu Tyr Leu Pro Asn Leu Thr Ala Asn Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 431
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 431

Val Asp Ala Lys Tyr Ala Lys Glu Arg Asn His Ala Ala His Glu Ile
1 5 10 15

Leu Tyr Leu Pro Asn Leu Thr Gln Asn Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 432
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 432

Val Asp Ala Lys Tyr Ala Lys Glu Arg Asn Thr Ala Ala Tyr Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 433
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 433

Val Asp Ala Lys Tyr Ala Lys Glu Arg Asn Arg Ala Ala Tyr Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 434
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 434

Val Asp Ala Lys Tyr Ala Lys Glu Arg Asn Gln Ala Ala Phe Glu Ile
1 5 10 15

Leu Asn Leu Pro Asn Leu Thr Asn Glu Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 435
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 435

Val Asp Ala Lys Tyr Ala Lys Glu Arg Asn Lys Ala Ala Val Glu Ile
1 5 10 15

Leu Glu Leu Pro Asn Leu Thr Asn Asp Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 436
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 436

Val Asp Ala Lys Tyr Ala Lys Glu Arg Asn Ser Ala Ala Gln Glu Ile
1 5 10 15

Leu Ser Leu Pro Asn Leu Thr Arg Ser Gln Val Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 437
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 437

Val Asp Ala Lys Tyr Ala Lys Glu Arg Asn Ala Ala Ala His Glu Ile
1 5 10 15

```
Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 438
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 438

Val Asp Ala Lys Tyr Ala Lys Glu Arg Asn Tyr Ala Ala Tyr Glu Ile
1               5                   10                  15

Leu Gln Leu Pro Asn Leu Thr Asn Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 439
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 439

Val Asp Ala Lys Tyr Ala Lys Glu Arg Asn Ala Ala Ala Phe Glu Ile
1               5                   10                  15

Leu Tyr Leu Pro Asn Leu Thr Glu Glu Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 440
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 440

Val Asp Ala Lys Tyr Ala Lys Glu Arg Asn Gln Ala Ala Tyr Glu Ile
1               5                   10                  15

Leu Tyr Leu Pro Asn Leu Thr Asn Lys Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 441
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 441

Val Asp Ala Lys Tyr Ala Lys Glu Arg Asn Glu Ala Ala Tyr Glu Ile
1               5                   10                  15

Leu Tyr Leu Pro Asn Leu Thr Lys Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 442
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 442

Val Asp Ala Lys Tyr Ala Lys Glu Arg Asn Lys Ala Ala His Glu Ile
1               5                   10                  15

Leu Tyr Leu Pro Asn Leu Thr Ser Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 443
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 443

Val Asp Ala Lys Tyr Ala Lys Glu Arg Asn Lys Ala Ala Ala Glu Ile
1               5                   10                  15

Leu Lys Leu Pro Asn Leu Thr Lys Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 444
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 444

Val Asp Ala Lys Tyr Ala Lys Glu Arg Asn Gln Ala Ala Tyr Glu Ile
1               5                   10                  15

Leu Gln Leu Pro Asn Leu Thr Arg Glu Gln Asp Trp Ala Phe Ile Trp
            20                  25                  30

Lys Leu Asp Asp Asp Pro Ser Gln Ser Ser Glu Leu Leu Ser Glu Ala 35 40 45

Lys Lys Leu Asn Asp Ser Gln Ala Pro Lys
50 55

<210> SEQ ID NO 445
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 445

Val Asp Ala Lys Tyr Ala Lys Glu Arg Asn Ile Ala Ala Gln Glu Ile
1 5 10 15

Leu Tyr Leu Pro Asn Leu Thr Arg Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 446
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 446

Val Asp Ala Lys Tyr Ala Lys Glu Arg Asn Asp Ala Ala Gln Glu Ile
1 5 10 15

Leu Tyr Leu Pro Asn Leu Thr Lys Lys Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 447
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 447

Val Asp Ala Lys Tyr Ala Lys Glu Arg Asn Ala Ala Ala Tyr Glu Ile
1 5 10 15

Leu Tyr Leu Pro Asn Leu Thr Ser Asp Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 448
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 448

Val Asp Ala Lys Tyr Ala Lys Glu Arg Asn Glu Ala Ala Tyr Glu Ile
1 5 10 15

Leu Tyr Leu Pro Asn Leu Thr Asn Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 449
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 449

Val Asp Ala Lys Tyr Ala Lys Glu Arg Asn Asp Ala Ala Tyr Glu Ile
1 5 10 15

Leu Tyr Leu Pro Asn Leu Thr Asn Ile Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 450
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 450

Val Asp Ala Lys Tyr Ala Lys Glu Arg Asn Tyr Ala Ala His Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 451
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 451

Val Asp Ala Lys Tyr Ala Lys Glu Arg Asn Glu Ala Ala Tyr Glu Ile
1 5 10 15

Leu Trp Leu Pro Asn Leu Thr His Asp Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 452
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 452

```
Val Asp Ala Lys Tyr Ala Lys Glu Arg Asn Asn Ala Ala Gln Glu Ile
1               5                   10                  15

Leu Glu Leu Pro Asn Leu Thr Trp Gly Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 453
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 453

```
Val Asp Ala Lys Tyr Ala Lys Glu Arg Asn Ser Ala Ala His Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 454
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 454

```
Val Asp Ala Lys Tyr Ala Lys Glu Arg Asn Asp Ala Ala Gln Glu Ile
1               5                   10                  15

Leu Asp Leu Pro Asn Leu Thr Asn Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 455
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 455

```
Val Asp Ala Lys Tyr Ala Lys Glu Arg Asn Ala Ala Ala Gln Glu Ile
1               5                   10                  15
```

Leu Tyr Leu Pro Asn Leu Thr Gln Ile Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 456
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 456

Val Asp Ala Lys Tyr Ala Lys Glu Arg Asn Ala Ala Ala His Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 457
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 457

Val Asp Ala Lys Tyr Ala Lys Glu Arg Asn Lys Ala Ala His Glu Ile
1 5 10 15

Leu Tyr Leu Pro Asn Leu Thr Ala Ser Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 458
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 458

Val Asp Ala Lys Tyr Ala Lys Glu Arg Asn Thr Ala Ala Tyr Glu Ile
1 5 10 15

Leu Tyr Leu Pro Asn Leu Thr Gln Ala Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 459
<211> LENGTH: 58

<212> TYPE: PRT
<213> ORGANISM: Artificial Sequence
<220> FEATURE:
<223> OTHER INFORMATION: Engineered PD-L1 binding polypeptide

<400> SEQUENCE: 459

Val Asp Ala Lys Tyr Ala Lys Glu Arg Asn Ile Ala Ala Gln Glu Ile
1 5 10 15

Leu Tyr Leu Pro Asn Leu Thr Gln Ser Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 460
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 460

Val Asp Ala Lys Tyr Ala Lys Glu Arg Asn Arg Ala Ala Gln Glu Ile
1 5 10 15

Leu Tyr Leu Pro Asn Leu Thr Lys Glu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 461
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 461

Val Asp Ala Lys Tyr Ala Lys Glu Arg Asn Ser Ala Ala Tyr Glu Ile
1 5 10 15

Leu Tyr Leu Pro Asn Leu Thr Lys Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 462
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 462

Val Asp Ala Lys Tyr Ala Lys Glu Arg Asn Ala Ala Ala Phe Glu Ile
1 5 10 15

Leu Tyr Leu Pro Asn Leu Thr Asn Arg Gln Lys Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 463
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 463

Val Asp Ala Lys Tyr Ala Lys Glu Arg Asn Glu Ala Ala Tyr Glu Ile
1               5                   10                  15

Leu Ala Leu Pro Asn Leu Thr Lys Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 464
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 464

Val Asp Ala Lys Tyr Ala Lys Glu Arg Asn Thr Ala Ala Phe Glu Ile
1               5                   10                  15

Leu Tyr Leu Pro Asn Leu Thr Asn Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 465
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 465

Val Asp Ala Lys Tyr Ala Lys Glu Arg Asn Ile Ala Ala Tyr Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 466
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 466

Val Asp Ala Lys Tyr Ala Lys Glu Arg Asn Asp Ala Ala Phe Glu Ile
1               5                   10                  15

Leu Tyr Leu Pro Asn Leu Thr Ser Arg Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 467
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 467

Val Asp Ala Lys Tyr Ala Lys Glu Arg Asn Thr Ala Ala Tyr Glu Ile
1               5                   10                  15

Leu Asn Leu Pro Asn Leu Thr Asn Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 468
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 468

Val Asp Ala Lys Tyr Ala Lys Glu Arg Asn Asp Ala Ala Tyr Glu Ile
1               5                   10                  15

Leu Asn Leu Pro Asn Leu Thr Gln Asn Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 469
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 469

Val Asp Ala Lys Tyr Ala Lys Glu Arg Asn Lys Ala Ala Tyr Glu Ile
1               5                   10                  15

Leu Tyr Leu Pro Asn Leu Thr Asn His Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys 50 55

<210> SEQ ID NO 470
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 470

Val Asp Ala Lys Tyr Ala Lys Glu Arg Asn Thr Ala Ala Ala Glu Ile
1 5 10 15

Leu Lys Leu Pro Asn Leu Thr Asn Ala Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 471
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 471

Val Asp Ala Lys Tyr Ala Lys Glu Arg Asn Ser Ala Ala Gln Glu Ile
1 5 10 15

Leu Tyr Leu Pro Asn Leu Thr Gln Ile Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 472
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 472

Val Asp Ala Lys Tyr Ala Lys Glu Arg Asn Ile Ala Ala Tyr Glu Ile
1 5 10 15

Leu Tyr Leu Pro Asn Leu Thr Thr Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 473
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 473

Val Asp Ala Lys Tyr Ala Lys Glu Arg Asn Thr Ala Ala Tyr Glu Ile

```
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 474
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 474

Val Asp Ala Lys Tyr Ala Lys Glu Arg Asn Ser Ala Ala Gln Glu Ile
1               5                   10                  15

Leu Tyr Leu Pro Asn Leu Thr Ala Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 475
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 475

Val Asp Ala Lys Tyr Ala Lys Glu Arg Asn Ser Ala Ala Tyr Glu Ile
1               5                   10                  15

Leu Tyr Leu Pro Asn Leu Thr His Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 476
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 476

Val Asp Ala Lys Tyr Ala Lys Glu Arg Asn Asp Ala Ala Tyr Glu Ile
1               5                   10                  15

Leu Asn Leu Pro Asn Leu Thr Ser Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 477
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 477

```
Val Asp Ala Lys Tyr Ala Lys Glu Arg Asn His Ala Ala His Glu Ile
1               5                   10                  15

Leu Tyr Leu Pro Asn Leu Thr Arg Arg Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 478
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 478

```
Val Asp Ala Lys Tyr Ala Lys Glu Arg Asn Ala Ala Ala Tyr Glu Ile
1               5                   10                  15

Leu Tyr Leu Pro Asn Leu Thr Asn Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 479
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 479

```
Val Asp Ala Lys Tyr Ala Lys Glu Arg Asn Gln Ala Ala Phe Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 480
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 480

```
Val Asp Ala Lys Tyr Ala Lys Glu Arg Asn Glu Ala Ala Gln Glu Ile
1               5                   10                  15

Leu Tyr Leu Pro Asn Leu Thr Gln Ala Gln Ile Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 481
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 481

Val Asp Ala Lys Tyr Ala Lys Glu Arg Asn Glu Ala Ala Phe Glu Ile
1               5                   10                  15

Leu Tyr Leu Pro Asn Leu Thr Ser Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 482
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 482

Val Asp Ala Lys Tyr Ala Lys Glu Arg Asn Arg Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 483
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 483

Val Asp Ala Lys Tyr Ala Lys Glu Arg Asn Thr Ala Ala Gln Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 484
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 484

Val Asp Ala Lys Tyr Ala Lys Glu Arg Asn Lys Ala Ala Tyr Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 485
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 485

Val Asp Ala Lys Tyr Ala Lys Glu Arg Asn Leu Ala Ala Phe Glu Ile
1 5 10 15

Leu Asn Leu Pro Asn Leu Thr Arg Lys Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 486
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 486

Val Asp Ala Lys Tyr Ala Lys Glu Arg Asn Ala Ala Ala Gln Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 487
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 487

Val Asp Ala Lys Tyr Ala Lys Glu Arg Asn Glu Ala Ala Tyr Glu Ile
1 5 10 15

Leu Tyr Leu Pro Asn Leu Thr Gln Gly Gln Lys Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 488
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 488

Val Asp Ala Lys Tyr Ala Lys Glu Arg Asn Ala Ala Ala Tyr Glu Ile
1               5                   10                  15

Leu Tyr Leu Pro Asn Leu Thr Gln Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 489
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 489

Val Asp Ala Lys Tyr Ala Lys Glu Arg Asn Ser Ala Ala Tyr Glu Ile
1               5                   10                  15

Leu Tyr Leu Pro Asn Leu Thr Gln His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 490
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 490

Val Asp Ala Lys Tyr Ala Lys Glu Arg Asn Asp Ala Ala Phe Glu Ile
1               5                   10                  15

Leu Tyr Leu Pro Asn Leu Thr Lys Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 491
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 491
```

-continued

Val Asp Ala Lys Tyr Ala Lys Glu Arg Asn Leu Ala Ala Gln Glu Ile
1 5 10 15

Leu Trp Leu Pro Asn Leu Thr Lys Glu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 492
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 492

Val Asp Ala Lys Tyr Ala Lys Glu Arg Asn Thr Ala Ala Tyr Glu Ile
1 5 10 15

Leu Tyr Leu Pro Asn Leu Thr Gln Ala Gln Lys Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 493
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 493

Val Asp Ala Lys Tyr Ala Lys Glu Arg Asn Ala Ala Ala Tyr Glu Ile
1 5 10 15

Leu Tyr Leu Pro Asn Leu Thr Trp Gly Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 494
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 494

Val Asp Ala Lys Tyr Ala Lys Glu Arg Asn Val Ala Ala Tyr Glu Ile
1 5 10 15

Leu Tyr Leu Pro Asn Leu Thr Asn Ser Gln Lys Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 495
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 495

```
Val Asp Ala Lys Tyr Ala Lys Glu Arg Asn Ala Ala Ala His Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 496
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 496

```
Val Asp Ala Lys Tyr Ala Lys Glu Arg Asn Glu Ala Ala Phe Glu Ile
1               5                   10                  15

Leu Tyr Leu Pro Asn Leu Thr Asn Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 497
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 497

```
Val Asp Ala Lys Tyr Ala Lys Glu Arg Asn Val Ala Ala His Glu Ile
1               5                   10                  15

Leu Tyr Leu Pro Asn Leu Thr Ser Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 498
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 498

```
Val Asp Ala Lys Tyr Ala Lys Glu Arg Asn Glu Ala Ala His Glu Ile
1               5                   10                  15

Leu Tyr Leu Pro Asn Leu Thr Gln Gly Gln Lys Trp Ala Phe Ile Trp
```

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 499
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 499

Val Asp Ala Lys Tyr Ala Lys Glu Arg Asn Ala Ala Ala Phe Glu Ile
1               5                   10                  15

Leu Tyr Leu Pro Asn Leu Thr Asn Tyr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 500
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 500

Val Asp Ala Lys Tyr Ala Lys Glu Arg Asn Lys Ala Ala Phe Glu Ile
1               5                   10                  15

Leu Asn Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 501
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 501

Val Asp Ala Lys Tyr Ala Lys Glu Arg Asn Asn Ala Ala Tyr Glu Ile
1               5                   10                  15

Leu Tyr Leu Pro Asn Leu Thr Ala Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 502
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 502

Val Asp Ala Lys Tyr Ala Lys Glu Arg Asn Gln Ala Ala Tyr Glu Ile
1 5 10 15

Leu Tyr Leu Pro Asn Leu Thr Ser Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 503
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 503

Val Asp Ala Lys Tyr Ala Lys Glu Arg Asn Asn Ala Ala Gln Glu Ile
1 5 10 15

Leu Glu Leu Pro Asn Leu Thr Ser Ser Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 504
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 504

Val Asp Ala Lys Tyr Ala Lys Glu Arg Asn Gln Ala Ala Phe Glu Ile
1 5 10 15

Leu Tyr Leu Pro Asn Leu Thr Asn Glu Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 505
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 505

Val Asp Ala Lys Tyr Ala Lys Glu Arg Asn Ser Ala Ala Tyr Glu Ile
1 5 10 15

Leu Tyr Leu Pro Asn Leu Thr Trp Ala Gln His Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 506
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 506

Val Asp Ala Lys Tyr Ala Lys Glu Arg Asn Glu Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 507
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 507

Val Asp Ala Lys Tyr Ala Lys Glu Arg Asn Ile Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 508
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 508

Val Asp Ala Lys Tyr Ala Lys Glu Arg Asn Thr Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 509
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 509
```

```
Val Asp Ala Lys Tyr Ala Lys Glu Arg Asn Ala Ala Ala Tyr Glu Ile
1               5                   10                  15

Leu Tyr Leu Pro Asn Leu Thr Ala Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 510
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 510

Val Asp Ala Lys Tyr Ala Lys Glu Arg Asn Lys Ala Ala His Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 511
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 511

Val Asp Ala Lys Tyr Ala Lys Glu Arg Asn Ala Ala Ala Phe Glu Ile
1               5                   10                  15

Leu Tyr Leu Pro Asn Leu Thr Asn Glu Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 512
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 512

Val Asp Ala Lys Tyr Ala Lys Glu Arg Asn Ser Ala Ala Phe Glu Ile
1               5                   10                  15

Leu Tyr Leu Pro Asn Leu Thr Asn Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 513
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 513

Val Asp Ala Lys Tyr Ala Lys Glu Arg Asn Glu Ala Ala Phe Glu Ile
1 5 10 15

Leu Tyr Leu Pro Asn Leu Thr Ser Ala Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 514
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 514

Val Asp Ala Lys Tyr Ala Lys Glu Arg Asn Leu Ala Ala His Glu Ile
1 5 10 15

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 515
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 515

Val Asp Ala Lys Tyr Ala Lys Glu Arg Asn Glu Ala Ala Tyr Glu Ile
1 5 10 15

Leu Tyr Leu Pro Asn Leu Thr Ser Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 516
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 516

Val Asp Ala Lys Tyr Ala Lys Glu Arg Asn Asn Ala Ala Tyr Glu Ile
1 5 10 15

Leu Tyr Leu Pro Asn Leu Thr Glu His Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 517
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 517

Val Asp Ala Lys Tyr Ala Lys Glu Arg Asn Leu Ala Ala Gln Glu Ile
1               5                   10                  15

Leu Tyr Leu Pro Asn Leu Thr Gln Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 518
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 518

Val Asp Ala Lys Tyr Ala Lys Glu Arg Asn Ala Ala Ala Tyr Glu Ile
1               5                   10                  15

Leu Lys Leu Pro Asn Leu Thr Trp Ala Gln Asn Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 519
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 519

Val Asp Ala Lys Tyr Ala Lys Glu Arg Asn Ser Ala Ala Gln Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 520
<211> LENGTH: 58
<212> TYPE: PRT

<213> ORGANISM: Artificial Sequence
<220> FEATURE:
<223> OTHER INFORMATION: Engineered PD-L1 binding polypeptide

<400> SEQUENCE: 520

Val Asp Ala Lys Tyr Ala Lys Glu Arg Asn Ile Ala Ala His Glu Ile
1 5 10 15

Leu Trp Leu Pro Asn Leu Thr Ser Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 521
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 521

Val Asp Ala Lys Tyr Ala Lys Glu Arg Asn Gln Ala Ala Tyr Glu Ile
1 5 10 15

Leu Tyr Leu Pro Asn Leu Thr Ser Gly Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 522
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 522

Val Asp Ala Lys Tyr Ala Lys Glu Arg Asn Glu Ala Ala Tyr Glu Ile
1 5 10 15

Leu Tyr Leu Pro Asn Leu Thr Asn Leu Gln Lys Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 523
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 523

Val Asp Ala Lys Tyr Ala Lys Glu Arg Asn Asp Ala Ala Tyr Glu Ile
1 5 10 15

Leu Tyr Leu Pro Asn Leu Thr Asn Gln Gln Lys Trp Ala Phe Ile Trp
20 25 30

Lys Leu Asp Asp Asp Pro Ser Gln Ser Ser Glu Leu Leu Ser Glu Ala 35 40 45

Lys Lys Leu Asn Asp Ser Gln Ala Pro Lys
50 55

<210> SEQ ID NO 524
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 524

Val Asp Ala Lys Tyr Ala Lys Glu Arg Asn Ala Ala Ala Tyr Glu Ile
1 5 10 15

Leu Tyr Leu Pro Asn Leu Thr Gln Asp Gln Lys Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 525
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 525

Val Asp Ala Lys Tyr Ala Lys Glu Arg Asn Glu Ala Ala Tyr Glu Ile
1 5 10 15

Leu Tyr Leu Pro Asn Leu Thr Asp Gly Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 526
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 526

Val Asp Ala Lys Tyr Ala Lys Glu Arg Asn Thr Ala Ala Tyr Glu Ile
1 5 10 15

Leu Tyr Leu Pro Asn Leu Thr Asn Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 527
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 527

Val Asp Ala Lys Tyr Ala Lys Glu Arg Asn Tyr Ala Ala Gln Glu Ile
1 5 10 15

Leu Tyr Leu Pro Asn Leu Thr Gln Ala Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 528
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 528

Val Asp Ala Lys Tyr Ala Lys Glu Arg Asn His Ala Ala Tyr Glu Ile
1 5 10 15

Leu Tyr Leu Pro Asn Leu Thr Gln Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 529
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 529

Val Asp Ala Lys Tyr Ala Lys Glu Arg Asn Glu Ala Ala Tyr Glu Ile
1 5 10 15

Leu Trp Leu Pro Asn Leu Thr Asn Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 530
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 530

Val Asp Ala Lys Tyr Ala Lys Glu Arg Asn Val Ala Ala Tyr Glu Ile
1 5 10 15

Leu Tyr Leu Pro Asn Leu Thr Asn Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 531
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 531

```
Val Asp Ala Lys Tyr Ala Lys Glu Arg Asn His Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 532
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 532

```
Val Asp Ala Lys Tyr Ala Lys Glu Arg Asn Leu Ala Ala His Glu Ile
1               5                   10                  15

Leu Tyr Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 533
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 533

```
Val Asp Ala Lys Tyr Ala Lys Glu Arg Asn Asp Ala Ala Phe Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 534
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 534

```
Val Asp Ala Lys Tyr Ala Lys Glu Arg Asn Asp Ala Ala Tyr Glu Ile
1               5                   10                  15
```

```
Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 535
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 535

Val Asp Ala Lys Tyr Ala Lys Glu Arg Asn His Ala Ala Gln Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 536
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 536

Val Asp Ala Lys Tyr Ala Lys Glu Arg Asn Phe Ala Ala His Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 537
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 537

Val Asp Ala Lys Tyr Ala Lys Glu Arg Asn Arg Ala Ala Phe Glu Ile
1               5                   10                  15

Leu Gln Leu Pro Asn Leu Thr Trp Ala Gln Asn Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 538
<211> LENGTH: 58
```

<212> TYPE: PRT
<213> ORGANISM: Artificial Sequence
<220> FEATURE:
<223> OTHER INFORMATION: Engineered PD-L1 binding polypeptide

<400> SEQUENCE: 538

Val Asp Ala Lys Tyr Ala Lys Glu Arg Asn Ile Ala Ala Gln Glu Ile
1 5 10 15

Leu Tyr Leu Pro Asn Leu Thr Gln Leu Gln Ile Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 539
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 539

Val Asp Ala Lys Tyr Ala Lys Glu Arg Asn Lys Ala Ala Phe Glu Ile
1 5 10 15

Leu Tyr Leu Pro Asn Leu Thr Asn Arg Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 540
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 540

Val Asp Ala Lys Tyr Ala Lys Glu Arg Asn Leu Ala Ala Phe Glu Ile
1 5 10 15

Leu Tyr Leu Pro Asn Leu Thr Asn Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 541
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 541

Val Asp Ala Lys Tyr Ala Lys Glu Arg Asn Glu Ala Ala Tyr Glu Ile
1 5 10 15

Leu Tyr Leu Pro Asn Leu Thr Ser Glu Gln Ile Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 542
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 542

Val Asp Ala Lys Tyr Ala Lys Glu Arg Asn Ser Ala Ala Tyr Glu Ile
1               5                   10                  15

Leu Tyr Leu Pro Asn Leu Thr Gln Arg Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 543
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 543

Val Asp Ala Lys Tyr Ala Lys Glu Arg Asn Ile Ala Ala Gln Glu Ile
1               5                   10                  15

Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 544
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 544

Val Asp Ala Lys Tyr Ala Lys Glu Arg Asn Ser Ala Ala Phe Glu Ile
1               5                   10                  15

Leu Asn Leu Pro Asn Leu Thr Lys Asp Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 545
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 545

Val Asp Ala Lys Tyr Ala Lys Glu Arg Asn Glu Ala Ala His Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 546
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 546

Val Asp Ala Lys Tyr Ala Lys Glu Arg Asn Asp Ala Ala Phe Glu Ile
1 5 10 15

Leu Gln Leu Pro Asn Leu Thr Lys Ala Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 547
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 547

Val Asp Ala Lys Tyr Ala Lys Glu Arg Asn Ser Ala Ala Phe Glu Ile
1 5 10 15

Leu Tyr Leu Pro Asn Leu Thr Gln Asn Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 548
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 548

Val Asp Ala Lys Tyr Ala Lys Glu Arg Asn Glu Ala Ala Phe Glu Ile
1 5 10 15

Leu Asn Leu Pro Asn Leu Thr Ser Ser Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys

```
    50                  55


<210> SEQ ID NO 549
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 549

Val Asp Ala Lys Tyr Ala Lys Glu Arg Asn Val Ala Ala Gln Glu Ile
1               5                   10                  15

Leu Tyr Leu Pro Asn Leu Thr Asn Glu Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 550
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 550

Val Asp Ala Lys Tyr Ala Lys Glu Arg Asn Ser Ala Ala His Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 551
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 551

Val Asp Ala Lys Tyr Ala Lys Glu Arg Asn Ala Ala Ala Phe Glu Ile
1               5                   10                  15

Leu Tyr Leu Pro Asn Leu Thr Gln Glu Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 552
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 552

Val Asp Ala Lys Tyr Ala Lys Glu Arg Asn Arg Ala Ala His Glu Ile
```

```
1               5                   10                  15

Leu Tyr Leu Pro Asn Leu Thr Gln Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 553
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 553

Val Asp Ala Lys Tyr Ala Lys Glu Arg Asn Glu Ala Ala Gln Glu Ile
1               5                   10                  15

Leu Asp Leu Pro Asn Leu Thr Arg Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 554
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 554

Val Asp Ala Lys Tyr Ala Lys Glu Arg Asn His Ala Ala Gln Glu Ile
1               5                   10                  15

Leu Tyr Leu Pro Asn Leu Thr Arg Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 555
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 555

Val Asp Ala Lys Tyr Ala Lys Glu Arg Asn Phe Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 556
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 556

Val Asp Ala Lys Tyr Ala Lys Glu Arg Asn Ala Ala Ala Tyr Glu Ile
1 5 10 15

Leu Tyr Leu Pro Asn Leu Thr Ser Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 557
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 557

Val Asp Ala Lys Tyr Ala Lys Glu Arg Asn Gln Ala Ala Gln Glu Ile
1 5 10 15

Leu Thr Leu Pro Asn Leu Thr Ala Glu Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 558
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 558

Val Asp Ala Lys Tyr Ala Lys Glu Arg Asn Asn Ala Ala Tyr Glu Ile
1 5 10 15

Leu Tyr Leu Pro Asn Leu Thr Gln Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 559
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 559

Val Asp Ala Lys Tyr Ala Lys Glu Arg Asn Lys Ala Ala Tyr Glu Ile
1 5 10 15

Leu Tyr Leu Pro Asn Leu Thr Gln Ser Gln Lys Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 560
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 560

Val Asp Ala Lys Tyr Ala Lys Glu Arg Asn Gln Ala Ala Ala Glu Ile
1               5                   10                  15

Leu Lys Leu Pro Asn Leu Thr Lys Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 561
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 561

Val Asp Ala Lys Tyr Ala Lys Glu Arg Asn Asn Ala Ala Glu Glu Ile
1               5                   10                  15

Leu Lys Leu Pro Asn Leu Thr Gln Gly Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 562
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 562

Val Asp Ala Lys Tyr Ala Lys Glu Arg Asn Asn Ala Ala Gln Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 563
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 563

Val Asp Ala Lys Tyr Ala Lys Glu Arg Asn Ala Ala Ala His Glu Ile
1 5 10 15

Leu Tyr Leu Pro Asn Leu Thr His Asn Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 564
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 564

Val Asp Ala Lys Tyr Ala Lys Glu Arg Asn Lys Ala Ala Glu Glu Ile
1 5 10 15

Leu Tyr Leu Pro Asn Leu Thr Gln Gly Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 565
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 565

Val Asp Ala Lys Tyr Ala Lys Glu Arg Asn Asp Ala Ala Phe Glu Ile
1 5 10 15

Leu Tyr Leu Pro Asn Leu Thr Glu Ala Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 566
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 566

Val Asp Ala Lys Tyr Ala Lys Glu Arg Asn Asp Ala Ala Tyr Glu Ile
1 5 10 15

Leu Tyr Leu Pro Asn Leu Thr Gln Ala Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
    50                  55

<210> SEQ ID NO 567
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 567

Val Asp Ala Lys Tyr Ala Lys Glu Arg Asn Ser Ala Ala Phe Glu Ile
1               5                   10                  15

Leu Tyr Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 568
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 568

Val Asp Ala Lys Tyr Ala Lys Glu Arg Asn Thr Ala Ala His Glu Ile
1               5                   10                  15

Leu Tyr Leu Pro Asn Leu Thr Asn Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 569
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 569

Val Asp Ala Lys Tyr Ala Lys Glu Arg Asn Ala Ala Ala Phe Glu Ile
1               5                   10                  15

Leu Tyr Leu Pro Asn Leu Thr Gln Ile Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 570
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 570

```
Val Asp Ala Lys Tyr Ala Lys Glu Arg Asn Arg Ala Ala Phe Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 571
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 571

Val Asp Ala Lys Tyr Ala Lys Glu Arg Asn Leu Ala Ala His Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 572
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 572

Val Asp Ala Lys Tyr Ala Lys Glu Arg Asn Lys Ala Ala His Glu Ile
1               5                   10                  15

Leu Tyr Leu Pro Asn Leu Thr Ala Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 573
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 573

Val Asp Ala Lys Tyr Ala Lys Glu Arg Asn Glu Ala Ala Thr Glu Ile
1               5                   10                  15

Leu Lys Leu Pro Asn Leu Thr Asn Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 574
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 574

```
Val Asp Ala Lys Tyr Ala Lys Glu Arg Asn Leu Ala Ala His Glu Ile
1               5                   10                  15

Leu Tyr Leu Pro Asn Leu Thr Asn Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 575
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 575

```
Val Asp Ala Lys Tyr Ala Lys Glu Arg Asn Gln Ala Ala Gln Glu Ile
1               5                   10                  15

Leu Tyr Leu Pro Asn Leu Thr Asn His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 576
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 576

```
Val Asp Ala Lys Tyr Ala Lys Glu Arg Asn Asp Ala Ala Gln Glu Ile
1               5                   10                  15

Leu Tyr Leu Pro Asn Leu Thr Asn His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 577
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 577

```
Val Asp Ala Lys Tyr Ala Lys Glu Arg Asn Ala Ala Ala Tyr Glu Ile
1               5                   10                  15

Leu Tyr Leu Pro Asn Leu Thr Asn Gln Gln Lys Trp Ala Phe Ile Trp
```

```
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 578
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 578

Val Asp Ala Lys Tyr Ala Lys Glu Arg Asn Thr Ala Ala His Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 579
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 579

Val Asp Ala Lys Tyr Ala Lys Glu Arg Asn His Ala Ala Gln Glu Ile
1               5                   10                  15

Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 580
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 580

Val Asp Ala Lys Tyr Ala Lys Glu Arg Asn Val Ala Ala His Glu Ile
1               5                   10                  15

Leu Tyr Leu Pro Asn Leu Thr Asn Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 581
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 581

Val Asp Ala Lys Tyr Ala Lys Glu Arg Asn His Ala Ala Tyr Glu Ile
1 5 10 15

Leu Asn Leu Pro Asn Leu Thr Gln Asp Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 582
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 582

Val Asp Ala Lys Tyr Ala Lys Glu Arg Asn Asp Ala Ala Tyr Glu Ile
1 5 10 15

Leu Tyr Leu Pro Asn Leu Thr Ser Ser Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 583
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 583

Val Asp Ala Lys Tyr Ala Lys Glu Arg Asn Asn Ala Ala Tyr Glu Ile
1 5 10 15

Leu Asn Leu Pro Asn Leu Thr Lys Ala Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 584
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 584

Val Asp Ala Lys Tyr Ala Lys Glu Arg Asn Glu Ala Ala Tyr Glu Ile
1 5 10 15

Leu Tyr Leu Pro Asn Leu Thr Asn Glu Gln Arg Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 585
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 585

Val Asp Ala Lys Tyr Ala Lys Glu Arg Asn Thr Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 586
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 586

Val Asp Ala Lys Tyr Ala Lys Glu Arg Asn Gln Ala Ala Tyr Glu Ile
1               5                   10                  15

Leu Tyr Leu Pro Asn Leu Thr Ser His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 587
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 587

Val Asp Ala Lys Tyr Ala Lys Glu Arg Asn Asp Ala Ala Tyr Glu Ile
1               5                   10                  15

Leu Tyr Leu Pro Asn Leu Thr Gln Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 588
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 588
```

```
Val Asp Ala Lys Tyr Ala Lys Glu Arg Asn Ile Ala Ala His Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 589
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 589

Val Asp Ala Lys Tyr Ala Lys Glu Arg Asn Ser Ala Ala Gln Glu Ile
1               5                   10                  15

Leu Tyr Leu Pro Asn Leu Thr Lys Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 590
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 590

Val Asp Ala Lys Tyr Ala Lys Glu Arg Asn Asn Ala Ala Phe Glu Ile
1               5                   10                  15

Leu Tyr Leu Pro Asn Leu Thr Gln Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 591
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 591

Val Asp Ala Lys Tyr Ala Lys Glu Arg Asn Ser Ala Ala His Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 592
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 592

Val Asp Ala Lys Tyr Ala Lys Glu Arg Asn Thr Ala Ala Tyr Glu Ile
1               5                   10                  15

Leu Tyr Leu Pro Asn Leu Thr Gln Glu Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 593
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 593

Val Asp Ala Lys Tyr Ala Lys Glu Arg Asn Ser Ala Ala His Glu Ile
1               5                   10                  15

Leu Tyr Leu Pro Asn Leu Thr Asn Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 594
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 594

Val Asp Ala Lys Tyr Ala Lys Glu Arg Asn Phe Ala Ala Tyr Glu Ile
1               5                   10                  15

Leu Tyr Leu Pro Asn Leu Thr Ser Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 595
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 595

Val Asp Ala Lys Tyr Ala Lys Glu Arg Asn Ser Ala Ala His Glu Ile
1               5                   10                  15
```

-continued

```
Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 596
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 596

Val Asp Ala Lys Tyr Ala Lys Glu Arg Asn Ser Ala Ala Tyr Glu Ile
1               5                   10                  15

Leu Asn Leu Pro Asn Leu Thr Lys Asn Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 597
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 597

Val Asp Ala Lys Tyr Ala Lys Glu Arg Asn Asp Ala Ala Phe Glu Ile
1               5                   10                  15

Leu Asn Leu Pro Asn Leu Thr Gln Ser Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 598
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 598

Val Asp Ala Lys Tyr Ala Lys Glu Arg Asn Ala Ala Ala Tyr Glu Ile
1               5                   10                  15

Leu Tyr Leu Pro Asn Leu Thr Arg Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 599
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 599

Val Asp Ala Lys Tyr Ala Lys Glu Arg Asn Ser Ala Ala His Glu Ile
1 5 10 15

Leu Tyr Leu Pro Asn Leu Thr Gln Ile Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 600
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 600

Val Asp Ala Lys Tyr Ala Lys Glu Arg Asn Asp Ala Ala His Glu Ile
1 5 10 15

Leu Tyr Leu Pro Asn Leu Thr Gln Glu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 601
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 601

Val Asp Ala Lys Tyr Ala Lys Glu Arg Asn Ser Ala Ala Tyr Glu Ile
1 5 10 15

Leu Tyr Leu Pro Asn Leu Thr Ser Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 602
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 602

Val Asp Ala Lys Tyr Ala Lys Glu Arg Asn Ala Ala Ala Tyr Glu Ile
1 5 10 15

Leu Tyr Leu Pro Asn Leu Thr Gln Asn Gln Lys Trp Ala Phe Ile Trp
20 25 30

Lys Leu Asp Asp Asp Pro Ser Gln Ser Ser Glu Leu Leu Ser Glu Ala

```
        35                  40                  45

Lys Lys Leu Asn Asp Ser Gln Ala Pro Lys
    50                  55


<210> SEQ ID NO 603
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 603

Val Asp Ala Lys Tyr Ala Lys Glu Arg Asn His Ala Ala Tyr Glu Ile
1               5                   10                  15

Leu Lys Leu Pro Asn Leu Thr Arg Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 604
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 604

Val Asp Ala Lys Tyr Ala Lys Glu Arg Asn Ala Ala Ala His Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 605
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 605

Val Asp Ala Lys Tyr Ala Lys Glu Arg Asn Lys Ala Ala Gln Glu Ile
1               5                   10                  15

Leu Glu Leu Pro Asn Leu Thr Asn Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 606
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 606

Val Asp Ala Lys Tyr Ala Lys Glu Arg Asn Val Ala Ala Tyr Glu Ile
1               5                   10                  15

Leu Tyr Leu Pro Asn Leu Thr Ser Glu Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 607
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 607

Val Asp Ala Lys Tyr Ala Lys Glu Arg Asn Lys Ala Ala Tyr Glu Ile
1               5                   10                  15

Leu Asn Leu Pro Asn Leu Thr Ser Glu Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 608
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 608

Val Asp Ala Lys Tyr Ala Lys Glu Arg Asn Ala Ala Ala His Glu Ile
1               5                   10                  15

Leu Tyr Leu Pro Asn Leu Thr Asn Val Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 609
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 609

Val Asp Ala Lys Tyr Ala Lys Glu Arg Asn Leu Ala Ala Tyr Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 610
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 610

Val Asp Ala Lys Tyr Ala Lys Glu Arg Asn Asp Ala Ala His Glu Ile
1               5                   10                  15

Leu Tyr Leu Pro Asn Leu Thr Asn Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 611
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 611

Val Asp Ala Lys Tyr Ala Lys Glu Arg Asn Asp Ala Ala Glu Glu Ile
1               5                   10                  15

Leu His Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 612
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 612

Val Asp Ala Lys Tyr Ala Lys Glu Arg Asn Ala Ala Ala Tyr Glu Ile
1               5                   10                  15

Leu Tyr Leu Pro Asn Leu Thr Asn Thr Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 613
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 613

Val Asp Ala Lys Tyr Ala Lys Glu Arg Asn Lys Ala Ala Tyr Glu Ile
1               5                   10                  15
```

```
Leu His Leu Pro Asn Leu Thr Lys Gly Gln His Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 614
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 614

Val Asp Ala Lys Tyr Ala Lys Glu Arg Asn Ala Ala Ala Phe Glu Ile
1               5                   10                  15

Leu His Leu Pro Asn Leu Thr Gln Ala Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 615
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 615

Val Asp Ala Lys Tyr Ala Lys Glu Arg Asn Ser Ala Ala Glu Glu Ile
1               5                   10                  15

Leu His Leu Pro Asn Leu Thr Ser Asn Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 616
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 616

Val Asp Ala Lys Tyr Ala Lys Glu Arg Asn Asp Ala Ala Tyr Glu Ile
1               5                   10                  15

Leu Tyr Leu Pro Asn Leu Thr Ser Thr Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 617
<211> LENGTH: 58
```

```
<212> TYPE: PRT
<213> ORGANISM: Artificial Sequence
<220> FEATURE:
<223> OTHER INFORMATION: Engineered PD-L1 binding polypeptide

<400> SEQUENCE: 617

Val Asp Ala Lys Tyr Ala Lys Glu Arg Asn Phe Ala Ala Gln Glu Ile
1               5                   10                  15

Leu His Leu Pro Asn Leu Thr Ala His Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 618
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 618

Val Asp Ala Lys Tyr Ala Lys Glu Arg Asn Arg Ala Ala His Glu Ile
1               5                   10                  15

Leu Lys Leu Pro Asn Leu Thr Ala Thr Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 619
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 619

Val Asp Ala Lys Tyr Ala Lys Glu Arg Asn Ala Ala Ala His Glu Ile
1               5                   10                  15

Leu Tyr Leu Pro Asn Leu Thr Asn Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 620
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 620

Val Asp Ala Lys Tyr Ala Lys Glu Arg Asn Ile Ala Ala Glu Glu Ile
1               5                   10                  15

Leu His Leu Pro Asn Leu Thr Gln Asp Gln Leu Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 621
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 621

Val Asp Ala Lys Tyr Ala Lys Glu Arg Asn Phe Ala Ala Asn Glu Ile
1               5                   10                  15

Leu Trp Leu Pro Asn Leu Thr Asn Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 622
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 622

Val Asp Ala Lys Tyr Ala Lys Glu Arg Asn Leu Ala Ala Gln Glu Ile
1               5                   10                  15

Leu His Leu Pro Asn Leu Thr Ala Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 623
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 623

Val Asp Ala Lys Tyr Ala Lys Glu Arg Asn Asn Ala Ala Phe Glu Ile
1               5                   10                  15

Leu His Leu Pro Asn Leu Thr Asn Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 624
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 624

Val Asp Ala Lys Tyr Ala Lys Glu Arg Asn Thr Ala Ala Tyr Glu Ile
1 5 10 15

Leu Tyr Leu Pro Asn Leu Thr Lys Thr Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 625
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 625

Val Asp Ala Lys Tyr Ala Lys Glu Arg Asn Ile Ala Ala Tyr Glu Ile
1 5 10 15

Leu His Leu Pro Asn Leu Thr Gln Asp Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 626
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 626

Val Asp Ala Lys Tyr Ala Lys Glu Arg Asn Val Ala Ala Glu Glu Ile
1 5 10 15

Leu His Leu Pro Asn Leu Thr Asn Gln Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 627
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 627

Val Asp Ala Lys Tyr Ala Lys Glu Arg Asn Ile Ala Ala Glu Glu Ile
1 5 10 15

Leu His Leu Pro Asn Leu Thr Gln Ala Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys 50 55

<210> SEQ ID NO 628
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 628

Val Asp Ala Lys Tyr Ala Lys Glu Arg Asn Asn Ala Ala Glu Glu Ile
1 5 10 15

Leu His Leu Pro Asn Leu Thr Ala Asn Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 629
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 629

Val Asp Ala Lys Tyr Ala Lys Glu Arg Asn His Ala Ala Gln Glu Ile
1 5 10 15

Leu His Leu Pro Asn Leu Thr Gln Ala Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 630
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 630

Val Asp Ala Lys Tyr Ala Lys Glu Arg Asn Tyr Ala Ala Glu Glu Ile
1 5 10 15

Leu His Leu Pro Asn Leu Thr Asn Gln Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 631
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 631

Val Asp Ala Lys Tyr Ala Lys Glu Arg Asn Ala Ala Ala Gln Glu Ile

```
1               5                   10                  15

Leu Tyr Leu Pro Asn Leu Thr Gln Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 632
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 632

Val Asp Ala Lys Tyr Ala Lys Glu Arg Asn Ala Ala Ala Gln Glu Ile
1               5                   10                  15

Leu Glu Leu Pro Asn Leu Thr Ala Thr Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 633
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 633

Val Asp Ala Lys Tyr Ala Lys Glu Arg Asn Glu Ala Ala His Glu Ile
1               5                   10                  15

Leu Tyr Leu Pro Asn Leu Thr Gln Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 634
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 634

Val Asp Ala Lys Tyr Ala Lys Glu Arg Asn Tyr Ala Ala Tyr Glu Ile
1               5                   10                  15

Leu His Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 635
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 635

```
Val Asp Ala Lys Tyr Ala Lys Glu Arg Asn Ser Ala Ala Tyr Glu Ile
1               5                   10                  15

Leu Tyr Leu Pro Asn Leu Thr Gln Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 636
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 636

```
Val Asp Ala Lys Tyr Ala Lys Glu Arg Asn Arg Ala Ala Phe Glu Ile
1               5                   10                  15

Leu Tyr Leu Pro Asn Leu Thr Asn Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 637
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 637

```
Val Asp Ala Lys Tyr Ala Lys Glu Arg Asn Gln Ala Ala Val Glu Ile
1               5                   10                  15

Leu His Leu Pro Asn Leu Thr Ala Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 638
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 638

```
Val Asp Ala Lys Tyr Ala Lys Glu Arg Asn Tyr Ala Ala Val Glu Ile
1               5                   10                  15

Leu His Leu Pro Asn Leu Thr His Gln Gln Val Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 639
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 639

Val Asp Ala Lys Tyr Ala Lys Glu Arg Asn Thr Ala Ala Tyr Glu Ile
1               5                   10                  15

Leu Tyr Leu Pro Asn Leu Thr Asn Thr Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 640
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 640

Val Asp Ala Lys Tyr Ala Lys Glu Arg Asn Asp Ala Ala Glu Glu Ile
1               5                   10                  15

Leu His Leu Pro Asn Leu Thr Gln Glu Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 641
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 641

Val Asp Ala Lys Tyr Ala Lys Glu Arg Asn Asp Ala Ala Tyr Glu Ile
1               5                   10                  15

Leu His Leu Pro Asn Leu Thr Lys Ala Gln Asn Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 642
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 642

Val Asp Ala Lys Tyr Ala Lys Glu Arg Asn Ala Ala Ala Ala Glu Ile
1 5 10 15

Leu His Leu Pro Asn Leu Thr Arg Asp Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 643
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 643

Val Asp Ala Lys Tyr Ala Lys Glu Arg Asn Glu Ala Ala Glu Glu Ile
1 5 10 15

Leu His Leu Pro Asn Leu Thr Trp Ser Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 644
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 644

Val Asp Ala Lys Tyr Ala Lys Glu Arg Asn Asp Ala Ala Phe Glu Ile
1 5 10 15

Leu His Leu Pro Asn Leu Thr Asn Ala Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 645
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 645

Val Asp Ala Lys Tyr Ala Lys Glu Arg Asn Glu Ala Ala Tyr Glu Ile
1 5 10 15

Leu Tyr Leu Pro Asn Leu Thr Asn Thr Gln Arg Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 646
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 646

Val Asp Ala Lys Tyr Ala Lys Glu Arg Asn Lys Ala Ala Glu Glu Ile
1               5                   10                  15

Leu His Leu Pro Asn Leu Thr Ser Ser Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 647
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 647

Val Asp Ala Lys Tyr Ala Lys Glu Arg Asn Thr Ala Ala Gln Glu Ile
1               5                   10                  15

Leu His Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 648
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 648

Val Asp Ala Lys Tyr Ala Lys Glu Arg Asn Asn Ala Ala Gln Glu Ile
1               5                   10                  15

Leu His Leu Pro Asn Leu Thr Ala Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 649
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 649
```

-continued

```
Val Asp Ala Lys Tyr Ala Lys Glu Arg Asn Asp Ala Ala Asn Glu Ile
1               5                   10                  15

Leu His Leu Pro Asn Leu Thr Asn Glu Gln Asn Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 650
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 650

Val Asp Ala Lys Tyr Ala Lys Glu Arg Asn His Ala Ala His Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 651
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 651

Val Asp Ala Lys Tyr Ala Lys Glu Arg Asn Gln Ala Ala Tyr Glu Ile
1               5                   10                  15

Leu Gln Leu Pro Asn Leu Thr Lys Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 652
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 652

Val Asp Ala Lys Tyr Ala Lys Glu Arg Asn Gln Ala Ala His Glu Ile
1               5                   10                  15

Leu Tyr Leu Pro Asn Leu Thr His Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 653
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 653

Val Asp Ala Lys Tyr Ala Lys Glu Arg Asn Lys Ala Ala Gln Glu Ile
1 5 10 15

Leu Tyr Leu Pro Asn Leu Thr Gln Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 654
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 654

Val Asp Ala Lys Tyr Ala Lys Glu Arg Asn Ile Ala Ala His Glu Ile
1 5 10 15

Leu Tyr Leu Pro Asn Leu Thr Ser Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 655
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 655

Val Asp Ala Lys Tyr Ala Lys Glu Arg Asn Thr Ala Ala His Glu Ile
1 5 10 15

Leu Tyr Leu Pro Asn Leu Thr Gln Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 656
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 656

Val Asp Ala Lys Tyr Ala Lys Glu Arg Asn Ser Ala Ala Tyr Glu Ile
1 5 10 15

Leu Tyr Leu Pro Asn Leu Thr Arg Asn Gln Lys Trp Ala Phe Ile Trp

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 657
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 657

Val Asp Ala Lys Tyr Ala Lys Glu Arg Asn Asp Ala Ala Phe Glu Ile
1               5                   10                  15

Leu Tyr Leu Pro Asn Leu Thr Gln Gly Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 658
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 658

Val Asp Ala Lys Tyr Ala Lys Glu Arg Asn Glu Ala Ala Tyr Glu Ile
1               5                   10                  15

Leu Tyr Leu Pro Asn Leu Thr Gln Asn Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 659
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 659

Val Asp Ala Lys Tyr Ala Lys Glu Arg Asn Arg Ala Ala Glu Glu Ile
1               5                   10                  15

Leu Tyr Leu Pro Asn Leu Thr Ser Gln Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 660
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 660

Val Asp Ala Lys Tyr Ala Lys Glu Arg Asn Tyr Ala Ala Phe Glu Ile
1 5 10 15

Leu Asn Leu Pro Asn Leu Thr Asn Gln Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 661
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 661

Val Asp Ala Lys Tyr Ala Lys Glu Arg Asn Ser Ala Ala Phe Glu Ile
1 5 10 15

Leu Asn Leu Pro Asn Leu Thr Asn Glu Gln Thr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 662
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 662

Val Asp Ala Lys Tyr Ala Lys Glu Arg Asn Asp Ala Ala Tyr Glu Ile
1 5 10 15

Leu Asn Leu Pro Asn Leu Thr Ala Ala Gln Asn Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 663
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 663

Val Asp Ala Lys Tyr Ala Lys Glu Arg Asn Ala Ala Ala Gln Glu Ile
1 5 10 15

Leu Asp Leu Pro Asn Leu Thr Gln Ala Gln Tyr Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 664
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 664

Val Asp Ala Lys Tyr Ala Lys Glu Arg Asn Asn Ala Ala Tyr Glu Ile
1               5                   10                  15

Leu Tyr Leu Pro Asn Leu Thr Gln Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 665
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 665

Val Asp Ala Lys Tyr Ala Lys Glu Arg Asn Gln Ala Ala Phe Glu Ile
1               5                   10                  15

Leu Asn Leu Pro Asn Leu Thr Lys Arg Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 666
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 666

Val Asp Ala Lys Tyr Ala Lys Glu Arg Asn Ala Ala Ala His Glu Ile
1               5                   10                  15

Leu Tyr Leu Pro Asn Leu Thr Asn Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 667
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 667
```

```
Val Asp Ala Lys Tyr Ala Lys Glu Arg Asn Lys Ala Ala Tyr Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 668
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 668

Val Asp Ala Lys Tyr Ala Lys Glu Arg Asn Ile Ala Ala Tyr Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 669
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 669

Val Asp Ala Lys Tyr Ala Lys Glu Arg Asn Leu Ala Ala Gln Glu Ile
1               5                   10                  15

Leu Tyr Leu Pro Asn Leu Thr Gln Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 670
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 670

Val Asp Ala Lys Tyr Ala Lys Glu Arg Asn Ser Ala Ala Tyr Glu Ile
1               5                   10                  15

Leu Tyr Leu Pro Asn Leu Thr His Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 671
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 671

```
Val Asp Ala Lys Tyr Ala Lys Glu Arg Asn Gln Ala Ala His Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 672
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 672

```
Val Asp Ala Lys Tyr Ala Lys Glu Arg Asn Gln Ala Ala Tyr Glu Ile
1               5                   10                  15

Leu Tyr Leu Pro Asn Leu Thr Gln His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 673
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 673

```
Val Asp Ala Lys Tyr Ala Lys Glu Arg Asn Thr Ala Ala Phe Glu Ile
1               5                   10                  15

Leu Tyr Leu Pro Asn Leu Thr Gln Gly Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 674
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 674

```
Val Asp Ala Lys Tyr Ala Lys Glu Arg Asn Val Ala Ala His Glu Ile
1               5                   10                  15
```

```
Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 675
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 675

Val Asp Ala Lys Tyr Ala Lys Glu Arg Asn Leu Ala Ala Gln Glu Ile
1               5                   10                  15

Leu Glu Leu Pro Asn Leu Thr Asn Glu Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 676
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 676

Val Asp Ala Lys Tyr Ala Lys Glu Arg Asn Ala Ala Ala Gln Glu Ile
1               5                   10                  15

Leu Glu Leu Pro Asn Leu Thr Asn Ser Gln Leu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 677
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 677

Val Asp Ala Lys Tyr Ala Lys Glu Arg Asn Lys Ala Ala Phe Glu Ile
1               5                   10                  15

Leu Tyr Leu Pro Asn Leu Thr Ser Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 678
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 678

Val Asp Ala Lys Tyr Ala Lys Glu Arg Asn Asp Ala Ala Tyr Glu Ile
1 5 10 15

Leu Tyr Leu Pro Asn Leu Thr Gln Lys Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 679
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 679

Val Asp Ala Lys Tyr Ala Lys Glu Arg Asn Leu Ala Ala Gln Glu Ile
1 5 10 15

Leu Tyr Leu Pro Asn Leu Thr Gln Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 680
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 680

Val Asp Ala Lys Tyr Ala Lys Glu Arg Asn Glu Ala Ala Tyr Glu Ile
1 5 10 15

Leu Tyr Leu Pro Asn Leu Thr Asp Arg Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 681
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 681

Val Asp Ala Lys Tyr Ala Lys Glu Arg Asn Gln Ala Ala Gln Glu Ile
1 5 10 15

Leu Tyr Leu Pro Asn Leu Thr Asn Gly Gln Arg Trp Ala Phe Ile Trp
20 25 30

Lys Leu Asp Asp Asp Pro Ser Gln Ser Ser Glu Leu Leu Ser Glu Ala 35 40 45

Lys Lys Leu Asn Asp Ser Gln Ala Pro Lys
50 55

<210> SEQ ID NO 682
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 682

Val Asp Ala Lys Tyr Ala Lys Glu Arg Asn His Ala Ala Gln Glu Ile
1 5 10 15

Leu Tyr Leu Pro Asn Leu Thr Ser Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 683
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 683

Val Asp Ala Lys Tyr Ala Lys Glu Arg Asn Asp Ala Ala Phe Glu Ile
1 5 10 15

Leu Tyr Leu Pro Asn Leu Thr Gln Glu Gln Val Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 684
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 684

Val Asp Ala Lys Tyr Ala Lys Glu Arg Asn Ile Ala Ala Tyr Glu Ile
1 5 10 15

Leu Tyr Leu Pro Asn Leu Thr Gln Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 685
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 685

Val Asp Ala Lys Tyr Ala Lys Glu Arg Asn Tyr Ala Ala His Glu Ile
1               5                   10                  15

Leu Tyr Leu Pro Asn Leu Thr Asn Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 686
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 686

Val Asp Ala Lys Tyr Ala Lys Glu Arg Asn Glu Ala Ala Gln Glu Ile
1               5                   10                  15

Leu Tyr Leu Pro Asn Leu Thr Gln Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 687
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 687

Val Asp Ala Lys Tyr Ala Lys Glu Arg Asn Ala Ala Ala Phe Glu Ile
1               5                   10                  15

Leu Ser Leu Pro Asn Leu Thr Lys Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 688
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 688

Val Asp Ala Lys Tyr Ala Lys Glu Arg Asn Thr Ala Ala Phe Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 689
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 689

Val Asp Ala Lys Tyr Ala Lys Glu Arg Asn Lys Ala Ala Tyr Glu Ile
1               5                   10                  15

Leu Tyr Leu Pro Asn Leu Thr Ser Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 690
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 690

Val Asp Ala Lys Tyr Ala Lys Glu Arg Asn Gln Ala Ala Phe Glu Ile
1               5                   10                  15

Leu Tyr Leu Pro Asn Leu Thr Asn Asn Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 691
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 691

Val Asp Ala Lys Tyr Ala Lys Glu Arg Asn Asp Ala Ala Tyr Glu Ile
1               5                   10                  15

Leu Tyr Leu Pro Asn Leu Thr Ser Gln Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 692
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 692

Val Asp Ala Lys Tyr Ala Lys Glu Arg Asn Val Ala Ala Gln Glu Ile
1               5                   10                  15
```

Leu Tyr Leu Pro Asn Leu Thr Lys Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 693
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 693

Val Asp Ala Lys Tyr Ala Lys Glu Arg Asn Ser Ala Ala His Glu Ile
1 5 10 15

Leu Tyr Leu Pro Asn Leu Thr Lys Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 694
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 694

Val Asp Ala Lys Tyr Ala Lys Glu Arg Asn Thr Ala Ala Tyr Glu Ile
1 5 10 15

Leu Tyr Leu Pro Asn Leu Thr Gln His Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 695
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 695

Val Asp Ala Lys Tyr Ala Lys Glu Arg Asn Val Ala Ala Gln Glu Ile
1 5 10 15

Leu Tyr Leu Pro Asn Leu Thr Gln Tyr Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 696
<211> LENGTH: 58

<212> TYPE: PRT
<213> ORGANISM: Artificial Sequence
<220> FEATURE:
<223> OTHER INFORMATION: Engineered PD-L1 binding polypeptide

<400> SEQUENCE: 696

```
Val Asp Ala Lys Tyr Ala Lys Glu Arg Asn Asn Ala Ala Tyr Glu Ile
1               5                   10                  15

Leu Asn Leu Pro Asn Leu Thr Ser Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 697
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 697

```
Val Asp Ala Lys Tyr Ala Lys Glu Arg Asn Ser Ala Ala Tyr Glu Ile
1               5                   10                  15

Leu Tyr Leu Pro Asn Leu Thr Gln Lys Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 698
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 698

```
Val Asp Ala Lys Tyr Ala Lys Glu Arg Asn Glu Ala Ala Tyr Glu Ile
1               5                   10                  15

Leu Tyr Leu Pro Asn Leu Thr Ser Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 699
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 699

```
Val Asp Ala Lys Tyr Ala Lys Glu Arg Asn Thr Ala Ala Gln Glu Ile
1               5                   10                  15

Leu Tyr Leu Pro Asn Leu Thr Gln Ser Gln Lys Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 700
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 700

Val Asp Ala Lys Tyr Ala Lys Glu Arg Asn Thr Ala Ala Tyr Glu Ile
1               5                   10                  15

Leu Tyr Leu Pro Asn Leu Thr Asn Phe Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 701
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 701

Val Asp Ala Lys Tyr Ala Lys Glu Arg Asn Ser Ala Ala Gln Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 702
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 702

Val Asp Ala Lys Tyr Ala Lys Glu Arg Asn Asp Ala Ala Phe Glu Ile
1               5                   10                  15

Leu Tyr Leu Pro Asn Leu Thr Gln Ser Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 703
<211> LENGTH: 58
<212> TYPE: PRT
<213> ORGANISM: Artificial Sequence
<220> FEATURE:
<223> OTHER INFORMATION: Engineered PD-L1 binding polypeptide
```

<400> SEQUENCE: 703

Val Asp Ala Lys Tyr Ala Lys Glu Arg Asn Lys Ala Ala His Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 704
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 704

Val Asp Ala Lys Tyr Ala Lys Glu Arg Asn Thr Ala Ala Tyr Glu Ile
1               5                   10                  15

Leu Tyr Leu Pro Asn Leu Thr Gln Arg Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 705
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 705

Val Asp Ala Lys Tyr Ala Lys Glu Arg Asn His Ala Ala His Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 706
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 706

Val Asp Ala Lys Tyr Ala Lys Glu Arg Asn Ser Ala Ala Tyr Glu Ile
1               5                   10                  15

Leu Tyr Leu Pro Asn Leu Thr Ala Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys 50 55

<210> SEQ ID NO 707
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 707

Val Asp Ala Lys Tyr Ala Lys Glu Arg Asn Ser Ala Ala Tyr Glu Ile
1 5 10 15

Leu Tyr Leu Pro Asn Leu Thr Asn Asn Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 708
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 708

Val Asp Ala Lys Tyr Ala Lys Glu Arg Asn Phe Ala Ala Gln Glu Ile
1 5 10 15

Leu Tyr Leu Pro Asn Leu Thr Lys Gly Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 709
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 709

Val Asp Ala Lys Tyr Ala Lys Glu Arg Asn Asp Ala Ala Tyr Glu Ile
1 5 10 15

Leu Tyr Leu Pro Asn Leu Thr Gln Asn Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 710
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 710

Val Asp Ala Lys Tyr Ala Lys Glu Arg Asn Thr Ala Ala Tyr Glu Ile

```
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 711
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 711

Val Asp Ala Lys Tyr Ala Lys Glu Arg Asn Ser Ala Ala Phe Glu Ile
1               5                   10                  15

Leu Tyr Leu Pro Asn Leu Thr Lys Asp Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 712
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 712

Val Asp Ala Lys Tyr Ala Lys Glu Arg Asn Leu Ala Ala Gln Glu Ile
1               5                   10                  15

Leu Glu Leu Pro Asn Leu Thr Ser Gln Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 713
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 713

Val Asp Ala Lys Tyr Ala Lys Glu Arg Asn Tyr Ala Ala Tyr Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 714
```

<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 714

Val Asp Ala Lys Tyr Ala Lys Glu Arg Asn Tyr Ala Ala His Glu Ile
1 5 10 15

Leu Tyr Leu Pro Asn Leu Thr Gln Asn Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 715
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 715

Val Asp Ala Lys Tyr Ala Lys Glu Arg Asn Gln Ala Ala Tyr Glu Ile
1 5 10 15

Leu Tyr Leu Pro Asn Leu Thr Gln Ala Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 716
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 716

Val Asp Ala Lys Tyr Ala Lys Glu Arg Asn Phe Ala Ala His Glu Ile
1 5 10 15

Leu Leu Leu Pro Asn Leu Thr Lys Gln Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 717
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 717

Val Asp Ala Lys Tyr Ala Lys Glu Arg Asn Thr Ala Ala Tyr Glu Ile
1 5 10 15

Leu Tyr Leu Pro Asn Leu Thr Ser Ala Gln Lys Trp Ala Phe Ile Trp
20 25 30

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 718
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 718

Val Asp Ala Lys Tyr Ala Lys Glu Arg Asn Ile Ala Ala Tyr Glu Ile
1               5                   10                  15

Leu Tyr Leu Pro Asn Leu Thr Asn Leu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 719
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 719

Val Asp Ala Lys Tyr Ala Lys Glu Arg Asn Asp Ala Ala Phe Glu Ile
1               5                   10                  15

Leu Tyr Leu Pro Asn Leu Thr Ser Glu Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 720
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 720

Val Asp Ala Lys Tyr Ala Lys Glu Arg Asn Asp Ala Ala Gln Glu Ile
1               5                   10                  15

Leu Glu Leu Pro Asn Leu Thr Trp Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 721
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 721

Val Asp Ala Lys Tyr Ala Lys Glu Arg Asn Tyr Ala Ala His Glu Ile
1               5                   10                  15

Leu Tyr Leu Pro Asn Leu Thr Gln Lys Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 722
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 722

Val Asp Ala Lys Tyr Ala Lys Glu Arg Asn Thr Ala Ala Tyr Glu Ile
1               5                   10                  15

Leu Tyr Leu Pro Asn Leu Thr Gln Gln Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 723
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 723

Val Asp Ala Lys Tyr Ala Lys Glu Arg Asn Ser Ala Ala Glu Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 724
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 724

Val Asp Ala Lys Tyr Ala Lys Glu Arg Asn Asp Ala Ala Phe Glu Ile
1               5                   10                  15

Leu Tyr Leu Pro Asn Leu Thr Gln Tyr Gln Ile Trp Ala Phe Ile Trp
            20                  25                  30

Lys Leu Asp Asp Asp Pro Ser Gln Ser Ser Glu Leu Leu Ser Glu Ala
        35                  40                  45

```
Lys Lys Leu Asn Asp Ser Gln Ala Pro Lys
    50                  55


<210> SEQ ID NO 725
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 725

Val Asp Ala Lys Tyr Ala Lys Glu Arg Asn Phe Ala Ala Gln Glu Ile
1               5                   10                  15

Leu Tyr Leu Pro Asn Leu Thr Gln Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 726
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 726

Val Asp Ala Lys Tyr Ala Lys Glu Arg Asn Ser Ala Ala Gln Glu Ile
1               5                   10                  15

Leu Tyr Leu Pro Asn Leu Thr Gln Arg Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 727
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 727

Val Asp Ala Lys Tyr Ala Lys Glu Arg Asn Ala Ala Ala Phe Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 728
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 728
```

```
Val Asp Ala Lys Tyr Ala Lys Glu Arg Asn His Ala Ala His Glu Ile
1               5                   10                  15

Leu Tyr Leu Pro Asn Leu Thr Gln Ala Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 729
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 729

Val Asp Ala Lys Tyr Ala Lys Glu Arg Asn Ala Ala Ala Tyr Glu Ile
1               5                   10                  15

Leu Phe Leu Pro Asn Leu Thr His Ser Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 730
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 730

Val Asp Ala Lys Tyr Ala Lys Glu Arg Asn Ile Ala Ala Gln Glu Ile
1               5                   10                  15

Leu His Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 731
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 731

Val Asp Ala Lys Tyr Ala Lys Glu Arg Asn Ala Ala Ala Phe Glu Ile
1               5                   10                  15

Leu Asn Leu Pro Asn Leu Thr Lys Ser Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 732
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 732

Val Asp Ala Lys Tyr Ala Lys Glu Arg Asn Gln Ala Ala Tyr Glu Ile
1 5 10 15

Leu Tyr Leu Pro Asn Leu Thr Gln Ser Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 733
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 733

Val Asp Ala Lys Tyr Ala Lys Glu Arg Asn Thr Ala Ala Tyr Glu Ile
1 5 10 15

Leu Tyr Leu Pro Asn Leu Thr Gln Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 734
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 734

Val Asp Ala Lys Tyr Ala Lys Glu Arg Asn Lys Ala Ala His Glu Ile
1 5 10 15

Leu Tyr Leu Pro Asn Leu Thr Asn Leu Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 735
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 735

Val Asp Ala Lys Tyr Ala Lys Glu Arg Asn Ser Ala Ala Glu Glu Ile
1 5 10 15

Leu Tyr Leu Pro Asn Leu Thr His Ser Gln Ile Trp Ala Phe Ile Trp

```
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 736
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 736

Val Asp Ala Lys Tyr Ala Lys Glu Arg Asn Leu Ala Ala Tyr Glu Ile
1               5                   10                  15

Leu Tyr Leu Pro Asn Leu Thr Gln Ser Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 737
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 737

Val Asp Ala Lys Tyr Ala Lys Glu Arg Asn Glu Ala Ala Tyr Glu Ile
1               5                   10                  15

Leu Tyr Leu Pro Asn Leu Thr Ala Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 738
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 738

Val Asp Ala Lys Tyr Ala Lys Glu Arg Asn Leu Ala Ala Tyr Glu Ile
1               5                   10                  15

Leu Tyr Leu Pro Asn Leu Thr Gln Ser Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 739
<211> LENGTH: 58
<212> TYPE: PRT
<213> ORGANISM: Artificial Sequence
```

<220> FEATURE:
<223> OTHER INFORMATION: Engineered PD-L1 binding polypeptide

<400> SEQUENCE: 739

Val Asp Ala Lys Tyr Ala Lys Glu Arg Asn Glu Ala Ala Tyr Glu Ile
1 5 10 15

Leu Gln Leu Pro Asn Leu Thr Ser Ser Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 740
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 740

Val Asp Ala Lys Tyr Ala Lys Glu Arg Asn Glu Ala Ala Tyr Glu Ile
1 5 10 15

Leu Tyr Leu Pro Asn Leu Thr Gln Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 741
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 741

Val Asp Ala Lys Tyr Ala Lys Glu Arg Asn Ala Ala Ala His Glu Ile
1 5 10 15

Leu Tyr Leu Pro Asn Leu Thr Gln Gly Gln Ile Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 742
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 742

Val Asp Ala Lys Tyr Ala Lys Glu Arg Asn Glu Ala Ala His Glu Ile
1 5 10 15

Leu Tyr Leu Pro Asn Leu Thr Ser Ser Gln Ile Trp Ala Phe Ile Trp
20 25 30

Lys Leu Asp Asp Asp Pro Ser Gln Ser Ser Glu Leu Leu Ser Glu Ala
35 40 45

```
Lys Lys Leu Asn Asp Ser Gln Ala Pro Lys
    50                  55


<210> SEQ ID NO 743
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 743

Val Asp Ala Lys Tyr Ala Lys Glu Arg Asn Val Ala Ala Phe Glu Ile
1               5                   10                  15

Leu Tyr Leu Pro Asn Leu Thr Asn Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 744
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 744

Val Asp Ala Lys Tyr Ala Lys Glu Arg Asn Lys Ala Ala Tyr Glu Ile
1               5                   10                  15

Leu Tyr Leu Pro Asn Leu Thr Gln Gln Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 745
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 745

Val Asp Ala Lys Tyr Ala Lys Glu Arg Asn Lys Ala Ala Tyr Glu Ile
1               5                   10                  15

Leu Tyr Leu Pro Asn Leu Thr Asn His Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 746
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 746
```

```
Val Asp Ala Lys Tyr Ala Lys Glu Arg Asn Glu Ala Ala Gln Glu Ile
1               5                   10                  15

Leu Tyr Leu Pro Asn Leu Thr Ser Ile Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 747
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 747

Val Asp Ala Lys Tyr Ala Lys Glu Arg Asn Thr Ala Ala Trp Glu Ile
1               5                   10                  15

Leu Gln Leu Pro Asn Leu Thr Arg Ala Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 748
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 748

Val Asp Ala Lys Tyr Ala Lys Glu Arg Asn Ala Ala Ala Gln Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 749
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 749

Val Asp Ala Lys Tyr Ala Lys Glu Arg Asn Thr Ala Ala Tyr Glu Ile
1               5                   10                  15

Leu Tyr Leu Pro Asn Leu Thr Ala Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 750
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 750

```
Val Asp Ala Lys Tyr Ala Lys Glu Arg Asn Asp Ala Ala Tyr Glu Ile
1               5                   10                  15

Leu Tyr Leu Pro Asn Leu Thr Ser Lys Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 751
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 751

```
Val Asp Ala Lys Tyr Ala Lys Glu Arg Asn Asn Ala Ala Gln Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 752
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 752

```
Val Asp Ala Lys Tyr Ala Lys Glu Arg Asn Val Ala Ala Tyr Glu Ile
1               5                   10                  15

Leu Tyr Leu Pro Asn Leu Thr Ser Asp Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 753
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 753

```
Val Asp Ala Lys Tyr Ala Lys Glu Arg Asn Tyr Ala Ala Gln Glu Ile
1               5                   10                  15
```

-continued

```
Leu Tyr Leu Pro Asn Leu Thr Gln Thr Gln Ile Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 754
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 754

Val Asp Ala Lys Tyr Ala Lys Glu Arg Asn Thr Ala Ala His Glu Ile
1               5                   10                  15

Leu Gln Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 755
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 755

Val Asp Ala Lys Tyr Ala Lys Glu Arg Asn Ser Ala Ala His Glu Ile
1               5                   10                  15

Leu Tyr Leu Pro Asn Leu Thr Ala Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 756
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 756

Val Asp Ala Lys Tyr Ala Lys Glu Arg Asn Gln Ala Ala Tyr Glu Ile
1               5                   10                  15

Leu Tyr Leu Pro Asn Leu Thr Gln Gly Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 757
<211> LENGTH: 58
<212> TYPE: PRT
```

<213> ORGANISM: Artificial Sequence
<220> FEATURE:
<223> OTHER INFORMATION: Engineered PD-L1 binding polypeptide

<400> SEQUENCE: 757

Val Asp Ala Lys Tyr Ala Lys Glu Arg Asn Asp Ala Ala Phe Glu Ile
1               5                   10                  15

Leu Ser Leu Pro Asn Leu Thr Arg Ala Gln Glu Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 758
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 758

Val Asp Ala Lys Tyr Ala Lys Glu Arg Asn Asn Ala Ala Gln Glu Ile
1               5                   10                  15

Leu Tyr Leu Pro Asn Leu Thr Gln Ser Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 759
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 759

Val Asp Ala Lys Tyr Ala Lys Glu Arg Asn His Ala Ala Asn Glu Ile
1               5                   10                  15

Leu Gln Leu Pro Asn Leu Thr Asn Glu Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 760
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 760

Val Asp Ala Lys Tyr Ala Lys Glu Arg Asn Ser Ala Ala His Glu Ile
1               5                   10                  15

Leu Tyr Leu Pro Asn Leu Thr Asn Lys Gln Lys Trp Ala Phe Ile Trp
            20                  25                  30

Lys Leu Asp Asp Asp Pro Ser Gln Ser Ser Glu Leu Leu Ser Glu Ala 35 40 45

Lys Lys Leu Asn Asp Ser Gln Ala Pro Lys
50 55

<210> SEQ ID NO 761
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 761

Val Asp Ala Lys Tyr Ala Lys Glu Arg Asn Leu Ala Ala Tyr Glu Ile
1 5 10 15

Leu Tyr Leu Pro Asn Leu Thr Gln Ala Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 762
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 762

Val Asp Ala Lys Tyr Ala Lys Glu Arg Asn Asp Ala Ala His Glu Ile
1 5 10 15

Leu Tyr Leu Pro Asn Leu Thr Gln Gln Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 763
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 763

Val Asp Ala Lys Tyr Ala Lys Glu Arg Asn Asp Ala Ala Tyr Glu Ile
1 5 10 15

Leu Tyr Leu Pro Asn Leu Thr Ala Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 764
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 764

Val Asp Ala Lys Tyr Ala Lys Glu Arg Asn Phe Ala Ala Gln Glu Ile
1 5 10 15

Leu Tyr Leu Pro Asn Leu Thr Ser Tyr Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 765
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 765

Val Asp Ala Lys Tyr Ala Lys Glu Arg Asn Trp Ala Ala Tyr Glu Ile
1 5 10 15

Leu Tyr Leu Pro Asn Leu Thr Asn Ala Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 766
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 766

Val Asp Ala Lys Tyr Ala Lys Glu Arg Asn Lys Ala Ala Tyr Glu Ile
1 5 10 15

Leu Lys Leu Pro Asn Leu Thr Arg Gly Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 767
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 767

Val Asp Ala Lys Tyr Ala Lys Glu Arg Asn Ala Ala Ala Gln Glu Ile
1 5 10 15

Leu Glu Leu Pro Asn Leu Thr Lys Ala Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 768
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 768

```
Val Asp Ala Lys Tyr Ala Lys Glu Arg Asn Leu Ala Ala Tyr Glu Ile
1               5                   10                  15

Leu Tyr Leu Pro Asn Leu Thr Gln Asn Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 769
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 769

```
Val Asp Ala Lys Tyr Ala Lys Glu Arg Asn Ser Ala Ala Tyr Glu Ile
1               5                   10                  15

Leu Tyr Leu Pro Asn Leu Thr His Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 770
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 770

```
Val Asp Ala Lys Tyr Ala Lys Glu Arg Asn Gln Ala Ala Tyr Glu Ile
1               5                   10                  15

Leu Tyr Leu Pro Asn Leu Thr Ser Ala Gln Arg Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 771
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 771

```
Val Asp Ala Lys Tyr Ala Lys Glu Arg Asn Gln Ala Ala His Glu Ile
1               5                   10                  15
```

Leu Tyr Leu Pro Asn Leu Thr Gln Lys Gln Lys Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 772
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 772

Val Asp Ala Lys Tyr Ala Lys Glu Arg Asn Asp Ala Ala Tyr Glu Ile
1 5 10 15

Leu Tyr Leu Pro Asn Leu Thr Asn His Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 773
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 773

Val Asp Ala Lys Tyr Ala Lys Glu Arg Asn Phe Ala Ala Tyr Glu Ile
1 5 10 15

Leu Tyr Leu Pro Asn Leu Thr Asn Gln Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 774
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 774

Val Asp Ala Lys Tyr Ala Lys Glu Arg Asn Ser Ala Ala Glu Glu Ile
1 5 10 15

Leu His Leu Pro Asn Leu Thr Met Gln Gln Leu Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 775
<211> LENGTH: 58

<212> TYPE: PRT
<213> ORGANISM: Artificial Sequence
<220> FEATURE:
<223> OTHER INFORMATION: Engineered PD-L1 binding polypeptide

<400> SEQUENCE: 775

```
Val Asp Ala Lys Tyr Ala Lys Glu Arg Asn Asn Ala Ala Thr Glu Ile
1               5                   10                  15

Leu Arg Leu Pro Asn Leu Thr Ala Gly Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 776
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 776

```
Val Asp Ala Lys Tyr Ala Lys Glu Arg Asn Asn Ala Ala Phe Glu Ile
1               5                   10                  15

Leu Arg Leu Pro Asn Leu Thr Asn Gly Gln His Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 777
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 777

```
Val Asp Ala Lys Tyr Ala Lys Glu Arg Asn Ala Ala Ala Phe Glu Ile
1               5                   10                  15

Leu Thr Leu Pro Asn Leu Thr Asn Glu Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 778
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 778

```
Val Asp Ala Lys Tyr Ala Lys Glu Arg Asn Arg Ala Ala Asn Glu Ile
1               5                   10                  15

Leu Gln Leu Pro Asn Leu Thr Lys Gly Gln Val Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 779
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 779

```
Val Asp Ala Lys Tyr Ala Lys Glu Arg Asn Arg Ala Ala Tyr Glu Ile
1               5                   10                  15

Leu Gln Leu Pro Asn Leu Thr His Gln Gln Thr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 780
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 780

```
Val Asp Ala Lys Tyr Ala Lys Glu Arg Asn Asp Ala Ala Tyr Glu Ile
1               5                   10                  15

Leu Gln Leu Pro Asn Leu Thr Lys Arg Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 781
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 781

```
Val Asp Ala Lys Tyr Ala Lys Glu Arg Asn Gln Ala Ala Val Glu Ile
1               5                   10                  15

Leu Gln Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 782
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 782

Val Asp Ala Lys Tyr Ala Lys Glu Arg Asn Asp Ala Ala Phe Glu Ile
1 5 10 15

Leu Gln Leu Pro Asn Leu Thr Asn Ser Gln His Trp Ala Phe Ile Trp
20 25 30

Lys Leu Glu Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 783
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 783

Val Asp Ala Lys Tyr Ala Lys Glu Arg Asn Asn Ala Ala Gln Glu Ile
1 5 10 15

Leu Gln Leu Pro Asn Leu Thr Gln Leu Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 784
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 784

Val Asp Ala Lys Tyr Ala Lys Glu Arg Asn Tyr Ala Ala Trp Glu Ile
1 5 10 15

Leu Arg Leu Pro Asn Leu Thr Ala Ser Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 785
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 785

Val Asp Ala Lys Tyr Ala Lys Glu Arg Asn Arg Ala Ala Gln Glu Ile
1 5 10 15

Leu Val Leu Pro Asn Leu Thr Arg Lys Gln Gln Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys 50 55

<210> SEQ ID NO 786
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 786

Val Asp Ala Lys Tyr Ala Lys Glu Arg Asn Ala Ala Ala Tyr Glu Ile
1 5 10 15

Leu Thr Leu Pro Asn Leu Thr Asn Lys Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 787
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 787

Val Asp Ala Lys Tyr Ala Lys Glu Arg Asn Asn Ala Ala Ser Glu Ile
1 5 10 15

Leu Ala Leu Pro Asn Leu Thr Gln Leu Gln Tyr Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 788
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 788

Val Asp Ala Lys Tyr Ala Lys Glu Arg Asn Arg Ala Ala Tyr Glu Ile
1 5 10 15

Leu Gln Leu Pro Asn Leu Thr Asn Gln Gln His Trp Ala Phe Ile Trp
20 25 30

Lys Leu Met Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 789
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 789

Val Asp Ala Lys Tyr Ala Lys Glu Arg Asn Arg Ala Ala Ser Glu Ile

```
1               5                   10                  15

Leu Leu Leu Pro Asn Leu Thr Arg Met Gln His Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 790
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 790

Val Asp Ala Lys Tyr Ala Lys Glu Arg Asn Leu Ala Ala Trp Glu Ile
1               5                   10                  15

Leu Gln Leu Pro Asn Leu Thr Asn Tyr Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 791
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 791

Val Asp Ala Lys Tyr Ala Lys Glu Arg Asn Gln Ala Ala Thr Glu Ile
1               5                   10                  15

Leu Val Leu Pro Asn Leu Thr His Gln Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 792
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 792

Val Asp Ala Lys Tyr Ala Lys Glu Arg Asn Thr Ala Ala Leu Glu Ile
1               5                   10                  15

Leu Tyr Leu Pro Asn Leu Thr Lys Asp Gln Val Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 793
```

```
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 793

Val Asp Ala Lys Tyr Ala Lys Glu Arg Asn Ala Ala Ala Glu Glu Ile
1               5                   10                  15

Leu Asp Leu Pro Asn Leu Thr Ala Gly Gln Met Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 794
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 794

Val Asp Ala Lys Tyr Ala Lys Glu Arg Asn Arg Ala Ala Trp Glu Ile
1               5                   10                  15

Leu Gln Leu Pro Asn Leu Thr Arg Thr Gln Trp Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 795
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 795

Val Asp Ala Lys Tyr Ala Lys Glu Arg Asn Ala Ala Ala Trp Glu Ile
1               5                   10                  15

Leu Arg Leu Pro Asn Leu Thr Arg His Gln Gln Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 796
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 796

Val Asp Ala Lys Tyr Ala Lys Glu Arg Asn Gln Ala Ala Tyr Glu Ile
1               5                   10                  15

Val Gln Leu Pro Asn Leu Thr Lys Gly Gln Thr Trp Ala Phe Ile Trp
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 797
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 797

Val Asp Ala Lys Tyr Ala Lys Glu Arg Asn Leu Ala Ala Ala Glu Ile
1               5                   10                  15

Ile Ala Leu Pro Asn Leu Thr Arg Gly Gln His Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 798
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 798

Val Asp Ala Lys Tyr Ala Lys Glu Arg Asn Tyr Ala Ala Ala Glu Ile
1               5                   10                  15

Leu Gln Leu Pro Asn Leu Thr Gly Leu Gln Thr Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 799
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 799

Val Asp Ala Lys Tyr Ala Lys Glu Arg Asn Arg Ala Ala Gln Glu Ile
1               5                   10                  15

Val Lys Leu Pro Asn Leu Thr His Gln Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 800
<211> LENGTH: 58
<212> TYPE: PRT
<213> ORGANISM: Artificial Sequence
<220> FEATURE:
```

<223> OTHER INFORMATION: Engineered PD-L1 binding polypeptide

<400> SEQUENCE: 800

Val Asp Ala Lys Tyr Ala Lys Glu Arg Asn Ala Ala Ala His Glu Ile
1 5 10 15

Leu Gln Leu Pro Asn Leu Thr Asn Thr Gln Arg Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 801
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 801

Val Asp Ala Lys Tyr Ala Lys Glu Arg Asn Ala Ala Ala His Glu Ile
1 5 10 15

Leu Gln Leu Pro Asn Leu Thr Thr Arg Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 802
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 802

Val Asp Ala Lys Tyr Ala Lys Glu Arg Asn Asp Ala Ala Val Glu Ile
1 5 10 15

Leu Arg Leu Pro Asn Leu Thr Ser Thr Gln Tyr Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 803
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 803

Val Asp Ala Lys Tyr Ala Lys Glu Arg Asn Gln Ala Ala Ala Glu Ile
1 5 10 15

Leu Ser Leu Pro Asn Leu Thr Gly Glu Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 804
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 804

Val Asp Ala Lys Tyr Ala Lys Glu Arg Asn Met Ala Ala Glu Glu Ile
1 5 10 15

Leu Gly Leu Pro Asn Leu Thr Ser His Gln His Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 805
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 805

Val Asp Ala Lys Tyr Ala Lys Glu Arg Asn His Ala Ala His Glu Ile
1 5 10 15

Leu Gly Leu Pro Asn Leu Thr Ala His Gln His Trp Ala Phe Ile Trp
20 25 30

Lys Leu Ala Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 806
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 806

Val Asp Ala Lys Tyr Ala Lys Glu Arg Asn Ala Ala Ala Phe Glu Ile
1 5 10 15

Leu Arg Leu Pro Asn Leu Thr Ser Ser Gln Phe Trp Ala Phe Ile Trp
20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 807
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 807

```
Val Asp Ala Lys Tyr Ala Lys Glu Arg Asn Ser Ala Ala His Glu Ile
1               5                   10                  15

Leu Tyr Leu Pro Asn Leu Thr Thr Asp Gln Gln Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 808
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 808

Val Asp Ala Lys Tyr Ala Lys Glu Arg Asn Ala Ala Ala Gly Glu Ile
1               5                   10                  15

Leu Arg Leu Pro Asn Leu Thr Ala Asn Gln His Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55


<210> SEQ ID NO 809
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 809

Ala Glu Ala Lys Tyr Ala Lys Glu Arg Asn Asn Ala Ala Phe Glu Ile
1               5                   10                  15

Leu Arg Leu Pro Asn Leu Thr Asn Gly Gln His Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60


<210> SEQ ID NO 810
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 810

Ala Glu Ala Lys Tyr Ala Lys Glu Arg Asn Gln Ala Ala Val Glu Ile
1               5                   10                  15

Leu Gln Leu Pro Asn Leu Thr Ala Ala Gln Tyr Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60
```

<210> SEQ ID NO 811
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 811

```
Ala Glu Ala Lys Tyr Ala Lys Glu Arg Asn Lys Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60
```

<210> SEQ ID NO 812
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 812

```
Ala Glu Ala Lys Tyr Ala Lys Glu Arg Asn Ala Ala Ala Tyr Glu Ile
1               5                   10                  15

Leu Tyr Leu Pro Asn Leu Thr Asn Ala Gln Lys Trp Ala Phe Ile Trp
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60
```

<210> SEQ ID NO 813
<211> LENGTH: 61
<212> TYPE: PRT
<213> ORGANISM: Artificial Sequence
<220> FEATURE:
<223> OTHER INFORMATION: Engineered PD-L1 binding polypeptide

<400> SEQUENCE: 813

```
Ala Glu Ala Lys Tyr Ala Lys Glu Arg Asn Asp Ala Ala Tyr Glu Ile
1               5                   10                  15

Leu Tyr Leu Pro Asn Leu Thr Asn Gln Gln Lys Trp Ala Phe Ile Trp
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60
```

<210> SEQ ID NO 814
<211> LENGTH: 58
<212> TYPE: PRT
<213> ORGANISM: Artificial Sequence
<220> FEATURE:
<223> OTHER INFORMATION: Engineered PD-L1 binding polypeptide

<400> SEQUENCE: 814

```
Ala Glu Ala Lys Tyr Ala Lys Glu Arg Asn Tyr Ala Ala Trp Glu Ile
1               5                   10                  15

Leu Arg Leu Pro Asn Leu Thr Ala Ser Gln Tyr Trp Ala Phe Ile Trp
```

20 25 30

Lys Leu Asp Asp Asp Pro Ser Gln Ser Ser Glu Leu Leu Ser Glu Ala
35 40 45

Lys Lys Leu Asn Asp Ser Gln Ala Pro Lys
50 55

<210> SEQ ID NO 815
<211> LENGTH: 447
<212> TYPE: PRT
<213> ORGANISM: Artificial Sequence
<220> FEATURE:
<223> OTHER INFORMATION: Heavy chain of antibody Lam

<400> SEQUENCE: 815

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile

```
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 816
<211> LENGTH: 218
<212> TYPE: PRT
<213> ORGANISM: Artificial Sequence
<220> FEATURE:
<223> OTHER INFORMATION: Light chain of antibody Lam

<400> SEQUENCE: 816

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 817
<211> LENGTH: 448
<212> TYPE: PRT
```

```
<213> ORGANISM: Artificial Sequence
<220> FEATURE:
<223> OTHER INFORMATION: Heavy chain of antibody Ipi

<400> SEQUENCE: 817

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 818
<211> LENGTH: 215
<212> TYPE: PRT
<213> ORGANISM: Artificial Sequence
<220> FEATURE:
<223> OTHER INFORMATION: Light chain of antibody Ipi

<400> SEQUENCE: 818

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 819
<211> LENGTH: 147
<212> TYPE: DNA
<213> ORGANISM: Artificial Sequence
<220> FEATURE:
<223> OTHER INFORMATION: Library oligonucleotide
<220> FEATURE:
<221> NAME/KEY: misc_feature
<222> LOCATION: (45)..(47)
<223> OTHER INFORMATION: n is a, c, g, or t
<220> FEATURE:
<221> NAME/KEY: misc_feature
<222> LOCATION: (54)..(56)
<223> OTHER INFORMATION: n is a, c, g, or t
<220> FEATURE:
```

<221> NAME/KEY: misc_feature
<222> LOCATION: (66)..(68)
<223> OTHER INFORMATION: n is a, c, g, or t
<220> FEATURE:
<221> NAME/KEY: misc_feature
<222> LOCATION: (84)..(89)
<223> OTHER INFORMATION: n is a, c, g, or t
<220> FEATURE:
<221> NAME/KEY: misc_feature
<222> LOCATION: (93)..(95)
<223> OTHER INFORMATION: n is a, c, g, or t
<220> FEATURE:
<221> NAME/KEY: misc_feature
<222> LOCATION: (117)..(119)
<223> OTHER INFORMATION: n is a, c, g, or t

<400> SEQUENCE: 819
aaataaatct cgaggtagat gccaaatacg ccaaagaacg taacnnngcg gctnnngaga 60
tcctgnnnct gcctaacctc accnnnnnnc aannntgggc cttcatctgg aaattannng 120
atgacccaag ccagagctca ttattta 147

<210> SEQ ID NO 820
<211> LENGTH: 16
<212> TYPE: PRT
<213> ORGANISM: Artificial Sequence
<220> FEATURE:
<223> OTHER INFORMATION: Linker

<400> SEQUENCE: 820

Gly Gly Gly Gly Ser Leu Val Pro Arg Gly Ser Gly Gly Gly Gly Ser
1 5 10 15

<210> SEQ ID NO 821
<211> LENGTH: 6
<212> TYPE: PRT
<213> ORGANISM: Artificial Sequence
<220> FEATURE:
<223> OTHER INFORMATION: Linker

<400> SEQUENCE: 821

Gly Ser Gly Ser Gly Ser
1 5

<210> SEQ ID NO 822
<211> LENGTH: 8
<212> TYPE: PRT
<213> ORGANISM: Artificial Sequence
<220> FEATURE:
<223> OTHER INFORMATION: Linker

<400> SEQUENCE: 822

Gly Ser Gly Ser Gly Ser Gly Ser
1 5

<210> SEQ ID NO 823
<211> LENGTH: 16
<212> TYPE: PRT
<213> ORGANISM: Artificial Sequence
<220> FEATURE:
<223> OTHER INFORMATION: Linker

<400> SEQUENCE: 823

Gly Ser Gly Ser Gly Ser Gly Ser Gly Ser Gly Ser Gly Ser Gly Ser
1 5 10 15

<210> SEQ ID NO 824
<211> LENGTH: 11

<212> TYPE: PRT
<213> ORGANISM: Artificial Sequence
<220> FEATURE:
<223> OTHER INFORMATION: Linker

<400> SEQUENCE: 824

Gly Gly Ser Gly Gly His Met Gly Ser Gly Gly
1 5 10

<210> SEQ ID NO 825
<211> LENGTH: 11
<212> TYPE: PRT
<213> ORGANISM: Artificial Sequence
<220> FEATURE:
<223> OTHER INFORMATION: Linker

<400> SEQUENCE: 825

Gly Gly Ser Gly Gly Ser Gly Gly Ser Gly Gly
1 5 10

<210> SEQ ID NO 826
<211> LENGTH: 5
<212> TYPE: PRT
<213> ORGANISM: Artificial Sequence
<220> FEATURE:
<223> OTHER INFORMATION: Linker

<400> SEQUENCE: 826

Gly Gly Ser Gly Gly
1 5

<210> SEQ ID NO 827
<211> LENGTH: 8
<212> TYPE: PRT
<213> ORGANISM: Artificial Sequence
<220> FEATURE:
<223> OTHER INFORMATION: Linker

<400> SEQUENCE: 827

Gly Gly Ser Gly Gly Gly Gly Gly
1 5

<210> SEQ ID NO 828
<211> LENGTH: 18
<212> TYPE: PRT
<213> ORGANISM: Artificial Sequence
<220> FEATURE:
<223> OTHER INFORMATION: Linker

<400> SEQUENCE: 828

Gly Gly Gly Ser Glu Gly Gly Gly Ser Glu Gly Gly Gly Ser Glu Gly
1 5 10 15

Gly Gly

<210> SEQ ID NO 829
<211> LENGTH: 8
<212> TYPE: PRT
<213> ORGANISM: Artificial Sequence
<220> FEATURE:
<223> OTHER INFORMATION: Linker

<400> SEQUENCE: 829

Ala Ala Gly Ala Ala Thr Ala Ala
1 5

<210> SEQ ID NO 830

<211> LENGTH: 5
<212> TYPE: PRT
<213> ORGANISM: Artificial Sequence
<220> FEATURE:
<223> OTHER INFORMATION: Linker

<400> SEQUENCE: 830

Gly Gly Gly Gly Gly
1 5

<210> SEQ ID NO 831
<211> LENGTH: 5
<212> TYPE: PRT
<213> ORGANISM: Artificial Sequence
<220> FEATURE:
<223> OTHER INFORMATION: Linker

<400> SEQUENCE: 831

Gly Gly Ser Ser Gly
1 5

<210> SEQ ID NO 832
<211> LENGTH: 11
<212> TYPE: PRT
<213> ORGANISM: Artificial Sequence
<220> FEATURE:
<223> OTHER INFORMATION: Linker

<400> SEQUENCE: 832

Gly Ser Gly Gly Gly Thr Gly Gly Gly Ser Gly
1 5 10

<210> SEQ ID NO 833
<211> LENGTH: 11
<212> TYPE: PRT
<213> ORGANISM: Artificial Sequence
<220> FEATURE:
<223> OTHER INFORMATION: Linker

<400> SEQUENCE: 833

Gly Ser Gly Gly Gly Thr Gly Gly Gly Ser Gly
1 5 10

<210> SEQ ID NO 834
<211> LENGTH: 12
<212> TYPE: PRT
<213> ORGANISM: Artificial Sequence
<220> FEATURE:
<223> OTHER INFORMATION: Linker

<400> SEQUENCE: 834

Gly Ser Gly Ser Gly Ser Gly Ser Gly Gly Ser Gly
1 5 10

<210> SEQ ID NO 835
<211> LENGTH: 14
<212> TYPE: PRT
<213> ORGANISM: Artificial Sequence
<220> FEATURE:
<223> OTHER INFORMATION: Linker

<400> SEQUENCE: 835

Gly Ser Gly Gly Ser Gly Gly Ser Gly Gly Ser Gly Gly Ser
1 5 10

<210> SEQ ID NO 836
<211> LENGTH: 14

```
<212> TYPE: PRT
<213> ORGANISM: Artificial Sequence
<220> FEATURE:
<223> OTHER INFORMATION: Linker

<400> SEQUENCE: 836

Gly Ser Gly Gly Ser Gly Ser Gly Gly Ser Gly Gly Ser Gly
1               5                   10


<210> SEQ ID NO 837
<211> LENGTH: 29
<212> TYPE: PRT
<213> ORGANISM: Artificial sequence
<220> FEATURE:
<223> OTHER INFORMATION: Engineered PD-L1 binding motif
<220> FEATURE:
<221> NAME/KEY: MISC_FEATURE
<222> LOCATION: (4)..(4)
<223> OTHER INFORMATION: X4 is selected from A, D, E, F, H, I, K, L, N,
      Q, R, S, T, V and Y
<220> FEATURE:
<221> NAME/KEY: MISC_FEATURE
<222> LOCATION: (7)..(7)
<223> OTHER INFORMATION: X7 is selected from A, E, F, H, N, Q, S, T, V,
      W and Y
<220> FEATURE:
<221> NAME/KEY: MISC_FEATURE
<222> LOCATION: (11)..(11)
<223> OTHER INFORMATION: X11 is selected from A, D, E, F, H, K, L, N, Q,
      R, S, T, V, W and Y
<220> FEATURE:
<221> NAME/KEY: MISC_FEATURE
<222> LOCATION: (16)..(16)
<223> OTHER INFORMATION: X16 is selected from N and T
<220> FEATURE:
<221> NAME/KEY: MISC_FEATURE
<222> LOCATION: (17)..(17)
<223> OTHER INFORMATION: X17 is selected from A, H, K, N, Q, R and S
<220> FEATURE:
<221> NAME/KEY: MISC_FEATURE
<222> LOCATION: (18)..(18)
<223> OTHER INFORMATION: X18 is selected from A, D, E, G, H, K, L, N, Q,
      R, S, T, V and Y
<220> FEATURE:
<221> NAME/KEY: MISC_FEATURE
<222> LOCATION: (20)..(20)
<223> OTHER INFORMATION: X20 is selected from H, I, K, L, N, Q, R, T, V
      and Y
<220> FEATURE:
<221> NAME/KEY: MISC_FEATURE
<222> LOCATION: (26)..(26)
<223> OTHER INFORMATION: X26 is selected from K and S
<220> FEATURE:
<221> NAME/KEY: MISC_FEATURE
<222> LOCATION: (28)..(28)
<223> OTHER INFORMATION: X28 is selected from A, D and E

<400> SEQUENCE: 837

Glu Arg Asn Xaa Ala Ala Xaa Glu Ile Leu Xaa Leu Pro Asn Leu Xaa
1               5                   10                  15

Xaa Xaa Gln Xaa Trp Ala Phe Ile Trp Xaa Leu Xaa Asp
            20                  25


<210> SEQ ID NO 838
<211> LENGTH: 21
<212> TYPE: PRT
<213> ORGANISM: Artificial Sequence
<220> FEATURE:
<223> OTHER INFORMATION: Engineered PD-L1 binding module
<220> FEATURE:
<221> NAME/KEY: MISC_FEATURE
<222> LOCATION: (2)..(2)
<223> OTHER INFORMATION: Engineered PD-L1 binding motif sequence
<220> FEATURE:
```

<221> NAME/KEY: MISC_FEATURE
<222> LOCATION: (8)..(8)
<223> OTHER INFORMATION: Xa is selected from A and S
<220> FEATURE:
<221> NAME/KEY: MISC_FEATURE
<222> LOCATION: (9)..(9)
<223> OTHER INFORMATION: Xb is selected from N and E
<220> FEATURE:
<221> NAME/KEY: MISC_FEATURE
<222> LOCATION: (12)..(12)
<223> OTHER INFORMATION: Xc is selected from A, S and C
<220> FEATURE:
<221> NAME/KEY: MISC_FEATURE
<222> LOCATION: (18)..(18)
<223> OTHER INFORMATION: Xd is selected from E, N and S
<220> FEATURE:
<221> NAME/KEY: MISC_FEATURE
<222> LOCATION: (19)..(19)
<223> OTHER INFORMATION: Xe is selected from D, E and S
<220> FEATURE:
<221> NAME/KEY: MISC_FEATURE
<222> LOCATION: (20)..(20)
<223> OTHER INFORMATION: Xf is selected from A and S

<400> SEQUENCE: 838

```
Lys Xaa Asp Pro Ser Gln Ser Xaa Xaa Leu Leu Xaa Glu Ala Lys Lys
1               5                   10                  15

Leu Xaa Xaa Xaa Gln
            20
```

<210> SEQ ID NO 839
<211> LENGTH: 5
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (3)..(3)
<223> OTHER INFORMATION: Engineered PD-L1 binding module sequence

<400> SEQUENCE: 839

```
Tyr Ala Xaa Ala Pro
1               5
```

<210> SEQ ID NO 840
<211> LENGTH: 5
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (3)..(3)
<223> OTHER INFORMATION: Engineered PD-L1 binding module sequence

<400> SEQUENCE: 840

```
Phe Asn Xaa Ala Pro
1               5
```

<210> SEQ ID NO 841
<211> LENGTH: 25
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (4)..(4)
<223> OTHER INFORMATION: Engineered PD-L1 binding motif sequence
<220> FEATURE:
<221> NAME/KEY: MISC_FEATURE
<222> LOCATION: (14)..(14)
<223> OTHER INFORMATION: Xc is selected from A and C

<400> SEQUENCE: 841

Phe Asn Lys Xaa Asp Pro Ser Gln Ser Ala Asn Leu Leu Xaa Glu Ala
1 5 10 15

Lys Lys Leu Asn Asp Ala Gln Ala Pro
20 25

<210> SEQ ID NO 842
<211> LENGTH: 25
<212> TYPE: PRT
<213> ORGANISM: artificial sequence
<220> FEATURE:
<223> OTHER INFORMATION: Engineered Pd-l1 binding polypeptide
<220> FEATURE:
<221> NAME/KEY: MISC_FEATURE
<222> LOCATION: (4)..(4)
<223> OTHER INFORMATION: Engineered PD-L1 binding motif sequence
<220> FEATURE:
<221> NAME/KEY: MISC_FEATURE
<222> LOCATION: (14)..(14)
<223> OTHER INFORMATION: Xc is selected from A, S and C

<400> SEQUENCE: 842

Phe Ala Lys Xaa Asp Pro Ser Gln Ser Ser Glu Leu Leu Xaa Glu Ala
1 5 10 15

Lys Lys Leu Ser Glu Ser Gln Ala Pro
20 25

<210> SEQ ID NO 843
<211> LENGTH: 25
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (4)..(4)
<223> OTHER INFORMATION: Engineered PD-L1 binding motif sequence
<220> FEATURE:
<221> NAME/KEY: MISC_FEATURE
<222> LOCATION: (14)..(14)
<223> OTHER INFORMATION: Xc is selected from A, S and C

<400> SEQUENCE: 843

Phe Ala Lys Xaa Asp Pro Ser Gln Ser Ser Glu Leu Leu Xaa Glu Ala
1 5 10 15

Lys Lys Leu Asn Asp Ser Gln Ala Pro
20 25

<210> SEQ ID NO 844
<211> LENGTH: 25
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (4)..(4)
<223> OTHER INFORMATION: Engineered PD-L1 binding motif sequence
<220> FEATURE:
<221> NAME/KEY: MISC_FEATURE
<222> LOCATION: (14)..(14)
<223> OTHER INFORMATION: Xc is selected from A, S and C

<400> SEQUENCE: 844

Tyr Ala Lys Xaa Asp Pro Ser Gln Ser Ser Glu Leu Leu Xaa Glu Ala
1 5 10 15

```
Lys Lys Leu Asn Asp Ser Gln Ala Pro
            20                  25


<210> SEQ ID NO 845
<211> LENGTH: 30
<212> TYPE: PRT
<213> ORGANISM: artificial
<220> FEATURE:
<223> OTHER INFORMATION: Engineered PD-L1 binding polypeptide
<220> FEATURE:
<221> NAME/KEY: MISC_FEATURE
<222> LOCATION: (8)..(9)
<223> OTHER INFORMATION: Engineered PD-L1 binding motif sequence

<400> SEQUENCE: 845

Ala Asp Asn Asn Phe Asn Lys Xaa Asp Pro Ser Gln Ser Ala Asn Leu
1               5                   10                  15

Leu Ser Glu Ala Lys Lys Leu Asn Glu Ser Gln Ala Pro Lys
            20                  25                  30


<210> SEQ ID NO 846
<211> LENGTH: 30
<212> TYPE: PRT
<213> ORGANISM: Artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif sequence

<400> SEQUENCE: 846

Ala Asp Asn Lys Phe Asn Lys Xaa Asp Pro Ser Gln Ser Ala Asn Leu
1               5                   10                  15

Leu Ala Glu Ala Lys Lys Leu Asn Asp Ala Gln Ala Pro Lys
            20                  25                  30


<210> SEQ ID NO 847
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif sequence

<400> SEQUENCE: 847

Ala Asp Asn Lys Phe Asn Lys Xaa Asp Pro Ser Val Ser Lys Glu Ile
1               5                   10                  15

Leu Ala Glu Ala Lys Lys Leu Asn Asp Ala Gln Ala Pro Lys
            20                  25                  30


<210> SEQ ID NO 848
<211> LENGTH: 33
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (11)..(11)
<223> OTHER INFORMATION: Engineered PD-L1 binding motif

<400> SEQUENCE: 848

Ala Asp Ala Gln Gln Asn Asn Phe Asn Lys Xaa Asp Pro Ser Gln Ser
```

1 5 10 15

Thr Asn Val Leu Gly Glu Ala Lys Lys Leu Asn Glu Ser Gln Ala Pro
20 25 30

Lys

<210> SEQ ID NO 849
<211> LENGTH: 28
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (6)..(6)
<223> OTHER INFORMATION: Engineered PD-L1 binding motif

<400> SEQUENCE: 849

Ala Gln His Asp Glu Xaa Asp Pro Ser Gln Ser Ala Asn Val Leu Gly
1 5 10 15

Glu Ala Gln Lys Leu Asn Asp Ser Gln Ala Pro Lys
20 25

<210> SEQ ID NO 850
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 850

Val Asp Asn Lys Phe Asn Lys Xaa Asp Pro Ser Gln Ser Ala Asn Leu
1 5 10 15

Leu Ala Glu Ala Lys Lys Leu Asn Asp Ala Gln Ala Pro Lys
20 25 30

<210> SEQ ID NO 851
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 851

Ala Glu Ala Lys Tyr Ala Lys Xaa Asp Pro Ser Glu Ser Ser Glu Leu
1 5 10 15

Leu Ser Glu Ala Lys Lys Leu Asn Lys Ser Gln Ala Pro Lys
20 25 30

<210> SEQ ID NO 852
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding polypeptide
<220> FEATURE:

<221> NAME/KEY: MISC_FEATURE
<222> LOCATION: (8)..(8)
<223> OTHER INFORMATION: Engineered PD-L1 binding motif

<400> SEQUENCE: 852

Val Asp Ala Lys Tyr Ala Lys Xaa Asp Pro Ser Gln Ser Ser Glu Leu
1 5 10 15

Leu Ala Glu Ala Lys Lys Leu Asn Asp Ala Gln Ala Pro Lys
20 25 30

<210> SEQ ID NO 853
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 853

Val Asp Ala Lys Tyr Ala Lys Xaa Asp Pro Ser Gln Ser Ser Glu Leu
1 5 10 15

Leu Ala Glu Ala Lys Lys Leu Asn Asp Ser Gln Ala Pro Lys
20 25 30

<210> SEQ ID NO 854
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: misc
<222> LOCATION: (8)..(8)
<223> OTHER INFORMATION: Engineered PD-L1 binding motif

<400> SEQUENCE: 854

Ala Glu Ala Lys Tyr Ala Lys Xaa Asp Pro Ser Gln Ser Ser Glu Leu
1 5 10 15

Leu Ser Glu Ala Lys Lys Leu Asn Asp Ser Gln Ala Pro Lys
20 25 30

<210> SEQ ID NO 855
<211> LENGTH: 29
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 855

Ala Glu Ala Lys Tyr Ala Lys Xaa Asp Pro Ser Gln Ser Ser Glu Leu
1 5 10 15

Leu Ser Glu Ala Lys Lys Leu Asn Asp Ser Gln Ala Pro
20 25

<210> SEQ ID NO 856
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 856

Ala Glu Ala Lys Phe Ala Lys Xaa Asp Pro Ser Gln Ser Ser Glu Leu
1 5 10 15

Leu Ser Glu Ala Lys Lys Leu Asn Asp Ser Gln Ala Pro Lys
20 25 30

<210> SEQ ID NO 857
<211> LENGTH: 29
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 857

Ala Glu Ala Lys Phe Ala Lys Xaa Asp Pro Ser Gln Ser Ser Glu Leu
1 5 10 15

Leu Ser Glu Ala Lys Lys Leu Asn Asp Ser Gln Ala Pro
20 25

<210> SEQ ID NO 858
<211> LENGTH: 30
<212> TYPE: PRT
<213> ORGANISM: Artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 858

Ala Glu Ala Lys Tyr Ala Lys Xaa Asp Pro Ser Gln Ser Ser Glu Leu
1 5 10 15

Leu Ala Glu Ala Lys Lys Leu Asn Asp Ala Gln Ala Pro Lys
20 25 30

<210> SEQ ID NO 859
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 859

Ala Glu Ala Lys Tyr Ala Lys Xaa Asp Pro Ser Gln Ser Ser Glu Leu
1 5 10 15

Leu Ser Glu Ala Lys Lys Leu Ser Glu Ser Gln Ala Pro Lys
20 25 30

<210> SEQ ID NO 860
<211> LENGTH: 29
<212> TYPE: PRT
<213> ORGANISM: artificial sequence
<220> FEATURE:

<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 860

Ala Glu Ala Lys Tyr Ala Lys Xaa Asp Pro Ser Gln Ser Ser Glu Leu
1 5 10 15

Leu Ser Glu Ala Lys Lys Leu Ser Glu Ser Gln Ala Pro
20 25

<210> SEQ ID NO 861
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 861

Ala Glu Ala Lys Phe Ala Lys Xaa Asp Pro Ser Gln Ser Ser Glu Leu
1 5 10 15

Leu Ser Glu Ala Lys Lys Leu Ser Glu Ser Gln Ala Pro Lys
20 25 30

<210> SEQ ID NO 862
<211> LENGTH: 29
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 862

Ala Glu Ala Lys Phe Ala Lys Xaa Asp Pro Ser Gln Ser Ser Glu Leu
1 5 10 15

Leu Ser Glu Ala Lys Lys Leu Ser Glu Ser Gln Ala Pro
20 25

<210> SEQ ID NO 863
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 863

Ala Glu Ala Lys Tyr Ala Lys Xaa Asp Pro Ser Gln Ser Ser Glu Leu
1 5 10 15

Leu Ala Glu Ala Lys Lys Leu Ser Glu Ala Gln Ala Pro Lys
20 25 30

<210> SEQ ID NO 864
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 864

```
Ala Glu Ala Lys Tyr Ala Lys Xaa Gln Pro Glu Gln Ser Ser Glu Leu
1               5                   10                  15

Leu Ser Glu Ala Lys Lys Leu Ser Glu Ser Gln Ala Pro Lys
            20                  25                  30
```

<210> SEQ ID NO 865
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 865

```
Ala Glu Ala Lys Tyr Ala Lys Xaa Asp Pro Ser Gln Ser Ser Glu Leu
1               5                   10                  15

Leu Ser Glu Ala Lys Lys Leu Glu Ser Ser Gln Ala Pro Lys
            20                  25                  30
```

<210> SEQ ID NO 866
<211> LENGTH: 29
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 866

```
Ala Glu Ala Lys Tyr Ala Lys Xaa Asp Pro Ser Gln Ser Ser Glu Leu
1               5                   10                  15

Leu Ser Glu Ala Lys Lys Leu Glu Ser Ser Gln Ala Pro
            20                  25
```

<210> SEQ ID NO 867
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 867

```
Ala Glu Ala Lys Tyr Ala Lys Xaa Asp Pro Ser Gln Ser Ser Glu Leu
1               5                   10                  15

Leu Ala Glu Ala Lys Lys Leu Glu Ser Ala Gln Ala Pro Lys
            20                  25                  30
```

<210> SEQ ID NO 868
<211> LENGTH: 30
<212> TYPE: PRT

<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 868

Ala Glu Ala Lys Tyr Ala Lys Xaa Gln Pro Glu Gln Ser Ser Glu Leu
1 5 10 15

Leu Ser Glu Ala Lys Lys Leu Glu Ser Ser Gln Ala Pro Lys
20 25 30

<210> SEQ ID NO 869
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 869

Ala Glu Ala Lys Tyr Ala Lys Xaa Asp Pro Ser Gln Ser Ser Glu Leu
1 5 10 15

Leu Ser Glu Ala Lys Lys Leu Ser Asp Ser Gln Ala Pro Lys
20 25 30

<210> SEQ ID NO 870
<211> LENGTH: 29
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 870

Ala Glu Ala Lys Tyr Ala Lys Xaa Asp Pro Ser Gln Ser Ser Glu Leu
1 5 10 15

Leu Ser Glu Ala Lys Lys Leu Ser Asp Ser Gln Ala Pro
20 25

<210> SEQ ID NO 871
<211> LENGTH: 30
<212> TYPE: PRT
<213> ORGANISM: artificial sequence
<220> FEATURE:
<223> OTHER INFORMATION: Engineered PD-L1 binding polypeptide
<220> FEATURE:
<221> NAME/KEY: MISC_FEATURE
<222> LOCATION: (8)..(8)
<223> OTHER INFORMATION: Engineered PD-L1 binding motif

<400> SEQUENCE: 871

Ala Glu Ala Lys Tyr Ala Lys Xaa Asp Pro Ser Gln Ser Ser Glu Leu
1 5 10 15

Leu Ala Glu Ala Lys Lys Leu Ser Asp Ser Gln Ala Pro Lys
20 25 30

<210> SEQ ID NO 872
<211> LENGTH: 30

<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding polypeptide

<400> SEQUENCE: 872

```
Ala Glu Ala Lys Tyr Ala Lys Xaa Asp Pro Ser Gln Ser Ser Glu Leu
1               5                   10                  15

Leu Ala Glu Ala Lys Lys Leu Ser Asp Ala Gln Ala Pro Lys
            20                  25                  30
```

<210> SEQ ID NO 873
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 873

```
Ala Glu Ala Lys Tyr Ala Lys Xaa Gln Pro Glu Gln Ser Ser Glu Leu
1               5                   10                  15

Leu Ser Glu Ala Lys Lys Leu Ser Asp Ser Gln Ala Pro Lys
            20                  25                  30
```

<210> SEQ ID NO 874
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 874

```
Val Asp Ala Lys Tyr Ala Lys Xaa Asp Pro Ser Gln Ser Ser Glu Leu
1               5                   10                  15

Leu Ser Glu Ala Lys Lys Leu Asn Asp Ser Gln Ala Pro Lys
            20                  25                  30
```

<210> SEQ ID NO 875
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 875

```
Val Asp Ala Lys Tyr Ala Lys Xaa Asp Pro Ser Gln Ser Ser Glu Leu
1               5                   10                  15

Leu Ala Glu Ala Lys Lys Leu Asn Asp Ala Gln Ala Pro Lys
            20                  25                  30
```

<210> SEQ ID NO 876

```
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 876

Val Asp Ala Lys Tyr Ala Lys Xaa Asp Pro Ser Gln Ser Ser Glu Leu
1               5                   10                  15

Leu Ser Glu Ala Lys Lys Leu Ser Glu Ser Gln Ala Pro Lys
            20                  25                  30


<210> SEQ ID NO 877
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 877

Val Asp Ala Lys Tyr Ala Lys Xaa Asp Pro Ser Gln Ser Ser Glu Leu
1               5                   10                  15

Leu Ala Glu Ala Lys Lys Leu Ser Glu Ala Gln Ala Pro Lys
            20                  25                  30


<210> SEQ ID NO 878
<211> LENGTH: 30
<212> TYPE: PRT
<213> ORGANISM: artificial sequence
<220> FEATURE:
<223> OTHER INFORMATION: engineered PD-L1 binding polyppetide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 878

Val Asp Ala Lys Tyr Ala Lys Xaa Gln Pro Glu Gln Ser Ser Glu Leu
1               5                   10                  15

Leu Ser Glu Ala Lys Lys Leu Ser Glu Ser Gln Ala Pro Lys
            20                  25                  30


<210> SEQ ID NO 879
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 879

Val Asp Ala Lys Tyr Ala Lys Xaa Asp Pro Ser Gln Ser Ser Glu Leu
1               5                   10                  15

Leu Ser Glu Ala Lys Lys Leu Glu Ser Ser Gln Ala Pro Lys
            20                  25                  30
```

<210> SEQ ID NO 880
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: enginerred PD-L1 binding motif

<400> SEQUENCE: 880

```
Val Asp Ala Lys Tyr Ala Lys Xaa Asp Pro Ser Gln Ser Ser Glu Leu
1               5                   10                  15

Leu Ala Glu Ala Lys Lys Leu Glu Ser Ala Gln Ala Pro Lys
            20                  25                  30
```

<210> SEQ ID NO 881
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 881

```
Val Asp Ala Lys Tyr Ala Lys Xaa Gln Pro Glu Gln Ser Ser Glu Leu
1               5                   10                  15

Leu Ser Glu Ala Lys Lys Leu Glu Ser Ser Gln Ala Pro Lys
            20                  25                  30
```

<210> SEQ ID NO 882
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 882

```
Val Asp Ala Lys Tyr Ala Lys Xaa Asp Pro Ser Gln Ser Ser Glu Leu
1               5                   10                  15

Leu Ser Glu Ala Lys Lys Leu Ser Asp Ser Gln Ala Pro Lys
            20                  25                  30
```

<210> SEQ ID NO 883
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 883

```
Val Asp Ala Lys Tyr Ala Lys Xaa Asp Pro Ser Gln Ser Ser Glu Leu
1               5                   10                  15

Leu Ala Glu Ala Lys Lys Leu Ser Asp Ser Gln Ala Pro Lys
            20                  25                  30
```

<210> SEQ ID NO 884
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 884

Val Asp Ala Lys Tyr Ala Lys Xaa Asp Pro Ser Gln Ser Ser Glu Leu
1 5 10 15

Leu Ala Glu Ala Lys Lys Leu Ser Asp Ala Gln Ala Pro Lys
20 25 30

<210> SEQ ID NO 885
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 885

Val Asp Ala Lys Tyr Ala Lys Xaa Gln Pro Glu Gln Ser Ser Glu Leu
1 5 10 15

Leu Ser Glu Ala Lys Lys Leu Ser Asp Ser Gln Ala Pro Lys
20 25 30

<210> SEQ ID NO 886
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 886

Val Asp Ala Lys Tyr Ala Lys Xaa Asp Pro Ser Gln Ser Ser Glu Leu
1 5 10 15

Leu Ala Glu Ala Lys Lys Leu Asn Lys Ala Gln Ala Pro Lys
20 25 30

<210> SEQ ID NO 887
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 887

Ala Glu Ala Lys Tyr Ala Lys Xaa Asp Pro Ser Gln Ser Ser Glu Leu
1 5 10 15

Leu Ala Glu Ala Lys Lys Leu Asn Lys Ala Gln Ala Pro Lys
20 25 30

<210> SEQ ID NO 888
<211> LENGTH: 30
<212> TYPE: PRT
<213> ORGANISM: artificial sequence
<220> FEATURE:
<223> OTHER INFORMATION: engineered PD-L1 binding polypeptide
<220> FEATURE:
<221> NAME/KEY: MISC_FEATURE
<222> LOCATION: (8)..(8)
<223> OTHER INFORMATION: engineered PD-L1 binding motif

<400> SEQUENCE: 888

```
Ala Asp Ala Lys Tyr Ala Lys Xaa Asp Pro Ser Gln Ser Ser Glu Leu
1               5                   10                  15

Leu Ser Glu Ala Lys Lys Leu Asn Asp Ser Gln Ala Pro Lys
            20                  25                  30
```

<210> SEQ ID NO 889
<211> LENGTH: 6
<212> TYPE: PRT
<213> ORGANISM: artificial sequence
<220> FEATURE:
<223> OTHER INFORMATION: His6-tag

<400> SEQUENCE: 889

```
His His His His His His
1               5
```

<210> SEQ ID NO 890
<211> LENGTH: 6
<212> TYPE: PRT
<213> ORGANISM: ARTIFICial sequence
<220> FEATURE:
<223> OTHER INFORMATION: HEHEHE tag

<400> SEQUENCE: 890

```
His Glu His Glu His Glu
1               5
```

<210> SEQ ID NO 891
<211> LENGTH: 5
<212> TYPE: PRT
<213> ORGANISM: artificial sequence
<220> FEATURE:
<223> OTHER INFORMATION: linker

<400> SEQUENCE: 891

```
Gly Gly Gly Gly Ser
1               5
```

<210> SEQ ID NO 892
<211> LENGTH: 5
<212> TYPE: PRT
<213> ORGANISM: artificial sequence
<220> FEATURE:
<223> OTHER INFORMATION: linker

<400> SEQUENCE: 892

```
Ser Ser Ser Ser Gly
1               5
```

<210> SEQ ID NO 893
<211> LENGTH: 15
<212> TYPE: PRT
<213> ORGANISM: artificial sequence
<220> FEATURE:

<223> OTHER INFORMATION: llinker

<400> SEQUENCE: 893

Ser Ser Ser Ser Gly Ser Ser Ser Ser Gly Ser Ser Ser Ser Gly
1 5 10 15

<210> SEQ ID NO 894
<211> LENGTH: 20
<212> TYPE: PRT
<213> ORGANISM: artificial sequence
<220> FEATURE:
<223> OTHER INFORMATION: linker

<400> SEQUENCE: 894

Ser Ser Ser Ser Gly Ser Ser Ser Ser Gly Ser Ser Ser Ser Gly Ser
1 5 10 15

Ser Ser Ser Gly
20

<210> SEQ ID NO 895
<211> LENGTH: 15
<212> TYPE: PRT
<213> ORGANISM: artificial sequence
<220> FEATURE:
<223> OTHER INFORMATION: linker

<400> SEQUENCE: 895

Gly Gly Gly Gly Ser Gly Gly Gly Gly Ser Gly Gly Gly Gly Ser
1 5 10 15

<210> SEQ ID NO 896
<211> LENGTH: 18
<212> TYPE: PRT
<213> ORGANISM: artificial sequence
<220> FEATURE:
<223> OTHER INFORMATION: fusion construct of Z variant with ABD
<220> FEATURE:
<221> NAME/KEY: MISC_FEATURE
<222> LOCATION: (9)..(9)
<223> OTHER INFORMATION: Z variant
<220> FEATURE:
<221> NAME/KEY: MISC_FEATURE
<222> LOCATION: (14)..(14)
<223> OTHER INFORMATION: Albumin binding domain (ABD)

<400> SEQUENCE: 896

Ala Gln His Asp Glu Ala Leu Glu Xaa Val Asp Tyr Val Xaa Tyr Val
1 5 10 15

Pro Gly

<210> SEQ ID NO 897
<211> LENGTH: 15
<212> TYPE: PRT
<213> ORGANISM: artificial sequence
<220> FEATURE:
<223> OTHER INFORMATION: subcloned encoded sequence with Z variant
<220> FEATURE:
<221> NAME/KEY: MISC_FEATURE
<222> LOCATION: (13)..(13)
<223> OTHER INFORMATION: Z variant

<400> SEQUENCE: 897

Met Gly Ser Ser His His His His His His Leu Gln Xaa Val Asp
1 5 10 15

POLYPEPTIDE

CROSS-REFERENCE TO RELATED APPLICATIONS

This application is a US National Stage application of International Patent Application Serial No. PCT/EP2016/076040 filed 28 Oct. 2016, which claims priority to European Patent Application Serial Nos. 15192364.6 filed 30 Oct. 2015 and 16157154.2 filed 24 Feb. 2016, all of which are incorporated by reference in their entireties herein.

SEQUENCE LISTING

A Sequence Listing, incorporated herein by reference, is submitted in electronic form as an ASCII text file, created May 1, 2020, named "8JA9262.TXT", size 544 KB.

FIELD OF THE INVENTION

The present disclosure relates to a class of engineered polypeptides having a binding affinity for programmed death-ligand 1 (in the following referred to as PD-L1). The present disclosure also relates to the use of such a PD-L1 binding polypeptide as a therapeutic, prognostic and/or diagnostic agent.

BACKGROUND

Under normal physiologic conditions, the immune checkpoints are crucial for maintaining self-tolerance (i.e. prevent autoimmunity) and for modulating the immune response to protect against tissue damage when the immune system is responding to pathogenic infections. At times, tumor cells can co-opt certain immune checkpoint pathways to escape from immunesurveillance mechanisms. Inhibition of immune checkpoints has therefore emerged as a promising approach in cancer immunotherapy. The two immune checkpoint receptors that have been most actively studied in this context are the cytotoxic T-lymphocyte-associated antigen (CTLA-4; also known as CD152) and programmed cell death protein 1 (PD-1; also known as CD279), which regulate the immune response at different levels. CTLA-4 primarily regulates immune responses early in T-cell activation, whereas PD-1 primarily limits the activity of T-cells in the effector phase within tissues and tumors (Pardoll, 2012, Nat. Rev. Cancer, 12:252-64).

PD-1 has two known ligands: programmed death-ligand 1 (PD-L1; also known as human B7 homolog 1, B7-H1, or cluster of differentiation 274, CD274) and programmed death-ligand 2 (PD-L2; also known as B7-DC and CD273). Both ligands belong to the B7 immunoglobulin superfamily and are type I transmembrane glycoproteins composed of IgC- and IgV-type extracellular domains. However, it was recently reported that PD-L1 and PD-L2, as well as PD-1, also exist in soluble forms in addition to being membrane bound. PD-L1 and PD-L2 share approximately 40% amino acid residue identity. Whereas the expression of PD-L2 is mainly limited to antigen presenting cells, PD-L1 is expressed in both hematopoietic and non-hematopoietic cells. High tumor expression of PD-L1 is associated with increased aggressiveness and worse prognosis (Dai et al, 2014, Cellular Immunology, 290:72-79).

The clinical significance of targeting immune checkpoint pathways has been demonstrated with several monoclonal antibodies inhibiting CTLA-4, PD-1 and PD-L1, which work by restoring protective immune responses to tumor cells. The anti-CTLA-4 antibody ipilimumab (Yervoy®, Bristol Myers Squibb) was approved by FDA in 2011 for the treatment patients with metastatic melanoma where a durable response was observed in 10-15% of the patients. However, ipilimumab is associated with immune-related toxicities, potentially due to its role in the priming phase of the immune response thereby also affecting normal tissues. A safer approach may be to target the PD-1/PD-L1 pathway to restore anti-tumor immunity selectively within the tumor microenvironment. Inhibition of the PD-1/PD-L1 pathway has demonstrated durable response in 30-35% of patients with advanced melanoma, which in 2014 resulted in the FDA approval of the anti-PD-1 antibodies pembrolizumab (formerly lambrolizumab; Keytruda®, Merck) and nivolumab (Bristol Myers Squibb and Ono Pharmaceutical) (Shin and Ribas, 2015, Curr. Opin. Immunol., 33:23-35; Philips and Atkins, 2015, International Immunology, 27:39-46). The first PD-L1 targeting antibody investigated in clinical trials was MDX-1105 which was evaluated in a Phase I study in patients with advanced solid tumors including melanoma, non-small cell lung cancer (NSCLC), colorectal cancer, renal cell carcinoma, ovarian cancer, pancreatic cancer, gastric cancer and breast cancer (Momtaz and Postow, 2014, Pharmgenomics Pers Med. 7:357-65). The results demonstrated potential benefits of PD-L1 blockade. Other antibodies against PD-L1 that are currently in Phase III clinical trials include atezolizumab (MDPL3280A, Genentech), durvalumab (MED14736, MedImmune/Astra Zeneca, Celgene), and avelumab (MSB0010718C, EMD Serono, Pfizer).

To improve the efficacy and increase the number of patients that respond to immunotherapy, it may be beneficial to target the antitumor immune response at multiple levels. This may be achieved through synergistic combinations. For instance, preclinical studies combining CTLA-4 and PD-1 blocking antibodies (ipilimumab and nivolumab) has demonstrated superior antitumor activity, but with a toxicity similar to anti-CTLA-4 monotherapy (Shin and Ribas, 2015, supra). Furthermore, PD-L1 is speculated to be a potential biomarker, due to its abundance in the tumor microenvironment and because tumor expression of PD-L1 has a strong association with response to anti-PD-1/PD-L1 therapy.

The high prevalence of cancer and infectious diseases, together with a high unmet medical need, warrants the development of new modes of treatment. Since tissue penetration rate is negatively associated with the size of the molecule, a relatively large antibody molecule inherently has poor tissue distribution and penetration capacity.

Thus, the use of monoclonal antibodies is not always optimal for therapy and there is continued need for provision of agents with a high affinity for PD-L1. Of great interest is also the provision of uses of such molecules in the treatment, diagnosis and prognosis of PD-L1 related disorders.

SUMMARY OF THE INVENTION

It is an object of the present disclosure to provide new PD-L1 binding agents, which could for example be used for therapeutic, prognostic and diagnostic applications.

It is an object of the present disclosure to provide a new multispecific agent, such as a bispecific agent, which has affinity for PD-L1 and at least one additional antigen.

It is an object of the present disclosure to provide a molecule allowing for efficient therapy of for example various forms of cancer and infectious disease, while alleviating the abovementioned and other drawbacks of current therapies.

It is an object of the present disclosure to provide a molecule suitable for prognostic and diagnostic applications, for example prognostic and diagnostic application in relation to various forms of cancer and infectious disease.

These and other objects, which are evident to the skilled person from the present disclosure, are met by the different aspects of the invention as claimed in the appended claims and as generally disclosed herein.

Thus, in the first aspect of the disclosure, there is provided a PD-L1 binding polypeptide, comprising a PD-L1 binding motif BM, which motif consists of an amino acid sequence selected from:

(SEQ ID NO: 837)

i) ERN$X_4$AA$X_7$EIL $X_{11}$LPNL$X_{16}$X17$X_{18}$Q$X_{20}$ WAFIW$X_{26}$L$X_{28}$D wherein, independently from each other, $X_4$ is selected from A, D, E, F, H, I, K, L, N, Q, R, S, T, V and Y;

$X_7$ is selected from A, E, F, H, N, Q, S, T, V, W and Y;

$X_{11}$ is selected from A, D, E, F, H, K, L, N, Q, R, S, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, N, Q, R, T, V and Y;

$X_{26}$ is selected from K and S; and $X_{28}$ is selected from A, D and E;

and ii) an amino acid sequence which has at least 96% identity to the sequence defined in i).

The above definition of a class of sequence related, PD-L1 binding polypeptides is based on a statistical analysis of a number of random polypeptide variants of a parent scaffold, that were selected for their interaction with PD-L1 in selection experiments. The identified PD-L1 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present disclosure, the random variation of binding surface residues and subsequent selection of variants have replaced the Fc interaction capacity with a capacity for interaction with PD-L1.

As the skilled person will realize, the function of any polypeptide, such as the PD-L1 binding capacity of the polypeptide of the present disclosure, is dependent on the tertiary structure of the polypeptide. It is therefore possible to make minor changes to the sequence of amino acids in a polypeptide without affecting the function thereof. Thus, the disclosure encompasses modified variants of the PD-L1 binding polypeptide, which have retained PD-L1 binding characteristics.

In this way, encompassed by the present disclosure is a PD-L1 binding polypeptide comprising an amino acid sequence with 96% or greater identity to a polypeptide as defined in i). For example, it is possible that an amino acid residue belonging to a certain functional grouping of amino acid residues (e.g. hydrophobic, hydrophilic, polar etc) could be exchanged for another amino acid residue from the same functional group.

In some embodiments, such changes may be made in any position of the sequence of the PD-L1 binding polypeptide as disclosed herein. In other embodiments, such changes may be made only in the non-variable positions, also denoted scaffold amino acid residues. In such cases, changes are not allowed in the variable positions. In other embodiments, such changes may be only in the variable positions. According to one definition of such "variable positions", these are positions denoted with an "X" in sequence i) as defined above. According to another definition, "variable positions" are those positions that are randomized in a selection library of Z variants prior to selection, and may thus for example be positions 2, 3, 4, 6, 7, 10, 11, 17, 18, 20, 21, 25 and 28 in sequence i), as illustrated in Example 1.

The term "% identity", as used throughout the specification, may for example be calculated as follows. The query sequence is aligned to the target sequence using the CLUSTAL W algorithm (Thompson et al., (1994) Nucleic Acids Research, 22: 4673-4680). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared and the percentage of positions in the query sequence that have identical correspondences in the target sequence is reported as % identity.

In another embodiment, there is provided a PD-L1 binding polypeptide wherein in sequence i)

$X_4$ is selected from A, D, E, F, H, I, K, L, N, Q, R, S, T, V and Y;

$X_7$ is selected from E, F, H, N, Q, S, T, V, W and Y;

$X_{11}$ is selected from A, D, H, L, Q, R, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, Q, R, T, V and Y;

$X_{26}$ is selected from K and S; and $X_{28}$ is selected from A, D and E.

In another embodiment, there is provided a PD-L1 binding polypeptide, wherein in sequence i)

$X_4$ is selected from A, D, E, F, H, I, K, L, N, Q, R, S, T, V and Y;

$X_7$ is selected from A, E, F, H, N, Q, S, T, V, W and Y;

$X_{11}$ is selected from A, D, E, F, H, K, L, N, Q, R, S, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, N, Q, R, T, V and Y;

$X_{26}$ is selected from K and S; and $X_{28}$ is selected from A, D and E.

In yet another embodiment, there is provided a PD-L1 binding polypeptide, wherein in sequence i)

$X_4$ is selected from A, D, E, F, H, I, K, L, N, Q, R, S, T and V;

$X_7$ is selected from F, H, Q and Y;

$X_{11}$ is selected from H, Q, W and Y;

$X_{16}$ is selected from N and T;

$X_{17}$ is selected from A, H, K, N, Q and S;

$X_{18}$ is selected from A, E, G, H, K, L, N, Q, R, S, T, V and Y;

$X_{20}$ is selected from H, I, K, Q, R and V;

$X_{26}$ is selected from K and S; and $X_{28}$ is selected from A and D.

As used herein, "$X_n$" and "$X_m$" are used to indicate amino acids in positions n and m in the sequence i) as defined above, wherein n and m are integers which indicate the position of an amino acid within said sequence as counted from the N-terminal end of said sequence. For example, $X_3$ and $X_7$ indicate the amino acid in position three and seven, respectively, from the N-terminal end of sequence i).

In embodiments according to the first aspect, there are provided polypeptides wherein $X_n$ in sequence i) is independently selected from a group of possible residues according to Table 1. The skilled person will appreciate that $X_n$ may be selected from any one of the listed groups of possible residues and that this selection is independent from the selection of amino acids in $X_m$, wherein n/m. Thus, any of the listed possible residues in position $X_n$ in Table 1 may be independently combined with any of the listed possible residues any other variable position in Table 1.

The skilled person will appreciate that Table 1 is to be read as follows: In one embodiment according to the first aspect, there is provided a polypeptide wherein amino acid residue "$X_n$" in sequence i) is selected from "Possible residues". Thus, Table 1 discloses several specific and individualized embodiments of the first aspect of the present disclosure. For example, in one embodiment according to the first aspect, there is provided a polypeptide wherein $X_4$ in sequence i) is selected from A, D, E, I, K, L, N, Q, S and T, and in another embodiment according to the first aspect, there is provided a polypeptide wherein $X_4$ in sequence i) is selected from A, D, E, I, K, Q, S and T. For avoidance of doubt, the listed embodiments may be freely combined in yet other embodiments. For example, one such combined embodiment is a polypeptide in which $X_4$ is selected from A, D, E, I, K, Q, S and T, while $X_7$ is selected from F, H, Q and Y, and $X_{18}$ is selected from A, L, K and S.

TABLE 1

| $X_n$ | Possible residues |
|---|---|
| $X_4$ | A, D, E, F, H, I, K, L, N, Q, R, S, T and V |
| $X_4$ | A, D, E, F, H, I, K, L, N, Q, R, S and T |
| $X_4$ | A, D, E, F, H, I, K, L, N, Q, S and T |
| $X_4$ | A, D, E, K, L, N, Q, S and T |
| $X_4$ | A, D, E, I, K, L, N, Q, S and T |
| $X_4$ | A, D, E, K, L, N, Q, and S |
| $X_4$ | A, D, E, I, K, Q, S and T |
| $X_4$ | A, E, K, L, N, Q, and S |
| $X_4$ | E, I, K, L, N, Q, S and T |
| $X_4$ | A, D, K, L, N, and S |
| $X_4$ | A, K, L, N, and S |
| $X_4$ | A, D, E, Q and S |
| $X_4$ | A, D, E, K, and S |
| $X_4$ | A, K, L, and S |
| $X_4$ | A, D, E and S |
| $X_4$ | A, E, Q and S |
| $X_4$ | A, E, K and S |
| $X_4$ | L, N, S and T |
| $X_4$ | L, S and T |
| $X_4$ | A, D and K |
| $X_4$ | A, E and S |
| $X_4$ | A, E and K |
| $X_4$ | A, D |
| $X_4$ | A, K |
| $X_4$ | D, K |
| $X_4$ | A, E |
| $X_4$ | A, S |
| $X_4$ | E, S |
| $X_4$ | E, K |
| $X_4$ | L, S |
| $X_4$ | L, T |
| $X_4$ | S, T |
| $X_4$ | E |
| $X_4$ | A |
| $X_4$ | D |
| $X_4$ | K |
| $X_4$ | S |
| $X_4$ | L |

TABLE 1-continued

| $X_n$ | Possible residues |
|---|---|
| $X_4$ | T |
| $X_7$ | E, F, H, N, Q, S, T, V, W and Y |
| $X_7$ | E, F, H, N, Q, S, V, W and Y |
| $X_7$ | E, F, H, N, Q, S, T, V and Y |
| $X_7$ | E, F, H, N, Q, S, T, W and Y |
| $X_7$ | E, F, H, Q, S, T, V, W and Y |
| $X_7$ | E, F, H, N, Q, S, V and Y |
| $X_7$ | E, F, H, N, Q, S and Y |
| $X_7$ | E, F, H, Q, S and Y |
| $X_7$ | E, F, H, Q and Y |
| $X_7$ | F, H, Q and Y |
| $X_7$ | F, Q and Y |
| $X_7$ | H, Q and Y |
| $X_7$ | F, Y |
| $X_7$ | F, Q |
| $X_7$ | Q, Y |
| $X_7$ | F |
| $X_7$ | Q |
| $X_7$ | Y |
| $X_7$ | H |
| $X_{11}$ | A, D, E, F, H, K, N, Q, R, S, T, W and Y |
| $X_{11}$ | D, E, F, H, K, N, Q, R, S, T, W and Y |
| $X_{11}$ | D, E, H, K, N, Q, R, S, T, W and Y |
| $X_{11}$ | E, H, K, N, Q, R, S, T, W and Y |
| $X_{11}$ | E, H, K, N, Q, S, T, W and Y |
| $X_{11}$ | E, H, K, N, Q, W and Y |
| $X_{11}$ | A, D, H, L, Q, R, T, V, W and Y |
| $X_{11}$ | H, Q, W and Y |
| $X_{11}$ | Q, Y |
| $X_{11}$ | W, Y |
| $X_{11}$ | H, Y |
| $X_{11}$ | H |
| $X_{11}$ | Y |
| $X_{16}$ | N |
| $X_{16}$ | T |
| $X_{17}$ | A, H, K, N, Q and S |
| $X_{17}$ | A, K, N, Q, R and S |
| $X_{17}$ | A, K, N, Q and S |
| $X_{17}$ | A, N, Q and S |
| $X_{17}$ | K, N, Q and S |
| $X_{17}$ | N, Q and S |
| $X_{17}$ | N, Q |
| $X_{17}$ | N, S |
| $X_{17}$ | N |
| $X_{17}$ | Q |
| $X_{17}$ | S |
| $X_{18}$ | A, E, G, H, K, L, N, Q, R, S, T, V and Y |
| $X_{18}$ | A, E, G, H, K, L, N, Q, R, S, T and Y |
| $X_{18}$ | A, E, G, H, K, L, N, Q, R, S, and Y |
| $X_{18}$ | A, E, G, H, K, L, N, Q, R and S |
| $X_{18}$ | A, E, G, K, N, Q, R and S |
| $X_{18}$ | A, G, H, L, N, Q, S and Y |
| $X_{18}$ | A, G, N, Q and S |
| $X_{18}$ | A, H, Q and S |
| $X_{18}$ | A, H and Q |
| $X_{18}$ | A, L, K and S |
| $X_{18}$ | A, K, Q and S |
| $X_{18}$ | A, Q and S |
| $X_{18}$ | A, G |
| $X_{18}$ | A, Q |
| $X_{18}$ | A |
| $X_{18}$ | Q |
| $X_{18}$ | G |
| $X_{18}$ | S |
| $X_{18}$ | H |
| $X_{20}$ | H, I, K, L, Q, R, T, V and Y |
| $X_{20}$ | H, I, K, L, Q, R, V and Y |
| $X_{20}$ | H, I, K, Q, R and V |
| $X_{20}$ | H, I, K and R |
| $X_{20}$ | H, I and K |
| $X_{20}$ | H, K and R |
| $X_{20}$ | K and R |
| $X_{20}$ | I, K |
| $X_{20}$ | I, H |
| $X_{20}$ | H, K |
| $X_{20}$ | H |
| $X_{20}$ | I |
| $X_{20}$ | K |

TABLE 1-continued

| $X_n$ | Possible residues |
|---|---|
| $X_{20}$ | R |
| $X_{26}$ | K |
| $X_{26}$ | S |
| $X_{28}$ | A, D |
| $X_{28}$ | A, E |
| $X_{28}$ | D, E |
| $X_{28}$ | A |
| $X_{28}$ | D |
| $X_{28}$ | E |

In one particular embodiment according to the first aspect, there is provided a polypeptide wherein sequence i) fulfills at least four of the seven conditions I-VII:

I. $X_7$ is selected from F, H, Q and Y;

II. $X_{11}$ is selected from H and Y;

III. $X_{16}$ is T;

IV. $X_{17}$ is selected from N, Q and S;

V. $X_{20}$ is selected from H, I, K and R;

VI. $X_{26}$ is K; and

VII. $X_{28}$ is A or D.

In one embodiment, sequence i) fulfills at least five of the seven conditions I-VII, such as least six of the seven conditions I-VII. In one particular embodiment, sequence i) fulfills all of the seven conditions I-VII.

In some embodiments of a PD-L1 binding polypeptide according to the first aspect, $X_7X_{11}X_{20}$ is selected from FYK and YYK. In some embodiments, $X_{11}X_{17}X_{20}$ is selected from YNK and YQK. In some embodiments, $X_{11}X_{18}X_{20}$ is YAK.

As described in detail in the experimental section to follow, the selection of PD-L1 binding polypeptide variants has led to the identification of a number of individual PD-L1 binding motif (BM) sequences. These sequences constitute individual embodiments of sequence i) according to this aspect. The sequences of individual PD-L1 binding motifs correspond to amino acid positions 8-36 in SEQ ID NO:1-808 presented in FIG. 1A-1CC. Hence, in one embodiment of the PD-L1 binding polypeptide according to this aspect, sequence i) corresponds to the sequence from position 8 to position 36 in a sequence selected from the group consisting of SEQ ID NO:1-808. In one embodiment, sequence i) corresponds to the sequence from position 8 to position 36 in a sequence selected from the group consisting of SEQ ID NO:1-93 and 774-796, such as the group consisting of SEQ ID NO:1-93 and 774-787. In one embodiment, sequence i) corresponds to the sequence from position 8 to position 36 in a sequence selected from the group consisting of SEQ ID NO:1-93, 775, 776, 779-781 and 784-786, such as the group consisting of SEQ ID NO:1-93, 776, 780, 781, 784 and 786, such as the group consisting of SEQ ID NO:1-93, 776, 781 and 784, such as the group consisting of SEQ ID NO:1-93, 776 and 784 or the group consisting of SEQ ID NO:1-93, 776 and 781, for example the group consisting of SEQ ID NO:1-93 and 776 or the group consisting of SEQ ID NO:1-93 and 781 or the group consisting of SEQ ID NO:1-93 and 784. In one embodiment, sequence i) corresponds to the sequence from position 8 to position 36 in a sequence selected from the group consisting of SEQ ID NO:1-93, 774, 775 and 780-786, such as the group consisting of SEQ ID NO:1-93, 775, 780, 781, 784 and 786. In one embodiment, sequence i) corresponds to the sequence from position 8 to position 36 in a sequence selected from the group consisting of SEQ ID NO:1, 2, 17, 776 and 781, such as the group consisting of SEQ ID NO: 1, 2 and 776. In one embodiment, sequence i) corresponds to the sequence from position 8 to position 36 in SEQ ID NO:1, SEQ ID NO:2 or SEQ ID NO:776. In one embodiment, sequence i) corresponds to the sequence from position 8 to position 36 in a sequence selected from the group consisting of SEQ ID NO:1-93. In one embodiment, sequence i) corresponds to the sequence from position 8 to position 36 in a sequence selected from the group consisting of SEQ ID NO:1, 3-8, 11, 13, 16, 18, 20, 22, 23, 43 and 73. In one embodiment, sequence i) corresponds to the sequence from position 8 to position 36 in a sequence selected from the group consisting of SEQ ID NO:1-24. For example, in one embodiment, sequence i) corresponds to the sequence from position 8 to position 36 in a sequence selected from the group consisting of SEQ ID NO:1-16, such as the group consisting of SEQ ID NO:1, 2, 4, 5, 7, 9 and 10. In another embodiment, sequence i) corresponds to the sequence from position 8 to position 36 in a sequence selected from the group consisting of SEQ ID NO:1, 3-6, 9-10, 12-21, 23 and 24, such as the group consisting of SEQ ID NO:1, 4-6, 9, 14 and 18-21. In one embodiment, sequence i) corresponds to the sequence from position 8 to position 36 in a sequence selected from the group consisting of SEQ ID NO:1-12, 14 and 17-21. In one embodiment, sequence i) corresponds to the sequence from position 8 to position 36 in a sequence selected from the group consisting of SEQ ID NO:1-12 and 17, such as the group consisting of SEQ ID NO:1-5 and 17, such as the group consisting of SEQ ID NO:1, 2 and 17. In one embodiment, sequence i) corresponds to the sequence from position 8 to position 36 in a sequence selected from the group consisting of SEQ ID NO:1, 4, 5, 6, 9, 14 and 18-21, such as the group consisting of SEQ ID NO:4, 5, 18 and 21, such as the group consisting of SEQ ID NO:4, 5 and 21. In one embodiment, sequence i) corresponds to the sequence from position 8 to position 36 in a sequence selected from the group consisting of SEQ ID NO:1, 2, 4, 5 and 21, such as the group consisting of SEQ ID NO:1 and 2. In one embodiment, sequence i) corresponds to the sequence from position 8 to position 36 in SEQ ID NO:1, SEQ ID NO:2, SEQ ID NO:4, SEQ ID NO:5 or SEQ ID NO:21.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Ca backbone of the polypeptide according to this embodiment of the invention is substantially the same as that of the three-helix bundle protein domain of which it forms a part, e.g. having the same elements of secondary structure in the same order etc. Thus, a BM according to the present disclosure "forms part" of a three-helix bundle domain if the polypeptide according to this embodiment has the same fold as the original domain, implying that the basic structural properties are shared, those properties e.g. resulting in similar CD spectra. The skilled person is aware of other parameters that are relevant.

In particular embodiments, the PD-L1 binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal Protein A (Wahlberg E et al, 2003, PNAS 100(6):3185-3190).

In some embodiments where the PD-L1 binding polypeptide as disclosed herein forms part of a three-helix bundle protein domain, the PD-L1 binding polypeptide may comprise a binding module (BMod), the amino acid sequence of which is selected from:

(SEQ ID NO: 838)
iii) K-[*BM*]-DPSQS$X_aX_b$LL$X_c$ EAKKL$X_dX_eX_f$Q;

wherein

[BM] is a PD-L1 binding motif as defined herein;

$X_a$ is selected from A and S;

$X_b$ is selected from N and E;

$X_c$ is selected from A, S and C;

$X_d$ is selected from E, N and S;

$X_e$ is selected from D, E and S; and $X_f$ is selected from A and S; and iv) an amino acid sequence which has at least 93% identity to a sequence defined in iii).

In some embodiments, said polypeptide may beneficially exhibit a high structural stability, such as resistance to chemical modifications, to changes in physical conditions and to proteolysis, during production and storage, as well as in vivo.

As discussed above, polypeptides comprising minor changes as compared to the above amino acid sequences, which do not largely affect the tertiary structure and the function of the polypeptide, are also within the scope of the present disclosure. Thus, in some embodiments, sequence iv) has at least 93%, such as at least 95%, such as at least 97% identity to a sequence defined by iii).

In one embodiment, $X_a$ in sequence iii) is A.

In one embodiment, $X_a$ in sequence iii) is S.

In one embodiment, $X_b$ in sequence iii) is N.

In one embodiment, $X_b$ in sequence iii) is E.

In one embodiment, $X_c$ in sequence iii) is A.

In one embodiment, $X_c$ in sequence iii) is S.

In one embodiment, $X_c$ in sequence iii) is C.

In one embodiment, $X_d$ in sequence iii) is E.

In one embodiment, $X_d$ in sequence iii) is N.

In one embodiment, $X_d$ in sequence iii) is S.

In one embodiment, $X_e$ in sequence iii) is D.

In one embodiment, $X_e$ in sequence iii) is E.

In one embodiment, $X_e$ in sequence iii) is S.

In one embodiment, $X_dX_e$ in sequence iii) is selected from EE, ES, SD, SE and SS.

In one embodiment, $X_dX_e$ in sequence iii) is ES.

In one embodiment, $X_dX_e$ in sequence iii) is SE.

In one embodiment, $X_dX_e$ in sequence iii) is SD.

In one embodiment, $X_f$ in sequence iii) is A.

In one embodiment, $X_f$ in sequence iii) is S.

In one embodiment, in sequence iii), $X_a$ is A; $X_b$ is N; $X_c$ is A and $X_f$ is A.

In one embodiment, in sequence iii), $X_a$ is S; $X_b$ is E; $X_c$ is A and $X_f$ is A.

In one embodiment, in sequence iii), $X_a$ is A; $X_b$ is N; $X_c$ is C and $X_f$ is A.

In one embodiment, in sequence iii), $X_a$ is S; $X_b$ is E; $X_c$ is S and $X_f$ is S.

In one embodiment, in sequence iii), $X_a$ is S; $X_b$ is E; $X_c$ is C and $X_f$ is S.

In one embodiment, in sequence iii), $X_a$ is A; $X_b$ is N; $X_c$ is A; $X_dX_e$ is ND and $X_f$ is A.

In one embodiment, in sequence iii), $X_a$ is S; $X_b$ is E; $X_c$ is A; $X_dX_e$ is ND and $X_f$ is A.

In one embodiment, in sequence iii), $X_a$ is A; $X_b$ is N; $X_c$ is C; $X_dX_e$ is ND and $X_f$ is A.

In one embodiment, in sequence iii), $X_a$ is S; $X_b$ is E; $X_c$ is S; $X_dX_e$ is ND and $X_f$ is S.

In one embodiment, in sequence iii), $X_a$ is S; $X_b$ is E; $X_c$ is C; $X_dX_e$ is ND and $X_f$ is S.

In one embodiment, in sequence iii), $X_a$ is A; $X_b$ is N; $X_c$ is A; $X_dX_e$ is SE and $X_f$ is A.

In one embodiment, in sequence iii), $X_a$ is S; $X_b$ is E; $X_c$ is A; $X_dX_e$ is SE and $X_f$ is A.

In one embodiment, in sequence iii), $X_a$ is A; $X_b$ is N; $X_c$ is C; $X_dX_e$ is SE and $X_f$ is A.

In one embodiment, in sequence iii), $X_a$ is S; $X_b$ is E; $X_c$ is S; $X_dX_e$ is SE and $X_f$ is S.

In one embodiment, in sequence iii), $X_a$ is S; $X_b$ is E; $X_c$ is C; $X_dX_e$ is SE and $X_f$ is S.

In one embodiment, in sequence iii), $X_a$ is A; $X_b$ is N; $X_c$ is A; $X_dX_e$ is SD and $X_f$ is A.

In one embodiment, in sequence iii), $X_a$ is S; $X_b$ is E; $X_c$ is A; $X_dX_e$ is SD and $X_f$ is A.

In one embodiment, in sequence iii), $X_a$ is A; $X_b$ is N; $X_c$ is C; $X_dX_e$ is SD and $X_f$ is A.

In one embodiment, in sequence iii), $X_a$ is S; $X_b$ is E; $X_c$ is S; $X_dX_e$ is SD and $X_f$ is S.

In one embodiment, in sequence iii), $X_a$ is S; $X_b$ is E; $X_c$ is C; $X_dX_e$ is SD and $X_f$ is S.

In yet a further embodiment, sequence iii) corresponds to the sequence from position 7 to position 55 in a sequence selected from the group consisting of SEQ ID NO:1-808 presented in FIG. 1A-1CC. Hence, in one embodiment of the PD-L1 binding polypeptide according to this aspect, sequence iii) corresponds to the sequence from position 7 to position 55 in a sequence selected from the group consisting of SEQ ID NO:1-808. In one embodiment, sequence iii) corresponds to the sequence from position 7 to position 55 in a sequence selected from the group consisting of SEQ ID NO:1-93 and 774-796, such as the group consisting of SEQ ID NO:1-93 and 774-787. In one embodiment, sequence iii) corresponds to the sequence from position 7 to position 55 in a sequence selected from the group consisting of SEQ ID NO:1-93, 775, 776, 779-781 and 784-786, such as the group consisting of SEQ ID NO:1-93, 776, 780, 781, 784 and 786, such as the group consisting of SEQ ID NO:1-93, 776, 781 and 784, such as the group consisting of SEQ ID NO:1-93, 776 and 784 or the group consisting of SEQ ID NO:1-93, 776 and 781, for example the group consisting of SEQ ID NO:1-93 and 776 or the group consisting of SEQ ID NO:1-93 and 781 or the group consisting of SEQ ID NO:1-93 and 784. In one embodiment, sequence iii) corresponds to the sequence from position 7 to position 55 in a sequence selected from the group consisting of SEQ ID NO:1-93, 774, 775 and 780-786, such as the group consisting of SEQ ID NO:1-93, 775, 780, 781, 784 and 786. In one embodiment, sequence iii) corresponds to the sequence from position 7 to position 55 in a sequence selected from the group consisting of SEQ ID NO:1, 2, 17, 776 and 781, such as the group consisting of SEQ ID NO: 1, 2 and 776. In one embodiment, sequence iii) corresponds to the sequence from position 7 to position 55 in SEQ ID NO:1, SEQ ID NO:2 or SEQ ID NO:776. In one embodiment, sequence iii) corresponds to the sequence from position 7 to position 55 in a sequence selected from the group consisting of SEQ ID NO:1-93. In one embodiment, sequence iii) corresponds to the sequence from position 7 to position 55 in a sequence selected from the group consisting of SEQ ID NO:1, 3-8, 11, 13, 16, 18, 20, 22, 23, 43 and 73. In one embodiment, sequence iii) corresponds to the sequence from position 7 to position 55 in a sequence selected from the group consisting of SEQ ID NO:1-24. For example, in one embodiment, sequence iii) corresponds to the sequence from position 7 to position 55 in a sequence selected from the group consisting of SEQ ID NO:1-16, such as the group consisting of SEQ ID NO:1, 2, 4, 5, 7, 9 and 10. In another embodiment, sequence iii) corresponds to the sequence from position 7 to position 55 in a sequence selected from the group consisting of SEQ ID NO:1, 3-6, 9-10, 12-21, 23 and 24, such as the group consisting of SEQ ID NO:1, 4-6, 9, 14 and 18-21. In one embodiment, sequence iii) corresponds to the sequence from position 7 to position 55 in a sequence selected from the group consisting of SEQ ID NO:1-12, 14 and 17-21. In one embodiment, sequence iii) corresponds to the sequence from position 7 to position 55 in a sequence selected from the group consisting of SEQ ID NO:1-12 and 17, such as the group consisting of SEQ ID NO:1-5 and 17, such as the group consisting of SEQ ID NO:1, 2 and 17. In one embodiment, sequence iii) corresponds to the sequence from position 7 to position 55 in a sequence selected from the group consisting of SEQ ID NO:1, 4, 5, 6, 9, 14 and 18-21, such as the group consisting of SEQ ID NO:4, 5, 18 and 21, such as the group consisting of SEQ ID NO:4, 5 and 21. In one embodiment, sequence iii) corresponds to the sequence from position 8 to position 36 in a sequence selected from the group consisting of SEQ ID NO:1, 2, 4, 5 and 21, such as the group consisting of SEQ ID NO:1 and 2. In one embodiment, sequence iii) corresponds to the sequence from position 7 to position 55 in SEQ ID NO:1, SEQ ID NO:2, SEQ ID NO:4, SEQ ID NO:5 or SEQ ID NO:21.

Also, in a further embodiment, there is provided a PD-L1 binding polypeptide, which comprises an amino acid sequence selected from:

```
                                    (SEQ ID NO: 839)
v)          YA-[BMod]-AP;
```

wherein [BMod] is a PD-L1 binding module as defined herein; and vi) an amino acid sequence which has at least 90% identity to a sequence defined in v).

Alternatively, there is provided a PD-L1 binding polypeptide, which comprises an amino acid sequence selected from:

```
                                    (SEQ ID NO: 840)
vii)        FN-[BMod]-AP;
```

wherein [BMod] is a PD-L1 binding module as defined herein; and viii) an amino acid sequence which has at least 90% identity to a sequence defined in vii).

For example, in one embodiment there is provided a PD-L1 binding polypeptide selected from the group consisting of

```
                                    (SEQ ID NO: 841)
ix)    FNK-[BM]-DPSQS ANLLXc EAKKL NDAQA P;
```

wherein [BM] is a PD-L1 binding motif as defined above and $X_c$ is selected from A and C; and x) an amino acid sequence which has at least 90% identity to a sequence defined in ix).

In another embodiment, there is provided a PD-L1 binding polypeptide selected from the group consisting of

```
                                    (SEQ ID NO: 842)
xi)    FAK-[BM]-DPSQS SELLXc EAKKL SESQA P;
```

wherein [BM] is a PD-L1 binding motif as defined above and $X_c$ is selected from A, S and C; and xii) an amino acid sequence which has at least 90% identity to a sequence defined in xi).

In another embodiment, there is provided a PD-L1 binding polypeptide selected from the group consisting of

```
                                    (SEQ ID NO: 843)
xiii)  FAK-[BM]-DPSQS SELLXc EAKKL NDSQA P;
```

wherein [BM] is a PD-L1 binding motif as defined above and $X_c$ is selected from A, S and C;

xiv) an amino acid sequence which has at least 90% identity to a sequence defined in xiii).

In yet another embodiment, there is provided a PD-L1 binding polypeptide selected from the group consisting of

```
                                    (SEQ ID NO: 844)
xv)    YAK-[BM]-DPSQS SELLXc EAKKL NDSQA P;
```

wherein [BM] is a PD-L1 binding motif as defined above and $X_c$ is selected from A, S and C;

xvi) and an amino acid sequence which has at least 90% identity to a sequence defined in xv).

As discussed above, polypeptides comprising minor changes as compared to the above amino acid sequences, which do not largely affect the tertiary structure and the function of the polypeptide, also fall within the scope of the present disclosure. Thus, in some embodiments, sequence vi), viii), x), xii), xiv) or xvi) may for example be at least 90%, such as at least 92%, such as at least 94%, such as at least 96%, such as at least 98% identical to a sequence defined by v, vii), ix), xi), xiii) and xv), respectively.

In some embodiments, the PD-L1 binding motif may form part of a polypeptide comprising an amino acid sequence selected from

```
ADNNFNK-[BM]-DPSQSANLLSEAKKLNESQAPK (SEQ ID NO: 845);
ADNKFNK-[BM]-DPSQSANLLAEAKKLNDAQAPK (SEQ ID NO: 846);
ADNKFNK-[BM]-DPSVSKEILAEAKKLNDAQAPK (SEQ ID NO: 847);
ADAQQNNFNK-[BM]-DPSQSTNVLGEAKKLNES  (SEQ ID NO: 848);
QAPK
AQHDE-[BM]-DPSQSANVLGEAQKLNDSQAPK   (SEQ ID NO: 849);
VDNKFNK-[BM]-DPSQSANLLAEAKKLNDAQAPK (SEQ ID NO: 850);
AEAKYAK-[BM]-DPSESSELLSEAKKLNKSQAPK (SEQ ID NO: 851);
VDAKYAK-[BM]-DPSQSSELLAEAKKLNDAQAPK (SEQ ID NO: 852);
```

-continued

VDAKYAK-[*BM*]-DPSQSSELLAEAKKLNDSQAPK (SEQ ID NO: 853);

AEAKYAK-[*BM*]-DPSQSSELLSEAKKLNDSQAPK (SEQ ID NO: 854);

AEAKYAK-[*BM*]-DPSQSSELLSEAKKLNDSQAP (SEQ ID NO: 855);

AEAKFAK-[*BM*]-DPSQSSELLSEAKKLNDSQAPK (SEQ ID NO: 856);

AEAKFAK-[*BM*]-DPSQSSELLSEAKKLNDSQAP (SEQ ID NO: 857);

AEAKYAK-[*BM*]-DPSQSSELLAEAKKLNDAQAPK (SEQ ID NO: 858);

AEAKYAK-[*BM*]-DPSQSSELLSEAKKLSESQAPK (SEQ ID NO: 859);

AEAKYAK-[*BM*]-DPSQSSELLSEAKKLSESQAP (SEQ ID NO: 860);

AEAKFAK-[*BM*]-DPSQSSELLSEAKKLSESQAPK (SEQ ID NO: 861);

AEAKFAK-[*BM*]-DPSQSSELLSEAKKLSESQAP (SEQ ID NO: 862);

AEAKYAK-[*BM*]-DPSQSSELLAEAKKLSEAQAPK (SEQ ID NO: 863);

AEAKYAK-[*BM*]-QPEQSSELLSEAKKLSESQAPK (SEQ ID NO: 864);

AEAKYAK-[*BM*]-DPSQSSELLSEAKKLESSQAPK (SEQ ID NO: 865);

AEAKYAK-[*BM*]-DPSQSSELLSEAKKLESSQAP (SEQ ID NO: 866);

AEAKYAK-[*BM*]-DPSQSSELLAEAKKLESAQAPK (SEQ ID NO: 867);

AEAKYAK-[*BM*]-QPEQSSELLSEAKKLESSQAPK (SEQ ID NO: 868);

AEAKYAK-[*BM*]-DPSQSSELLSEAKKLSDSQAPK (SEQ ID NO: 869);

AEAKYAK-[*BM*]-DPSQSSELLSEAKKLSDSQAP (SEQ ID NO: 870);

AEAKYAK-[*BM*]-DPSQSSELLAEAKKLSDSQAPK (SEQ ID NO: 871);

AEAKYAK-[*BM*]-DPSQSSELLAEAKKLSDAQAPK (SEQ ID NO: 872);

AEAKYAK-[*BM*]-QPEQSSELLSEAKKLSDSQAPK (SEQ ID NO: 873);

VDAKYAK-[*BM*]-DPSQSSELLSEAKKLNDSQAPK (SEQ ID NO: 874);

VDAKYAK-[*BM*]-DPSQSSELLAEAKKLNDAQAPK (SEQ ID NO: 875);

VDAKYAK-[*BM*]-DPSQSSELLSEAKKLSESQAPK (SEQ ID NO: 876);

VDAKYAK-[*BM*]-DPSQSSELLAEAKKLSEAQAPK (SEQ ID NO: 877);

VDAKYAK-[*BM*]-QPEQSSELLSEAKKLSESQAPK (SEQ ID NO: 878);

VDAKYAK-[*BM*]-DPSQSSELLSEAKKLESSQAPK (SEQ ID NO: 879);

VDAKYAK-[*BM*]-DPSQSSELLAEAKKLESAQAPK (SEQ ID NO: 880);

VDAKYAK-[*BM*]-QPEQSSELLSEAKKLESSQAPK (SEQ ID NO: 881);

VDAKYAK-[*BM*]-DPSQSSELLSEAKKLSDSQAPK (SEQ ID NO: 882);

VDAKYAK-[*BM*]-DPSQSSELLAEAKKLSDSQAPK (SEQ ID NO: 883);

VDAKYAK-[*BM*]-DPSQSSELLAEAKKLSDAQAPK (SEQ ID NO: 884);

VDAKYAK-[*BM*]-QPEQSSELLSEAKKLSDSQAPK (SEQ ID NO: 885);

VDAKYAK-[*BM*]-DPSQSSELLAEAKKLNKAQAPK (SEQ ID NO: 886);

AEAKYAK-[*BM*]-DPSQSSELLAEAKKLNKAQAPK (SEQ ID NO: 887); and

ADAKYAK-[*BM*]-DPSQSSELLSEAKKLNDSQAPK (SEQ ID NO: 888);

wherein [BM] is a PD-L1 binding motif as defined herein.

In one embodiment, the PD-L1 binding polypeptide comprises an amino acid sequence selected from:

(SEQ ID NO: 874)
xvii) VDAKYAK-[*BM*]-DPSQSSELLSEAKKLNDSQAPK;

wherein [BM] is a PD-L1 binding motif as defined herein; and xviii) an amino acid sequence which has at least 89% identity to the sequence defined in xvii).

In one embodiment, the PD-L1 binding polypeptide comprises an amino acid sequence selected from:

(SEQ ID NO: 861)
xix) AEAKFAK-[*BM*]-DPSQSSELLSEAKKLSESQAPK;

wherein [BM] is a PD-L1 binding motif as defined herein; and xx) an amino acid sequence which has at least 89% identity to the sequence defined in xix).

In one embodiment, the PD-L1 binding polypeptide comprises an amino acid sequence selected from:

xxi)
(SEQ ID NO: 854)
AEAKYAK-[*BM*]-DPSQSSELLSEAKKLNDSQAPK;

wherein [BM] is a PD-L1 binding motif as defined herein; and xxii) an amino acid sequence which has at least 89% identity to the sequence defined in xxi).

In one embodiment, the PD-L1 binding polypeptide comprises an amino acid sequence selected from:

xxiii)
(SEQ ID NO: 856)
AEAKFAK-[*BM*]-DPSQSSELLSEAKKLNDSQAPK;

wherein [BM] is a PD-L1 binding motif as defined herein; and xxiv) an amino acid sequence which has at least 89% identity to the sequence defined in xxiii).

Again, polypeptides comprising minor changes as compared to the above amino acid sequences, which do not largely affect the tertiary structure and the function of the polypeptide, also fall within the scope of the present disclosure. Thus, in some embodiments, sequence xviii), xx), xxii) or xxiv) may for example be at least 89%, such as at least 91%, such as at least 93%, such as at least 94%, such as at least 96%, such as at least 98% identical to a sequence defined by xvii), xix), xxi) and xxiii), respectively.

Sequence xvii) or xxi) in such a polypeptide may be selected from the group consisting of SEQ ID NO:1-814 presented in FIG. 1A-1CC. In one embodiment of the PD-L1 binding polypeptide according to this aspect, sequence xvii) or xxi) corresponds to the sequence from position 1 to position 58 in a sequence selected from the group consisting of SEQ ID NO:1-808. In one embodiment, sequence xvii) or xxi) corresponds to the sequence from position 1 to position 58 in a sequence selected from the group consisting of SEQ ID NO:1-93, 774-796 and 809-814, such as the group consisting of SEQ ID NO:1-93, 774-787 and 809-814. In one embodiment, sequence xvii) or xxi) corresponds to the sequence from position 1 to position 58 in a sequence selected from the group consisting of SEQ ID NO:1-93, 775, 776, 779-781, 784-786 and 809-814, such as the group consisting of SEQ ID NO:1-93, 776, 780, 781, 784, 786 and 809-814, such as the group consisting of SEQ ID NO:1-93, 776, 781, 784 and 809-814, such as the group consisting of SEQ ID NO:1-93, 776, 784, 809 and 811-814 or the group consisting of SEQ ID NO:1-93, 776, 781, 809 and 811-814. In one embodiment, sequence xvii) or xxi) corresponds to the sequence from position 1 to position 58 in a sequence selected from the group consisting of SEQ ID NO:1-93, 776, 809 and 811-814 or the group consisting of SEQ ID NO:1-93, 781, 809 and 811-814 or the group consisting of SEQ ID NO:1-93, 784 and 811-814. In one embodiment, sequence xvii) or xxi) corresponds to the sequence from position 1 to position 58 in a sequence selected from the group consisting of SEQ ID NO:1-93, 774, 775, 780-786 and 810-814, such as the group consisting of SEQ ID NO:1-93, 775, 780, 781, 784, 786 and 810-814. In one embodiment, sequence xvii) or xxi) corresponds to the sequence from position 1 to position 58 in a sequence selected from the group consisting of SEQ ID NO:1-93, 776, 781 and 809-813, such as the group consisting of SEQ ID NO:1-93, 781 and 810-813. In one embodiment, sequence xvii) or xxi) corresponds to the sequence from position 1 to position 58 in a sequence selected from the group consisting of SEQ ID NO:1, 2, 17, 776, 781, 809-812, such as the group consisting of SEQ ID NO: 1, 2, 776, 809, 811 and 812. In one embodiment, sequence xvii) corresponds to the sequence from position 1 to position 58 in a sequence selected from the group consisting of SEQ ID NO:1-93, 776 and 781, such as the group consisting of SEQ ID NO:1-93 and 781. In one embodiment, sequence xvii) corresponds to the sequence from position 1 to position 58 in a sequence selected from the group consisting of SEQ ID NO:1, 2, 17, 776 and 781, such as the group consisting of SEQ ID NO: 1, 2 and 776. In one embodiment, sequence xvii) corresponds to the sequence from position 1 to position 58 in SEQ ID NO:1, SEQ ID NO:2 or SEQ ID NO:776. In one embodiment, sequence xvii) or xxi) corresponds to the sequence from position 1 to position 58 in a sequence selected from the group consisting of SEQ ID NO:1-93 and 811-813. In one embodiment, sequence xvii) or xxi) corresponds to the sequence from position 1 to position 58 in a sequence selected from the group consisting of SEQ ID NO:1, 3-8, 11, 13, 16, 18, 22, 23, 43, 73 and 811-813. In one embodiment, sequence xvii) or xxi) corresponds to the sequence from position 1 to position 58 in a sequence selected from the group consisting of SEQ ID NO:1-24 and 811-813. For example, in one embodiment, sequence xvii) or xxi) corresponds to the sequence from position 1 to position 58 in a sequence selected from the group consisting of SEQ ID NO:1-16 and 811-813, such as the group consisting of SEQ ID NO:1, 2, 4, 5, 7, 9, 10, 811 and 812. In another embodiment, sequence xvii) or xxi) corresponds to the sequence from position 1 to position 58 in a sequence selected from the group consisting of SEQ ID NO:1, 3-6, 9-10, 12-21, 23, 24, 811 and 812, such as the group consisting of SEQ ID NO:1, 4-6, 9, 14, 18-21, 811 and 812. In one embodiment, sequence xvii) or xxi) corresponds to the sequence from position 1 to position 58 in a sequence selected from the group consisting of SEQ ID NO:1-12, 14, 17-21 and 811-812. In one embodiment, sequence xvii) or xxi) corresponds to the sequence from position 1 to position 58 in a sequence selected from the group consisting of SEQ ID NO:1-12, 17, 811 and 812, such as the group consisting of SEQ ID NO:1-5, 17, 811 and 812, such as the group consisting of SEQ ID NO:1, 2, 17, 811 and 812. In one embodiment, sequence xvii) or xxi) corresponds to the sequence from position 1 to position 58 in a sequence selected from the group consisting of SEQ ID NO:1, 4, 5, 6, 9, 14, 18, 19, 20, 21 and 811, such as the group consisting of SEQ ID NO:4, 5, 18 and 21, such as the group consisting of SEQ ID NO:4, 5 and 21. In one embodiment, sequence xvii)) corresponds to the sequence from position 8 to position 36 in a sequence selected from the group consisting of SEQ ID NO:1, 2, 4, 5 and 21, such as the group consisting of SEQ ID NO:1 and 2. In one embodiment, sequence xvii) or xxi) corresponds to the sequence from position 1 to position 58 in SEQ ID NO:1 or 811. In one embodiment, sequence xvii) or xxi) corresponds to the sequence from position 1 to position 58 in SEQ ID NO:2 or 812. In one embodiment, sequence xvii) corresponds to the sequence from position 1 to position 58 in SEQ ID NO:4, SEQ ID NO:5 or SEQ ID NO:21.

The terms "PD-L1 binding" and "binding affinity for PD-L1" as used in this specification refer to a property of a polypeptide which may be tested for example by ELISA or by the use of surface plasmon resonance (SPR) technology.

For example as described in the examples below, PD-L1 binding affinity may be tested in an experiment in which samples of the polypeptide are captured on antibody-coated ELISA plates and biotinylated PD-L1 is added followed by streptavidin-conjugated HRP. TMB substrate is added and the absorbance at 450 nm is measured using a multi-well plate reader, such as Victor$^3$ (Perkin Elmer). The skilled person may then interpret the results obtained by such experiments to establish at least a qualitative measure of the binding affinity of the polypeptide for PD-L1. If a quantitative measure is desired, for example to determine the EC50 value (the half maximal effective concentration) for the interaction, ELISA may also be used. The response of the polypeptide against a dilution series of biotinylated PD-L1 is measured using ELISA as described above. The skilled person may then interpret the results obtained by such experiments, and EC50 values may be calculated from the results using for example GraphPad Prism 5 and non-linear regression.

PD-L1 binding affinity may also be tested in an experiment in which PD-L1, or a fragment thereof, is immobilized on a sensor chip of a surface plasmon resonance (SPR) instrument, and the sample containing the polypeptide to be tested is passed over the chip. Alternatively, the polypeptide to be tested is immobilized on a sensor chip of the instrument, and a sample containing PD-L1, or a fragment thereof, is passed over the chip. The skilled person may then interpret the results obtained by such experiments to establish at least a qualitative measure of the binding affinity of the polypeptide for PD-L1. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. PD-L1 is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

The terms "albumin binding" and "binding affinity for albumin" as used in this disclosure refer to a property of a polypeptide which may be tested for example by the use of SPR technology in a Biacore instrument or ProteOn XPR36 instrument, in an analogous way to the example described above for PD-L1.

In one embodiment, the PD-L1 binding polypeptide is capable of binding to PD-L1 such that the $K_D$ value of the interaction with PD-L1 is at most $2\times10^{-8}$ M, such as at most $1\times10^{-8}$ M, such as at most $1\times10^{-9}$ M, such as at most $5\times10^{-10}$ M, such as at most $3\times10^{-10}$ M.

In one embodiment, the PD-L1 binding polypeptide is capable of binding to PD-L1 such that the $k_d$ value of the interaction with PD-L1 is at most $1\times10^{-3}$ $s^{-1}$, such as at most $6\times10^{-4}$ $s^{-1}$.

In one embodiment, there is provided a PD-L1 binding polypeptide according to any preceding item which is capable of binding to PD-L1 such that the EC50 value of the interaction is at most $1\times10^{-9}$ M, such as at most $1\times10^{-10}$ M, such as at most $7\times10^{-11}$ M.

Binding of a polypeptide as defined herein to PD-L1 may interfere either with signaling via PD-L1 in vivo or in vitro. When PD-L1 binds to PD-1, the ligand/receptor interaction dampens the T-lymphocyte response by e.g. inhibiting kinases involved in T-lymphocyte activation. Thus, blocking the binding of PD-L1 to PD-1 restores the T-lymphocyte response. Blocking activity may for example be quantified by the half maximal inhibitory concentration (IC50), which is a measure of the effectiveness of a substance in inhibiting a specific biological or biochemical function. This quantitative measure indicates how much of a particular substance is needed to inhibit a given biological process by half, and is commonly used in the art.

Thus, in one embodiment, there is provided a PD-L1 binding polypeptide as defined herein which is capable of blocking PD-L1 dependent signaling. In one embodiment, the half maximal inhibitory concentration (IC50) of the blocking is at most $5\times10^{-8}$ M, such as at most $1\times10^{-8}$ M, such as at most $5\times10^{-9}$ M, such as at most $3.5\times10^{-9}$ M, such as at most $1\times10^{-9}$ M, such as at most $5\times10^{-10}$ M, such as at most $1\times10^{-10}$ M. In one embodiment, the PD-L1 binding polypeptide is capable of blocking the interaction of PD-L1 with PD-1.

In one embodiment, said PD-L1 is human PD-L1. In another embodiment, said PD-L1 is rhesus monkey PD-1.

The skilled person will understand that various modifications and/or additions can be made to a PD-L1 binding polypeptide according to any aspect disclosed herein in order to tailor the polypeptide to a specific application without departing from the scope of the present disclosure. For example, in one embodiment, there is provided a PD-L1 binding polypeptide as described herein, which polypeptide has been extended by and/or comprises additional amino acids at the C terminus and/or N terminus. Such a polypeptide should be understood as a polypeptide having one or more additional amino acid residues at the very first and/or the very last position in the polypeptide chain. Thus, a PD-L1 binding polypeptide may comprise any suitable number of additional amino acid residues, for example at least one additional amino acid residue. Each additional amino acid residue may individually or collectively be added in order to, for example, improve and/or simplify production, purification, stabilization in vivo or in vitro, coupling or detection of the polypeptide. Such additional amino acid residues may comprise one or more amino acid residues added for the purpose of chemical coupling. One example of this is the addition of a cysteine residue. Additional amino acid residues may also provide a "tag" for purification or detection of the polypeptide, such as a $His_6$ (SEQ ID NO:889) tag, a $(HisGlu)_3$ (SEQ ID NO:890) tag ("HEHEHE" tag) or a "myc" (c-myc) tag or a "FLAG" tag for interaction with antibodies specific to the tag or immobilized metal affinity chromatography (IMAC) in the case of a $His_6$ (SEQ ID NO:889)-tag.

In one embodiment, there is provided a PD-L1 binding polypeptide as described herein which comprises additional amino acids at the C-terminal and/or N-terminal end. For example, in one embodiment of the PD-L1 binding polypeptide as disclosed herein, it consists of any one of the sequences disclosed herein, having from 0 to 15 additional C-terminal and/or N-terminal residues, such as from 0 to 7 additional C-terminal and/or N-terminal residues. In one embodiment, the PD-L1 binding polypeptide consists of any one of the sequences disclosed herein, having from 0 to 15, such as from 0 to 4, such as 3 additional C-terminal residues. In one particular embodiment, the PD-L1 binding polypeptide as described herein comprises the additional C-terminal residues VDC or VEC.

The further amino acids as discussed above may be coupled to the PD-L1 binding polypeptide by means of chemical conjugation (using known organic chemistry methods) or by any other means, such as expression of the PD-L1 binding polypeptide as a fusion protein or joined in any other fashion, either directly or via a linker, for example an amino acid linker.

A further polypeptide domain may moreover provide another PD-L1 binding moiety. Thus, in a further embodiment, there is provided a PD-L1 binding polypeptide in a multimeric form. Said multimer is understood to comprise at least two PD-L1 binding polypeptides as disclosed herein as monomer units, the amino acid sequences of which may be the same or different. Multimeric forms of the polypeptides may comprise a suitable number of domains, each having a PD-L1 binding motif, and each forming a monomer within the multimer. These domains may have the same amino acid sequence, but alternatively, they may have different amino acid sequences. In other words, the PD-L1 binding polypeptide of the invention may form homo- or heteromultimers, for example homo- or heterodimers. In one embodiment, there is provided a PD-L1 binding polypeptide, wherein said monomer units are covalently coupled together. In another embodiment, said PD-L1 binding polypeptide monomer units are expressed as a fusion protein. In one embodiment, there is provided a PD-L1 binding polypeptide in dimeric form.

In one particular embodiment, said dimeric form is a homodimeric form. In another embodiment, said dimeric form is a heterodimeric form. For the sake of clarity, throughout this disclosure, the term "PD-L1 binding polypeptide" is used to encompass PD-L1 binding polypeptides in all forms, i.e. monomeric and multimeric forms.

The further amino acids as discussed above may for example comprise one or more further polypeptide domain (s). A further polypeptide domain may provide the PD-L1 binding dimer with another function, such as for example another binding function, or an enzymatic function, or a toxic function or a fluorescent signaling function, or combinations thereof.

Furthermore, it may be beneficial that the PD-L1 binding polypeptide as defined herein is part of a fusion protein or a conjugate comprising a second or further moieties. Second and further moiety/moieties of the fusion polypeptide or conjugate in such a protein may suitably have a desired biological activity.

Thus, in a second aspect of the present disclosure, there is provided a fusion protein or a conjugate, comprising a first moiety consisting of a PD-L1 binding polypeptide according to the first aspect, and a second moiety consisting of a polypeptide having a desired biological activity. In another embodiment, said fusion protein or conjugate may additionally comprise further moieties, comprising desired biological activities that can be either the same as or different from the biological activity of the second moiety.

Non-limiting examples of a desired biological activity comprise a therapeutic activity, a binding activity and an enzymatic activity. In one embodiment, the second moiety having a desired biological activity is a therapeutically active polypeptide. In one embodiment, said second moiety is an immune response modifying agent. In another embodiment, said second moiety is an anti-cancer agent.

In one embodiment of either the first or second aspect of the present disclosure, there is provided a PD-L1 binding polypeptide, fusion protein or conjugate which comprises an immune response modifying agent. Non-limiting examples of additional immune response modifying agents include immunomodulating agents or other anti-inflammatory agents In one embodiment of either the first or second aspect of the present disclosure, there is provided a PD-L1 binding polypeptide, fusion protein or conjugate which comprises an anti-cancer agent. Non-limiting examples of anti-cancer agents include agents selected from the group consisting of auristatin, anthracycline, calicheamycin, combretastatin, doxorubicin, duocarmycin, the CC-1065 anti-tumor-antibiotic, ecteinsascidin, geldanamycin, maytansinoid, methotrexate, mycotoxin, taxol, ricin, bouganin, gelonin, *pseudomonas* exotoxin 38 (PE38), diphtheria toxin (DT), and their analogues, and derivates thereof and combinations thereof. A skilled person would appreciate that the non-limiting examples of anti-cancer agents include all possible variants of said agents, for example the agent auristatin is intended to include for example auristatin E, auristatin F, auristatin PE, and derivatives thereof.

Non-limiting examples of therapeutically active polypeptides are biomolecules, such as molecules selected from the group consisting of human endogenous enzymes, hormones, growth factors, chemokines, cytokines and lymphokines.

Non-limiting examples of binding activities are binding activities which increase the in vivo half-life of the fusion protein or conjugate, and binding activities which act to block a biological activity. One example of such a binding activity is a binding activity, which increases the in vivo half-life of a fusion protein or conjugate. In one embodiment of said fusion protein or conjugate, the in vivo half-life of said fusion protein or conjugate is longer than the in vivo half-life of the polypeptide having the desired biological activity per se. In one embodiment, said in vivo half-life is increased at least 10 times, such as at least 25 times, such as at least 50 times, such as at least 75 times, such as at least 100 times compared the in vivo half-life of the fusion protein or conjugate per se.

The fusion protein or conjugate may comprise at least one further moiety. In one particular embodiment, said target is albumin, binding to which increases the in vivo half-life of said fusion protein or conjugate. In one embodiment, said albumin binding activity is provided by an albumin binding domain (ABD) of streptococcal protein G or a derivative thereof. Thus, said fusion protein may for example comprise a PD-L1 binding polypeptide in monomeric or multimeric form (such as a homodimeric or heterodimeric form) as defined herein and an albumin binding domain of streptococcal protein G or a derivative thereof.

In another embodiment, said there is provided a fusion protein or a conjugate wherein said second moiety having a desired binding activity is a protein based on protein Z, derived from the B domain of protein A from *Staphylococcus aureus*, which has a binding affinity for a target other than PD-L1.

For example, said fusion protein or conjugate, comprising at least one further moiety, may comprise [PD-L1 binding polypeptide]-[albumin binding moiety]-[moiety with affinity for selected target]. It is to be understood that the three moieties in this example may be arranged in any order from the N- to the C-terminal of the polypeptide.

The skilled person is aware that the construction of a fusion protein often involves the use of linkers between the functional moieties to be fused, and there are different kinds of linkers with different properties, such as flexible amino acid linkers, rigid amino acid linkers and cleavable amino acid linkers. Linkers have been used to for example increase stability or improve folding of fusion proteins, to increase expression, improve biological activity, enable targeting and alter pharmacokinetics of fusion proteins. Thus, in one embodiment, the polypeptide according to any aspect disclosed herein further comprises at least one linker, such as at least one linker selected from flexible amino acid linkers, rigid amino acid linkers and cleavable amino acid linkers. In one embodiment, said linker is arranged between said PD-L1 binding polypeptide and a further polypeptide domain, such as between a PD-L1 binding domain as disclosed herein and an antibody or antigen binding fragment thereof (as described in further detail below). Flexible linkers are often used in the art when the joined domains require a certain degree of movement or interaction, and may be particularly useful in some embodiments of the complex. Such linkers are generally composed of small, non-polar (for example G) or polar (for example S or T) amino acids. Some flexible linkers primarily consist of stretches of G and S residues, for example $(GGGGS)_p$, where GGGGS is SEQ ID NO: 891. Adjusting the copy number "p" allows for optimization of linker in order to achieve appropriate separation between the functional moieties or to maintain necessary inter-moiety interaction. Apart from G and S linkers, other flexible linkers are known in the art, such as G and S linkers containing additional amino acid residues, such as T and A, to maintain flexibility, as well as polar amino acid residues to improve solubility. Additional non-limiting examples of linkers include GGGGSLVPRGSGGGGS, $(GS)_3$, $(GS)_4$, $(GS)_8$, GGSGGHMGSGG, GGSGGSGGSGG, GGSGG, GGSGGGGG, GGGSEGGGSEGGGSEGGG, AAGAATAA, GGGGG, GGSSG, GSGGGTGGGSG, GSGGGTGGGSG, GSGSGSGSGGSG, GSGGSGGSGGSGGS and GSGGSGSGGSGGSG, corresponding to SEQ ID NO:820-836, respectively, and GT. The skilled person is aware of other suitable linkers.

In one embodiment, said linker is a flexible linker comprising glycine (G), serine (S) and/or threonine (T) residues. In one embodiment, said linker has a general formula selected from $(G_nS_m)_p$ and $(S_nG_m)_p$, wherein, independently, n=1-7, m=0-7, n+m<8 and p=1-7. In one embodiment, n=1-5. In one embodiment, m=0-5. In one embodiment, p=1-5. In a more specific embodiment, n=4, m=1 and p=1-4. In one embodiment, said linker is selected from the group consisting of $S_4G$ (SEQ ID NO:892), $(S_4G)_3$ (SEQ ID NO:893) and $(S_4G)_4$ (SEQ ID NO:894). In one embodiment, said linker is selected from the group consisting of $G_4S$ (SEQ ID NO: 891) and $(G_4S)_3$ (SEQ ID NO:895). In one particular embodiment, said linker is $G_4S$ (SEQ ID NO: 891) and in another embodiment said linker is $(G_4S)_3$ (SEQ ID NO:895).

With regard to the description above of fusion proteins or conjugates incorporating a PD-L1 binding polypeptide according to the disclosure, it is to be noted that the designation of first, second and further moieties is made for clarity reasons to distinguish between PD-L1 binding polypeptide or polypeptides according to the invention on the one hand, and moieties exhibiting other functions on the other hand. These designations are not intended to refer to the actual order of the different domains in the polypeptide chain of the fusion protein or conjugate. Similarly, the designations first and second monomer units are made for clarity reasons to distinguish between said units. Thus, for example, said first moiety (or monomer unit) may without restriction appear at the N-terminal end, in the middle, or at the C-terminal end of the fusion protein or conjugate.

Recently, considerable progress has been made in the development of multispecific agents, such as antibodies with the ability to bind to more than one antigen, for example through engineering of the complementarity determining regions (CDRs) to address two antigens in a single antibody combining site (Bostrom et al, 2009, Science 323(5921): 1610-1614; Schaefer et al, 2011, Cancer Cell 20(4):472-486), via construction of heterodimeric antibodies using engineered Fc units (Carter, 2001, J Immunol Methods 248(1-2):7-15; Schaefer et al, 2011, Proc Natl Acad Sci USA 108(27):11187-11192) and via genetic fusion of auxiliary recognition units to N- or C-termini of light or heavy chains of full-length antibodies (Kanakaraj et al, 2012, MAbs 4(5):600-613; LaFleur et al, 2013, MAbs 5(2):208-218). Thus, it may be beneficial for a molecule incorporating an affinity for PD-L1 as disclosed herein to also exhibit affinity for another factor, such as a factor associated with cancer or an immune response associated factor.

Thus, in third aspect of the present disclosure, there is provided a complex comprising at least one PD-L1 binding polypeptide and at least one antibody or an antigen binding fragment thereof, wherein the PD-L1 binding polypeptide is as described herein.

When used herein, the term "complex" is intended to refer to two or more associated polypeptide chains, at least one having an affinity for PD-L1 and at least one being an antibody or an antigen binding fragment thereof. These polypeptide chains may each contain different protein domains, and the resulting multiprotein complex can have multiple functions. "Complex" intends to refer to two or more polypeptides as defined herein, connected by covalent bonds, for example two or more polypeptide chains connected by covalent bonds through expression thereof as a recombinant fusion protein, or associated by chemical conjugation.

As is well known, antibodies are immunoglobulin molecules capable of specific binding to a target (an antigen), such as a carbohydrate, polynucleotide, lipid, polypeptide or other, through at least one antigen recognition site located in the variable region of the immunoglobulin molecule. As used herein, the term "antibody or an antigen binding fragment thereof" encompasses not only full-length or intact polyclonal or monoclonal antibodies, but also antigen-binding fragments thereof, such as Fab, Fab', $F(ab')_2$, $Fab_3$, Fv and variants thereof, fusion proteins comprising one or more antibody portions, humanized antibodies, chimeric antibodies, minibodies, diabodies, triabodies, tetrabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies and covalently modified antibodies. Further examples of modified antibodies and antigen binding fragments thereof include nanobodies, AlbudAbs, DARTs (dual affinity re-targeting), BiTEs (bispecific T-cell engager), TandAbs (tandem diabodies), DAFs (dual acting Fab), two-in-one antibodies, SMIPs (small modular immunopharmaceuticals), FynomAbs (fynomers fused to antibodies), DVD-Igs (dual variable domain immunoglobulin), CovX-bodies (peptide modified antibodies), duobodies and triomAbs. This listing of variants of antibodies and antigen binding fragments thereof is not to be seen as limiting, and the skilled person is aware of other suitable variants.

A full-length antibody comprises two heavy chains and two light chains. Each heavy chain contains a heavy chain variable region ($V_H$) and first, second and third constant regions ($C_H1$, $C_H2$ and $C_H3$). Each light chain contains a light chain variable region ($V_L$) and a light chain constant region ($C_L$). Depending on the amino acid sequence of the constant domain of its heavy chains, antibodies are assigned to different classes. There are six major classes of antibodies: IgA, IgD, IgE, IgG, IgM and IgY, and several of these may be further divided into subclasses (isotypes), e.g., IgG1, IgG2, IgG3, IgG4, IgA1 and IgA2. The term "full-length antibody" as used herein refers to an antibody of any class, such as IgD, IgE, IgG, IgA, IgM or IgY (or any sub-class thereof). The subunit structures and three-dimensional configurations of different classes of antibodies are well known.

An "antigen binding fragment" is a portion or region of an antibody molecule, or a derivative thereof, that retains all or a significant part of the antigen binding of the corresponding full-length antibody. An antigen binding fragment may comprise the heavy chain variable region ($V_H$), the light chain variable region ($V_L$), or both. Each of the $V_H$ and $V_L$ typically contains three complementarity determining regions CDR1, CDR2 and CDR3. The three CDRs in $V_H$ or $V_L$ are flanked by framework regions (FR1, FR2, FR3 and FR4). As briefly listed above, examples of antigen binding fragments include, but are not limited to: (1) a Fab fragment, which is a monovalent fragment having a $V_L$-$C_L$ chain and a $V_H$-$C_H1$ chain; (2) a Fab' fragment, which is a Fab fragment with the heavy chain hinge region, (3) a $F(ab')_2$ fragment, which is a dimer of Fab' fragments joined by the heavy chain hinge region, for example linked by a disulfide bridge at the hinge region; (4) an Fc fragment; (5) an Fv fragment, which is the minimum antibody fragment having the $V_L$ and $V_H$ domains of a single arm of an antibody; (6) a single chain Fv (scFv) fragment, which is a single polypeptide chain in which the $V_H$ and $V_L$ domains of an scFv are linked by a peptide linker; (7) an $(scFv)_2$, which comprises two $V_H$ domains and two $V_L$ domains, which are associated through the two $V_H$ domains via disulfide bridges and (8) domain antibodies, which can be antibody single variable domain ($V_H$ or $V_L$) polypeptides that specifically bind antigens.

Antigen binding fragments can be prepared via routine methods. For example, $F(ab')_2$ fragments can be produced by pepsin digestion of a full-length antibody molecule, and Fab fragments can be generated by reducing the disulfide bridges of $F(ab')_2$ fragments. Alternatively, fragments can be prepared via recombinant technology by expressing the heavy and light chain fragments in suitable host cells (e.g., *E. coli*, yeast, mammalian, plant or insect cells) and having them assembled to form the desired antigen-binding fragments either in vivo or in vitro. A single-chain antibody can be prepared via recombinant technology by linking a nucleotide sequence coding for a heavy chain variable region and a nucleotide sequence coding for a light chain variable region. For example, a flexible linker may be incorporated between the two variable regions. The skilled person is aware of methods for the preparation of both full-length antibodies and antigen binding fragments thereof.

Thus, in one embodiment, this aspect of the disclosure provides a complex as defined herein, wherein said at least one antibody or antigen binding fragment thereof is selected from the group consisting of full-length antibodies, Fab fragments, Fab' fragments, $F(ab')_2$ fragments, Fc fragments, Fv fragments, single chain Fv fragments, $(scFv)_2$ and domain antibodies. In one embodiment, said at least one antibody or antigen binding fragment thereof is selected from full-length antibodies, Fab fragments and scFv fragments. In one particular embodiment, said at least one antibody or antigen binding fragment thereof is a full-length antibody.

In one embodiment of said complex as defined herein, the antibody or antigen binding fragment thereof is selected from the group consisting of monoclonal antibodies, human antibodies, humanized antibodies, chimeric antibodies, and antigen-binding fragments thereof.

The term "monoclonal antibodies" as used herein refers to antibodies having monovalent affinity, meaning that each antibody molecule in a sample of the monoclonal antibody binds to the same epitope on the antigen, whereas the term "polyclonal antibodies" as used herein refers to a collection of antibodies that react against a specific antigen, but in which collection there may be different antibody molecules for example identifying different epitopes on the antigen. Polyclonal antibodies are typically produced by inoculation of a suitable mammal and are purified from the mammal's serum. Monoclonal antibodies are made by identical immune cells that are clones of a unique parent cell (for example a hybridoma cell line). The term "human antibody" as used herein refers to antibodies having variable and constant regions corresponding substantially to, or derived from, antibodies obtained from human subjects. The term "chimeric antibodies" as used herein, refers to recombinant or genetically engineered antibodies, such as for example mouse monoclonal antibodies, which contain polypeptides or domains from a different species, for example human, introduced to reduce the antibodies' immunogenicity. The term "humanized antibodies" refers to antibodies from non-human species whose protein sequences have been modified to increase their similarity to antibody variants produced naturally in humans, in order to reduce immunogenicity.

The complex as described herein may for example be present in the form of a fusion protein or a conjugate. Thus, said at least one PD-L1 binding polypeptide and said at least one antibody, or antigen binding fragment thereof, may be coupled by means of chemical conjugation (using known organic chemistry methods) or by any other means, such as expression of the complex as a fusion protein or joined in any other fashion, either directly or via a linker, for example an amino acid linker. The skilled person will appreciate that the above description of linker sequences in relation to fusion polypeptides is equally relevant for the complex as disclosed herein.

Thus in one embodiment, there is provided a complex as defined herein, wherein said complex is a fusion protein or a conjugate. In one embodiment, said complex is a fusion protein. In another embodiment, said complex is a conjugate. In one embodiment of said complex, said PD-L1 binding polypeptide is attached to the N-terminus or C-terminus of the heavy chain of said antibody or antigen binding fragment thereof. In another embodiment, said PD-L1 binding polypeptide is attached to the N-terminus or C-terminus of the light chain of said antibody or antigen binding fragment thereof. In one embodiment, said PD-L1 binding polypeptide is attached to the N-terminus and/or C-terminus of the light chain and heavy chain of said antibody or antigen binding fragment thereof. For example, the PD-L1 binding polypeptide may be attached to only the N-terminus of the heavy chain(s), only the N-terminus of the light chain(s), only the C-terminus of the heavy chain(s), only the C-terminus of the light chain(s), both the N-terminus and the C-terminus of the heavy chain(s), both the N-terminus and the C-terminus of the light chain(s), only the C-terminus of the light chain(s) and the N-terminus of the heavy chain(s), only the C-terminus of the heavy chain(s) and the N-terminus of the light chain(s), of said antibody or antigen binding fragment thereof.

In one embodiment there is provided a complex, wherein said PD-L1 binding polypeptide is attached either to the C-terminus or the N-terminus of the heavy chain or the light chain of said antibody or antigen binding fragment thereof.

In one particular embodiment, there is provided a complex according to any preceding item, wherein said antibody or antigen binding fragment thereof has affinity for an antigen, for example an antigen associated with an infectious disease, or an antigen associated with cancer. For example, said antigen may be PD-1 or CTLA-4.

In one embodiment there is provided a fusion protein, conjugate or complex as described herein, wherein the said second or further moiety/moieties or antibody or antigen binding fragment thereof is an inhibitor selected from the group consisting of inhibitors of: PD-1, CTLA-4, T-cell immunoglobulin and mucin containing protein-3 (TIM-3), galectin-9 (GAL-9), lymphocyte activation gene-3 (LAG-3), PD-L2, B7 homolog 3 (B7-H3), B7 homolog 4 (B7-H4), V-domain Ig suppressor of T-cell activation (VISTA), carcinoembryonic antigen-related cell adhesion molecule 1 (CEACAM1), B and T lymphocyte attenuator (BTLA), colony stimulating factor 1 receptor (CSF1R), herpes virus entry mediator (HVEM), killer immunoglobulin receptor (KIR), adenosine, adenosine A2a receptor (A2aR), CD200-CD200R and T cell Ig and ITIM domain.

In one embodiment, said second moiety or antibody or antigen binding fragment thereof is an inhibitor of PD-1, such as an inhibitor selected from the group consisting of nivolumab, pidilizumab, BMS 936559, MPDL3280A (Roche) and pembrolizumab. In a specific embodiment, the inhibitor is pembrolizumab.

In one embodiment, said second moiety or antibody or antigen binding fragment thereof is an inhibitor of CTLA-4, such as an inhibitor selected from the group consisting of belatacept, abatacept, tremelimumab and ipilimumab. In a specific embodiment, the inhibitor is ipilimumab.

In one embodiment there is provide a fusion protein, conjugate or complex as described herein, wherein said second moiety or antibody or antigen binding fragment thereof is an agonist selected from the group consisting of agonists of CD134, CD40, 4-1BB and glucocorticoid-induced TNFR-related protein (GITR).

The above aspects furthermore encompass polypeptides in which the PD-L1 binding polypeptide according to the first aspect, the PD-L1 binding polypeptide as comprised in a fusion protein or conjugate according to the second aspect or in a complex according to the third aspect, further comprises a label, such as a label selected from the group consisting of fluorescent dyes and metals, chromophoric dyes, chemiluminescent compounds, bioluminescent proteins, enzymes, radionuclides, radioactive particles and pretargeting recognition tags. Such labels may for example be used for detection of the polypeptide. For example, in some embodiments, such labeled polypeptide may for example be used for labeling or targeting tumors which have a high expression of PD-1.

Indirect labeling of a Z variant polypeptide was recently shown using pretargeting recognition tags (Westerlund et al (2015), Bioconjugate Chem 26:1724-1736). Similarly, the disclosure provides a PD-L1 binding polypeptide as described herein labeled with a pretargeting moiety, which may then be used for indirect labeling with a moiety complementary to the pretargeting moiety. When comprising a pretargeting moiety, a PD-L1 binding agent of the present disclosure is able to associate with a complementary pretargeting moiety, and such complementary pretargeting moiety may then comprise or be attached to a suitable radionuclide. The skilled person is aware of suitable radionuclides for therapeutic, diagnostic and/or prognostic purposes. Such a radionuclide may be chelated to said complementary pretargeting moiety via a chelating environment as generally described for the PD-L1 binding agent below.

In one embodiment, the complementary pair of pretargeting moieties comprise stept(avidin)/biotin, oligonucleotide/complementary oligonucleotide such as DNA/complementary DNA, RNA/complementary RNA, phosphorothioate nucleic acid/complementary phosphorothioate nucleic acid and peptide nucleic acid (PNA)/complementary peptide nucleic acid (cPNA) and morpholinos/complementary morpholinos. In one particular embodiment, said pretargeting moiety is a PNA oligonucleotide, such as a 10-20-mer PNA sequence, such as a 15-mer PNA sequence.

In embodiments in which the polypeptide, fusion protein, conjugate or complex is labeled, directly or indirectly (e.g. via pretargeting as described above), with an imaging agent (e.g. radioactive agent), measuring the amount of labeled polypeptide present in a tumor may be done using imaging equipment, such as through acquiring radioactivity counts or images of radiation density, or derivatives thereof such as radiation concentration. Non-limiting examples of radionuclides, suitable for either direct labeling of the PD-L1 binding agent according to any aspect disclosed herein, or for indirect labeling by labeling of a complementary pretargeting moiety, include $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I, $^{76}$Br, $^{111}$In, $^{99m}$Tc, $^{123}$I, $^{131}$I and $^{67}$Ga.

In one embodiment, the imaging equipment used in such measurements is positron emission tomography (PET) equipment, in which case the radionuclide is selected such that it is suitable for PET. The skilled person is aware of radionuclides suitable for use with PET. For example, a PET radionuclide is selected from the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I and $^{76}$Br.

In another embodiment, the imaging equipment used is single-photon emission computed tomography (SPECT) equipment, in which case the radionuclide is selected such that it is suitable for SPECT. The skilled person is aware of radionuclides suitable for use with SPECT. For example, a SPECT radionuclide is selected from the group consisting of $^{111}$In, $^{99m}$Tc, $^{123}$I, $^{131}$I and $^{67}$Ga.

Thus, in one embodiment there is provided a PD-L1 binding polypeptide, fusion protein or complex as described herein, which comprises a direct or indirect radionuclide label, such as a radionuclide selected from the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I, $^{76}$Br, $^{111}$In, $^{99m}$Tc, $^{123}$I, $^{131}$I and $^{67}$Ga, such as the group consisting of $^{68}$Ga, $^{110m}$In, $^{18}$F, $^{45}$Ti, $^{44}$Sc, $^{61}$Cu, $^{66}$Ga, $^{64}$Cu, $^{55}$Co, $^{72}$As, $^{86}$Y, $^{89}$Zr, $^{124}$I and $^{76}$Br, such as $^{18}$F.

In some embodiments, the labeled PD-L1 binding polypeptide is present as a moiety in a fusion protein, conjugate or complex also comprising a second moiety having a desired biological activity. The label may in some instances be coupled only to the PD-L1 binding polypeptide, and in some instances both to the PD-L1 binding polypeptide and to the second moiety of the fusion protein or conjugate and/or the antibody or antigen binding fragment thereof the complex. Furthermore, it is also possible that the label may be coupled to a second moiety, or antibody or antigen binding fragment thereof only and not to the PD-L1 binding moiety. Hence, in yet another embodiment, there is provided a PD-L1 binding polypeptide comprising a second moiety, wherein said label is coupled to the second moiety only. In another embodiment, there is provided a complex as defined herein, wherein said label is coupled to the antibody or antigen binding fragment thereof only.

When reference is made to a labeled polypeptide, this should be understood as a reference to all aspects of polypeptides as described herein, including PD-L1 binding polypeptides, fusion proteins, conjugates and complexes comprising a PD-L1 binding polypeptide. Thus, a labeled polypeptide may contain only the PD-L1 binding polypeptide and e.g. a therapeutic radionuclide, which may be chelated or covalently coupled to the PD-L1 binding polypeptide, or contain the PD-L1 binding polypeptide, a therapeutic radionuclide and a second moiety such as a small molecule having a desired biological activity, for example a therapeutic efficacy. A labeled polypeptide may contain a PD-L1 binding polypeptide in heterodimeric form and e.g. a therapeutic radionuclide, which may be chelated or covalently coupled to the PD-L1 binding polypeptide, or contain the PD-L1 binding polypeptide in heterodimeric form, a therapeutic radionuclide and a second moiety such as a small molecule having a desired biological activity, for example a therapeutic efficacy. Also envisioned is a complex which contains a PD-L1 binding polypeptide as defined herein, an antibody or antigen binding fragment thereof and a e.g. a therapeutic radionuclide, which may be chelated or covalently coupled to the PD-L1 binding polypeptide or to the antibody or antigen binding fragment thereof. The skilled person is aware of other possible variants.

In embodiments where the PD-L1 binding polypeptide, fusion protein, conjugate or complex is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the PD-L1 binding polypeptide, fusion protein, conjugate or complex, the incorporation of a radionuclide is enabled through the provision of a chelating environment, through which the radionuclide may be coordinated, chelated or complexed to the polypeptide. One example of a chelator is the polyaminopolycarboxylate type of chelator. Two classes of such polyaminopolycarboxylate chelators can be distinguished: macrocyclic and acyclic chelators.

In one embodiment, the PD-L1 binding polypeptide, fusion protein, conjugate or complex comprises a chelating environment provided by a polyaminopolycarboxylate chelator conjugated to the PD-L1 binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the PD-L1 binding polypeptide, PD-L1 binding polypeptide in heterodimeric form, fusion protein, conjugate or complex is provided by DOTA or a derivative thereof. More specifically, in one embodiment, a chelating polypeptide encompassed by the present disclosure is obtained by reacting the DOTA derivative 1,4,7,10-tetraazacyclododecane-1,4,7-trisacetic acid-10-maleimidoethylacetamide (maleimidomonoamide-DOTA) with said polypeptide. In one embodiment, a chelating polypeptide encompassed by the present disclosure is obtained by reacting the DOTA derivative DOTAGA (2,2',2"-(10-(2,6-dioxotetrahydro-2H-pyran-3-yl)-1,4,7,10-tetraazacyclododecane-1,4,7-triyl)triacetic acid) with said polypeptide. Additionally, 1,4,7-triazacyclononane-1,4,7-triacetic acid (NOTA) and derivatives thereof may be used as chelators. Hence, in one embodiment, a chelating environment of the PD-L1 binding polypeptide, PD-L1 binding polypeptide in heterodimeric form, fusion protein, conjugate or complex is provided by NOTA or a derivative thereof. In one embodiment, a chelating polypeptide encompassed by the present disclosure is obtained by reacting the NOTA derivative NODAGA (2,2'-(7-(1-carboxy-4-((2,5-dioxopyrrolidin-1-yl)oxy)-4-oxobutyl)-1,4,7-triazonane-1,4-diyl)diacetic acid) with said polypeptide. The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

In further aspects of the present disclosure, there is provided a polynucleotide encoding a PD-L1 binding polypeptide, fusion protein or complex as described herein; an expression vector comprising said polynucleotide; and a host cell comprising said expression vector.

Also encompassed by this disclosure is a method of producing PD-L1 binding polypeptide, fusion protein or complex as described above, comprising culturing said host cell under conditions permissive of expression of said polypeptide from its expression vector, and isolating the polypeptide.

The PD-L1 binding polypeptide, fusion protein or complex of the present disclosure may alternatively be produced by non-biological peptide synthesis using amino acids and/or amino acid derivatives having protected reactive side-chains, the non-biological peptide synthesis comprising step-wise coupling of the amino acids and/or the amino acid derivatives to form a polypeptide, fusion protein or complex as described herein having protected reactive side-chains, removal of the protecting groups from the reactive side-chains of the polypeptide fusion protein or complex, and folding of the polypeptide in aqueous solution.

A complex as disclosed herein may also be produced by the conjugation of at least one PD-L1 binding polypeptide or fusion protein as described herein to at least one antibody or antigen binding fragment thereof. The skilled person is aware of conjugation methods, such as conventional chemical conjugation methods, for example using charged succinimidyl esters or carbodiimides.

It should be understood that the PD-L1 binding polypeptide according to the present disclosure may be useful as a therapeutic, diagnostic and/or prognostic agent in its own right or as a means for targeting other therapeutic or diagnostic agents, with e.g. direct or indirect effects on PD-L1. A direct therapeutic effect may for example be accomplished by inhibiting PD-L1 signaling. An indirect therapeutic effect may for example be accomplished by pretargeting using PD-L1 binding polypeptides as described above.

Thus, in another aspect, there is provided a composition comprising a PD-L1 binding polypeptide, fusion protein, conjugate or complex as described herein and at least one pharmaceutically acceptable excipient or carrier. In one embodiment, said composition further comprises at least one additional active agent, such as at least two additional active agents, such as at least three additional active agents. Non-limiting examples of additional active agents that may prove useful in such combination are immune response modifying agents and anti-cancer agents as described herein.

The small size and robustness of the PD-L1 binding polypeptides of the present disclosure confer several advantages over conventional monoclonal antibody based therapies. Such advantages include advantages in formulation, modes of administration, such as alternative routes of administration, administration at higher doses than antibodies and absence of Fc-mediated side effects. The agents of the present disclosure are contemplated for oral, topical, intravenous, intraperitoneal, subcutaneous, pulmonary, transdermal, intramuscular, intranasal, buccal, sublingual or suppository administration, such as for topical administration. Also, many diseases and disorders, such as cancers and infectious disease, are associated with more than one factor. Thus, a complex as defined herein confers the advantage of targeting an additional antigen together with PD-L1.

In another aspect of the present disclosure, there is provided a PD-L1 binding polypeptide, fusion protein, conjugate, complex or composition as described herein for use as a medicament, a prognostic agent and/or a diagnostic agent. In one embodiment, there is provided a PD-L1 binding polypeptide, fusion protein, conjugate, complex or composition for use in the treatment, diagnosis or prognosis of a PD-L1 related disorder.

In one embodiment, said PD-L1 binding polypeptide, fusion protein, conjugate, complex or composition is provided for use as a medicament. In a more specific embodiment, there is provided a PD-L1 binding polypeptide, fusion protein, conjugate, complex or composition as described herein, for use as a medicament to modulate PD-L1 function in vivo. As used herein, the term "modulate" refers to changing the activity, such as rendering PD-L1 function hypomorph, partially inhibiting or fully inhibiting PD-L1 function.

In one embodiment, there is provided a PD-L1 binding polypeptide, fusion protein, conjugate, complex or composition for use in the treatment of a PD-L1 related disorder.

In one embodiment, there is provided a PD-L1 binding polypeptide, fusion protein, conjugate, complex or composition for use in the diagnosis of a PD-L1 related disorder.

In one embodiment, there is provided a PD-L1 binding polypeptide, fusion protein, conjugate, complex or composition for use in the prognosis of a PD-L1 related disorder.

As used herein, the term "PD-L1 related disorder" refers to any disorder, disease or condition in which PD-L1 signalling plays a regulatory role. Examples of such PD-L1 related disorder include infectious diseases and cancers.

It is to be understood that said PD-L1 binding polypeptide, fusion protein, conjugate, complex or composition may be used as the sole diagnostic or prognostic agent or as a companion diagnostic and/or prognostic agent.

In one embodiment, said PD-L1 related disorder is selected from the group consisting infectious diseases and cancers. Non-limiting examples of infectious diseases include chronic viral infection, for example selected from the group consisting of human immunodeficiency virus (HIV), hepatitis B virus (HBV) and hepatitis C virus (HCV).

The skilled person will appreciate that a cancer suitable for treatment, diagnosis and/or prognosis using PD-L1 binding polypeptide, fusion protein, conjugate, complex or composition may be a solid tumor cancer or a non-solid tumor cancer characterized by over-expression of PD-L1. Non-limiting examples of such cancers include skin cancer; such as melanoma and nonmelanoma skin cancer (NMSC); lung cancers such as small cell lung cancer, non-small cell lung cancer (NSCLC); head and neck cancer, renal cell carcinoma (RCC), bladder cancer, breast cancer, colorectal cancer, gastric cancer, ovarian cancer, pancreatic cancer, prostate cancer, glioma, glioblastoma, liver carcinoma, gallbladder cancer, thyroid cancer, bone cancer, cervical cancer, uterine cancer, vulval cancer, endometrial cancer, testicular cancer, kidney cancer, esophageal carcinoma, brain/CNS cancers, neuronal cancers, mesothelioma, sarcomas, small bowel adenocarcinoma and pediatric malignancies; leukaemia, acute myeloid leukaemia, acute lymphoblastic leukaemia and multiple myeloma.

In one particular embodiment, said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as a cancer selected from the group consisting of melanoma, NSCLC, head and neck cancer, RCC and bladder cancer.

In one embodiment, it may be beneficial to administer a therapeutically effective amount of a PD-L1 binding polypeptide, fusion protein, conjugate, complex or composition as described herein together with at least one second drug substance, such as an anti-cancer agent or an immune response modifying agent.

In one embodiment, there is provided a PD-L1 binding polypeptide, fusion protein, conjugate, complex or composition for use in prognosis and/or diagnosis together with at least one cell proliferation marker. Non-limiting examples of contemplated cell proliferation markers are those selected from the group consisting of Ki-67, AgNOR, choline, claspin, cyclin A, CYR61, Cdk1, histone H3, HsMCM2, IL-2, Ki-S1, Ki-S2, Ligl, MCM2, MCM6, MCM7, mitosin, p120, PCNA, PDPK, PLK, STK1, TK-1, topoisomerase II alpha and TPS.

In a related aspect, there is provided a method of treatment of a PD-L1 related disorder, comprising administering to a subject in need thereof an effective amount of a PD-L1 binding polypeptide, fusion protein, conjugate, complex or composition as described herein. In a more specific embodiment of said method, the PD-L1 binding polypeptide, fusion protein, conjugate, complex or composition as described herein modulates PD-L1 function in vivo. The skilled person will appreciate that any description in relation to the use of PD-L1 binding polypeptide, fusion protein, conjugate, complex or composition as described herein for treatment of a disease or disorder is equally relevant for the related therapeutic method. For the sake of brevity, such description will not be repeated here.

In one particular embodiment, said method of treatment, particularly relevant for the treatment of PD-L1 related cancers, comprises the steps of contacting the subject with a PD-L1 binding polypeptide, fusion protein, conjugate or complex comprising a pretargeting moiety as described herein, or with a composition comprising said PD-L1 binding polypeptide, fusion protein, conjugate or complex comprising a pretargeting moiety, and contacting the subject with a complementary pretargeting moiety comprising a radionuclide.

In another aspect of the present disclosure, there is provided a method of detecting PD-L1, comprising providing a sample suspected to contain PD-L1, contacting said sample with a PD-L1 binding polypeptide, fusion protein, conjugate, complex or composition as described herein, and detecting the binding of the PD-L1 binding polypeptide, fusion protein, conjugate, complex or composition to indicate the presence of PD-L1 in the sample.

In one embodiment, said method further comprises an intermediate washing step for removing non-bound polypeptide, fusion protein, conjugate, complex or composition, after contacting the sample.

In another embodiment, said method is a diagnostic or prognostic method for determining the presence of PD-L1 in a subject, the method comprising the steps:

a) contacting the subject, or a sample isolated from the subject, with a PD-L1 binding polypeptide, fusion protein, conjugate, complex or composition as described herein, and b) obtaining a value corresponding to the amount of the PD-L1 binding polypeptide, fusion protein, conjugate, complex or composition that has bound in said subject or to said sample.

In one embodiment, said method further comprises an intermediate washing step for removing non-bound polypeptide, fusion protein, conjugate or composition, after contacting the subject or sample and before obtaining a value.

In one embodiment of this diagnostic or prognostic method, said PD-L1 binding polypeptide, fusion protein, conjugate or complex comprises a pretargeting moiety as described herein, and the contacting step a) of the method further comprises contacting the subject with a complementary pretargeting moiety labeled with a detectable label, such as a radionuclide label.

In one embodiment, said method further comprises a step of comparing said value to a reference. Said reference may be by a numerical value, a threshold or a visual indicator, for example based on a color reaction. The skilled person will appreciate that different ways of comparison to a reference are known in the art and may be suitable for use.

In one embodiment of such a method, said subject is a mammalian subject, such as a human subject. In one embodiment, said method is performed in vivo. In another embodiment, said method is performed in vitro.

In one embodiment, the diagnostic or prognostic method is a method for medical imaging in vivo as discussed above. Such a method comprises the systemic administration of a PD-L1 binding entity as disclosed herein (i.e. the polypeptide per se, or the fusion protein, conjugate, complex or composition containing it) to a mammalian subject. The PD-L1 binding entity is directly or indirectly labelled, with a label comprising a radionuclide suitable for medical imaging (see above for a list of contemplated radionuclides). Furthermore, the method for medical imaging comprises obtaining one or more images of at least a part of the subject's body using a medical imaging instrument, said image(s) indicating the presence of the radionuclide inside the body.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 1A-1CC is a listing of the amino acid sequences of examples of PD-L1 binding polypeptides of the present disclosure (SEQ ID NO:1-814), as well as the heavy chain ($HC_{Lam}$; SEQ ID NO:815) and the light chain ($LC_{Lam}$; SEQ ID NO:816) of the PD-1 binding monoclonal antibody Lam and the heavy chain ($HC_{Ipi}$; SEQ ID NO:817) and the light chain ($LC_{Ipi}$; SEQ ID NO:818) of the CTLA-4 binding monoclonal antibody Ipi. In the PD-L1 binding polypeptides of the present disclosure, the deduced PD-L1 binding motifs (BM) extend from residue 8 to residue 36 in each sequence. The amino acid sequences of the 49 amino acid residues long polypeptides (BMod) predicted to constitute the complete three-helix bundle within each of these Z variants extend from residue 7 to residue 55.

FIG. 8 shows dual binding specificity of complexes analyzed in a Biacore capture assay as described in Example 8. (A) Z15170-$HC_{Lam}$ and (B) Z15170-$LC_{Lam}$ were injected for 5 min over chip surfaces immobilized with PD-1, followed by injection of PD-L1 at a concentration of 100 and/or 500 nM, respectively. (C) Z15170-$HC_{Ipi}$ and (D) Z15170-$LC_{Ipi}$ were injected for 5 min over chip surfaces immobilized with CTLA-4, followed by injection of PD-L1 at a concentration of 100 and 500 nM, respectively.

FIG. 9 shows the result of inhibition of PD-L1 and CTLA-4 by Ipi-based complexes, analyzed in a mixed lymphocyte assay as described in Example 8. (A) Reduction in the number of MDA-MB231 cells and (B) increasing number of CD3+ T-cells with increasing concentrations of the Ipi-based complexes $HC_{Ipi}$-Z15170, $LC_{Ipi}$-Z15170, Z15170-$HC_{Ipi}$ and Z15170-$LC_{Ipi}$.

FIG. 10 shows PET maximum intensity projection (MIP) images of xenograft mice. (A) MIPs of mice with LOX tumor (left) and SUDHL6 tumor (right) xenografts, 30-90 min after administration of $[^{18}F]$AlF-NOTA-Z15168. (B) MIPs of mice with LOX tumor xenografts, 30-90 min after administration of $[^{18}F]$AlF-NOTA-Z15168 (left) at baseline and (right) following pre-block with 400 μg NOTA-Z15168.

FIG. 11 shows ex vivo biodistribution results for LOX and SUDHL6 mouse xenograft models, as analyzed directly after PET data acquisition. The results are displayed in units of (A) Standard Uptake Value (SUV) and (B) tumor:blood ratio. Error bars represent standard deviation.

FIG. 12 shows the result of whole body scan of rhesus monkeys. MIPs (summed over 90-180 min; colour inverted images) of rhesus monkeys administered with (A) $[^{18}F]$AlF-NOTA-Z15168 and (B) $[^{18}F]$AlF-NOTA-Z18609. (C) Average tracer uptake over 120-180 min in different organs displayed in the units of SUV. Error bars represent standard deviation.

EXAMPLES

Summary

Figure 2A:
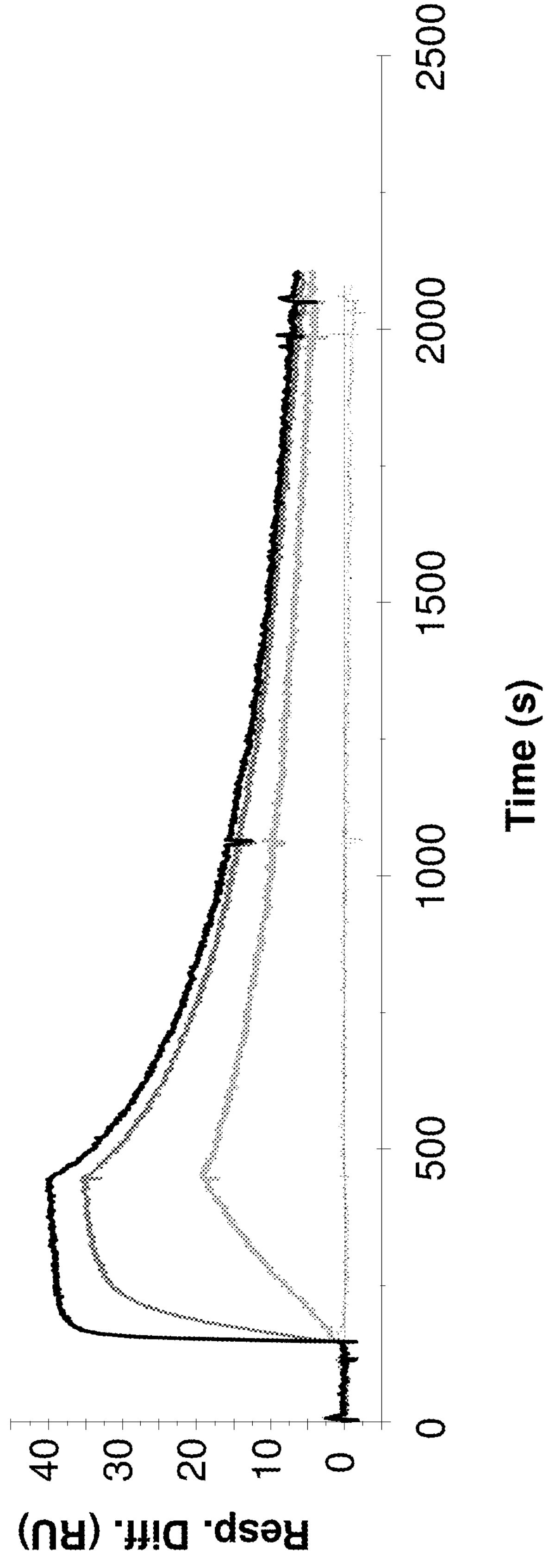
FIG. 2 shows binding of two first generation polypeptides to human PD-L1 analyzed by Biacore as described in Example 3. Z variants (A) Z13091 (SEQ ID NO:776) and (B) Z13156 (SEQ ID NO:781 were injected at concentrations of 50 nM (black), 5 nM (dark grey) and 0.5 nM (light grey) over a CM5 chip with immobilized hPD-L1.

The following Examples disclose the development of novel Z variant molecules targeted to human programmed death-ligand 1 (PD-L1), also known as human B7 homolog 1 (B7-H1) and cluster of differentiation 274 (CD274), based on phage display technology. The PD-L1 binding polypeptides described herein were sequenced, and their amino acid sequences are listed in FIG. 1A-1CC with the sequence identifiers SEQ ID NO:1-808. The Examples further describe the characterization of PD-L1 binding polypeptides and demonstrate in vitro functionality of said polypeptides.

Example 1

Selection and Screening of PD-L1 Binding Z Variants

In this Example, human PD-L1 (hPD-L1) was used as target in phage display selections using a phage library of Z variants. Selected clones were DNA sequenced, produced in *E. coli* periplasmic fractions and assayed against PD-L1 in ELISA (enzyme-linked immunosorbent assay).

Materials and Methods

Biotinylation of target protein: hPD-L1 (human PD-L1 Fc Chimera, R&D Systems, cat. no. 156-B7-100) was biotinylated using No-Weigh EZ-Link Sulfo-NHS-LC-Biotin (Thermo Scientific, cat. no. 21327) at a 10× molar excess, according to the manufacturer's recommendations. The reaction was performed at room temperature (RT) for 40 min. Subsequent buffer exchange to PBS (10 mM phosphate, 137 mM NaCl, 2.68 mM KCl, pH 7.4) was performed using a Slide-a-lyzer dialysis cassette (10000 MWCO, Thermo Scientific, cat. no. 66383) according to the manufacturer's instructions.

Phage display selection of PD-L1 binding Z variants: A library of random variants of protein Z displayed on bacteriophage, constructed in phagemid pAY02592 essentially as described in Grönwall et al. (2007) J Biotechnol, 128:162-183, was used to select PD-L1 binding Z variants. In this library, an albumin binding domain (ABD, GA3 of protein G from *Streptococcus* strain G148) is used as fusion partner to the Z variants. The library is denoted Zlib006Naive.II and has a size of $1.5\times10^{10}$ library members (Z variants). *E. coli* RRIAM15 cells (Ruther et al., (1982) Nucleic Acids Res 10:5765-5772) from a glycerol stock containing the phagemid library Zlib006Naive.II were inoculated in 20 l of a defined proline free medium [3 g/l $KH_2PO_4$, 2 g/l $K_2HPO_4$, 0.02 g/l uracil, 6.7 g/l YNB (Difco™ Yeast Nitrogen Base w/o amino acids, Becton Dickinson), 5.5 g/l glucose monohydrate, 0.3 g/l L-alanine, 0.24 g/l L-arginine monohydrochloride, 0.11 g/l L-asparagine monohydrate, 0.1 g/l L-cysteine, 0.3 g/l L-glutamic acid, 0.1 g/l L-glutamine, 0.2 g/l glycine, 0.05 g/l L-histidine, 0.1 g/l L-isoleucine, 0.1 g/l L-leucine, 0.25 g/l L-lysine monohydrochloride, 0.1 g/l L-methionine, 0.2 g/l L-phenylalanine, 0.3 g/l L-serine, 0.2 g/l L-threonine, 0.1 g/l L-tryptophane, 0.05 g/l L-tyrosine, 0.1 g/l L-valine], supplemented with 100 μg/ml ampicillin. The cultivations were grown at 37° C. in a fermenter (Belach Bioteknik, BR20). When the cells reached an optical density at 600 nm ($OD_{600}$) of 0.75, approximately 2.6 l of the cultivation was infected using a 10× molar excess of M13K07 helper phage (New England Biolabs, cat. no. N0315S). The cells were incubated for 30 min, whereupon the fermenter was filled up to 20 l with cultivation medium (2.5 g/l $(NH_4)_2SO_4$; 5.0 g/l Yeast Extract (Merck 1.03753.0500); 25 g/l Peptone (Scharlau 07-119); 2 g/l $K_2HPO_4$; 3 g/l $KH_2PO_4$; 1.25 g/l $Na_3C_6H_5O_7.2H_2O$; 0.1 ml/l Breox FMT30 antifoaming agent) supplemented with 100 μM isopropyl-β-D-1-thiogalactopyranoside (IPTG) for induction of expression and with 50 μg/ml ampicillin, 12.5 μg/ml carbenicillin, 25 μg/ml kanamycin, 35 ml/l of 1.217 M $MgSO_4$ and 10 ml of a trace element solution [129 mM $FeCl_3$; 36.7 mM $ZnSO_4$; 10.6 mM $CuSO_4$; 78.1 mM $MnSO_4$; 94.1 mM $CaCl_2$, dissolved in 1.2 M HCl]. A glucose-limited fed-batch cultivation was started where a 600 g/l glucose solution was fed to the reactor (15 g/h in the start, 40 g/h at the end of the fermentation after 17 h). pH was controlled at 7 through the automatic addition of 25% $NH_4OH$, air was supplemented (10 l/min), and the stirrer was set to keep the dissolved oxygen level above 30%. The cells in the cultivation were removed by tangential flow filtration.

The phage particles were precipitated from the supernatant twice in PEG/NaCl (polyethylene glycol/sodium chloride), filtered and dissolved in PBS and glycerol as described in Grönwall et al., supra. Phage stocks were stored at −80° C. before use.

Selections against biotinylated hPD-L1 were performed in four cycles initially divided in two different tracks (1 and 2). As selection proceeded, the tracks were further divided according to target concentration and number and/or time of washes to finally end up in nine tracks in cycle 4. More precisely, the first track (1) was divided in the second to the fourth cycles, resulting in a total of two tracks (1-1 to 1-2) in cycle 2, four tracks (1-1-1 to 1-2-2) in cycle 3 and six tracks (1-1-1-1 to 1-2-2-1) in cycle 4. The second track (2) was divided in the third to the fourth cycles, resulting in a total of two tracks (2-1-1 to 2-1-2) in cycle 3, three tracks (2-1-1-1 to 2-1-2-1) in cycle 4. In track 1 with descendants, Dynabeads® M-280 Streptavidin (SA-beads, Invitrogen, cat. no. 11206D) were used to catch the hPD-L1:Z variant complexes. In track 2, Dynabeads® Protein A (SPA-beads, Invitrogen, cat. no. 10002D) were used instead to catch the hPD-L1:Z variant complexes by binding to the Fc part of the hPD-L1 Fc chimeric protein.

Phage stock preparation, selection procedure and amplification of phage between selection cycles were performed essentially as described for selection against another biotinylated target in WO2009/077175 with the following exception: the selection buffer consisted of PBS supplemented with % Fetal Bovine Serum (FBS, Gibco, cat. no. 10108-165) and 0.1% Tween20 (Acros Organics, cat. no. 233362500).

In order to reduce the amount of background binders, a pre-selection was performed in each cycle. In the pre-selection, the same types of beads were used as during the selection, i.e. SA-beads in track 1 and SPA-beads in track 2. In all tracks of cycle 1-4, pre-selections were performed using SA- or SPA-beads coated with biotinylated human IgG-Fc (Jackson ImmunoResearch Lab, cat. no. 009-060-008). Furthermore in cycle 1, track 1, the pre-selection was performed using SA-beads coated with a mix of hPD-L2 (human PD-L2 Fc Chimera; R&D Systems, cat. no. 1224-PL-100), hB7-H3 (human B7-H3 Fc Chimera; R&D Systems, cat. no. 1027-B3-100), hB7-H4 (human B7-H4; R&D Systems, cat. no. 6576-B7-50), biotinylated previously as described for hPD-L1. In cycle 1, track 2, the pre-selection was performed using SPA-beads coated with a mix of biotinylated PD-L2 and biotinylated B7-H3. During pre-selection the phage stock was incubated with coated beads end-over end for 30-90 min at RT. All tubes and beads used in the pre-selections or selection were pre-blocked with PBS supplemented with 3% Bovine Serum Albumin (BSA, Sigma A3059-100G) and 0.1% Tween20. Selection was performed in solution at RT and the time for selection was approximately 120 min followed by wash with PBS+0.1% Tween20 and catch of target-phage complexes on SA-beads or SPA-beads using 1 mg beads per 1.6 or 8.5 μg biotinylated hPD-L1, respectively.

For amplification of phage particles between selection cycle 1 and 2, *E. coli* strain ER2738 cells (Lucigen, Middleton, Wis., USA) were used for infection and grown in medium supplemented with 20 μg/ml tetracycline. A 5× excess of M13K07 helper phage compared to bacteria were allowed to infect log phase bacteria.

TABLE 2

Selection against biotinylated hPD-L1 Fc chimera

| Cycle | Selection track | Phage stock from library or selection track | Proteins used in pre-selection | Target conc. (nM) | Number of washes | Duration of last wash (h) |
|---|---|---|---|---|---|---|
| 1 | 1 | Zlib006Naive.II | IgG-Fc, hPD-L2, hB7-H3, hB7-H4 | 100 | 2 | |
| 1 | 2 | Zlib006Naive.II | IgG-Fc, hPD-L2, hB7-H3 | 100 | 2 | |

TABLE 2-continued

Selection against biotinylated hPD-L1 Fc chimera

| Cycle | Selection track | Phage stock from library or selection track | Proteins used in pre-selection | Target conc. (nM) | Number of washes | Duration of last wash (h) |
|---|---|---|---|---|---|---|
| 2 | 1-1 | 1 | IgG-Fc | 66 | 4 | |
| 2 | 1-2 | 1 | IgG-Fc | 10 | 4 | |
| 2 | 2-1 | 2 | IgG-Fc | 66 | 4 | |
| 3 | 1-1-1 | 1-1 | IgG-Fc | 44 | 6 | |
| 3 | 1-1-2 | 1-1 | IgG-Fc | 10 | 6 | |
| 3 | 1-2-1 | 1-2 | IgG-Fc | 1 | 6 | |
| 3 | 1-2-2 | 1-2 | IgG-Fc | 0.5 | 10 | |
| 3 | 2-1-1 | 2-1 | IgG-Fc | 44 | 6 | |
| 3 | 2-1-2 | 2-1 | IgG-Fc | 10 | 6 | |
| 4 | 1-1-1-1 | 1-1-1 | IgG-Fc | 30 | 10 | |
| 4 | 1-1-1-2 | 1-1-1 | IgG-Fc | 10 | 31 | 1 |
| 4 | 1-1-2-1 | 1-1-2 | IgG-Fc | 10 | 31 | 15 |
| 4 | 1-2-1-1 | 1-2-1 | IgG-Fc | 0.5 | 10 | |
| 4 | 1-2-1-2 | 1-2-1 | IgG-Fc | 0.2 | 31 | 64 [4° C.] |
| 4 | 1-2-2-1 | 1-2-2 | IgG-Fc | 0.05 | 31 | 15 |
| 4 | 2-1-1-1 | 2-1-1 | IgG-Fc | 30 | 10 | |
| 4 | 2-1-1-2 | 2-1-1 | IgG-Fc | 10 | 31 | 1 |
| 4 | 2-1-2-1 | 2-1-2 | IgG-Fc | 10 | 31 | 15 |

The amplification of phage particles between selection cycles 2 and 4 was done by performing infection of bacteria in solution as follows. After infection of log phase *E. coli* ER2738 with phage particles, TSB supplemented with 2% glucose, 10 μg/ml tetracycline and 100 μg/ml ampicillin was added, followed by incubation with rotation for 30 min at 37° C. Thereafter, the bacteria were infected with M13K07 helper phage in 5× excess. The infected bacteria were pelleted by centrifugation, re-suspended in TSB-YE medium supplemented with 100 μM IPTG, 25 μg/ml kanamycin and 100 μg/ml ampicillin, and grown overnight at 30° C. The overnight cultures were centrifuged, and phage particles in the supernatant were precipitated twice with PEG/NaCl buffer. Finally, the phage particles were re-suspended in selection buffer before entering the next selection cycle.

In the final selection cycle, log phase bacteria were infected with eluate and diluted before spreading onto TBAB plates (30 g/l tryptose blood agar base, Oxoid, cat. no. CM0233B) supplemented with 0.2 g/l ampicillin in order to form single colonies to be used in ELISA screening. An overview of the selection strategy, describing an increased stringency in subsequent cycles, using a lowered target concentration and an increased number of washes, is shown in Table 2. Washes were performed for 1 min, if nothing else is stated in Table 2, using PBST 0.1% (PBS supplemented with 0.1% Tween-20) and elution was carried out as described in WO2009/077175.

Production of Z variants for ELISA: Z variants were produced by inoculating single colonies from the selections into 1 ml TSB-YE medium supplemented with 100 μg/ml ampicillin and 1 mM IPTG in deep-well plates (Nunc, cat. no. 278752). The plates were incubated with rotation for 24 h at 37° C. Cells were pelleted by centrifugation, re-suspended in 200 μl PBST 0.05% and frozen at −80° C. to release the periplasmic fraction of the cells. Frozen samples were thawed in a water bath and the freeze-thawing procedure was repeated eight times. 600 μl PBST 0.05% was added to the thawed samples and cells were pelleted by centrifugation.

The final supernatant of the periplasmic extract contained the Z variants as fusions to ABD, expressed as AQHDEALE-[Z#####]-VDYV-[ABD]-YVPG (SEQ ID NO:896) (Grönwall et al., supra). Z##### refers to individual, 58 amino acid residue Z variants.

ELISA screening of Z variants: The binding of Z variants to hPD-L1 was analyzed in ELISA assays. Half-area 96-well ELISA plates (Costar, cat. no. 3690) were coated at 4° C. overnight with 2 μg/ml of an anti-ABD goat antibody (produced in-house) diluted in coating buffer (50 mM sodium carbonate, pH 9.6; Sigma, cat. no. C3041). The antibody solution was poured off and the wells were washed in water and blocked with 100 μl of PBSC (PBS supplemented with 0.5% casein; Sigma, cat. no. C8654) for 1 to 3 h at RT. The blocking solution was discarded and 50 μl periplasmic solutions, diluted 1:1 with PBST 0.05%, were added to the wells and incubated for 1.5 to 2.5 h at RT under slow agitation. As a blank control, PBST 0.05% was added instead of a periplasmic sample. The supernatants were poured off and the wells were washed 4 times with PBST 0.05%. Then, 50 μl of biotinylated hPD-L1 at a concentration of 0.32 nM in PBSC was added to each well. The plates were incubated for 1 h at RT followed by washes as described above. Streptavidin conjugated HRP (Thermo Scientific, cat. no. N100) diluted 1:30,000 in PBSC, was added to the wells and the plates were incubated for approximately 1 h. After washing as described above, 50 μl ImmunoPure TMB substrate (Thermo Scientific, cat. no. 34021) was added to the wells and the plates were treated according to the manufacturer's recommendations. The absorbance at 450 nm was measured using a multi-well plate reader, Victor[3] (Perkin Elmer).

Sequencing: In parallel with the ELISA screening, all clones were sequenced. PCR fragments were amplified from single colonies, sequenced and analyzed essentially as described in WO2009/077175.

EC50 analysis of Z variants: A selection of PD-L1 binding Z variants was subjected to an analysis of the response against a dilution series of biotinylated hPD-L1 following the procedure described above. The Z variants were diluted 1:1 in PBST 0.05%. Biotinylated hPD-L1 was added at a concentration of 40 nM and diluted stepwise 1:4 down to 32 pM. As a background control, all Z variants were also assayed with no target protein added. Periplasm samples containing the PD-L1 binding Z variant Z13112 (SEQ ID.NO:777) were included on each plate and analyzed as positive control. Periplasm containing the ABD moiety only was used as negative control. In the same assay, the specificity of the Z variants was tested by incubating periplasm samples with the four different biotinylated control proteins hPD-L2, hB7-H3, hB7-H4 and IgGFc, respectively, added at a concentration of 8 nM. Data were analyzed using GraphPad Prism 5 and non-linear regression, and EC50 values (the half maximal effective concentration) were calculated.

Results

Phage display selection of PD-L1 binding Z variants: Individual clones were obtained after four cycles of phage display selections against biotinylated hPD-L1.

ELISA screening of Z variants: The clones obtained after four cycles of selection were produced in 96-well plates and screened for hPD-L1 binding activity in ELISA. Several unique Z variants were found to give a response of 0.3 AU or higher (corresponding to at least 3× the blank control) against hPD-L1 at a concentration of 0.32 nM. The average response of the blank controls was 0.067 AU.

Sequencing: Sequencing was performed for clones obtained after four cycles of selection. Each variant was given a unique identification number #####, and individual variants are referred to as Z#####. The amino acid sequences of the 58 amino acid residues long Z variants are listed in FIG. 1A-1CC and in the sequence listing as SEQ ID NO:774-808. The deduced PD-L1 binding motifs extend from residue 8 to residue 36 in each sequence. The amino acid sequences of the 49 amino acid residues long polypeptides predicted to constitute the complete three-helix bundle within each of these Z variants extend from residue 7 to residue 55.

EC50 analysis of Z variants: A subset of Z variants having the highest ELISA values in the ELISA screening experiment described above was selected and subjected to a target titration in ELISA format. Periplasm samples were incubated with a serial dilution of biotinylated hPD-L1. A periplasm sample containing Z13112 (SEQ ID NO:777), confirmed to bind PD-L1 in the ELISA screen, was selected as a positive control and used to normalize different plates to each other. Obtained values were analyzed and their respective EC50 values were calculated (Table 3).

No significant binding was detected to any of the included control proteins of the B7-family (hPD-L2, hB7-H3 and hB7-H4), nor to the control protein IgGFc (included here because Fc chimeric proteins were used in the selection and screening). These results indicate that the selected Z variants are specific to PD-L1.

TABLE 3

Calculated EC50 values from ELISA titration analysis

| Z variant | SEQ ID NO: | EC50 (M) |
|---|---|---|
| Z13080 | 774 | $2.8 \times 10^{-10}$ |
| Z13088 | 775 | $3.8 \times 10^{-10}$ |
| Z13091 | 776 | $2.2 \times 10^{-10}$ |
| Z13104 | 788 | $4.1 \times 10^{-10}$ |
| Z13112 | 777 | $2.2 \times 10^{-10}$ |
| Z13115 | 789 | $4.0 \times 10^{-10}$ |
| Z13117 | 790 | $2.9 \times 10^{-10}$ |
| Z13134 | 791 | $4.5 \times 10^{-10}$ |
| Z13147 | 779 | $2.8 \times 10^{-10}$ |
| Z13154 | 780 | $1.1 \times 10^{-10}$ |
| Z13158 | 782 | $2.5 \times 10^{-10}$ |
| Z13164 | 783 | $2.2 \times 10^{-10}$ |
| Z13165 | 784 | $2.4 \times 10^{-10}$ |

TABLE 3-continued

Calculated EC50 values from ELISA titration analysis

| Z variant | SEQ ID NO: | EC50 (M) |
|---|---|---|
| Z13169 | 785 | $1.5 \times 10^{-10}$ |
| Z13186 | 792 | $4.7 \times 10^{-10}$ |
| Z13190 | 793 | $2.6 \times 10^{-10}$ |
| Z13198 | 786 | $1.6 \times 10^{-10}$ |
| Z13210 | 794 | $3.5 \times 10^{-10}$ |
| Z13304 | 787 | $3.2 \times 10^{-10}$ |
| Z13368 | 795 | $4.8 \times 10^{-10}$ |
| Z13447 | 796 | $2.9 \times 10^{-10}$ |

Example 2

Subcloning and Production of a Subset of Primary PD-L1 Binding Z Variants

Materials and Methods

Subcloning of Z variants with a Hiss-tag: The DNA of 14 PD-L1 binding Z variants, Z13080 (SEQ ID NO:774), Z13088 (SEQ ID NO:775), Z13091 (SEQ ID NO:776), Z13112 (SEQ ID NO:777), Z13120 (SEQ ID NO:778), Z13147 (SEQ ID NO:779), Z13154 (SEQ ID NO:780), Z13156 (SEQ ID NO:781), Z13158 (SEQ ID NO:782), Z13164 (SEQ ID NO:783), Z13165 (SEQ ID NO:784), Z13169 (SEQ ID NO:785), Z13198 (SEQ ID NO:786) and Z13304 (SEQ ID NO:787) were amplified from the library vector pAY02592. A subcloning strategy for construction of monomeric Z variant molecules with N-terminal Hiss-tag was applied using standard molecular biology techniques (essentially as described in detail in WO2009/077175 for Z variants binding another target). The Z gene fragments were subcloned into the expression vector pAY01448 resulting in the encoded sequence MGSSHHHHHHLQ-[Z#####]-VD (seq ID NO:897.

Subcloning of Z variants with a C-terminal Cys: Two Z variants, Z13091 (SEQ ID NO:776) and Z13156 (SEQ ID NO:781) were mutated to start with the N-terminal amino acids AE instead of VD and further subcloned with the C-terminal addition of the amino acids VDC (incorporating a unique cysteine in the polypeptide) using standard molecular biology techniques. The resulting encoding sequences are referred to as Z15168-Cys (SEQ ID NO:809) and Z15169-Cys (SEQ ID NO:810), respectively.

Cultivation: *E. coli* T7E2 cells (GeneBridges) were transformed with plasmids containing the gene fragments of each respective PD-L1 binding Z variant and cultivated at 37° C. in 940 ml of TSB-YE medium supplemented with 50 μg/ml kanamycin. In order to induce protein expression, IPTG was added to a final concentration of 0.2 mM at $OD_{600}$=2 and the cultivation was incubated at 37° C. for another 5 h. The cells were harvested by centrifugation.

Purification of PD-L1 binding Z variants with a Hiss-tag: Approximately 1-2 g of each cell pellet was resuspended in 30 ml of binding buffer (20 mM sodium phosphate, 0.5 M NaCl, 20 mM imidazole, pH 7.4) supplemented with Benzonase® (Merck, cat. no. 1.01654.0001) to a concentration of 15 U/ml. After cell disruption by sonication, cell debris was removed by centrifugation and each supernatant was applied on a 1 ml His GraviTrap IMAC column (GE Healthcare, cat. no. 11-0033-99). Contaminants were removed by washing with wash buffer (20 mM sodium phosphate, 0.5 M NaCl, 60 mM imidazole, pH 7.4) and the PD-L1 binding Z variants were subsequently eluted with elution buffer (20 mM sodium phosphate, 0.5 M NaCl, 500 mM imidazole, pH 7.4). After the IMAC purification, the protein buffer was exchanged to PBS using PD-10 columns (GE Healthcare, cat. no. 17-0851-01).

Purification of PD-L1 binding Z variants with a C-terminal Cys: The respective cell pellet was resuspended in 20 mM Tris-HCl, pH 8 (10 ml buffer/g cell pellet) and lysed by heat treatment in a water bath at 90° C. for 10 min, followed by cooling on ice to approximately 20° C. Benzonase® was added (1 μl/g cell pellet) and each cell lysate was incubated at RT for 30 min, before cell debris was removed by centrifugation. For reduction of disulfides, dithiothreitol (DTT; Acros organics, cat. no. 165680250) was added to a final concentration of 20 mM followed by incubation at RT for 1 h. Purification was performed by anion exchange followed by reverse phase chromatography (RPC). Buffer exchange to 20 mM HEPES, 1 mM EDTA, pH 7.2 was carried out using HiPrep 26/10 columns (GE Healthcare, cat. no. 17-5087-01). Finally, each Z variant was purified on EndoTrap® red columns (Hyglos, cat. no. 321063) to ensure low endotoxin content.

For each protein purified by any method described above, the concentration was determined by measuring the absorbance at 280 nm, using a NanoDrop® ND-1000 spectrophotometer and the extinction coefficient of the protein. The purity was analyzed by SDS-PAGE stained with Coomassie Blue and the identity of each purified Z variant was confirmed using HPLC-MS analysis (HPLC-MS 1100; Agilent Technologies).

Results

Cultivation and purification: The PD-L1 binding Z variants with a Hiss-tag or a C-terminal Cys were expressed as soluble gene products in *E. coli*. SDS-PAGE analysis of each final protein preparation showed that these predominantly contained the PD-L1 binding Z variant. The correct identity and molecular weight of each Z variant were confirmed by HPLC-MS analysis.

Example 3

Characterization of Primary PD-L1 Binding Z Variants

In this Example, a subset of Z variants was characterized in terms of stability and in vitro binding properties. The specificity and affinity for human PD-L1 of the Z variants were analyzed by SPR and binding to PD-L1 expressing cells was analyzed using Fluorescence Activated Cell Sorting (FACS). Furthermore, the ability of Z variants to block the binding of PD-L1 to its receptor PD1 was investigated using AlphaLISA.

Materials and Methods

Biacore kinetic and specificity analysis: Kinetic constants ($k_a$ and $k_d$) and affinities ($K_D$) for hPD-L1 were determined for 14 Hiss-tagged Z variants using a Biacore 2000 instrument (GE Healthcare). Some of the Z variants were also tested for binding against the sequence-related proteins hPD-L2, hB7-H3, hB7-H4 and mPD-L1 (mouse PD-L1 Fc Chimera, R&D Systems, cat. no. 1019-B7).

hPD-L1, hPD-L2, hB7-H3, hB7-H4 and mPD-L1 were immobilized in separate flow cells on the carboxylated dextran layer of different CM5 chip surfaces (GE Healthcare, cat. no. BR100012). The immobilization was performed using amine coupling chemistry according to the manufacturer's protocol and using HBS-EP as running buffer (0.01 M HEPES pH 7.4, 0.15 M NaCl, 3 mM EDTA, 0.005% v/v Surfactant P20, GE Healthcare, cat. no. BR100188). The ligand immobilization levels on the surfaces were 468-894 RU for hPD-L1, 537-742 RU for hPD-L2, 383 RU for hB7-H3, 538-659 RU for hB7-H4 and 482 RU for mPD-L1. One flow cell surface on each chip was activated and deactivated for use as blank during analyte injections. In the kinetic experiment, HBS-EP was used as running buffer and the flow rate was 50 μl/min. The analytes, i.e. the Z variants, were each diluted in HBS-EP buffer within a concentration range of 1000 to 0.01 nM and injected for 5 min, followed by dissociation in running buffer for 15-25 min. After dissociation, the surfaces were regenerated with one or two injections of 0.1% SDS. Kinetic constants were calculated from the sensorgrams using the Langmuir 1:1 model of BiaEvaluation software 4.1 (GE Healthcare).

AlphaLISA blocking assay: The potential of Z variants to inhibit binding of PD-L1 to PD-1 was analyzed by AlphaLISA and recordings in an EnSpire multiplate reader 2300 (Perkin Elmer). hPD-1 (human PD-1 Fc-chimera; R&D Systems, cat. no. 1086-PD-050) was immobilized on AlphaLISA Acceptor beads (Perkin Elmer, cat. no. 6772002) according to the manufacturer's recommendations. Stepwise serial dilutions 1:3 of Hiss-tagged Z variants to final concentrations of 250 nM to 12 pM were made in a 384 plate (Perkin Elmer, cat. no. 6005350) and incubated for 1 h with 10 nM biotinylated hPD-L1 in AlphaLISA buffer (Perkin Elmer, cat. no. AL000F). hPD-1-coated Acceptor beads were added to a final concentration of 10 μg/ml and incubated for 1 h. Finally, streptavidin coated Donor beads (Perkin Elmer, cat. no. 6772002) were added to a final concentration of 40 μg/ml and incubated for 30 min. All incubations were performed at RT in the dark. The plate was analyzed in the EnSpire instrument and the IC50 values were calculated using GraphPad Prism 5.

Cell binding analysis by FACS: The potential of Z variants to bind PD-L1 expressing cells was investigated using Fluorescence Activated Cell Sorting (FACS). THP-1 cells, cultivated in RPMI (Lonza, cat. no. BE12-702F) containing 10% FBS were stimulated with 10 ng/ml IFNg (R&D Systems, cat. no. 285-IF-100) overnight which results in up-regulation of PD-L1. 150,000 stimulated and unstimulated cells were pipetted per well of a v-bottomed 96 well plate (Nunc, cat. no. 277143) and the cells in the plate were subsequently pelleted at 400 g for 3 min at RT. The supernatants were removed and the cells were resuspended in 100 μl PBS plus 2.5% FBS (staining buffer) containing 10 μg/ml of the different His-tagged Z variants. A mouse anti-PD-L1 antibody (R&D Systems, cat. no. MAB1561) at 1 μg/ml was used as a positive control. Cells incubated with buffer alone were used as negative controls. The cells were incubated for 1 h at 8° C. in the dark, washed twice with 100 μl staining buffer and resuspended in 100 μl of staining buffer containing a goat anti-Z antibody (produced in house) at a concentration of 5 μg/ml. Cells stained with the positive control were treated with buffer only. The cells were incubated for 1 h at 8° C. in the dark, washed twice with 100 μl staining buffer and resuspended in 100 μl of staining buffer containing an Alexa Fluor 647 chicken anti-goat IgG antibody (Life technologies, cat. no. A21469) or an Alexa Fluor 647 goat anti-mouse IgG antibody (Life technologies cat. no. A21236). The cells were once again incubated for 1 h at 8° C. in the dark, washed twice with 100 μl staining buffer and resuspended in 200 μl of staining buffer. Data from 10,000 cells were obtained using a FACS Calibur (Beckman Coulter) and the data was analyzed using Flowing software 2.5.0 (Turku University). Mean fluorescence intensity (MFI) was used as a read out of binding capacity.

Circular dichroism (CD) spectroscopy analysis: Two purified Z variants with a C-terminal cysteine, Z15168-Cys (SEQ ID NO:809) and Z15169-Cys (SEQ ID NO:810), were diluted to 0.5 mg/ml in 20 mM HEPES, 1 mM EDTA, pH 7.2. For each diluted Z variant, a CD spectrum at 250-195 nm was obtained at 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. A new CD spectrum was obtained at 20° C. after the heating procedure in order to study the refolding ability of the Z variants. The CD measurements were performed on a Jasco J-810 spectropolarimeter (Jasco Scandinavia AB) using a cell with an optical path length of 1 mm.

Results

Figure 2B:
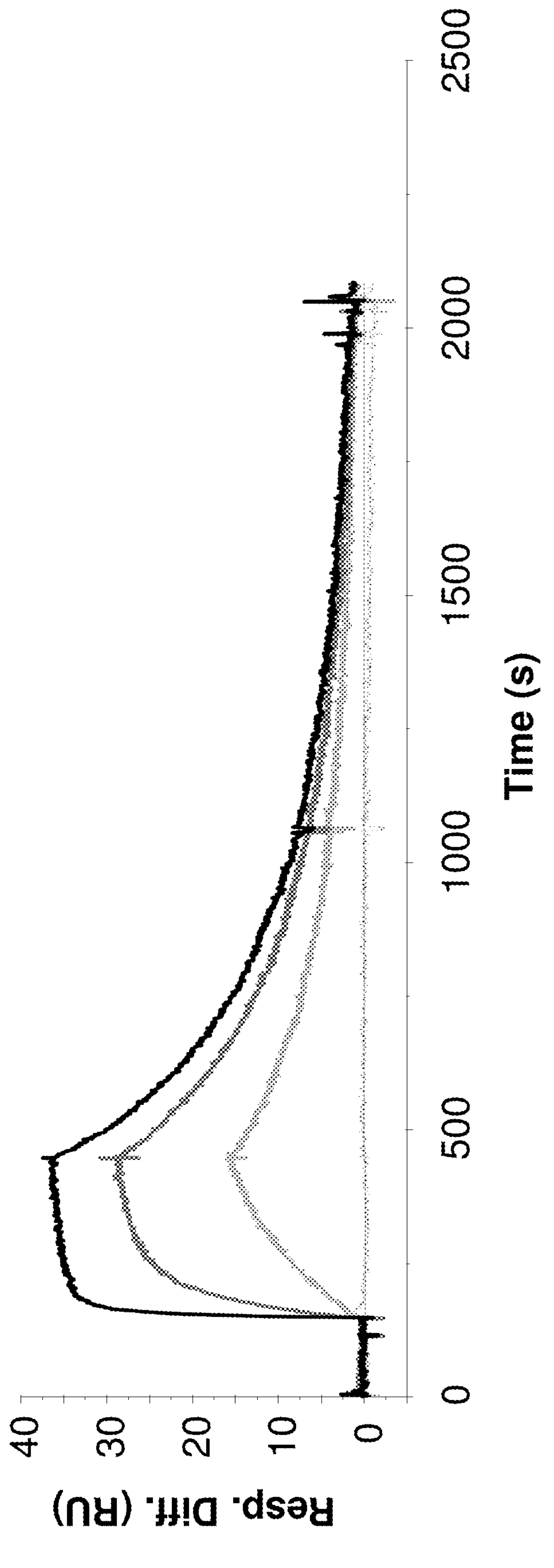

Biacore kinetic and specificity analysis: The interactions of 14 Hiss-tagged PD-L1-binding Z variants with hPD-L1 were analyzed in a Biacore instrument by injecting various concentrations of the Z variants over a surface containing immobilized hPD-L1. All tested Z variants showed binding to hPD-L1. A summary of the kinetic parameters ($K_D$, $k_a$ and $k_d$) for binding of the Z variants to hPD-L1 obtained using a 1:1 interaction model is given in Table 4. Typical resulting curves, where responses from a blank surface were substracted, are displayed in FIG. 2 for two selected Z variants, Z13091 (SEQ ID NO:776) and Z13156 (SEQ ID NO:781).

TABLE 4

Kinetic parameters for binding of Z variants to hPD-L1

| Z variant | SEQ ID NO: | hPD-L1 $k_a$ (1/Ms) | hPD-L1 $k_d$ (1/s) | hPD-L1 $K_D$ (M) |
|---|---|---|---|---|
| Z13080 | 774 | $1.4 \times 10^{6}$ | $9.2 \times 10^{-3}$ | $6.6 \times 10^{-9}$ |
| Z13088 | 775 | $1.4 \times 10^{6}$ | $3.7 \times 10^{-3}$ | $2.6 \times 10^{-9}$ |
| Z13091 | 776 | $3.1 \times 10^{6}$ | $1.4 \times 10^{-3}$ | $4.6 \times 10^{-10}$ |
| Z13112 | 777 | $6.1 \times 10^{5}$ | $1.5 \times 10^{-3}$ | $2.5 \times 10^{-9}$ |
| Z13120 | 778 | $2.0 \times 10^{6}$ | $1.2 \times 10^{-2}$ | $6.0 \times 10^{-9}$ |
| Z13147 | 779 | $1.0 \times 10^{6}$ | $1.7 \times 10^{-3}$ | $1.6 \times 10^{-9}$ |
| Z13154 | 780 | $2.3 \times 10^{6}$ | $3.1 \times 10^{-3}$ | $1.4 \times 10^{-9}$ |
| Z13156 | 781 | $1.7 \times 10^{6}$ | $2.5 \times 10^{-3}$ | $1.5 \times 10^{-9}$ |
| Z13158 | 782 | $6.7 \times 10^{5}$ | $5.6 \times 10^{-3}$ | $8.3 \times 10^{-9}$ |
| Z13164 | 783 | $7.9 \times 10^{5}$ | $8.7 \times 10^{-3}$ | $1.1 \times 10^{-8}$ |
| Z13165 | 784 | $2.0 \times 10^{6}$ | $1.3 \times 10^{-3}$ | $6.4 \times 10^{-10}$ |
| Z13169 | 785 | $2.4 \times 10^{6}$ | $3.5 \times 10^{-3}$ | $1.5 \times 10^{-9}$ |
| Z13198 | 786 | $5.8 \times 10^{6}$ | $5.6 \times 10^{-3}$ | $9.7 \times 10^{-10}$ |
| Z13304 | 787 | $1.6 \times 10^{6}$ | $6.4 \times 10^{-3}$ | $4.1 \times 10^{-9}$ |

Figure 3:
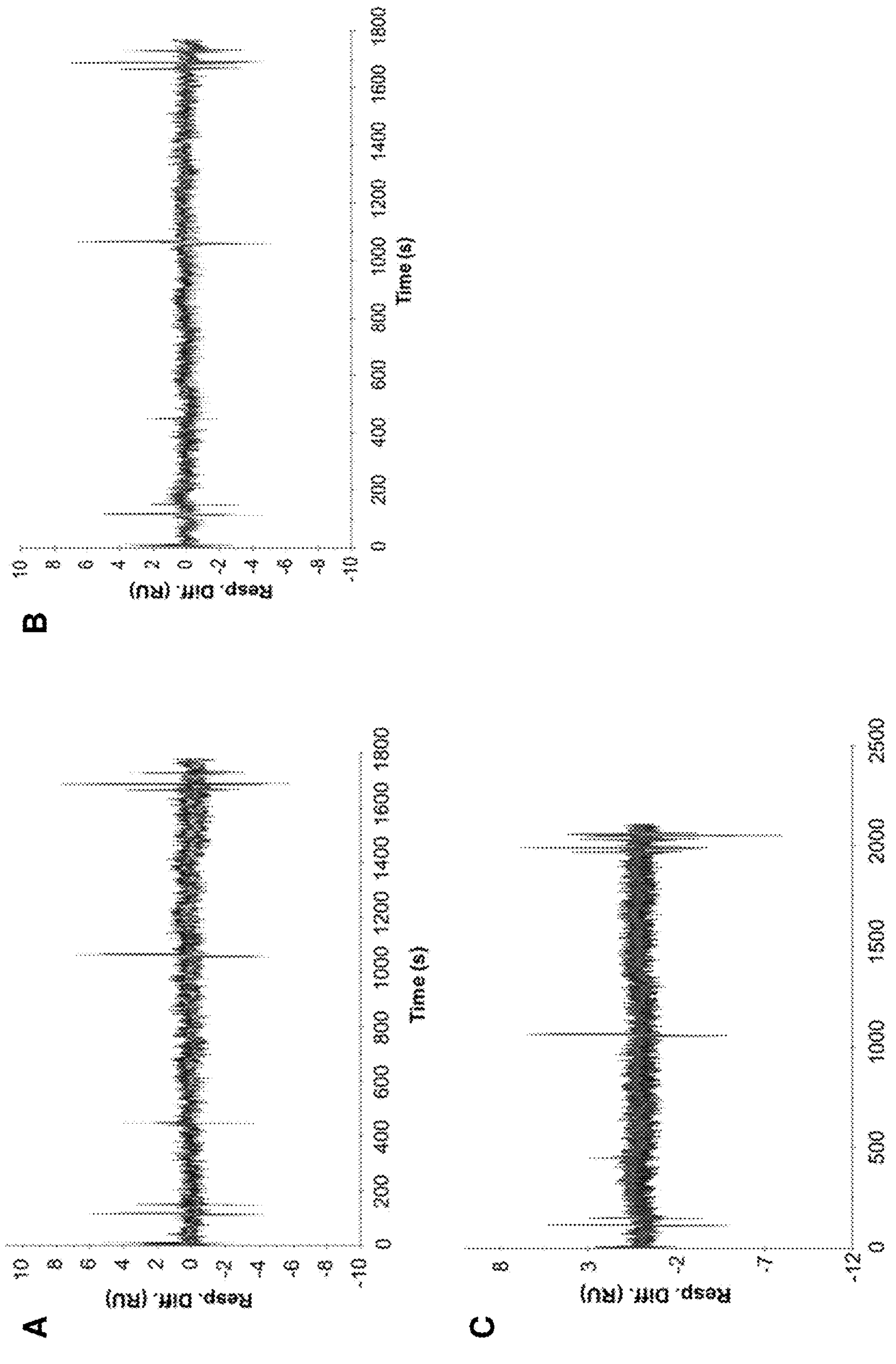
FIG. 3 shows absence of SPR response against (A) hPD-L2, (B) hB7-H3 and (C) hB7-H4, here illustrated with the PD-L1 binding polypeptides Z13091 (SEQ ID NO:776) and Z13156 (SEQ ID NO:781) injected at concentrations of 50 nM, 5 nM and 0.5 nM.

A subset of the Z variants was also tested for binding against four immobilized, sequence-related proteins: hPD-L2, hB7-H3, hB7-H4 and mPD-L1. No binding against hPD-L2, hB7-H3, hB7-H4 or mPD-L1 was detected at Z variant concentrations up to 50 nM. When injecting 1000 nM of a few selected Z variants (Z13088, Z13091, Z13112, Z13147, Z13154, Z13156, Z13165, Z13169, Z13198) some response against B7-H4 was observed for Z13156 and Z13165. The result of the binding specificity analysis is summarized in Table 5. Typical non-interacting traces from the SPR analysis against hPD-L2, hB7-H3 and hB7-H4 are shown in FIG. 3.

TABLE 5

Binding specificity against mPD-L1, hPD-L2, hB7-H3 and hB7-H4

| Z variant | SEQ ID NO: | mPD-L1 | hPD-L2 | hB7-H3 | hB7-H4 |
|---|---|---|---|---|---|
| Z13080 | 774 | n.a. | n.d. | n.d. | n.a. |
| Z13088 | 775 | n.d. | n.d. | n.d. | n.d. |
| Z13091 | 776 | n.d. | n.d. | n.d. | n.d. |
| Z13112 | 777 | n.a. | n.d. | n.a. | n.d. |
| Z13120 | 778 | n.a. | n.d. | n.d. | n.a. |
| Z13147 | 779 | n.d. | n.d. | n.a. | n.d. |
| Z13154 | 780 | n.d. | n.d. | n.d. | n.d. |
| Z13156 | 781 | n.d. | n.d. | n.d. | $K_D$ > 5 μM |
| Z13158 | 782 | n.a. | n.d. | n.d. | n.a. |
| Z13164 | 783 | n.a. | n.d. | n.d. | n.a. |
| Z13165 | 784 | n.d. | n.d. | n.d. | $K_D$ > 5 μM |
| Z13169 | 785 | n.d. | n.d. | n.d. | n.d. |
| Z13198 | 786 | n.d. | n.d. | n.d. | n.d. |
| Z13304 | 787 | n.a. | n.d. | n.a. | n.d. |

n.a. not assayed;
n.d. no binding detected

AlphaLISA blocking assay: The ability of 14 Hiss-tagged Z variants to inhibit hPD-L1 binding to hPD-1 was tested in an AlphaLISA blocking assay. Serial dilutions of the Z variants were incubated with biotinylated hPD-L1 and the blocking ability of each respective variant was measured after addition of hPD-1 coated Acceptor beads and subsequently streptavidin coated Donor beads. Inhibition could be measured as a decrease in AlphaLISA counts for positive Z variants. The calculated IC50 values for the 14 variants that were all shown to block PD-L1 binding to PD-1 in this assay are shown in Table 6.

TABLE 6

IC50 values for Z variants inhibiting binding of PD-L1 to PD-1

| Z variant | SEQ ID NO: | IC50 (M) |
|---|---|---|
| Z13080 | 774 | $2.7 \times 10^{-9}$ |
| Z13088 | 775 | $8.8 \times 10^{-10}$ |
| Z13091 | 776 | $6.9 \times 10^{-9}$ |
| Z13112 | 777 | $3.9 \times 10^{-9}$ |
| Z13120 | 778 | $4.2 \times 10^{-9}$ |
| Z13147 | 779 | $5.6 \times 10^{-9}$ |
| Z13154 | 780 | $1.1 \times 10^{-9}$ |
| Z13156 | 781 | $1.4 \times 10^{-9}$ |
| Z13158 | 782 | $2.4 \times 10^{-9}$ |
| Z13164 | 783 | $2.3 \times 10^{-9}$ |
| Z13165 | 784 | $1.3 \times 10^{-9}$ |
| Z13169 | 785 | $2.2 \times 10^{-9}$ |
| Z13198 | 786 | $1.3 \times 10^{-9}$ |
| Z13304 | 787 | $4.2 \times 10^{-8}$ |

TABLE 7

Normalized MFI for binding of Z variants to THP-1 cells

| Z variant | SEQ ID NO: | MFI (normalized) |
|---|---|---|
| Z13080 | 774 | 1.06 |
| Z13088 | 775 | 1.00 |
| Z13091 | 776 | 1.00 |
| Z13112 | 777 | 0.76 |
| Z13120 | 778 | 0.71 |
| Z13147 | 779 | 0.56 |
| Z13154 | 780 | 1.04 |
| Z13156 | 781 | 1.09 |
| Z13158 | 782 | 0.91 |
| Z13164 | 783 | 0.81 |
| Z13165 | 784 | 1.24 |
| Z13169 | 785 | 0.91 |

TABLE 7-continued

| Normalized MFI for binding of Z variants to THP-1 cells | | |
|---|---|---|
| Z variant | SEQ ID NO: | MFI (normalized) |
| Z13198 | 786 | 0.89 |
| Z13304 | 787 | 0.75 |
| anti-PD-L1 antibody | — | 0.40 |

Cell binding analysis by FACS: This experiment confirmed binding of the PD-L1 specific Z variants to PD-L1 expressing cells. THP-1 cells stimulated with IFNγ overnight, which increases the PD-L1 expression, were stained with 10 μg/ml of each of the Hiss-tagged Z variants. The analyses were performed at two different occasions and the MFI values, normalized against Z13091 included in both assays, are presented in Table 7.

Figure 4:
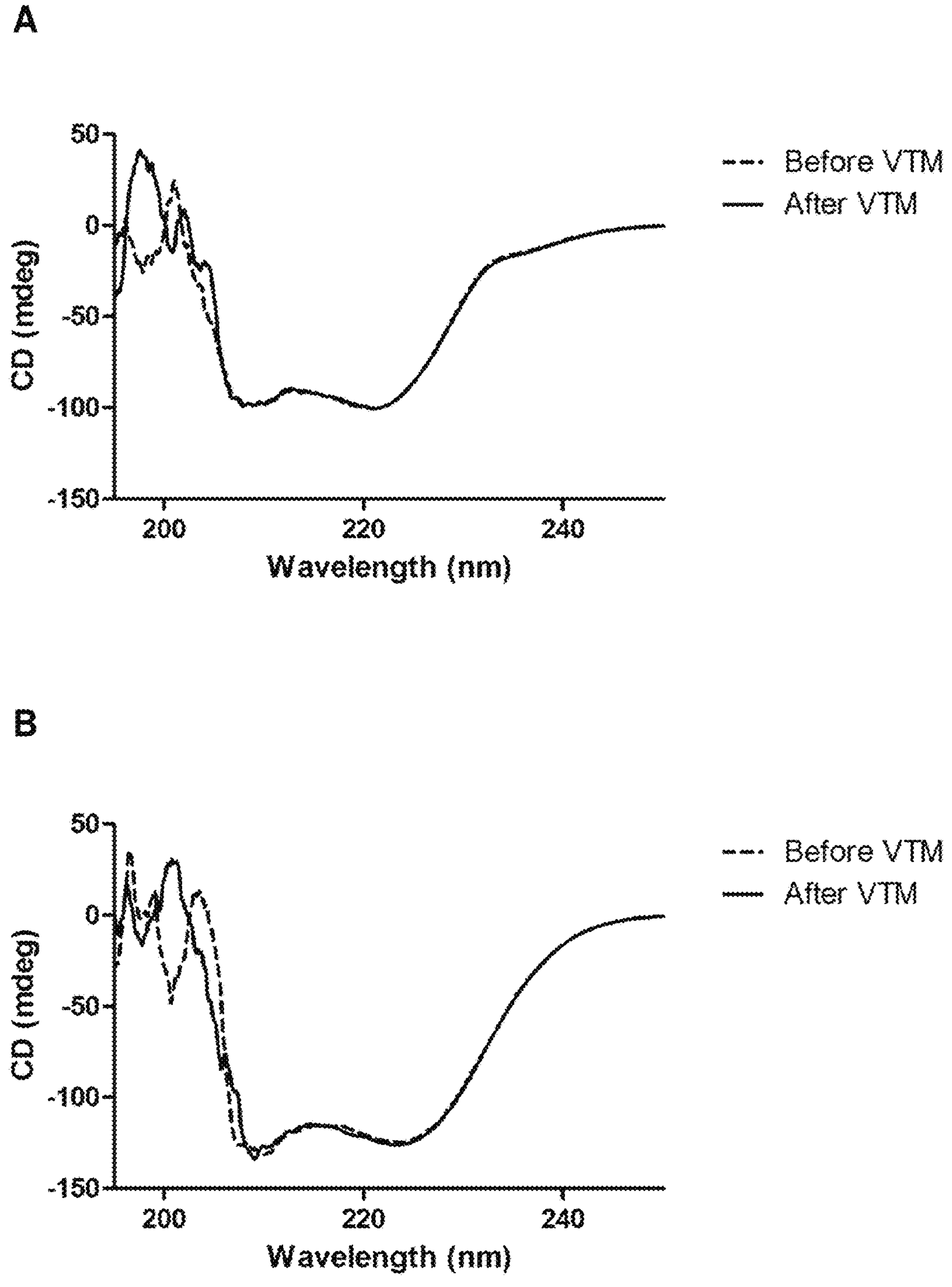
FIG. 4 shows circular dichroism (CD) spectra of two first generation PD-L1 binding polypeptides. The CD spectra at wavelengths ranging from 250 to 195 nm collected at 20° C. before (broken line) and after (solid line) variable temperature measurement (VTM) are shown for (A) Z15168-Cys (SEQ ID NO:809) and (B) Z15169-Cys (SEQ ID NO:810).

CD analysis: The CD spectra determined for two selected PD-L1 binding Z variants with a C-terminal cysteine, Z15168-Cys (SEQ ID NO:809) and Z15169-Cys (SEQ ID NO:810) showed that both variants had an α-helical structure at 20° C. based on the typical minima at 208 and 222 nm. Reversible folding was seen for both Z variants when overlaying spectra measured before and after heating to 90° C. (FIG. 4). The noisy signal observed in the far UV region is expected to result from buffer effects (HEPES, which was used as analysis buffer, absorbs strongly at 200 nM and below). The melting temperatures (Tm) were determined to 50° C. and 58° C. for Z15168-Cys and Z15169-Cys, respectively (Table 8).

TABLE 8

| Melting temperatures (Tm) | | |
|---|---|---|
| Z variant | SEQ ID NO: | Tm (° C.) |
| Z15168-Cys | 809 | 50 |
| Z15169-Cys | 810 | 58 |

Example 4

Design and Construction of a Maturated Library of PD-L1 Binding Z Variants

In this Example, a maturated library was constructed. The library was used for selections of PD-L1 binding Z variants. Selections from maturated libraries may result in binders with increased affinity (Orlova et al., (2006) Cancer Res 66(8):4339-48). In this study, randomized single stranded oligonucleotides are generated, using split-pool DNA synthesis enabling incorporation of defined codons in desired positions in the synthesis.

Materials and Methods

Library design: The library was based on the sequences of the PD-L1 binding Z variants identified and characterized as described in Example 1 and Example 3. In the new library, 13 variable positions in the Z molecule scaffold were biased towards certain amino acid residues, according to a strategy based on the Z variant sequences defined in SEQ ID NO:774-808. Two oligonucleotides, one forward and one reverse complementary, with complementary 3'-ends were generated using split-pool synthesis. The two oligonucleotides were annealed and extended by PCR, using outer primers, to yield one gene fragment covering 147 bp corresponding to partially randomized helix 1 and 2 of the amino acid sequence: 5'-AA ATA AAT CTC GAG GTA GAT GCC AAA TAC GCC AAA GAA CGT AAC NNN GCG GCT NNN GAG ATC CTG NNN CTG CCT AAC CTC ACC NNN NNN CAA NNN TGG GCC TTC ATC TGG AAA TTA NNN GAT GAC CCA AGC CAG AGC TCA TTA TTT A-3' (SEQ ID NO:819; randomized codons are illustrated as NNN) flanked by restriction sites XhoI and SacI. The oligonucleotides were ordered from Ella Biotech GmbH (Martinsried Germany).

TABLE 9

| Design of maturated library | | | |
|---|---|---|---|
| Amino acid position in the Z variant molecule | Randomization (amino acid abbreviations) | No of amino acids | Proportion |
| 9 | R | 1 | 1/1 |
| 10 | N | 1 | 1/1 |
| 11 | A, D, E, F, H, I, K, L, N, Q, R, S, T, V, W, Y | 16 | 1/16 |
| 13 | A | 1 | 1/1 |
| 14 | A, D, E, F, H, I, K, L, N, Q, R, S, T, V, W, Y | 16 | 1/16 |
| 17 | L | 1 | 1/1 |
| 18 | A, D, E, F, H, I, K, L, N, Q R, S, T, V, W, Y | 16 | 1/16 |
| 24 | A, D, E, F, H, I, K, L, N, Q R, S, T, V, W, Y | 16 | 1/16 |
| 25 | A, D, E, F, G, H, I, K, L, N, Q, R, S, T, V, W, Y | 17 | 1/17 |
| 27 | A, D, E, F, H, I, K, L, N, Q R, S, T, V, W, Y | 16 | 1/16 |
| 28 | W | 1 | 1/1 |
| 32 | W | 1 | 1/1 |
| 35 | 50% D, 30% A, 20% E | 3 | 1/2 (D), 3/10 (A), 1/5 (E) |

The theoretical distributions of amino acid residues in the new library including 7 variable positions (11, 14, 18, 24, 25, 27 and 35) in the Z molecule scaffold are given in Table 9. The resulting theoretical library size is $5.3\times10^7$ variants.

Library construction: The library was amplified using AmpliTaq Gold polymerase (Life Technologies, cat. no. 4311816) during 12 cycles of PCR and pooled products were purified with QiAquick PCR Purification Kit (QIAGEN, cat. no. 28106) according to the supplier's recommendations. The purified pool of randomized library fragments was digested with restriction enzymes XhoI and SacI-HF (New England Biolabs, cat. no. R0146L, and cat. no. R3156M, respectively) and concentrated using a PCR Purification Kit. Subsequently, the product was run on a preparative 2.5% agarose (NuSieve GTG® Agarose, Lonza, cat. no. 50080) gel electrophoresis and purified using QIAGEN Gel Extraction Kit (QIAGEN, cat. no. 28706) according to the supplier's recommendations.

The phagemid vector pAY02592 (essentially as pAffi1 described in Grönwall et al., supra) was restricted with the same enzymes and purified using phenol/chloroform extraction and ethanol precipitation. The restricted fragments and the restricted vector were ligated in a molar ratio of 5:1 with T4 DNA ligase (Thermo Scientific, cat. no. EL0011) for 2 h at RT, followed by overnight incubation at 4° C. The ligated DNA was recovered by phenol/chloroform extraction and ethanol precipitation, followed by dissolution in 10 mM Tris-HCl, pH 8.5. Thus, the resulting library in vector pAY02592 encoded Z variants each fused to an albumin binding domain (ABD) derived from streptococcal protein G.

The ligation reactions (approximately 160 ng DNA/transformation) were electroporated into electrocompetent *E. coli* ER2738 cells (Lucigen, Middleton, Wis., USA, 50 μl).

Immediately after electroporation, approximately 1 ml of recovery medium (supplied with *E. coli* ER2738 cells) was added. The transformed cells were incubated at 37° C. for 60 min. Samples were taken for titration and for determination of the number of transformants. The cells were thereafter pooled and cultivated overnight at 37° C. in 1 l of TSB-YE medium, supplemented with 2% glucose, 10 μg/ml tetracycline and 100 μg/ml ampicillin. The cells were pelleted for 15 min at 4,000 g and resuspended in a PBS/glycerol solution (approximately 40% glycerol). The cells were aliquoted and stored at −80° C. Clones from the library of Z variants were sequenced in order to verify the content and to evaluate the outcome of the constructed library vis-à-vis the library design. Sequencing was performed as described in Example 1 and the amino acid distribution was verified.

Preparation of phage stock: Cells from a glycerol stock containing the phagemid library were inoculated in 3.5 l of TSB-YE supplemented with 1 g/l glucose, 100 mg/l ampicillin and 10 mg/l tetracycline. The cells were cultivated at 37° C. with orbital shaking (100 RPM). When the cells reached an optical density at 600 nm (OD600) of 0.59, approximately 620 ml of the cultivation was infected using a 5× molar excess of M13K07 helper phage. The cells were incubated for 30 min, whereupon the cells were pelleted by centrifugation at 3,000 g and resuspended in 3 l fresh TSB-YE supplemented with 100 mg/l ampicillin, 25 mg/l kanamycin, and 0.1 mM IPTG. The cultivation was split into 6x5 l shaker flasks at and incubated at 30° C. with orbital shaking and after ~18 h the cells were pelleted by centrifugation at 4,700 g. The phage particles were precipitated from the supernatant twice in PEG/NaCl, filtered and dissolved in PBS and glycerol as described in Example 1. Phage stocks were stored at −80° C. until use in selection.

Results

Library construction: The new library was designed based on a set of PD-L1 binding Z variants with verified binding properties (Example 1 and 3). The theoretical size of the designed library was $5.3\times10^7$ Z variants. The actual size of the library, determined by titration after transformation to *E. coli*. ER2738 cells, was $2.8\times10^9$ transformants.

The library quality was tested by sequencing of 116 transformants and by comparing their actual sequences with the theoretical design. The contents of the actual library compared to the designed library were shown to be satisfactory. A maturated library of potential binders to PD-L1 was thus successfully constructed.

Example 5

Selection, Screening and Characterization of Z Variants from a Maturated Library Materials and Methods Phage display selection of PD-L1 binding Z variants: The target protein PD-L1 was biotinylated as described in Example 1. Phage display selections, using the new library of Z variant molecules constructed as described in Example 4, were performed in four cycles against hPD-L1 essentially as described in Example 1, with the following exceptions: Exception 1: SA-beads were used to catch the PD-L1:Z variant complexes in all selection tracks. Exception 2: pre-selection was performed against SA-beads coated with biotinylated human IgG-Fc only before cycle 1 and 2. Furthermore in cycle 1, another pre-selection was performed against SA-beads coated with a mix of PD-L2, B7-H3, and B7-H4 as previously described in Example 1. Exception 3: selections against biotinylated human PD-L1 was performed in four cycles initially divided in two different tracks (1 and 2). As selection proceeded, the tracks were further divided according to target concentration and number and/or time of washes to finally end up in 11 tracks in cycle four. More precisely, the first track (1) was divided in the second to the fourth cycles, resulting in a total of 2 tracks (1-1 to 1-2) in cycle 2, four tracks (1-1-1 to 1-2-2) in cycle 3 and seven tracks (1-1-1-1 to 1-2-2-2) in cycle 4. The second track (2) was divided in the second to the fourth cycles, resulting in a total of 2 tracks (2-1 to 2-2) in cycle 2, four tracks (2-1-1 to 2-2-2) in cycle 3 and four tracks (2-1-1-1 to 2-2-2-1) in cycle four. Exception 4: during the 19 h washing step in selection cycle 1-1-2-3 a 20-fold molecular excess of non-biotinylated hPD-L1 was added to the wash buffer. An overview of the selection strategy, describing an increased stringency in subsequent cycles obtained by using a lowered target concentration and an increased number of washes, is shown in Table 10.

TABLE 10

Selection against biotinylated hPD-L1 Fc using a maturated library

| Cycle | Selection track | Phage stock from library or selection track | Proteins used in pre-selection | Target conc. (nM) | Number of washes | Duration of last wash (h) | Addition to last wash buffer |
|---|---|---|---|---|---|---|---|
| 1 | 1 | Zlib006PD-L1.I | IgG-Fc, PD-L2, B7-H3, B7-H4 | 50 | 2 | | |
| 1 | 2 | Zlib006PD-L1.I | IgG-Fc, PD-L2, B7-H3, B7-H4 | 25 | 2 | | |
| 2 | 1-1 | 1 | IgG-Fc | 25 | 8 | | |
| 2 | 1-2 | 1 | IgG-Fc | 10 | 12 | | |
| 2 | 2-1 | 2 | IgG-Fc | 2.5 | 12 | | |
| 2 | 2-2 | 2 | IgG-Fc | 0.5 | 12 | | |
| 3 | 1-1-1 | 1-1 | no pre-selection | 5 | 20 | | |
| 3 | 1-1-2 | 1-1 | no pre-selection | 5 | 20 | 18 | |
| 3 | 1-2-1 | 1-2 | no pre-selection | 2.5 | 20 | | |
| 3 | 1-2-2 | 1-2 | no pre-selection | 1 | 20 | 18 | |
| 3 | 2-1-1 | 2-1 | no pre-selection | 0.5 | 20 | | |
| 3 | 2-1-2 | 2-1 | no pre-selection | 0.1 | 20 | 18 | |
| 3 | 2-2-1 | 2-2 | no pre-selection | 0.05 | 20 | 18 | |
| 3 | 2-2-2 | 2-2 | no pre-selection | 0.005 | 20 | | |
| 4 | 1-1-1-1 | 1-1-1 | no pre-selection | 2.5 | 20 | | |
| 4 | 1-1-2-1 | 1-1-2 | no pre-selection | 2.5 | 20 | | |

TABLE 10-continued

Selection against biotinylated hPD-L1 Fc using a maturated library

| Cycle | Selection track | Phage stock from library or selection track | Proteins used in pre-selection | Target conc. (nM) | Number of washes | Duration of last wash (h) | Addition to last wash buffer |
|---|---|---|---|---|---|---|---|
| 4 | 1-1-2-2 | 1-1-2 | no pre-selection | 2.5 | 20 | 19 | |
| 4 | 1-1-2-3 | 1-1-2 | no pre-selection | 2.5 | 20 | 19 | 50 nM hPD-L1 |
| 4 | 1-2-1-1 | 1-2-1 | no pre-selection | 0.1 | 20 | | |
| 4 | 1-2-2-1 | 2-1-2 | no pre-selection | 0.5 | 20 | | |
| 4 | 1-2-2-2 | 1-2-2 | no pre-selection | 0.5 | 20 | 19 | |
| 4 | 2-1-1-1 | 2-1-1 | no pre-selection | 0.05 | 20 | | |
| 4 | 2-1-2-1 | 2-1-2 | no pre-selection | 0.1 | 30 | 19 | |
| 4 | 2-2-1-1 | 2-2-1 | no pre-selection | 0.01 | 30 | 19 | |
| 4 | 2-2-2-1 | 2-2-2 | no pre-selection | 0.05 | 20 | 19 | |

Production of Z variants for ELISA: The Z variants were produced by inoculating single colonies from the selections into 1.2 ml TSB-YE medium supplemented with 100 μg/ml ampicillin and 1 mM IPTG in deep-well plates (Nunc, cat. no. 278752). The plates were incubated with rotation for 24 h at 37° C. Cells were pelleted by centrifugation at 3300 g and re-suspended in 150 μl PBST 0.05% and frozen at −80° C. to release the periplasmic fraction of the cells. Frozen samples were thawed in a water bath and the freeze-thawing procedure was repeated eight times before the periplasmic fraction was isolated in deep-well plates (Axygen, cat. no. 391-01-101) by filtration using filter plates (EMD Millipore, cat. no. MSNANLY50). The final supernatant of the periplasmic extract contained the Z variants as fusions to ABD, expressed as AQHDEALE-[Z#####]-VDYV-[ABD]-YVPG (SEQ ID NO:896) (Grönwall et al., supra). Z##### refers to individual, 58 amino acid residue Z variants.

ELISA screening of Z variants: The binding of Z variants to human PD-L1 was analyzed in ELISA assays as described previously in Example 1 with the following exceptions. Exception 1: The periplasmic fraction was diluted 1:8 with PBST 0.05% before added to the wells and incubated for 1.7 h. Exception 2: instead of a blank control a negative control of a periplasmic fraction containing the fusion protein ABD with no Z-fusion partner was used. Exception 3: periplasm samples containing the primary PD-L1 binding Z variant Z13091 (SEQ ID.NO:776) was included in duplicates on each plate and analyzed as positive controls. Exception 4: 50 μl of biotinylated hPD-L1 at a concentration of 40 pM in PBSC was added to each well and the plates were incubated for 1.8 h at RT.

Sequencing: In parallel with the ELISA screening, all clones were sequenced as described in Example 1.

ELISA EC50 analysis: A selection of PD-L1 binding Z variants was subjected to an analysis of the response against a dilution series of biotinylated human PD-L1 as described in Example 1 with the following exceptions. Exception 1: the Z variants were diluted 1:8 in PBST 0.05% before added to the wells. Exception 2: biotinylated human PD-L1 was added at a concentration of 15 nM and diluted stepwise 1:3 down to 0.25 pM. Exception 3: a periplasm sample containing the primary PD-L1 binding Z variant Z13091 (SEQ ID.NO:776) was included for comparison and analyzed together with the maturated Z variants.

Results

Phage display selection of PD-L1 binding Z variants: Individual clones were obtained after four cycles of phage display selection against biotinylated hPD-L1.

ELISA screening of Z variants: The clones obtained after four cycles of selection were produced in 96-well plates and screened for hPD-L1 binding activity in ELISA. A majority of the unique Z variants were found to give a higher response than average response of the positive control Z13091 (average 0.264 AU) against hPD-L1 at a concentration of 40 pM. The average response of the negative controls was 0.051 AU.

Sequencing: Sequencing was performed for clones obtained after four cycles of selection. Each variant was given a unique identification number, Z#####, as described in Example 1. The amino acid sequences of the 58 amino acid residues long Z variants are listed in FIG. 1A-1CC and in the sequence listing as SEQ ID NO:1-773. The deduced PD-L1 binding motifs extend from position 8 to position 36 in each sequence. The amino acid sequences of the 49 amino acid residues long polypeptides predicted to constitute the complete three-helix bundle within each of these Z variants extend from residue 7 to residue 55.

EC50 analysis of Z variants: A subset of Z variants having the highest ELISA values in the ELISA screening experiment described above was selected and subjected to a target titration in ELISA format. Periplasm samples were incubated with a serial dilution of biotinylated hPD-L1. A periplasm sample containing Z13091 (SEQ ID NO:776), the isolated primary Z variant that showed the highest binding affinity to hPD-L1, was included as a positive control. Obtained values were analyzed and their respective EC50 values were calculated using GraphPad Prism 5 (Table 11). All maturated Z variants showed lower EC50 values than the top primary Z variant Z13091.

TABLE 11

Calculated EC50 values of Z-ABD variants from maturation

| Z variant | SEQ ID NO: | EC50 (M) | Z variant | SEQ ID NO: | EC50 (M) | Z variant | SEQ ID NO: | EC50 (M) |
|---|---|---|---|---|---|---|---|---|
| Z17746 | 8 | $6.7 \times 10^{-11}$ | Z18054 | 22 | $6.2 \times 10^{-11}$ | Z18135 | 67 | $8.5 \times 10^{-11}$ |
| Z17748 | 11 | $6.7 \times 10^{-11}$ | Z18060 | 44 | $8.3 \times 10^{-11}$ | Z18137 | 68 | $7.4 \times 10^{-11}$ |

TABLE 11-continued

Calculated EC50 values of Z-ABD variants from maturation

| Z variant | SEQ ID NO: | EC50 (M) | Z variant | SEQ ID NO: | EC50 (M) | Z variant | SEQ ID NO: | EC50 (M) |
|---|---|---|---|---|---|---|---|---|
| Z17756 | 7 | $6.7 \times 10^{-11}$ | Z18064 | 1 | $6.8 \times 10^{-11}$ | Z18138 | 69 | $7.4 \times 10^{-11}$ |
| Z17758 | 25 | $8.0 \times 10^{-11}$ | Z18065 | 45 | $7.1 \times 10^{-11}$ | Z18140 | 70 | $8.7 \times 10^{-11}$ |
| Z17772 | 26 | $8.8 \times 10^{-11}$ | Z18066 | 12 | $7.3 \times 10^{-11}$ | Z18143 | 71 | $7.8 \times 10^{-11}$ |
| Z17825 | 5 | $6.7 \times 10^{-11}$ | Z18069 | 46 | $7.8 \times 10^{-11}$ | Z18144 | 72 | $7.9 \times 10^{-11}$ |
| Z17843 | 27 | $8.6 \times 10^{-11}$ | Z18070 | 10 | $7.6 \times 10^{-11}$ | Z18148 | 73 | $7.0 \times 10^{-11}$ |
| Z17911 | 3 | $7.0 \times 10^{-11}$ | Z18074 | 6 | $7.0 \times 10^{-11}$ | Z18149 | 18 | $6.9 \times 10^{-11}$ |
| Z17928 | 28 | $8.3 \times 10^{-11}$ | Z18078 | 47 | $7.8 \times 10^{-11}$ | Z18150 | 74 | $7.6 \times 10^{-11}$ |
| Z17950 | 29 | $7.8 \times 10^{-11}$ | Z18090 | 17 | $8.8 \times 10^{-11}$ | Z18152 | 75 | $8.0 \times 10^{-11}$ |
| Z17964 | 2 | $7.7 \times 10^{-11}$ | Z18092 | 48 | $7.7 \times 10^{-11}$ | Z18153 | 76 | $8.0 \times 10^{-11}$ |
| Z17968 | 30 | $8.2 \times 10^{-11}$ | Z18095 | 49 | $7.3 \times 10^{-11}$ | Z18156 | 77 | $8.0 \times 10^{-11}$ |
| Z17972 | 19 | $7.4 \times 10^{-11}$ | Z18096 | 50 | $8.0 \times 10^{-11}$ | Z18158 | 78 | $8.7 \times 10^{-11}$ |
| Z17975 | 31 | $8.9 \times 10^{-11}$ | Z18099 | 51 | $8.7 \times 10^{-11}$ | Z18164 | 79 | $7.6 \times 10^{-11}$ |
| Z17978 | 13 | $6.5 \times 10^{-11}$ | Z18101 | 23 | $6.7 \times 10^{-11}$ | Z18167 | 80 | $8.4 \times 10^{-11}$ |
| Z17990 | 32 | $8.0 \times 10^{-11}$ | Z18104 | 52 | $7.5 \times 10^{-11}$ | Z18172 | 81 | $7.6 \times 10^{-11}$ |
| Z17995 | 33 | $8.4 \times 10^{-11}$ | Z18106 | 53 | $8.3 \times 10^{-11}$ | Z18174 | 82 | $8.4 \times 10^{-11}$ |
| Z17997 | 34 | $7.7 \times 10^{-11}$ | Z18108 | 54 | $7.8 \times 10^{-11}$ | Z18176 | 83 | $8.9 \times 10^{-11}$ |
| Z17999 | 35 | $7.5 \times 10^{-11}$ | Z18110 | 55 | $8.1 \times 10^{-11}$ | Z18179 | 84 | $8.7 \times 10^{-11}$ |
| Z18000 | 36 | $7.9 \times 10^{-11}$ | Z18111 | 56 | $7.8 \times 10^{-11}$ | Z18185 | 85 | $8.1 \times 10^{-11}$ |
| Z18005 | 37 | $7.8 \times 10^{-11}$ | Z18115 | 57 | $7.7 \times 10^{-11}$ | Z18220 | 86 | $8.4 \times 10^{-11}$ |
| Z18008 | 38 | $7.3 \times 10^{-11}$ | Z18116 | 58 | $7.4 \times 10^{-11}$ | Z18228 | 87 | $8.8 \times 10^{-11}$ |
| Z18021 | 39 | $8.8 \times 10^{-11}$ | Z18117 | 59 | $8.1 \times 10^{-11}$ | Z18233 | 21 | $8.6 \times 10^{-11}$ |
| Z18022 | 9 | $7.4 \times 10^{-11}$ | Z18118 | 60 | $7.9 \times 10^{-11}$ | Z18240 | 88 | $7.8 \times 10^{-11}$ |
| Z18027 | 40 | $8.0 \times 10^{-11}$ | Z18119 | 61 | $1.0 \times 10^{-10}$ | Z18243 | 89 | $8.1 \times 10^{-11}$ |
| Z18036 | 41 | $7.6 \times 10^{-11}$ | Z18124 | 62 | $8.4 \times 10^{-11}$ | Z18252 | 90 | $8.5 \times 10^{-11}$ |
| Z18037 | 42 | $7.7 \times 10^{-11}$ | Z18128 | 63 | $7.7 \times 10^{-11}$ | Z18268 | 91 | $8.9 \times 10^{-11}$ |
| Z18038 | 43 | $6.9 \times 10^{-11}$ | Z18129 | 16 | $6.2 \times 10^{-11}$ | Z18353 | 15 | $7.7 \times 10^{-11}$ |
| Z18039 | 20 | $6.9 \times 10^{-11}$ | Z18130 | 64 | $7.4 \times 10^{-11}$ | Z18374 | 92 | $1.0 \times 10^{-10}$ |
| Z18048 | 4 | $6.5 \times 10^{-11}$ | Z18131 | 65 | $8.7 \times 10^{-11}$ | Z18377 | 93 | $7.8 \times 10^{-11}$ |
| Z18052 | 14 | $7.1 \times 10^{-11}$ | Z18133 | 66 | $7.7 \times 10^{-11}$ | Z18418 | 24 | $8.0 \times 10^{-11}$ |
| | | | | | | Z13091 | 776 | $1.2 \times 10^{-10}$ |

Example 6

Subcloning and Production of a Subset of Maturated PD-L1 Binding Z Variants

Materials and Methods

Subcloning of Z variants with a Hiss-tag: The DNA of 24 maturated PD-L1 binding Z variants, (Z17746 (SEQ ID NO:8), Z17748 (SEQ ID NO:11), Z17756 (SEQ ID NO:7), Z17825 (SEQ ID NO:5), Z17911 (SEQ ID NO:3), Z17964 (SEQ ID NO:2), Z17972 (SEQ ID NO:19), Z17978 (SEQ ID NO:13), Z18022 (SEQ ID NO:9), Z18039 (SEQ ID NO:20), Z18048 (SEQ ID NO:4), Z18052 (SEQ ID NO:14), Z18054 (SEQ ID NO:22), Z18064 (SEQ ID NO:1), Z18066 (SEQ ID NO:12), Z18070 (SEQ ID NO:10), Z18074 (SEQ ID NO:6), Z18090 (SEQ ID NO:17), Z18101 (SEQ ID NO:23), Z18129 (SEQ ID NO:16), Z18149 (SEQ ID NO:18), Z18233 (SEQ ID NO:21), Z18353 (SEQ ID NO:15) and Z18418 (SEQ ID NO:24)) were amplified from the library vector pAY02592 and subcloned with a Hiss-tag as described in Example 2 above.

Subcloning of Z variants with a C-terminal Cys: Three Z variants, Z18064 (SEQ ID NO:1), Z17964 (SEQ ID NO:2) and Z18090 (SEQ ID NO:17) were mutated to start with the N-terminal amino acids AE instead of VD and further subcloned with the C-terminal addition of the amino acids VDC (incorporating a unique cysteine in the polypeptide) using standard molecular biology techniques. The resulting sequences are referred to as Z18608-Cys (SEQ ID NO:811), Z18609-Cys (SEQ ID NO:812) and Z18610-Cys (SEQ ID NO:813), respectively.

Cultivation: Generally, *E. coli* T7E2 cells (GeneBridges) were transformed with plasmids containing the gene fragments of each respective PD-L1 binding Z variant and cultivated at 37° C. in approximately 940 ml of TSB-YE medium supplemented with 50 μg/ml kanamycin. In order to induce protein expression, IPTG was added to a final concentration of 0.2 mM at $OD_{600}$=2 and the cultivation was incubated at 37° C. for another 5 h. The cells were harvested by centrifugation. Specifically, Z18608-Cys and Z18609-Cys were fed-batch cultivated at 37° C. in approximately 700 ml of defined mineral medium supplemented with 50 μg/ml kanamycin. In order to induce protein expression, IPTG was added to a final concentration of 0.5 mM at $OD_{600}$=75 and the cultivation was incubated for another 7 h. The cells were harvested by centrifugation.

Purification of PD-L1 binding Z variants with a Hiss-tag: IMAC purifications, buffer exchange to PBS and concentration determinations were performed essentially as described in Example 2.

Purification of PD-L1 binding Z variants with a C-terminal Cys: The respective cell pellet was re-suspended in 20 mM Tris-HCl, 0.5 mM EDTA, 0.1% Tween 80, pH 7.5 (10 ml buffer/g cell pellet) and lysed by heat treatment in a water bath at 80° C. for 10 min, followed by cooling on ice to approximately 20° C. Benzonase® was added (1 μl/g cell pellet) and each cell lysate was incubated at RT for 30 min, before cell debris was removed by centrifugation. For reduction of disulfides, dithiothreitol (DTT; Acros Organics, cat. no. 165680250) was added to a final concentration of 10 mM followed by incubation at RT for 20 min. Thereafter, the lysate was filtered through a 0.45 μm syringe filter (Millipore). Purification was performed by anion exchange followed by reverse phase chromatography (RPC). Buffer exchange to 20 mM HEPES, 1 mM EDTA, pH 7.2 was carried out using Sephadex G-25 medium (GE Healthcare) packed in an XK-50 column.

For any protein purified by either method described above, the concentration was determined by measuring the absorbance at 280 nm, using a NanoDrop® ND-1000 spectrophotometer and the extinction coefficient of the protein. The purity was analyzed by SDS-PAGE stained with Coomassie Blue, and the identity of each purified Z variant was confirmed using HPLC-MS analysis (HPLC-MS 1100; Agilent Technologies).

Results

Cultivation and purification: The PD-L1 binding Z variants were expressed as soluble gene products in *E. coli*. The amount of purified protein from approximately 2.0-2.4 g bacterial pellet was determined spectrophotometrically by measuring the absorbance at 280 nm and ranged from approximately 18 mg to 29 mg for the different Hiss-tagged PD-L1 binding Z variants. SDS-PAGE analysis of each final protein preparation showed that these predominantly contained the PD-L1 binding Z variant. The correct identity and molecular weight of each Z variant were confirmed by HPLC-MS analysis.

Example 7

Additional Characterization of a Subset of Primary PD-L1 Binding Z Variants

In this Example, a subset of Z variants was characterized in terms of stability and various binding properties. The specificity and affinity for PD-L1 of the Z variants were analyzed by Biacore and the ability of Z variants to block the binding of PD-L1 to its receptor PD-1 was investigated using AlphaLISA.

Materials and Methods

Biacore kinetic and specificity analysis: Kinetic constants ($k_a$ and $k_d$) and affinities ($K_D$) for human PD-L1 and rhesus monkey PD-L1 (RhPD-L1; rhesus PD-L1/Fc Chimera, Sino Biological Inc., cat. no. 90251-C02H) were determined for 24 matured Hiss-tagged Z variants (specified in Example 6). The Z variants were also tested for binding against the sequence-related proteins hPD-L2, hB7-H3 and hB7-H4. The Biacore analyses were performed essentially as described in Example 3, however a flow rate of 30 µl/min was used. The ligand immobilization levels on the surfaces were 1030 RU for hPD-L1, 1060 RU for RhPD-L1, 1070 RU for hPD-L2, 1090 RU for hB7-H3, and 770 RU for hB7-H4. In a first binding kinetic analysis, the 24 Z variants were injected at concentrations of 5 and 50 nM over chips immobilized with hPD-L1 and RhPD-L1, respectively. The 12 maturated PD-L1 binding Z variants that showed the highest affinity to hPD-L1 in the first experiment were analyzed in more detail and injected at concentrations of 135, 45, 15, 5 and 1.67 nM over immobilized hPD-L1 and RhPD-L1. In the specificity test, i.e. the binding analysis against hPD-L2, hB7-H3 and hB7-H4, the 24 Z variants were injected at a concentration of 500 nM.

AlphaLISA blocking assay: The potential of the Z variants to inhibit binding of PD-L1 to its natural ligand PD-1 was analyzed in an AlphaLISA assay as described in Example 3 with the following exceptions: Exception 1: stepwise serial dilutions 1:3 of Hiss-tagged Z variants to final concentrations of 250 nM to 4 pM were made in a 384SW plate (Perkin Elmer, cat. no. 6008350) and incubated for 45 min with 8 nM biotinylated hPD-L1 (R&D Systems) in AlphaLISA buffer (Perkin Elmer, cat. no. AL000F). Exception 2: hPD-1-coated Acceptor beads were added to a final concentration of 10 µg/ml and incubated for 50 min.

Circular dichroism (CD) spectroscopy analysis: A subset of the purified Hiss-tagged Z variants were analyzed by CD spectroscopy as described in Example 3, but with the exceptions that the analysis buffer was PBS and that the temperature was raised to 80° C. in the VTM.

Results

Biacore kinetic and specificity analysis: The interactions of 24 maturated Hiss-tagged Z variants with human and rhesus monkey PD-L1, were analyzed in a Biacore instrument by injecting various concentrations of the Z variants over surfaces containing immobilized hPD-L1 and RhPD-L1, respectively. A first kinetic analysis was performed in order to rank the Z variants in terms of their affinity for hPD-L1 and RhPD-L1, as well as to compare their binding kinetics with the primary PD-L1 binding Z variant Z13091. A summary of the approximate affinity constants from the ranking experiment, which were obtained by using a 1:1 interaction model, is given in Table 12.

Figure 5:
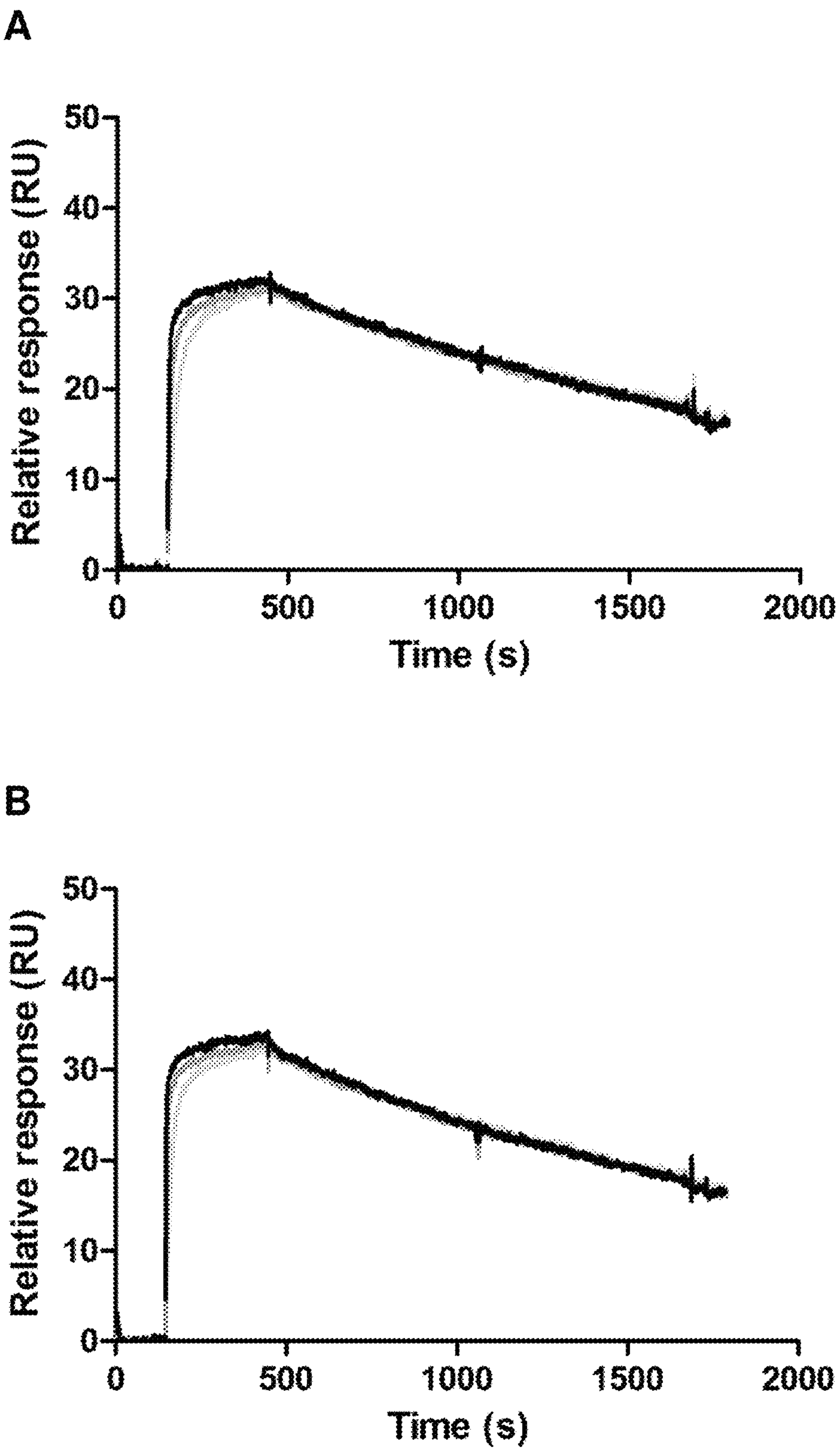
FIG. 5 shows binding of two second generation polypeptides to human PD-L1 analyzed by Biacore as described in Example 7. Z variants (A) Z17964 (SEQ ID NO:2) and (B) Z18064 (SEQ ID NO:1) were injected at concentrations of 135 nM (black), 45 nM (dark grey) and 15 nM (light grey) over a CM5 chip with immobilized hPD-L1.

The 12 maturated Z variants that showed the highest binding affinity to hPD-L1 were further analyzed and the more precisely determined kinetic parameters for these 12 Z variants are given in Table 13. Typical resulting curves, where responses from a blank surface were subtracted, are displayed for two selected variants in FIG. 5.

TABLE 12

Approximate affinity constants for binding of Z variants to hPD-L1 and RhPD-L1

| Z variant | SEQ ID NO of Z variant | hPD-L1 $K_D$ (M) | RhPD-L1 $K_D$ (M) |
|---|---|---|---|
| Z13091 | 776 | $7.4 \times 10^{-10}$ | $5.2 \times 10^{-9}$ |
| Z17746 | 8 | $3.8 \times 10^{-10}$ | $5.2 \times 10^{-10}$ |
| Z17748 | 11 | $4.5 \times 10^{-10}$ | $7.4 \times 10^{-10}$ |
| Z17756 | 7 | $2.4 \times 10^{-10}$ | $2.1 \times 10^{-9}$ |
| Z17825 | 5 | $2.5 \times 10^{-10}$ | $1.2 \times 10^{-9}$ |
| Z17911 | 3 | $3.6 \times 10^{-10}$ | $2.2 \times 10^{-9}$ |
| Z17964 | 2 | $3.0 \times 10^{-10}$ | $2.0 \times 10^{-9}$ |
| Z17972 | 19 | $5.4 \times 10^{-10}$ | $2.7 \times 10^{-9}$ |
| Z17978 | 13 | $4.5 \times 10^{-10}$ | $1.0 \times 10^{-9}$ |
| Z18022 | 9 | $3.4 \times 10^{-10}$ | $1.4 \times 10^{-9}$ |
| Z18039 | 20 | $6.3 \times 10^{-10}$ | $1.9 \times 10^{-9}$ |
| Z18048 | 4 | $3.5 \times 10^{-10}$ | $1.8 \times 10^{-9}$ |
| Z18052 | 14 | $4.5 \times 10^{-10}$ | $1.2 \times 10^{-9}$ |
| Z18054 | 22 | $7.6 \times 10^{-10}$ | $1.2 \times 10^{-9}$ |
| Z18064 | 1 | $1.3 \times 10^{-10}$ | $1.5 \times 10^{-9}$ |
| Z18066 | 12 | $4.3 \times 10^{-10}$ | $2.1 \times 10^{-9}$ |
| Z18070 | 10 | $3.1 \times 10^{-10}$ | $2.5 \times 10^{-9}$ |
| Z18074 | 6 | $3.6 \times 10^{-10}$ | $2.9 \times 10^{-9}$ |
| Z18090 | 17 | $5.1 \times 10^{-10}$ | $2.3 \times 10^{-9}$ |
| Z18101 | 23 | $9.3 \times 10^{-10}$ | $2.4 \times 10^{-9}$ |
| Z18129 | 16 | $4.8 \times 10^{-10}$ | $1.2 \times 10^{-9}$ |
| Z18149 | 18 | $5.3 \times 10^{-10}$ | $9.6 \times 10^{-10}$ |
| Z18233 | 21 | $7.2 \times 10^{-10}$ | $4.4 \times 10^{-9}$ |
| Z18353 | 15 | $4.6 \times 10^{-10}$ | $1.6 \times 10^{-9}$ |
| Z18418 | 24 | $1.9 \times 10^{-9}$ | $4.1 \times 10^{-9}$ |

Furthermore, all 24 maturated Hiss-tagged Z variants were also tested for binding against the three sequence-related proteins, hPD-L2, hB7-H3, and hB7-H4. In line with the results in Example 3, no binding to either of the control proteins were detected at a Z variant concentration of 500 nM.

TABLE 13

Kinetic parameters for binding of Z variants to hPD-L1 and RhPD-L1

| | | hPD-L1 | | | RhPD-L1 | | |
|---|---|---|---|---|---|---|---|
| Z variant | SEQ ID NO: | $k_a$ (1/Ms) | $k_d$ (1/s) | $K_D$ (M) | $k_a$ (1/Ms) | $k_d$ (1/s) | $K_D$ (M) |
| Z13091 | 776 | $1.8 \times 10^{6}$ | $1.1 \times 10^{-3}$ | $6.3 \times 10^{-10}$ | $1.9 \times 10^{6}$ | $1.0 \times 10^{-3}$ | $5.4 \times 10^{-10}$ |
| Z17746 | 8 | $1.6 \times 10^{6}$ | $4.6 \times 10^{-4}$ | $2.8 \times 10^{-10}$ | $1.4 \times 10^{6}$ | $4.0 \times 10^{-4}$ | $2.8 \times 10^{-10}$ |
| Z17748 | 11 | $1.7 \times 10^{6}$ | $5.7 \times 10^{-4}$ | $3.4 \times 10^{-10}$ | $1.8 \times 10^{6}$ | $5.1 \times 10^{-4}$ | $2.9 \times 10^{-10}$ |
| Z17756 | 7 | $2.0 \times 10^{6}$ | $5.4 \times 10^{-4}$ | $2.8 \times 10^{-10}$ | $2.7 \times 10^{6}$ | $4.5 \times 10^{-4}$ | $1.7 \times 10^{-10}$ |
| Z17825 | 5 | $2.0 \times 10^{6}$ | $4.7 \times 10^{-4}$ | $2.4 \times 10^{-10}$ | $1.9 \times 10^{6}$ | $3.9 \times 10^{-4}$ | $2.1 \times 10^{-10}$ |
| Z17911 | 3 | $2.3 \times 10^{6}$ | $4.9 \times 10^{-4}$ | $2.1 \times 10^{-10}$ | $2.1 \times 10^{6}$ | $4.2 \times 10^{-4}$ | $2.0 \times 10^{-10}$ |
| Z17964 | 2 | $2.1 \times 10^{6}$ | $4.3 \times 10^{-4}$ | $2.1 \times 10^{-10}$ | $3.4 \times 10^{6}$ | $3.8 \times 10^{-4}$ | $1.1 \times 10^{-10}$ |
| Z18022 | 9 | $1.7 \times 10^{6}$ | $4.9 \times 10^{-4}$ | $2.8 \times 10^{-10}$ | $1.6 \times 10^{6}$ | $4.6 \times 10^{-4}$ | $2.8 \times 10^{-10}$ |
| Z18048 | 4 | $1.9 \times 10^{6}$ | $4.4 \times 10^{-4}$ | $2.3 \times 10^{-10}$ | $1.6 \times 10^{6}$ | $3.8 \times 10^{-4}$ | $2.4 \times 10^{-10}$ |
| Z18064 | 1 | $3.5 \times 10^{6}$ | $4.3 \times 10^{-4}$ | $1.3 \times 10^{-10}$ | $3.5 \times 10^{6}$ | $3.4 \times 10^{-4}$ | $9.6 \times 10^{-11}$ |
| Z18066 | 12 | $1.5 \times 10^{6}$ | $5.4 \times 10^{-4}$ | $3.7 \times 10^{-10}$ | $1.4 \times 10^{6}$ | $4.7 \times 10^{-4}$ | $3.5 \times 10^{-10}$ |
| Z18070 | 10 | $2.0 \times 10^{6}$ | $5.7 \times 10^{-4}$ | $2.9 \times 10^{-10}$ | $1.7 \times 10^{6}$ | $4.7 \times 10^{-4}$ | $2.8 \times 10^{-10}$ |
| Z18074 | 6 | $2.0 \times 10^{6}$ | $5.4 \times 10^{-4}$ | $2.7 \times 10^{-10}$ | $1.7 \times 10^{6}$ | $4.6 \times 10^{-4}$ | $2.7 \times 10^{-10}$ |

AlphaLISA blocking assay: The ability of 24 maturated Hiss-tagged monomeric Z variants to inhibit hPD-L1 binding to hPD-1 was tested in an AlphaLISA blocking assay. The primary Z variant Z13091 was included as a reference. Serial dilutions of the Z variants were incubated with biotinylated hPD-L1 and the blocking ability of each respective variant was measured after addition of hPD-1 coated Acceptor beads and subsequently streptavidin coated Donor beads. Inhibition could be measured as a decrease in AlphaLISA counts for positive Z variants. The calculated IC50 values for the variants that were shown to block PD-L1 binding to PD-1 in this assay are shown in Table 14.

TABLE 14

IC50 values for Z variants blocking the PD-1/PD-L1 interaction

| Z variant | SEQ ID NO: | IC50 AlphaLISA (M) |
|---|---|---|
| Z13091 | 776 | $1.1 \times 10^{-9}$ |
| Z17746 | 8 | $1.3 \times 10^{-9}$ |
| Z17748 | 11 | $1.1 \times 10^{-9}$ |
| Z17756 | 7 | $1.5 \times 10^{-9}$ |
| Z17825 | 5 | $1.6 \times 10^{-10}$ |
| Z17911 | 3 | $5.7 \times 10^{-10}$ |
| Z17964 | 2 | $8.9 \times 10^{-9}$ |
| Z17972 | 19 | $2.9 \times 10^{-10}$ |
| Z17978 | 13 | $6.2 \times 10^{-10}$ |
| Z18022 | 9 | $3.1 \times 10^{-10}$ |
| Z18039 | 20 | $2.9 \times 10^{-10}$ |
| Z18048 | 4 | $1.5 \times 10^{-10}$ |
| Z18052 | 14 | $3.4 \times 10^{-10}$ |
| Z18054 | 22 | $1.1 \times 10^{-9}$ |
| Z18064 | 1 | $3.9 \times 10^{-10}$ |
| Z18066 | 12 | $8.3 \times 10^{-10}$ |
| Z18070 | 10 | $8.6 \times 10^{-10}$ |
| Z18074 | 6 | $3.1 \times 10^{-10}$ |
| Z18090 | 17 | $6.7 \times 10^{-10}$ |
| Z18101 | 23 | $6.2 \times 10^{-10}$ |
| Z18129 | 16 | $6.0 \times 10^{-10}$ |
| Z18149 | 18 | $1.9 \times 10^{-10}$ |
| Z18233 | 21 | $1.5 \times 10^{-10}$ |
| Z18353 | 15 | $7.2 \times 10^{-10}$ |
| Z18418 | 24 | $5.7 \times 10^{-10}$ |

Figure 6:
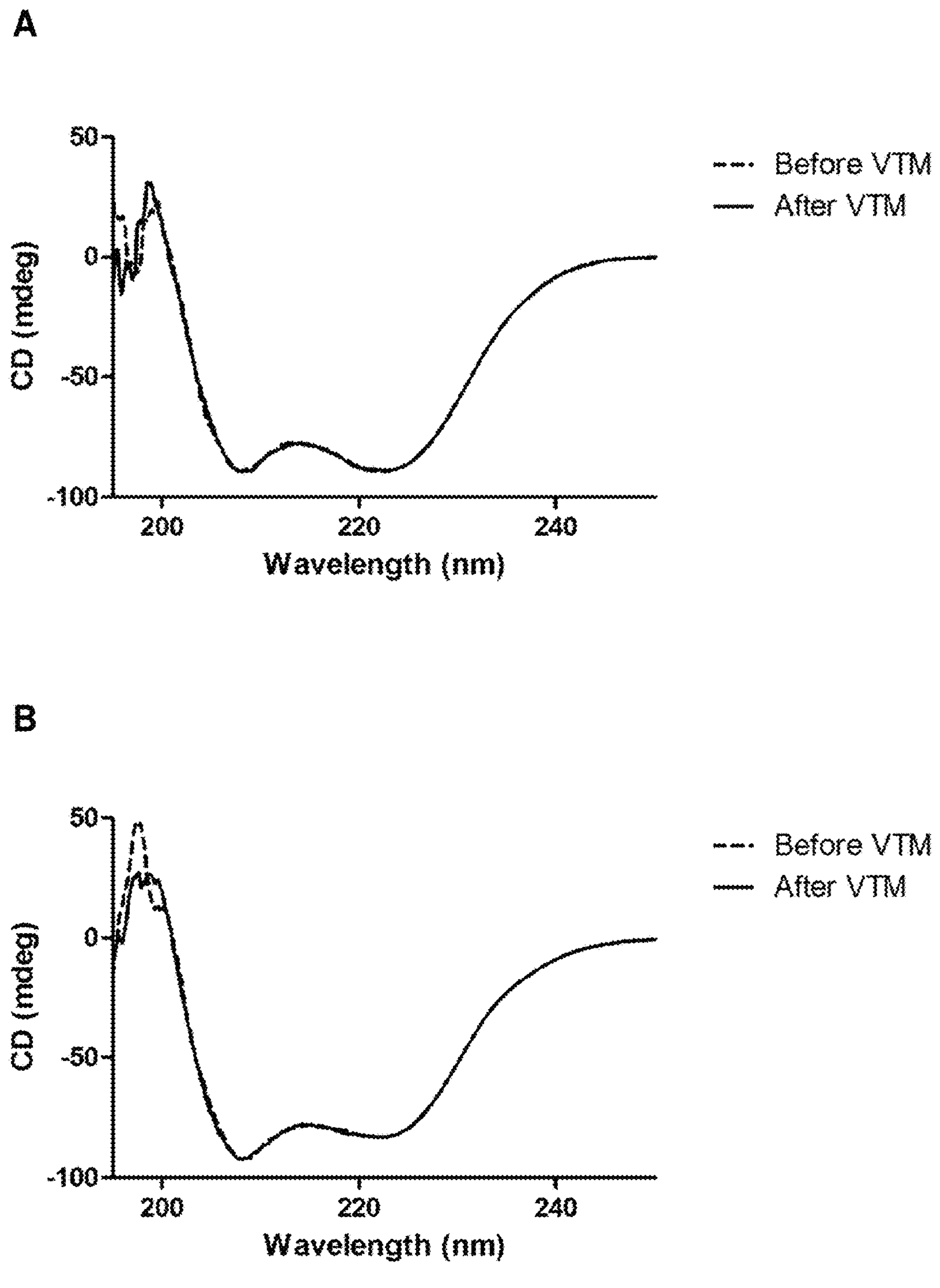
FIG. 6 shows circular dichroism (CD) spectra of two second generation PD-L1 binding polypeptides. The CD spectra at wavelengths ranging from 250 to 195 nm collected at 20° C. before (broken line) and after (solid line) the variable temperature measurement (VTM) are shown for (A) Z18064 (SEQ ID NO:1) and (B) Z18090 (SEQ ID NO:17).

CD analysis: The CD spectra determined for 24 maturated PD-L1 binding Z variants with a $His_6$ tag showed that each had an α-helical structure at 20° C. The melting temperatures (Tm) were determined using variable temperature measurements (Table 15). Reversible folding was observed for all PD-L1 binding Z variants when overlaying spectra measured at 20° C. before and after heating to 80° C., as shown for two selected Z variants in FIG. 6.

TABLE 15

Melting temperatures of maturated PD-L1 binding Z variants

| Z variant | SEQ ID NO: | Tm (° C.) |
|---|---|---|
| Z17746 | 8 | 59 |
| Z17748 | 11 | 63 |
| Z17756 | 7 | 63 |
| Z17825 | 5 | 60 |
| Z17911 | 3 | 59 |
| Z17964 | 2 | 62 |
| Z17978 | 13 | 59 |
| Z18022 | 9 | 59 |
| Z18039 | 20 | 55 |
| Z18048 | 4 | 60 |
| Z18064 | 1 | 62 |
| Z18066 | 12 | 58 |
| Z18070 | 10 | 60 |
| Z18074 | 6 | 62 |
| Z18090 | 17 | 68 |
| Z18129 | 16 | 63 |
| Z18233 | 21 | 57 |

Example 8

Characterization of Anti-PD-L1/PD-1 and Anti-PD-L1/CTLA-4 Complexes

Materials and Methods

Production of complexes and control antibodies: Four different complexes targeting PD-L1 and PD-1, and four different complexes targeting PD-L1 and CTLA-4 were constructed, as well as a control antibody targeting PD-1. An antibody denoted "Lam", having the same CDR sequences and specificity as the commercially available, PD-1 targeting monoclonal antibody pembrolizumab (formerly lambrolizumab), was constructed using the heavy chain (HC) and light chain (LC) sequences $HC_{Lam}$ (SEQ ID NO:815) and $LC_{Lam}$ (SEQ ID NO:816). An antibody denoted "Ipi", having the same CDR sequences and specificity as the commercially available, CTLA-4 targeting monoclonal antibody ipilimumab, was constructed using the heavy chain (HC) and light chain (LC) sequences $HC_{Ipi}$; (SEQ ID NO:817) and $LC_{Ipi}$ (SEQ ID NO:818). The PD-L1 targeting Z variant Z15170 (SEQ ID NO:814; identical to Z13165 (SEQ ID NO:784) but starting with the amino acid residues AE instead of VD) with a C-terminal VD sequence was genetically fused, via a flexible 15 residue $(GGGGS)_3$ linker, to the N-termini of $HC_{Lam}$, $LC_{Lam}$, $HC_{Ipi}$ and $LC_{Ipi}$, respectively, resulting in the complexes Z15170-$HC_{Lam}$, Z15170-$LC_{Lam}$, Z15170-$HC_{Ipi}$ and Z15170-$LC_{Ipi}$, respectively; or to the C-termini of the same chains, resulting in the complexes $HC_{Lam}$-Z15170, $LC_{Lam}$-Z15170, $HC_{Ipi}$-Z15170 and $LC_{Ipi}$-Z15170, respectively. Gene synthesis, cloning, production by transient gene expression in CHO cells as well as purification by Protein A chromatography and verification of constructs by gel electrophoresis were performed by Evitria AG (Switzerland).

Biacore kinetic analyses: Kinetic constants ($k_a$ and $k_d$) and affinities ($K_D$) for hPD-L1, human PD-1 (hPD-1; R&D Systems cat. no. 1086-PD-050) and human CTLA-4 (hCTLA-4; R&D Systems cat. no. 325-CT-200) were determined for all eight complexes produced and using a Biacore 2000 instrument (GE Healthcare). The control antibody Lam was also analyzed for binding against PD-1. 5 μg/ml solutions of each of the proteins hPD-L1, hPD-1 and hCTLA-4 were prepared in 10 mM NaAc buffer (pH 5.0 for PD-L1, and pH 4.5 for PD-1 and CTLA-4) and used for immobilization in separate flow cells on the carboxylated dextran layer of different CM5 chip surfaces (GE Healthcare, cat. no. BR100012). The immobilization was performed using amine coupling chemistry according to the manufacturer's protocol and using HBS-EP with 500 mM NaCl as running buffer. Immobilization levels obtained were ~110-140 RU. A series of 3.33, 10, 30, 90, 270 nM concentrations of the respective complex and Lam were injected and the responses recorded, except for analysis of binding to PD-L1 for constructs with Z15170 positioned on the C-terminus of the respective antibody, for which a concentration series of 30, 90, 270 and 900 nM was used.

In a separate experiment, the dual binding specificity was evaluated by a capture assay using the Biacore 2000 instrument. The complexes Z15170-$HC_{Lam}$, Z15170-$LC_{Lam}$, Z15170-$HC_{Ipi}$ and Z15170-$LC_{Ipi}$, Lam and ipilimumab (Yervoy®, Bristol-Myers Squibb/Astra Zeneca via Apoteket AB, cat. no. 065544, lot no. 4A85968), at a concentration of 300 nM, were injected over chip surfaces immobilized with PD-1 or CTLA-4 as described above. In all cases, the duration of the injection was 5 min at a flow rate of 30 μl/min with a wait/dissociation step of 5 min before a second injection (5 min) of 100 or 500 nM PD-L1 was made. HBS-EP with 500 mM NaCl was used as a running buffer and for protein dilutions.

Cell binding analysis by FACS: The potential of the complexes to bind PD-L1 expressing cells was investigated using FACS. 150 000 cells of the breast cancer cell line MDA-MB-231, cultivated in DMEM (ATCC cat. no. 30-2002) containing 10% FBS, were pipetted per well of a v-bottomed 96-well plate (Nunc, cat. no. 277143) and the cells in the plate were subsequently pelleted at 400 g for 3 min at RT. The supernatants were removed and the cells were resuspended in 100 μl PBS plus 2.5% FBS (staining buffer) containing 0.625 μg/ml of the complexes Z15170-$HC_{Lam}$, Z15170-$LC_{Lam}$, $HC_{Lam}$-Z15170, $LC_{Lam}$-Z15170, Z15170-$HC_{Ipi}$, Z15170-$LC_{Ipi}$, $HC_{Ipi}$-Z1 5170 and $LC_{Ipi}$-Z15170, respectively, or 0.625 μg/ml of the antibodies Lam or ipilimumab. A mouse anti-PD-L1 antibody (RnD Systems, cat. no. MAB1561) at a concentration of 1 μg/ml was used as a positive control. Cells incubated with buffer alone were used as negative controls. The cells were incubated for 1 h at 8° C. in the dark, washed twice with 100 μl staining buffer, and resuspended in 100 μl of staining buffer containing 2.5 μg/ml of a goat-anti-human IgG-Alexa488 (Molecular Probes, cat. no. A11013) or, for cells stained with the positive control antibody, goat anti-mouse IgG-Alexa647 antibody (Life Technologies, cat. No. A21236). The cells were incubated for 1 h at 8° C. in the dark, washed twice with 100 μl staining buffer and resuspended in 300 μl of staining buffer. Data from 10,000 cells were obtained using a FACS Calibur (Beckman Coulter) and the data was analyzed using Flowing software 2.5.0 (Turku University). Mean fluorescence intensity (MFI) was used as a read out of binding capacity.

Co-culture of MDA-MB-231 and PBMC: A mixed lymphocyte assay was used to analyze if the Ipi-based complexes could affect proliferation or the cytotoxic effect of T-cells and thereby increase the elimination of cancer cells. Herein, peripheral blood mononuclear cells (PBMC) and MDA-MB-231 cells were co-cultivated for six days and the number of T-cells and cancer cells were assessed. 20000 MDA-MB-231 cells, cultivated in DMEM containing 10% FBS, were pipetted per well of a flat-bottomed 96-well plate and were left to adhere to the bottom of the well by incubation at 37° C. in a humidified 5% $CO_2$ atmosphere. Day 2 of the experiment, serial dilutions (200-0.064 nM) of the Ipi-based complexes were prepared in a separate plate using RPM11640 with L-glut (Lonza) supplemented with 10% FCS, and 1% Pen-Strep (Lonza, cat. no. DE17-603E). The DMEM medium was discarded from the MDA-MB-231 cells and 100 μl of the diluted complexes were added. PBMC were prepared form a buffy coat using Ficoll Paque PLUS (GE Healthcare, cat no. 17-1440-02). In brief, the buffy coat was diluted 2× in PBS. 10 ml of the diluted buffy coat were layered on the top of 5 ml Ficoll in 15 ml falcon tubes and centrifuged at RT for 30 min at 400 g. The lymphocyte layer was collected and the cells were washed twice in the supplemented RPM11640 medium described above. The cells were counted and adjusted to 1 million cells per ml in supplemented RPMI medium. 100 μl of the cell suspension were added to the plate with the MDA-MB-231 cells. The plates were incubated for 6 days at 37° C. in a humidified 5% $CO_2$ atmosphere. At day 7 of the experiment, the number of MDA-MD-231 cells and CD3+ T-cells were counted by FACS. The PBMC were transferred to a v-bottom plate, washed two times with PBS containing 2% FBS (also used as staining buffer) and stained with a mouse anti-CD3 antibody (EXBIO Praha, cat no. 12-631-M001) at a concentration of 2 μg/ml for 1 h at 4° C. The MDA-MB231 cells were trypsinated (20 μl/well) and transferred to another v-bottom shaped plate washed two times with PBS containing 2% FBS and stained with a rabbit anti-EGFR antibody (Abcam, cat no. ab2430-1) at a concentration of 2 μg/ml for 1 h at 4° C. The cells were washed two times with PBS containing 2% FBS and an Alexa-fluor 488-goat-anti-rabbit antibody (Invitrogen, cat no. A11008) and Alexa-fluor 647-goat-anti-mouse antibody (Life technologies, cat no. A21236) were used as detection antibodies at a concentration of 1 μg/ml and incubated for 1 h at 4° C.

Results

Figure 7:
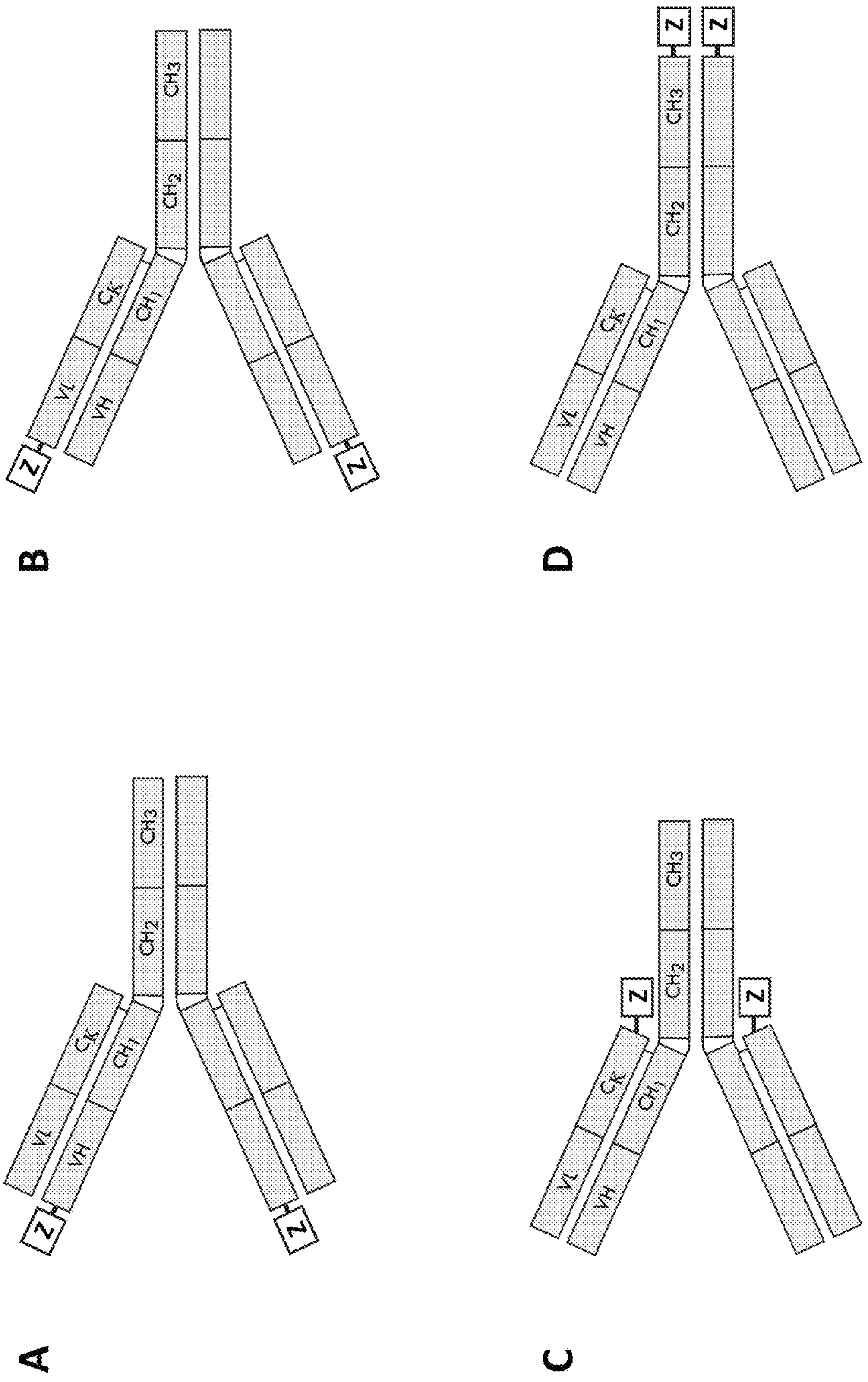
FIG. 7 is a schematic representation of the design of complexes according to the disclosure, produced as described in Example 8. "Z" denotes the PD-L1 targeting Z variant Z15170 (SEQ ID NO:814), which was genetically fused to the N-termini (7A and 7B) or the C-termini (7C and 7D) of the heavy (7A and 7D) or the light (7B and 7C) chains of the anti-PD-1 monoclonal antibody Lam or the anti-CTLA-4 monoclonal antibody Ipi via a 15 residue $(GGGGS)_3$-linker (SEQ ID NO:895).

Production of complex constructs: A schematic representation of the design of each of the four types of produced complexes is shown in FIG. 7.

Biacore kinetic analyses: The affinity to the target proteins PD-L1, PD-1 and CTLA-4, respectively, were determined for each relevant complex. The control antibody Lam was also analyzed against its target PD-1. The kinetic parameters for the interactions with PD-L1 are summarized in Table 16. The capability of the Z moiety of the complex to interact with PD-L1 was maintained, although the affinity was reduced as well as affected by the positioning of the Z moiety on the antibody. For comparison, the $K_D$ of the Hiss-Z13165 interaction with PD-L1 was 0.64 nM (as presented in Example 3) whereas the $K_D$ for complexes with N-terminally positioned Z moieties was 1.5-2.6 nM and the $K_D$ for C-terminally positioned Z moieties was 12-41 nM. Thus, N-terminal positioning of the Z moiety was superior to the C-terminal positioning, with approximately 10 times higher affinity. This effect was evident with both Lam- and Ipi-based constructs. Whether the fusions were made to the heavy or light chains of the antibodies were of less importance for the N-terminally positioned Z moiety, but had major impact on the C-terminally positioned Z moiety, where the light chain fusions had a $K_D$ of 12-18 nM compared to a $K_D$ of 29-41 nM for the heavy chain fusions.

TABLE 16

Kinetic parameters for binding of indicated complexes to hPD-L1

| Analyte | $k_a$ (1/MS) | $k_d$ (1/s) | $K_D$ (M) |
|---|---|---|---|
| $HC_{Lam}$-Z15170 | $2.44 \times 10^4$ | $7.17 \times 10^{-4}$ | $2.9 \times 10^{-8}$ |
| $LC_{Lam}$-Z15170 | $3.06 \times 10^4$ | $3.58 \times 10^{-4}$ | $1.2 \times 10^{-8}$ |
| Z15170-$HC_{Lam}$ | $1.16 \times 10^5$ | $2.84 \times 10^{-4}$ | $2.4 \times 10^{-9}$ |
| Z15170-$LC_{Lam}$ | $2.33 \times 10^5$ | $6.01 \times 10^{-4}$ | $2.6 \times 10^{-9}$ |
| $HC_{Ipi}$-Z15170 | $1.78 \times 10^4$ | $7.27 \times 10^{-4}$ | $4.1 \times 10^{-8}$ |
| $LC_{Ipi}$-Z15170 | $3.07 \times 10^4$ | $5.63 \times 10^{-4}$ | $1.8 \times 10^{-8}$ |
| Z15170-$HC_{Ipi}$ | $2.05 \times 10^5$ | $4.83 \times 10^{-4}$ | $2.4 \times 10^{-9}$ |
| Z15170-$LC_{Ipi}$ | $2.30 \times 10^5$ | $3.49 \times 10^{-4}$ | $1.5 \times 10^{-9}$ |

The interactions of the complexes with PD-1 and CTLA-4, respectively, followed a bivalent model. The $K_{D1}$, $K_{D2}$, $k_{a1}$, $k_{a2}$, $k_{d1}$ and $k_{d2}$ are summarized in Table 17 and Table 18 for PD-1 and CTLA-4, respectively. The affinity constant $K_{D1}$ for the interaction of PD-1 with the produced Lam control antibody was determined to 18.6 nM. The affinity was stronger for all the Lam based complexes, with a $K_{D1}$ range of 0.8-2.7 nM. A somewhat slower association and rate, $k_a1$, was seen for Z15170-$HC_{Lam}$, but generally the differences between the complexes were small, i.e. the positioning of the Z moiety on the antibody seems to have minor impact on the interaction between the antibody and PD-1.

TABLE 17

Parameters for binding of indicated complexes and Lam to hPD-1

| Analyte | $k_{a1}$ (1/Ms) | $k_{d1}$ (1/s) | $K_{D1}$ (M) | $k_{a2}$ (1/RUs) | $k_{d2}$ (1/s) | $K_{D2}$ (RU) |
|---|---|---|---|---|---|---|
| Lam | $4.35 \times 10^4$ | $8.10 \times 10^{-4}$ | $1.9 \times 10^{-8}$ | $1.88 \times 10^{-3}$ | $1.83 \times 10^{-3}$ | 0.97 |
| $HC_{Lam}$-Z15170 | $1.17 \times 10^5$ | $1.64 \times 10^{-4}$ | $1.4 \times 10^{-9}$ | $3.35 \times 10^0$ | $1.65 \times 10^1$ | 4.9 |
| $LC_{Lam}$-Z15170 | $1.78 \times 10^5$ | $1.34 \times 10^{-4}$ | $7.5 \times 10^{-10}$ | $2.92 \times 10^{-1}$ | $7.89 \times 10^{-1}$ | 2.7 |
| Z15170-$HC_{Lam}$ | $4.27 \times 10^4$ | $1.17 \times 10^{-4}$ | $2.7 \times 10^{-9}$ | $1.93 \times 10^{-2}$ | $7.87 \times 10^{-2}$ | 4.1 |
| Z15170-$LC_{Lam}$ | $1.14 \times 10^5$ | $1.56 \times 10^{-4}$ | $1.4 \times 10^{-9}$ | $2.22 \times 10^{-2}$ | $1.72 \times 10^{-1}$ | 7.7 |

TABLE 18

Kinetic parameters for binding of indicated complexes to hCTLA-4

| Analyte | $k_{a1}$ (1/Ms) | $k_{d1}$ (1/s) | $K_{D1}$ (M) | $k_{a2}$ (1/RUs) | $k_{d2}$ (1/s) | $K_{D2}$ (RU) |
|---|---|---|---|---|---|---|
| $HC_{Ipi}$-Z15170 | $6.79 \times 10^4$ | $5.40 \times 10^{-4}$ | $8.0 \times 10^{-9}$ | $6.76 \times 10^{-2}$ | $4.10 \times 10^{-1}$ | 6.1 |
| $LC_{Ipi}$-Z15170 | $5.48 \times 10^4$ | $4.41 \times 10^{-4}$ | $8.0 \times 10^{-9}$ | $4.04 \times 10^{-2}$ | $2.88 \times 10^{-1}$ | 7.1 |
| Z15170-$HC_{Ipi}$ | $3.33 \times 10^4$ | $2.79 \times 10^{-4}$ | $8.4 \times 10^{-9}$ | $1.38 \times 10^{-2}$ | $8.20 \times 10^{-2}$ | 5.9 |
| Z15170-$LC_{Ipi}$ | $4.55 \times 10^4$ | $4.49 \times 10^{-4}$ | $9.9 \times 10^{-9}$ | $9.74 \times 10^{-3}$ | $4.22 \times 10^{-2}$ | 4.3 |

The affinity constant $K_{D1}$ for the interaction of complexes with CTLA-4 was in the range of 8-10 nM and this is in line with the reported $K_D$ for ipilimumab (5.25±3.62 nM; European Medicines Agency's assessment report 2011: EMA/CHMP/557664/2011). The kinetic profiles were similar for all Ipi-based constructs, but with somewhat slower association and dissociation rates for Z15170-$HC_{Ipi}$.

The Biacore capture assay confirmed the dual binding specificity of all complexes included in the assay, i.e. Z15170-$HC_{Lam}$, Z15170-$LC_{Lam}$, Z15170-$HC_{Ipi}$ and Z15170-$LC_{Ipi}$. FIG. 8 shows that the complexes first bind to immobilized PD-1 or CTLA-4 and that PD-L1 subsequently binds to the respective captured complex. In separate control experiments, it was shown that PD-L1 does not bind to CTLA-4 or Ipi and that no additional binding by PD-L1 was seen following injection of PD-L1 to Lam captured on PD-1.

Cell binding analysis by FACS: This experiment was performed to analyze whether the complexes could bind to PD-L1 expressing cells. MDA-MB-231 cells that naturally express PD-L1 were stained with 0.625 μg/ml of the respective complex. The MFI values are presented in Table 19 and shows that the complexes had the ability to bind PD-L1 expressing cells. For both the Ipi- and Lam-based complexes, the highest MFI values were obtained for N-terminal positioning of the Z moiety on the light chain of the antibody.

TABLE 19

MFI for binding of complexes to PD-L1 expressing cells

| Analyte | MFI |
|---|---|
| Lam | 62 |
| Z15170-$HC_{Lam}$ | 161 |
| $HC_{Lam}$-Z15170 | 274 |
| Z15170-$LC_{Lam}$ | 327 |
| $LC_{Lam}$-Z15170 | 145 |
| Ipilimumab | 64 |

TABLE 19-continued

| MFI for binding of complexes to PD-L1 expressing cells | |
|---|---|
| Analyte | MFI |
| Z15170-$HC_{Ipi}$ | 488 |
| $HC_{Ipi}$-Z15170 | 264 |
| Z15170-$LC_{Ipi}$ | 582 |
| $LC_{Ipi}$-Z15170 | 192 |
| Negative control | 69 |
| Anti-PD-L1 antibody | 610 |

Co-culture of MDA-MB-231 and PBMC: To assess whether the Ipi-based complexes could affect the inhibitory mechanisms caused by CTLA-4 and PD-L1, a mixed lymphocyte assay was used. Breast cancer cells MDA-MB-231 were co-cultivated with PBMC for six days and the number of cancer cells and T-cells were evaluated. The analysis revealed a concentration dependent effect of the complexes, with an increased amount of T-cells and a lowered number of cancer cells. FIG. 9A shows the reduction in number of MDA-MB231 cells with increasing concentration of the complexes. This reduction was evident for all complexes with the best effect achieved with the construct in which the Z moiety is situated at the N-terminus of the light chain of the antibody. In contrast, the ipilimumab control antibody did not induce a concentration dependent decrease of the cancer cells. Thus, blocking of the interaction PD-1/PD-L1 appears essential to reduce the amount of cancer cells. FIG. 9B shows the increase in the number of T-cells with an increasing concentration of the complexes. Again, the effect is most prominent with the construct in which the Z moiety is situated at the N-terminus of the light chain of the antibody.

Example 9

Conjugation and Radiolabeling of PD-L1 Binding Z Variants

This Example describes the conjugation and radiolabeling of Z15168-Cys (SEQ ID NO:809), Z18608-Cys (SEQ ID NO:811), Z18609-Cys (SEQ ID NO:812) and Z18610-Cys (SEQ ID NO:813), cloned and produced as described in Example 2 and Example 6, and further used for the in vivo imaging studies described in Example 10 and 11.

Materials and Methods

Reduction and NOTA conjugation: To 5 mg of Z variant in [20 mM HEPES, 1 mM EDTA, pH 7.2] was added three molar equivalents of tris(2-carboxyethyl)phosphine (TCEP) in 0.5 ml of degassed 0.2 M ammonium acetate buffer (pH 7.0). The reaction was kept at RT for 60 min before being transferred to an Ultracel 3K Centrifugal Filter and centrifuged at 4000 rpm for 90 min. The flow-through was discarded and an additional 1 ml of 0.2 M ammonium acetate buffer added, and the process repeated. The reduced Z variant was then transferred to a second reaction vessel in 2 ml of oxygen free 0.2 M ammonium acetate buffer (pH 7.0). 4 mg of NOTA-maleimide (Macrocyclics) in 0.5 ml of 0.2 M ammonium acetate buffer (pH 7.0) was then added, and the reaction vessel purged with argon before heating to 40° C. for 3 h, at which point the reaction mixture was transferred to an Ultracel 3K Centrifugal Filter and centrifuged for 90 min at 4000 rpm. The flow-through was discarded and 2 ml milliQ water added. Centrifugation was performed for an additional 90 min and the flow-through discarded. Purified NOTA-conjugated Z variant was collected in 1 ml milliQ water, lyophilized and stored at −70° C. prior to use. Purity of the final product was determined by LC/MS.

Radiolabeling: A cartridge containing [$^{18}$F]-fluoride was first washed with 1.5 ml of ultrapure water, then [$^{18}$F]-fluoride was eluted with 1.0 ml of 0.4 M $KHCO_3$. 100 μl of the eluted [$^{18}$F]-fluoride solution was added to a stem vial charged with 10 μl acetic acid, 50 μl $AlCl_3$ (2 mM in 0.1 M NaOAc buffer, pH 4) and 125 μl 0.1 M NaOAc pH 4. The solution was incubated for 2 min at RT before 1 mg of NOTA-conjugated Z variant in 400 μl of a 1:1 solution of acetrontrile and 0.1 M NaOAc pH 4 was added, then heated to 100° C. for 15 min. After heating was complete, the sample was transferred to a vial containing 0.7 ml of 0.1% formic acid, mixed and purified by HPLC [Waters Xselect CSH C18 column (250×10 mm, 130 μm)] using a gradient of 10-30% MeCN over 15 min at a flow rate of 5 ml/min, the balance being 0.1% formic acid. The peak corresponding to [$^{18}$F]AlF-NOTA-Z##### was collected, the MeCN was removed in vacuo, and transferred to a sterile vial using physiologic saline as a rinse to give [$^{18}$F]AlF-NOTA-Z#####. Specific activity and radiochemical purity was determined via a Waters Acquity LC/MS system (Milford, Mass., USA) and a R-RAM Model 4 Radio-HPLC detector (IN/US Systems, Brandon, Fla., USA).

Results

The PD-L1 binding Z variants, Z15168-Cys (SEQ ID NO:809), Z18608-Cys (SEQ ID NO:811), Z18609-Cys (SEQ ID NO:812) and Z18610-Cys (SEQ ID NO:813), were site specifically conjugated with NOTA at their respective unique C-terminal cysteine residue. Subsequent radiolabeling with [$^{18}$F]AlF typically resulted in radiochemical purities of 97-100% and specific activities of 14.6±6.5 GBq/mmol. The radiolabeled Z variants will be referred to as [$^{18}$F]AlF-NOTA-Z[#####].

Example 10

In Vivo Imaging and Biodistribution in Tumor Bearing Mice

Materials and Methods

Animal models: Female SCID Beige mice (6-8 week old, Charles River Laboratories) were housed in a temperature and humidity controlled room and kept on a regular diet. LOXIMVI (human melanoma cell line, PD-L1 positive) or SUDHL-6 (PD-L1 negative) cells were cultured in complete growth medium containing RPMI 1640 medium with 10% fetal bovine serum at 37° C. with 5% $CO_2$. The growth medium was changed 2 or 3 times per week and the cells subcultured at a ratio of 1:10 when needed. Tumors were implanted at the right shoulder by subcutaneous injection of $1×10^6$ LOXIMVI cells in 100 μl PBS or $10×10^6$ SUDHL-6 cells in 100 μl PBS+Growth Factor Reduced Matrigel (1:1). The mice were used for micro-PET and ex vivo studies about 5-7 days and 3 weeks after the injection of LOXIMVI and SUDHL-6 cells, respectively, when tumors reached a mass of 100-400 mg.

PET data acquisition: Mice were anesthetized with isoflurane (4-5% induction, 1-3% maintenance), prepared with tail vein catheters, and placed in a dedicated small animal PET scanner (microPET Focus220, Siemens Preclinical Solutions). A 20 min transmission scan with $^{57}$Co was obtained to correct for photon attenuation and scatter. Then, 0.2-0.6 MBq of the respective [$^{18}$F]-labelled Z variant was administered via the tail vein catheters, and PET data were collected for 90 min. In a separate pre-blocking experiment, 400 µg non-labelled NOTA-conjugated Z15168-Cys was administered prior to administration of [$^{18}$F]AIF-NOTA-Z15168.

Ex vivo biodistribution measurements: Immediately after PET acquisition, mice were euthanized. Tumor, heart, lung, spleen, liver, kidneys, blood, plasma and muscle were collected and measured using a gamma counter (PerkinElmer). For each mouse, biodistribution measurements were converted into units of Standard Uptake Value (SUV). Regions of Interest (ROI) were drawn on all tumors that could be identified in PET images, and time activity curves (TACs) were calculated.

Results

Representative PET images following injection of [$^{18}$F]-labelled Z variants into tumor-bearing mice showed the highest uptake in kidney and bladder. PD-L1 positive LOX tumors could be clearly seen in images, while PD-L1 negative SUDHL6 tumors were not visible. Representative PET images are shown in FIG. 10A for [$^{18}$F]AIF-NOTA-Z15168. Ex vivo biodistribution measurements at 90 min post-injection were in agreement with PET images. The uptake of [$^{18}$F]-labelled Z variants Z15168-Cys (SEQ ID NO:809), Z18608-Cys (SEQ ID NO:811), Z18609-Cys (SEQ ID NO:812) and Z18610-Cys (SEQ ID NO:813) was significantly higher in LOX tumors than in SUDHL6 tumors and the tumor uptake increased with the PD-L1 binding affinity of the Z variants (FIG. 11A-B). Target specificity was confirmed in a pre-blocking experiment in which pre-administration of 400 µg NOTA-Z15168 caused a reduction in [$^{18}$F]AIF-NOTA-Z15168 uptake in LOX tumors (FIG. 101B). Changes in distribution, including faster clearance as indicated by reduced blood uptake at 90 min, was also seen. The kidney tracer retention (average SUV ranged between 57 to 84 in LOX tumor xenographs) is likely due to tubular reuptake of proteins, where [$^{18}$F]AIF label is trapped after cleavage of the Z variants. To summarize, the results show that Z variant ligands are effective in targeting PD-L1 positive tumors in vivo, exhibiting specific binding and a rapid clearance.

Example 11

In Vivo Imaging in Rhesus Monkey

Materials and Methods

Fasted rhesus monkeys were sedated with Ketamine (10 mg/kg, intramuscular). An intrevenous catheter was inserted into the right and left saphenous veins and the animals were maintained on propofol anesthesia (5 mg/kg for induction and 0.45 mg/kg/min throughout the scanning procedure). Following the initial induction with propofol, the animal was intubated and maintained on ventilated oxygen/air gas mixture at approximately 10 cm$^3$/kg/breath, and 23 respirations per minute. Animals were instrumented with a temperature probe, a pulse oximeter and an end tidal $CO_2$ monitor. Body temperature was maintained using K-module heating pads. General fluid therapy was maintained with Lactated Ringer's solution (10 ml/kg/h i.v.) throughout the scanning procedure. 84-138 MBq of [$^{18}$F]AIF-NOTA-Z15168 and 147-227 MBq of [$^{18}$F]AIF-NOTA-Z18609, respectively, were administered as a 2 min infusion. Whole body dynamic scan was initiated at the start of the tracer injection and acquired for 180 min using a Siemens Biograph 64 TPTV PET/CT scanner. Whole body reconstruction was performed using the PET/CT scanner vendor supplied software. PET image analysis was performed using customized Matlab based software.

Results

Representative maximum intensity projection images of rhesus monkeys administered with[$^{18}$F]AIF-NOTA-Z15168 and [$^{18}$F]AIF-NOTA-Z18609, respectively, are shown in FIGS. 12A-B and graphs of the average tracer uptake (~120-180 min) are shown in FIG. 12C. As in mice, the highest uptake was seen in kidney (SUV 100-112) and bladder, but also lymph node and spleen targeting was observed, which is consistent with PD-L1 expression.

ITEMIZED LIST OF EMBODIMENTS

1. PD-L1 binding polypeptide, comprising a PD-L1 binding motif BM, which motif consists of an amino acid sequence selected from:

i)

(SEQ ID NO: 837)

ERN$X_4$AA$X_7$EIL $X_{11}$LPNL$X_{16}X_{17}X_{18}$Q$X_{20}$ WAFIW$X_{26}$L$X_{28}$D wherein, independently from each other, $X_4$ is selected from A, D, E, F, H, I, K, L, N, Q, R, S, T, V and Y;

$X_7$ is selected from A, E, F, H, N, Q, S, T, V, W and Y;

$X_{11}$ is selected from A, D, E, F, H, K, L, N, Q, R, S, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, N, Q, R, T, V and Y;

$X_{26}$ is selected from K and S; and $X_{28}$ is selected from A, D and E;

and ii) an amino acid sequence which has at least 96% identity to the sequence defined in i).

2. PD-L1 binding polypeptide according to item 1, wherein in sequence i)

$X_4$ is selected from A, D, E, F, H, I, K, L, N, Q, R, S, T, V and Y;

$X_7$ is selected from E, F, H, N, Q, S, T, V, W and Y;

$X_{11}$ is selected from A, D, H, L, Q, R, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, Q, R, T, V and Y;

$X_{26}$ is selected from K and S; and $X_{28}$ is selected from A, D and E.

3. PD-L1 binding polypeptide according to item 1, wherein in sequence i)

$X_4$ is selected from A, D, E, F, H, I, K, L, N, Q, R, S, T, V and Y;

$X_7$ is selected from A, E, F, H, N, Q, S, T, V, W and Y;

$X_{11}$ is selected from A, D, E, F, H, K, L, N, Q, R, S, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, N, Q, R, T, V and Y;

$X_{26}$ is selected from K and S; and $X_{28}$ is selected from A, D and E.

4. PD-L1 binding polypeptide according to item 2 or 3, wherein in sequence i)

$X_4$ is selected from A, D, E, F, H, I, K, L, N, Q, R, S, T and V;

$X_7$ is selected from F, H, Q and Y;

$X_{11}$ is selected from H, Q, W and Y;

$X_{16}$ is selected from N and T;

$X_{17}$ is selected from A, H, K, N, Q and S;

$X_{18}$ is selected from A, E, G, H, K, L, N, Q, R, S, T, V and Y;

$X_{20}$ is selected from H, I, K, Q, R and V;

$X_{26}$ is selected from K and S; and $X_{28}$ is selected from A and D.

5. PD-L1 binding polypeptide according to any one of item 1-4, wherein sequence i) fulfills at least four of the seven conditions I-VII:

I. $X_7$ is selected from F, H, Q and Y;

II. $X_{11}$ is selected from H and Y;

III. $X_{16}$ is T;

IV. $X_{17}$ is selected from N, Q and S;

V. $X_{20}$ is selected from H, I, K and R;

VI. $X_{26}$ is K; and

VII. $X_{28}$ is A or D.

6. PD-L1 binding polypeptide according to item 5, wherein sequence i) fulfills at least five of the seven conditions I-VII.

7. PD-L1 binding polypeptide according to item 6, wherein sequence i) fulfills at least six of the seven conditions I-VII.

8. PD-L1 binding polypeptide according to item 7, wherein sequence i) fulfills all of the seven conditions I-VII.

9. PD-L1 binding polypeptide according to any one of items 1-8, wherein $X_7X_{11}X_{20}$ is selected from FYK and YYK.

10. PD-L1 binding polypeptide according to any one of items 1-9, wherein $X_{11}X_{17}X_{20}$ is selected from YNK and YQK.

11. PD-L1 binding polypeptide according to any one of items 1-10, wherein $X_{11}X_{18}X_{20}$ is YAK.

12. PD-L1 binding polypeptide according to any preceding item, wherein sequence i) corresponds to the sequence from position 8 to position 36 in a sequence selected from the group consisting of SEQ ID NO:1-808.

13. PD-L1 binding polypeptide according to item 12, wherein sequence i) corresponds to the sequence from position 8 to position 36 in a sequence selected from the group consisting of SEQ ID NO:1-93 and 774-796.

14. PD-L1 binding polypeptide according to item 13, wherein sequence i) corresponds to the sequence from position 8 to position 36 in a sequence selected from the group consisting of SEQ ID NO:1-93 and 774-787.

15. PD-L1 binding polypeptide according to item 14, wherein sequence i) corresponds to the sequence from position 8 to position 36 in a sequence selected from the group consisting of SEQ ID NO:1-93, 775, 776, 779-781 and 784-786, such as the group consisting of SEQ ID NO:1-93, 776, 780, 781, 784 and 786, such as the group consisting of SEQ ID NO:1-93, 776, 781 and 784, such as the group consisting of SEQ ID NO:1-93, 776 and 784 or the group consisting of SEQ ID NO:1-93, 776 and 781, for example the group consisting of SEQ ID NO:1-93 and 776 or the group consisting of SEQ ID NO:1-93 and 781 or the group consisting of SEQ ID NO:1-93 and 784.

16. PD-L1 binding polypeptide according to item 15, wherein sequence i) corresponds to the sequence from position 8 to position 36 in a sequence selected from the group consisting of SEQ ID NO:1-93, 774, 775, 780-786, such as the group consisting of SEQ ID NO:1-93, 775, 780, 781, 784 and 786.

17. PD-L1 binding polypeptide according to any one of items 14-16, wherein sequence i) corresponds to the sequence from position 8 to position 36 in a sequence selected from the group consisting of SEQ ID NO:1-93.

18. PD-L1 binding polypeptide according to item 17, wherein sequence i) corresponds to the sequence from position 8 to position 36 in a sequence selected from the group consisting of SEQ ID NO:1-24.

19. PD-L1 binding polypeptide according to item 18, wherein sequence i) corresponds to the sequence from position 8 to position 36 in a sequence selected from the group consisting of SEQ ID NO:1-12, 14 and 17-21.

20. PD-L1 binding polypeptide according to item 19, wherein sequence i) corresponds to the sequence from position 8 to position 36 in a sequence selected from the group consisting of SEQ ID NO:1-12 and 17, such as the group consisting of SEQ ID NO:1-5 and 17, such as the group consisting of SEQ ID NO:1, 2 and 17.

21. PD-L1 binding polypeptide according to item 19, wherein sequence i) corresponds to the sequence from position 8 to position 36 in a sequence selected from the group consisting of SEQ ID NO:1, 4, 5, 6, 9, 14 and 18-21, such as the group consisting of SEQ ID NO:4, 5, 18 and 21, such as the group consisting of SEQ ID NO:4, 5 and 21.

22. PD-L1 binding polypeptide according to item 20 or 21, wherein sequence i) corresponds to the sequence from position 8 to position 36 in SEQ ID NO:1.

23. PD-L1 binding polypeptide according to item 20 or 21, wherein sequence i) corresponds to the sequence from position 8 to position 36 in SEQ ID NO:4.

24. PD-L1 binding polypeptide according to item 20 or 21, wherein sequence i) corresponds to the sequence from position 8 to position 36 in SEQ ID NO:5.

25. PD-L1 binding polypeptide according to item 21, wherein sequence i) corresponds to the sequence from position 8 to position 36 in SEQ ID NO:21.

26. PD-L1 binding polypeptide according to any preceding item, wherein said PD-L1 binding motif forms part of a three-helix bundle protein domain.

27. PD-L1 binding polypeptide according to item 26, wherein said PD-L1 binding motif essentially forms part of two helices with an interconnecting loop, within said three-helix bundle protein domain.

28. PD-L1 binding polypeptide according to item 27, wherein said three-helix bundle protein domain is selected from bacterial receptor domains.

29. PD-L1 binding polypeptide according to item 28, wherein said three-helix bundle protein domain is selected from domains of protein A from *Staphylococcus aureus* or derivatives thereof.

30. PD-L1 binding polypeptide according to any preceding item, which comprises a binding module BMod, the amino acid sequence of which is selected from:

iii)

(SEQ ID NO: 838)

K-[*BM*]-DPSQS$X_aX_b$LL$X_c$ EAKKL$X_dX_eX_f$Q;

wherein

[BM] is a PD-L1 binding motif as defined in any one of items 1-25;

$X_a$ is selected from A and S;

$X_b$ is selected from N and E;

$X_c$ is selected from A, S and C;

$X_d$ is selected from E, N and S;

$X_e$ is selected from D, E and S; and $X_f$ is selected from A and S; and iv) an amino acid sequence which has at least 93% identity to a sequence defined in iii).

31. PD-L1 binding polypeptide according to any preceding item, wherein sequence iii) corresponds to the sequence from position 7 to position 55 in a sequence selected from the group consisting of SEQ ID NO:1-808.

32. PD-L1 binding polypeptide according to item 31, wherein sequence iii) corresponds to the sequence from position 7 to position 55 in a sequence selected from the group consisting of SEQ ID NO:1-93 and 774-796.

33. PD-L1 binding polypeptide according to item 32, wherein sequence iii) corresponds to the sequence from position 7 to position 55 in a sequence selected from the group consisting of SEQ ID NO:1-93 and 774-787.

34. PD-L1 binding polypeptide according to item 33, wherein sequence iii) corresponds to the sequence from position 7 to position 55 in a sequence selected from the group consisting of SEQ ID NO:1-93, 775, 776, 779-781 and 784-786, such as the group consisting of SEQ ID NO:1-93, 776, 780, 781, 784 and 786, such as the group consisting of SEQ ID NO:1-93, 776, 781 and 784, such as the group consisting of SEQ ID NO:1-93, 776 and 784 or the group consisting of SEQ ID NO:1-93, 776 and 781, for example the group consisting of SEQ ID NO:1-93 and 776 or the group consisting of SEQ ID NO:1-93 and 781 or the group consisting of SEQ ID NO:1-93 and 784.

35. PD-L1 binding polypeptide according to item 33, wherein sequence iii) corresponds to the sequence from position 7 to position 55 in a sequence selected from the group consisting of SEQ ID NO:1-93, 774, 775 and 780-786, such as the group consisting of SEQ ID NO:1-93, 775, 780, 781, 784 and 786.

36. PD-L1 binding polypeptide according to any one of items 33-35, wherein sequence iii) corresponds to the sequence from position 7 to position 55 in a sequence selected from the group consisting of SEQ ID NO:1-93.

37. PD-L1 binding polypeptide according to item 36, wherein sequence iii) corresponds to the sequence from position 7 to position 55 in a sequence selected from the group consisting of SEQ ID NO:1-24.

38. PD-L1 binding polypeptide according to item 37, wherein sequence iii) corresponds to the sequence from position 7 to position 55 in a sequence selected from the group consisting of SEQ ID NO:1-12, 14 and 17-21.

39. PD-L1 binding polypeptide according to item 38, wherein sequence iii) corresponds to the sequence from position 7 to position 55 in a sequence selected from the group consisting of SEQ ID NO:1-12 and 17, such as the group consisting of SEQ ID NO:1-5 and 17, such as the group consisting of SEQ ID NO:1, 2 and 17.

40. PD-L1 binding polypeptide according to item 38, wherein sequence iii) corresponds to the sequence from position 7 to position 55 in a sequence selected from the group consisting of SEQ ID NO:1, 4, 5, 6, 9, 14 and 18-21, such as the group consisting of SEQ ID NO:4, 5, 18 and 21, such as the group consisting of SEQ ID NO:4, 5 and 21.

41. PD-L1 binding polypeptide according to item 40 or 41, wherein sequence iii) corresponds to the sequence from position 7 to position 55 in SEQ ID NO:1.

42. PD-L1 binding polypeptide according to item 40 or 41, wherein sequence iii) corresponds to the sequence from position 7 to position 55 in SEQ ID NO:4.

43. PD-L1 binding polypeptide according to item 40 or 41, wherein sequence iii) corresponds to the sequence from position 7 to position 55 in SEQ ID NO:5.

44. PD-L1 binding polypeptide according to item 41, wherein sequence iii) corresponds to the sequence from position 7 to position 55 in SEQ ID NO:21.

45. PD-L1 binding polypeptide according to any preceding item, which comprises an amino acid sequence selected from:

v)
YA-[*BMod*]-AP; (SEQ ID NO: 839)

wherein [BMod] is a PD-L1 binding module as defined in any one of items 30-44; and vi) an amino acid sequence which has at least 90% identity to a sequence defined in v).

46. PD-L1 binding polypeptide according to any one of items 1-44, which comprises an amino acid sequence selected from:

vii)
FN-[*BMod*]-AP; (SEQ ID NO: 840)

wherein [BMod] is a PD-L1 binding module as defined in any one of items 30-44; and viii) an amino acid sequence which has at least 90% identity to a sequence defined in vii).

47. PD-L1 binding polypeptide according to any preceding item, which comprises an amino acid sequence selected from:

ADNNFNK-[*BM*]-DPSQSANLLSEAKKLNESQAPK; (SEQ ID NO: 845)

ADNKFNK-[*BM*]-DPSQSANLLAEAKKLNDAQAPK; (SEQ ID NO: 846)

ADNKFNK-[*BM*]-DPSVSKEILAEAKKLNDAQAPK; (SEQ ID NO: 847)

ADAQQNNFNK-[*BM*]-DPSQSTNVLGEAKKLNESQAPK; (SEQ ID NO: 848)

AQHDE-[*BM*]-DPSQSANVLGEAQKLNDSQAPK; (SEQ ID NO: 849)

VDNKFNK-[*BM*]-DPSQSANLLAEAKKLNDAQAPK; (SEQ ID NO: 850)

AEAKYAK-[*BM*]-DPSESSELLSEAKKLNKSQAPK; (SEQ ID NO: 851)

VDAKYAK-[*BM*]-DPSQSSELLAEAKKLNDAQAPK; (SEQ ID NO: 852)

VDAKYAK-[*BM*]-DPSQSSELLAEAKKLNDSQAPK; (SEQ ID NO: 853)

AEAKYAK-[*BM*]-DPSQSSELLSEAKKLNDSQAPK; (SEQ ID NO: 854)

AEAKYAK-[*BM*]-DPSQSSELLSEAKKLNDSQAP; (SEQ ID NO: 855)

AEAKFAK-[*BM*]-DPSQSSELLSEAKKLNDSQAPK; (SEQ ID NO: 856)

AEAKFAK-[*BM*]-DPSQSSELLSEAKKLNDSQAP; (SEQ ID NO: 857)

AEAKYAK-[*BM*]-DPSQSSELLAEAKKLNDAQAPK; (SEQ ID NO: 858)

AEAKYAK-[*BM*]-DPSQSSELLSEAKKLSESQAPK; (SEQ ID NO: 859)

-continued (SEQ ID NO: 860)
AEAKYAK-[*BM*]-DPSQSSELLSEAKKLSESQAP;

(SEQ ID NO: 861)
AEAKFAK-[*BM*]-DPSQSSELLSEAKKLSESQAPK;

(SEQ ID NO: 862)
AEAKFAK-[*BM*]-DPSQSSELLSEAKKLSESQAP;

(SEQ ID NO: 863)
AEAKYAK-[*BM*]-DPSQSSELLAEAKKLSEAQAPK;

(SEQ ID NO: 864)
AEAKYAK-[*BM*]-QPEQSSELLSEAKKLSESQAPK;

(SEQ ID NO: 865)
AEAKYAK-[*BM*]-DPSQSSELLSEAKKLESSQAPK;

(SEQ ID NO: 866)
AEAKYAK-[*BM*]-DPSQSSELLSEAKKLESSQAP;

(SEQ ID NO: 867)
AEAKYAK-[*BM*]-DPSQSSELLAEAKKLESAQAPK;

(SEQ ID NO: 868)
AEAKYAK-[*BM*]-QPEQSSELLSEAKKLESSQAPK;

(SEQ ID NO: 869)
AEAKYAK-[*BM*]-DPSQSSELLSEAKKLSDSQAPK;

(SEQ ID NO: 870)
AEAKYAK-[*BM*]-DPSQSSELLSEAKKLSDSQAP;

(SEQ ID NO: 871)
AEAKYAK-[*BM*]-DPSQSSELLAEAKKLSDSQAPK;

(SEQ ID NO: 872)
AEAKYAK-[*BM*]-DPSQSSELLAEAKKLSDAQAPK;

(SEQ ID NO: 873)
AEAKYAK-[*BM*]-QPEQSSELLSEAKKLSDSQAPK;

(SEQ ID NO: 874)
VDAKYAK-[*BM*]-DPSQSSELLSEAKKLNDSQAPK;

(SEQ ID NO: 875)
VDAKYAK-[*BM*]-DPSQSSELLAEAKKLNDAQAPK;

(SEQ ID NO: 876)
VDAKYAK-[*BM*]-DPSQSSELLSEAKKLSESQAPK;

(SEQ ID NO: 877)
VDAKYAK-[*BM*]-DPSQSSELLAEAKKLSEAQAPK;

(SEQ ID NO: 878)
VDAKYAK-[*BM*]-QPEQSSELLSEAKKLSESQAPK;

(SEQ ID NO: 879)
VDAKYAK-[*BM*]-DPSQSSELLSEAKKLESSQAPK;

(SEQ ID NO: 880)
VDAKYAK-[*BM*]-DPSQSSELLAEAKKLESAQAPK;

(SEQ ID NO: 881)
VDAKYAK-[*BM*]-QPEQSSELLSEAKKLESSQAPK;

(SEQ ID NO: 882)
VDAKYAK-[*BM*]-DPSQSSELLSEAKKLSDSQAPK;

(SEQ ID NO: 883)
VDAKYAK-[*BM*]-DPSQSSELLAEAKKLSDSQAPK;

(SEQ ID NO: 884)
VDAKYAK-[*BM*]-DPSQSSELLAEAKKLSDAQAPK;

(SEQ ID NO: 885)
VDAKYAK-[*BM*]-QPEQSSELLSEAKKLSDSQAPK;

(SEQ ID NO: 886)
VDAKYAK-[*BM*]-DPSQSSELLAEAKKLNKAQAPK;

-continued (SEQ ID NO: 887)
AEAKYAK-[*BM*]-DPSQSSELLAEAKKLNKAQAPK;
and (SEQ ID NO: 888)
ADAKYAK-[*BM*]-DPSQSSELLSEAKKLNDSQAPK;

wherein [BM] is a PD-L1 binding motif as defined in any one of items 1-25.

48. PD-L1 binding polypeptide according to any one of items 1-47, which comprises an amino acid sequence selected from:

xvii)
(SEQ ID NO: 874)
VDAKYAK-[*BM*]-DPSQSSELLSEAKKLNDSQAPK;

wherein [BM] is a PD-L1 binding motif as defined in any one of items 1-25; and xviii) an amino acid sequence which has at least 89% identity to the sequence defined in xvii).

49. PD-L1 binding polypeptide according to any one of items 1-47, which comprises an amino acid sequence selected from:

xix)
(SEQ ID NO: 861)
AEAKFAK-[*BM*]-DPSQSSELLSEAKKLSESQAPK;

wherein [BM] is a PD-L1 binding motif as defined in any one of items 1-25; and xx) an amino acid sequence which has at least 89% identity to the sequence defined in xix).

50. PD-L1 binding polypeptide according to any one of items 1-47, which comprises an amino acid sequence selected from:

xxi)
(SEQ ID NO: 854)
AEAKYAK-[*BM*]-DPSQSSELLSEAKKLNDSQAPK;

wherein [BM] is a PD-L1 binding motif as defined in any one of items 1-25; and xxii) an amino acid sequence which has at least 89% identity to the sequence defined in xxi).

51. PD-L1 binding polypeptide according to any one of items 1-47, which comprises an amino acid sequence selected from:

xxiii)
(SEQ ID NO: 856)
AEAKFAK-[*BM*]-DPSQSSELLSEAKKLNDSQAPK;

wherein [BM] is a PD-L1 binding motif as defined in any one of items 1-25; and xxiv) an amino acid sequence which has at least 89% identity to the sequence defined in xxiii).

52. PD-L1 binding polypeptide according to any preceding item, wherein sequence xvii) or xxi) corresponds to the sequence from position 1 to position 58 in a sequence selected from the group consisting of SEQ ID NO:1-814.

53. PD-L1 binding polypeptide according to item 52, wherein sequence xvii) or xxi) corresponds to the sequence from position 1 to position 58 in a sequence selected from the group consisting of SEQ ID NO:1-93, 774-796 and 809-814.

54. PD-L1 binding polypeptide according to item 53, wherein sequence xvii) or xxi) corresponds to the sequence from position 1 to position 58 in a sequence selected from the group consisting of SEQ ID NO:1-93, 774-787 and 809-814.

55. PD-L1 binding polypeptide according to item 54, wherein sequence xvii) or xxi) corresponds to the sequence from position 1 to position 58 in a sequence selected from the group consisting of SEQ ID NO:1-93, 775, 776, 779-781, 784-786 and 809-814, such as the group consisting of SEQ ID NO:1-93, 776, 780, 781, 784, 786 and 809-814, such as the group consisting of SEQ ID NO:1-93, 776, 781, 784 and 809-814, such as the group consisting of SEQ ID NO:1-93, 776, 784, 809 and 811-814 or the group consisting of SEQ ID NO:1-93, 776, 781, 809 and 811-814, for example the group consisting of SEQ ID NO:1-93, 776, 809 and 811-814 or the group consisting of SEQ ID NO:1-93, 781, 809 and 811-814 or the group consisting of SEQ ID NO:1-93, 784 and 811-814.

56. PD-L1 binding polypeptide according to item 55, wherein sequence xvii) or xxi) corresponds to the sequence from position 1 to position 58 in a sequence selected from the group consisting of SEQ ID NO:1-93, 774, 775, 780-786 and 810-814, such as the group consisting of SEQ ID NO:1-93, SEQ ID NO:775, 780, 781, 784, 786 and 810-814.

57. PD-L1 binding polypeptide according to any one of items 54-56, wherein sequence xvii) or xxi) corresponds to the sequence from position 1 to position 58 in a sequence selected from the group consisting of SEQ ID NO:1-93 and 811-813.

58. PD-L1 binding polypeptide according to item 57, wherein sequence xvii) or xxi) corresponds to the sequence from position 1 to position 58 in a sequence selected from the group consisting of SEQ ID NO:1-24 and 811-813.

59. PD-L1 binding polypeptide according to item 58, wherein sequence xvii) or xxi) corresponds to the sequence from position 1 to position 58 in a sequence selected from the group consisting of SEQ ID NO:1-12, 14, 17-21 and SEQ ID NO:811-812.

60. PD-L1 binding polypeptide according to item 59, wherein sequence xvii) or xxi) corresponds to the sequence from position 1 to position 58 in a sequence selected from the group consisting of SEQ ID NO:1-12, 17, 811 and 812, such as the group consisting of SEQ ID NO:1-5, 17, 811 and 812, such as the group consisting of SEQ ID NO:1, 2, 17, 811 and 812.

61. PD-L1 binding polypeptide according to item 58, wherein sequence xvii) or xxi) corresponds to the sequence from position 1 to position 58 in a sequence selected from the group consisting of SEQ ID NO:1, 4, 5, 6, 9, 14, 18, 19, 20, 21 and 811, such as the group consisting of SEQ ID NO:4, 5, 18 and 21, such as the group consisting of SEQ ID NO:4, 5 and 21.

62. PD-L1 binding polypeptide according to item 60 or 61, wherein sequence xvii) or xxi) corresponds to the sequence from position 1 to position 58 in SEQ ID NO:1 or 811.

63. PD-L1 binding polypeptide according to item 60, wherein sequence xvii) or xxi) corresponds to the sequence from position 1 to position 58 in SEQ ID NO:2 or 812.

64. PD-L1 binding polypeptide according to item 60 or 61, wherein sequence xvii) corresponds to the sequence from position 1 to position 58 in SEQ ID NO:4.

65. PD-L1 binding polypeptide according to item 60 or 61, wherein sequence xvii) corresponds to the sequence from position 1 to position 58 in SEQ ID NO:5.

66. PD-L1 binding polypeptide according to item 61, wherein sequence xvii) corresponds to the sequence from position 1 to position 58 in SEQ ID NO:21.

67. PD-L1 binding polypeptide according to any preceding item, which is capable of blocking PD-L1 dependent signaling.

68. PD-L1 binding polypeptide according to item 67, wherein the half maximal inhibitory concentration (IC50) of the blocking is at most $5\times10^{-8}$ M, such as at most $1\times10^{-8}$ M, such as at most $5\times10^{-9}$ M, such as at most $3.5\times10^{-9}$ M, such as at most $1\times10^{-9}$ M, such as at most $5\times10^{-1o}$ M, such as at most $1\times10^{-10}$ M.

69. PD-L1 binding polypeptide according to any preceding item, which is capable of blocking the interaction of PD-L1 with PD-1.

70. PD-L1 binding polypeptide according to any preceding item, which is capable of binding to PD-L1 such that the $K_D$ value of the interaction is at most $2\times10^{-8}$ M, such as at most $1\times10^{-8}$ M, such as at most $1\times10^{-9}$ M, such as at most $5\times10^{-10}$ M, such as at most $3\times10^{-10}$ M.

71. PD-L1 binding polypeptide according to any preceding item, which is capable of binding to PD-L1 such that the $k_d$ value of the interaction is at most $1\times10^{-3}$ $s^{-1}$. such as at most $6\times10^{-4}$ $s^{-1}$.

72. PD-L1 binding polypeptide according to any preceding item, which is capable of binding to PD-L1 such that the EC50 value of the interaction is at most $1\times10^{-9}$ M, such as at most $1\times10^{-1o}$ M, such as at most $7\times10^{-11}$ M.

73. PD-L1 binding polypeptide according to any preceding item, wherein said PD-L1 is human PD-L1.

74. PD-L1 binding polypeptide according to any preceding item which comprises additional amino acids at the C-terminal and/or N-terminal end.

75. PD-L1 binding polypeptide according to item 74, wherein said additional amino acid(s) improve(s) production, purification, stabilization in vivo or in vitro, coupling or detection of the polypeptide.

76. PD-L1 binding polypeptide according to any preceding item in multimeric form, comprising at least two PD-L1 binding polypeptide monomer units, whose amino acid sequences may be the same or different.

77. PD-L1 binding polypeptide according to item 76, wherein said PD-L1 binding polypeptide monomer units are covalently coupled together.

78. PD-L1 binding polypeptide according to item 77, wherein the PD-L1 binding polypeptide monomer units are expressed as a fusion protein.

79. PD-L1 binding polypeptide according to any one of items 76-78, in dimeric form.

80. Fusion protein or conjugate comprising a first moiety consisting of a PD-L1 binding polypeptide according to any preceding item, and a second moiety consisting of a polypeptide having a desired biological activity.

81. Fusion protein or conjugate according to item 80, wherein said desired biological activity is a therapeutic activity.

82. Fusion protein or conjugate according to item 80, wherein said desired biological activity is a binding activity.

83. Fusion protein or conjugate according to item 80, wherein said desired biological activity is an enzymatic activity.

84. Fusion protein or conjugate according to item 82, wherein said binding activity is albumin binding activity which increases in vivo half-life of the fusion protein or conjugate.

85. Fusion protein or conjugate according to item 84, wherein said second moiety comprises the albumin binding domain of streptococcal protein G or a derivative thereof.

86. Fusion protein or conjugate according to item 82, wherein said binding activity acts to block a biological activity.

87. Fusion protein or conjugate according to item 81, wherein the second moiety is a therapeutically active polypeptide.

88. Fusion protein or conjugate according to item 87, wherein the second moiety is an immune response modifying agent.

89. Fusion protein or conjugate according to item 87, wherein the second moiety is an anti-cancer agent.

90. Fusion protein or conjugate according to any one of items 80-83 and 86-89, wherein the second moiety is selected from the group consisting of human endogenous enzymes, hormones, growth factors, chemokines, cytokines and lymphokines.

91. Fusion protein according to any one of items 80-91, wherein the second moiety further comprises a linker.

92. Complex, comprising at least one PD-L1 binding polypeptide according to any one of the preceding items and at least one antibody or an antigen binding fragment thereof.

93. Complex according to item 92, wherein said at least one antibody or antigen binding fragment thereof is selected from the group consisting of full-length antibodies, Fab fragments, Fab' fragments, $F(ab')_2$ fragments, Fc fragments, Fv fragments, single chain Fv (scFv) fragments, $(scFv)_2$ and domain antibodies.

94. Complex according to item 93, wherein said at least one antibody or antigen binding fragment thereof is selected from the group consisting of full-length antibodies, Fab fragments and scFv fragments.

95. Complex according to item 94, wherein said at least one antibody or antigen binding fragment thereof is a full-length antibody.

96. Complex according to any one of items 92-95, wherein said antibody or antigen binding fragment thereof is a monoclonal antibody or an antigen binding fragment thereof.

97. Complex according to any one of items 92-96, wherein said antibody or antigen binding fragment thereof is selected from the group consisting of human antibodies, humanized antibodies and chimeric antibodies, and antigen binding fragments thereof.

98. Complex according to item 97, wherein said antibody or antigen binding fragment thereof is a human or humanized antibody, or an antigen binding fragment thereof.

99. Complex according to any one of items 92-98, wherein said PD-L1 binding polypeptide is attached at either the C-terminus or the N-terminus of the heavy chain or the light chain of said antibody or antigen binding fragment thereof.

100. Complex according to any one of items 92-99, further comprising a linker.

101. Complex according to any one of items 92-100, wherein said antibody or antigen binding fragment thereof has affinity for an antigen, for example an antigen associated with an infectious disease, or an antigen associated with cancer.

102. Fusion protein or conjugate according to any one of items 79-90 or complex according to any one of items 92-101, wherein said second moiety or said antibody or antigen binding fragment thereof is an inhibitor selected from the group consisting of inhibitors of: PD-1, CTLA-4, T-cell immunoglobulin and mucin containing protein-3 (TIM-3), galectin-9 (GAL-9), lymphocyte activation gene-3 (LAG-3), PD-L2, B7 homolog 3 (B7-H3), B7 homolog 4 (B7-H4), V-domain Ig suppressor of T-cell activation (VISTA), carcinoembryonic antigen-related cell adhesion molecule 1 (CEACAM1), B and T lymphocyte attenuator (BTLA), colony stimulating factor 1 receptor (CSF1R), herpes virus entry mediator (HVEM), killer immunoglobulin receptor (KIR), adenosine, adenosine A2a receptor (A2aR), CD200-CD200R and T cell Ig and ITIM domain.

103. Fusion protein, conjugate or complex according to item 102, wherein said second moiety, antibody or antigen binding fragment thereof is an inhibitor of PD-1, such as an inhibitor selected from the group consisting of nivolumab, pidilizumab, BMS 936559, MPDL3280A and pembrolizumab, such as pembrolizumab.

104. Fusion protein, conjugate or complex according to item 102, wherein said second moiety, antibody or antigen binding fragment thereof is an inhibitor of CTLA-4, such as an inhibitor selected from the group consisting of belatacept, abatacept and ipilimumab, such as ipilimumab.

105. Fusion protein or conjugate according to any one of items 80-91 or complex according to any one of items 92-101, wherein said second moiety or antibody or antigen binding fragment thereof is an agonist selected from the group consisting of agonists of CD134, CD40, 4-11BB and glucocorticoid-induced TNFR-related protein (GITR).

106. PD-L1 binding polypeptide, fusion protein, conjugate or complex according to any one of items 1-105, further comprising a label.

107. PD-L1 binding polypeptide, fusion protein, conjugate or complex according to item 106, wherein said label is selected from the group consisting of fluorescent dyes and metals, chromophoric dyes, chemiluminescent compounds and bioluminescent proteins, enzymes, radionuclides, radioactive particles and pretargeting recognition tags.

108. PD-L1 binding polypeptide, fusion protein, conjugate or complex according to item 107, comprising a chelating environment provided by a polyaminopolycarboxylate chelator conjugated to the PD-L1 binding polypeptide via a thiol group of a cysteine residue or an amine group of a lysine residue.

109. PD-L1 binding polypeptide, fusion protein, conjugate or complex according to item 106, which comprises a pretargeting recognition tag forming part of a complementary pair of pretargeting moieties, for example selected from stept(avidin)/biotin, oligonucleotide/complementary oligonucleotide such as DNA/complementary DNA, RNA/complementary RNA, phosphorothioate nucleic acid/complementary phosphorothioate nucleic acid and peptide nucleic acid/complementary peptide nucleic acid and morpholinos/complementary morpholinos.

110. PD-L1 binding polypeptide, fusion protein, conjugate or complex according to item 109, wherein said pretargeting recognition tag is a peptide nucleic acid tag.

111. PD-L1 binding polypeptide, fusion protein, conjugate or complex according to any one of item 110, wherein said pretargeting recognition tag is a 10-20-mer peptide nucleic acid sequence, such as a 15-mer peptide nucleic acid sequence.

112. A polynucleotide encoding a polypeptide according to any one of items 1-105.

113. Expression vector comprising a polynucleotide according to item 112.

114. Host cell comprising an expression vector according to item 113.

115. Method of producing a polypeptide according to any one of items 1-105, comprising culturing a host cell according to item 114 under conditions permissive of expression of said polypeptide from said expression vector, and isolating said polypeptide.

116. Composition comprising a PD-L1 binding polypeptide, fusion protein, conjugate or complex according to any one of items 1-111 and at least one pharmaceutically acceptable excipient or carrier.

117. Composition according to item 116, further comprising at least one additional active agent, such as an agent selected from an immune response modifying agent and an anti-cancer agent.

118. PD-L1 binding polypeptide, fusion protein, conjugate or complex according to any one of items 1-111 or a composition according to any one of items 116-117 for oral, topical, intravenous, intraperitoneal, subcutaneous, pulmonary, transdermal, intramuscular, intranasal, buccal, sublingual or suppository administration, such as for topical administration.

119. PD-L1 binding polypeptide, fusion protein, conjugate or complex according to any one of items 1-111 or a composition according to any one of items 116-117 for use as a medicament, a diagnostic agent and/or a prognostic agent.

120. PD-L1 binding polypeptide, fusion protein, conjugate, complex or composition for use according to item 119 as a medicament.

121. PD-L1 binding polypeptide, fusion protein, conjugate, complex or composition for use according to item 119 as a diagnostic agent and/or a prognostic agent.

122. PD-L1 binding polypeptide, fusion protein, conjugate, complex or composition for use as a medicament according to item 120, wherein said polypeptide, fusion protein, conjugate or composition modulates PD-L1 function in vivo.

123. PD-L1 binding polypeptide, fusion protein, conjugate, complex or composition for use according to any one of items 119-121 in the treatment, prognosis or diagnosis of a PD-L1 related disorder.

124. PD-L1 binding polypeptide, fusion protein, conjugate, complex or composition for use according to item 122, wherein said PD-L1 related disorder is selected from the group consisting of infectious diseases and cancers.

125. PD-L1 binding polypeptide, fusion protein, conjugate, complex or composition for use according to item 124, wherein said PD-L1 related disorder is an infectious disease, such as a chronic viral infection, for example selected from the group consisting of human immunodeficiency virus (HIV), hepatitis B virus (HBV) and hepatitis C virus (HCV).

126. PD-L1 binding polypeptide, fusion protein, conjugate, complex or composition for use according to item 124, wherein said PD-L1 related disorder is cancer, such as a cancer selected from the group consisting of:

cancers manifesting solid tumors, for example selected from the group consisting of skin cancer, such as melanoma and nonmelanoma skin cancer (NMSC); lung cancers, such as small cell lung cancer, non-small cell lung cancer (NSCLC); head and neck cancer; renal cell carcinoma (RCC); bladder cancer; breast cancer; colorectal cancer; gastric cancer; ovarian cancer; pancreatic cancer; prostate cancer; glioma; glioblastoma; liver carcinoma; gallbladder cancer; thyroid cancer; bone cancer; cervical cancer; uterine cancer; vulval cancer; endometrial cancer; testicular cancer; kidney cancer; esophageal carcinoma; brain/CNS cancers; neuronal cancers: mesothelioma; sarcomas; small bowel adenocarcinoma; and pediatric malignancies; and cancers manifesting non-solid tumors, for example leukaemia, acute myeloid leukaemia, acute lymphoblastic leukaemia and multiple myeloma.

127. PD-L1 binding polypeptide, fusion protein, conjugate, complex or composition for use according to item 126, wherein said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as selected from the group consisting of melanoma, NSCLC, head and neck cancer, RCC and bladder cancer.

128. Method of treatment of a PD-L1 related disorder, comprising administering to a subject in need thereof an effective amount of a PD-L1 binding polypeptide, fusion protein, conjugate or complex according to any one of items 1-111 or a composition according to any one of items 116-117.

129. Method according to item 128, wherein said PD-L1 related disorder is selected from the group consisting of infectious disease and cancer.

130. Method according to item 129, wherein said PD-L1 related disorder is an infectious disease, such as a chronic viral infection, for example selected from the group consisting of human immunodeficiency virus (HIV), hepatitis B virus (HBV) and hepatitis C virus (HCV).

131. Method according to item 129, wherein said PD-L1 related disorder is cancer, such as a cancer selected from the group consisting of:

cancers manifesting solid tumors, for example selected from the group consisting of skin cancer, such as melanoma and nonmelanoma skin cancer (NMSC); lung cancers, such as small cell lung cancer, non-small cell lung cancer (NSCLC); head and neck cancer; renal cell carcinoma (RCC); bladder cancer; breast cancer; colorectal cancer; gastric cancer; ovarian cancer; pancreatic cancer; prostate cancer; glioma; glioblastoma; liver carcinoma; gallbladder cancer; thyroid cancer; bone cancer; cervical cancer; uterine cancer; vulval cancer; endometrial cancer; testicular cancer; kidney cancer; esophageal carcinoma; brain/CNS cancers; neuronal cancers: mesothelioma; sarcomas; small bowel adenocarcinoma; and pediatric malignancies; and cancers manifesting non-solid tumors, for example leukaemia, acute myeloid leukaemia, acute lymphoblastic leukaemia and multiple myeloma.

132. Method according to item 131, in which said cancer is selected from the group consisting of melanoma, NSCLC, head and neck cancer, RCC, bladder cancer, breast cancer, colorectal cancer, gastric cancer, ovarian cancer, pancreatic cancer and prostate cancer, such as selected from the group consisting of melanoma, NSCLC, head and neck cancer, RCC and bladder cancer.

133. Method according to any one of items 131-132, comprising the steps of:

contacting the subject with a PD-L1 binding polypeptide, fusion protein, conjugate or complex according to any one of items 109-111 comprising a pretargeting recognition tag, or with a composition comprising such a PD-L1 binding polypeptide, fusion protein, conjugate or complex, and contacting the subject with a complementary pretargeting moiety, comprising a radionuclide.

134. Method of detecting PD-L1, comprising providing a sample suspected to contain PD-L1, contacting said sample with a PD-L1 binding polypeptide, fusion protein, conjugate or complex according to any one of items 1-111 or a composition according to any one of items 116-117, and detecting the binding of the PD-L1 binding polypeptide, fusion protein, conjugate, complex or composition to indicate the presence of PD-L1 in the sample.

135. Method for determining the presence PD-L1 in a subject, comprising the steps of:

a) contacting the subject, or a sample isolated from the subject, with a PD-L1 binding polypeptide, fusion protein, conjugate or complex according to any one of items 1-111 or a composition according to any one of items 116-117, and b) obtaining a value corresponding to the amount of the PD-L1 binding polypeptide, fusion protein, conjugate or composition that has bound in said subject or to said sample.

136. Method according to item 135, in which said PD-L1 binding polypeptide, fusion protein, conjugate or complex is according to any one of items 109-111, or said composition comprises such a PD-L1 binding polypeptide, fusion protein, conjugate or complex, and step a) further comprises contacting the subject with a complementary pretargeting moiety labeled with a detectable label, such as a radionuclide label.

137. Method according to item 135 or 136, further comprising a step of comparing said value to a reference.

138. Method according to any one of items 134-137, wherein said subject is a mammalian subject, such as a human subject.

139. Method according to any one of items 134-138, wherein the method is performed in vivo.

140. Method according to item 139, which is a method for medical imaging in which step a) comprises the systemic administration of said PD-L1 binding polypeptide, fusion protein, conjugate, complex or composition to a mammalian subject;

said PD-L1 binding polypeptide, fusion protein, conjugate, complex, composition or pretargeting moiety comprises a radionuclide label suitable for medical imaging; and step b) comprises obtaining one or more images of at least a part of the subject's body using a medical imaging instrument, said image(s) indicating the presence of the radionuclide inside the body.

The invention claimed is:

1. A PD-L1 binding polypeptide, comprising a PD-L1 binding motif BM, which motif consists of the amino acid sequence selected from:

i) (SEQ ID NO: 837)
$ERNX_4AAX_7EIL\ X_{11}LPNLX_{16}X_{17}X_{18}QX_{20}WAFIWX_{26}LX_{28}D$ wherein, independently from each other, $X_4$ is selected from A, D, E, F, H, I, K, L, N, Q, R, S, T, V and Y;

$X_7$ is selected from A, E, F, H, N, Q, S, T, V, W and Y;

$X_{11}$ is selected from A, D, E, F, H, K, L, N, Q, R, S, T, V, W and Y;

$X_{16}$ is selected from N and T;

$X_{17}$ is selected from A, H, K, N, Q, R and S;

$X_{18}$ is selected from A, D, E, G, H, K, L, N, Q, R, S, T, V and Y;

$X_{20}$ is selected from H, I, K, L, N, Q, R, T, V and Y;

$X_{26}$ is selected from K and S; and $X_{28}$ is selected from A, D and E; and ii) the amino acid sequence which has at least 96% identity to the sequence defined in i).

2. The PD-L1 binding polypeptide according to claim 1, wherein sequence i) corresponds to the sequence from position 8 to position 36 in a sequence selected from the group consisting of SEQ ID NO:1-808.

3. The PD-L1 binding polypeptide according to claim 1, wherein said PD-L1 binding motif forms part of a three-helix bundle protein domain.

4. The PD-L1 binding polypeptide according to claim 1, which comprises a binding module BMod, the amino acid sequence of which is selected from:

iii) (SEQ ID NO: 838)
$K\text{-}[BM]\text{-}DPSQSX_aX_bLLX_c\ EAKKLX_dX_eX_fQ$;

wherein

[BM] is a PD-L1 binding motif as defined in claim 1;

$X_a$ is selected from A and S;

$X_b$ is selected from N and E;

$X_c$ is selected from A, S and C;

$X_d$ is selected from E, N and S;

$X_e$ is selected from D, E and S; and $X_f$ is selected from A and S;

iv) the amino acid sequence which has at least 93% identity to a sequence defined in iii).

5. The PD-L1 binding polypeptide according to claim 1, which comprises the amino acid sequence selected from:

xvii) (SEQ ID NO: 874)
VDAKYAK-[*BM*]-DPSQSSELLSEAKKLNDSQAPK;

wherein [BM] is a PD-L1 binding motif as defined in claim 1; and xviii) the amino acid sequence which has at least 89% identity to the sequence defined in xvii).

6. The PD-L1 binding polypeptide according to claim 1, which comprises the amino acid sequence selected from:

xxi) (SEQ ID NO: 854)
AEAKYAK-[*BM*]-DPSQSSELLSEAKKLNDSQAPK;

wherein [BM] is a PD-L1 binding motif as defined in claim 1; and xxii) the amino acid sequence which has at least 89% identity to the sequence defined in xxi).

7. The PD-L1 binding polypeptide according to claim 5 or 6, wherein sequence xvii) or xxi) corresponds to the sequence from position 1 to position 58 in a sequence selected from the group consisting of SEQ ID NO:1-814.

8. The PD-L1 binding polypeptide according to claim 7, wherein sequence xvii) or xxi) corresponds to the sequence from position 1 to position 58 in a sequence selected from the group consisting of SEQ ID NO:1-93 and 811-813.

9. The PD-L1 binding polypeptide according to claim 7, wherein sequence xvii) or xxi) corresponds to the sequence from position 1 to position 58 in a sequence selected from the group consisting of SEQ ID NO:1, 2, 4, 5, 21, 811 and 812.

10. The PD-L1 binding polypeptide according to claim 7, wherein sequence xvii) or xxi) corresponds to the sequence from position 1 to position 58 in a sequence selected from the group consisting of SEQ ID NO:1 and 2 or SEQ ID NO:811 and 812.

11. The PD-L1 binding polypeptide according to claim 1, which is capable of blocking PD-L1 dependent signaling.

12. The PD-L1 binding polypeptide according to claim 11, wherein the half maximal inhibitory concentration (IC50) of the blocking is at most $5\times10^{-8}$ M.

13. The PD-L1 binding polypeptide according to claim 11, wherein the half maximal inhibitory concentration (IC50) of the blocking is at most $1\times10^{-8}$ M.

14. The PD-L1 binding polypeptide according to claim 11, wherein the half maximal inhibitory concentration (IC50) of the blocking is at most $5\times10^{-9}$ M.

15. The PD-L1 binding polypeptide according to claim 11, wherein the half maximal inhibitory concentration (IC50) of the blocking is at most $3.5\times10^{-9}$ M.

16. The PD-L1 binding polypeptide according to claim 11, wherein the half maximal inhibitory concentration (IC50) of the blocking is at most $1\times10^{-9}$ M.

17. The PD-L1 binding polypeptide according to claim 11, wherein the half maximal inhibitory concentration (IC50) of the blocking is at most $5\times10^{-10}$ M.

18. The PD-L1 binding polypeptide according to claim 11, wherein the half maximal inhibitory concentration (IC50) of the blocking is at most $1\times10^{-10}$ M.

19. The PD-L1 binding polypeptide according to claim 1, which is capable of blocking the interaction of PD-L1 with PD-1.

20. The PD-L1 binding polypeptide according to claim 1, which is capable of binding to PD-L1 such that the $K_D$ value of the interaction is at most $2\times10^{-8}$ M.

21. The PD-L1 binding polypeptide according to claim 20, which is capable of binding to PD-L1 such that the $K_D$ value of the interaction is at most $1\times10^{-8}$ M.

22. The PD-L1 binding polypeptide according to claim 20, which is capable of binding to PD-L1 such that the $K_D$ value of the interaction is at most $1\times10^{-9}$ M.

23. The PD-L1 binding polypeptide according to claim 20, which is capable of binding to PD-L1 such that the $K_D$ value of the interaction is at most $5\times10^{-10}$ M.

24. The PD-L1 binding polypeptide according to claim which is capable of binding to PD-L1 such that the $K_D$ value of the interaction is at most $3\times10^{-10}$ M.

25. The PD-L1 binding polypeptide according to claim 1, wherein sequence i) corresponds to the sequence from position 8 to position 36 in a sequence selected from the group consisting of SEQ ID NO:1-93.

26. The PD-L1 binding polypeptide according to claim 1, wherein sequence i) corresponds to the sequence from position 8 to position 36 in a sequence selected from the group consisting of SEQ ID NO:1-24.

27. The PD-L1 binding polypeptide according to claim 1, wherein sequence i) corresponds to the sequence from position 8 to position 36 in a sequence selected from the group consisting of SEQ ID NOs:1, 2, 4, 5, and 21.

28. The PD-L1 binding polypeptide according to claim 1, wherein sequence i) corresponds to the sequence from position 8 to position 36 in a sequence selected from the group consisting of SEQ ID NO:1 and 2.

29. A Fusion protein or conjugate comprising
- a first moiety consisting of a PD-L1 binding polypeptide according to claim 1; and
- a second moiety consisting of a polypeptide having a desired biological activity.

30. A complex, comprising at least one PD-L1 binding polypeptide according to claim 1 and at least one antibody or an antigen binding fragment thereof.

31. A polynucleotide encoding a polypeptide according to claim 1.

32. A composition comprising a PD-L1 binding polypeptide-according to claim 1, and at least one pharmaceutically acceptable excipient or carrier.

33. A method of treating a PD-L1 related disorder, comprising administering to a subject in need thereof an effective amount of a PD-L1 binding polypeptide according to claim 1.

34. The method of claim 33, wherein said PD-L1 related disorder is selected from the group consisting of infectious disease and cancer.

* * * * *

UNITED STATES PATENT AND TRADEMARK OFFICE

CERTIFICATE OF CORRECTION

PATENT NO. : 11,155,596 B2
APPLICATION NO. : 15/770956
DATED : October 26, 2021
INVENTOR(S) : Elisabet Wahlberg and Elin Gunneriusson It is certified that error appears in the above-identified patent and that said Letters Patent is hereby corrected as shown below:

On the Title Page

Under (30) Foreign Application Priority Data, please add --Oct. 30, 2015 (EP) 15192364--

Signed and Sealed this
Twelfth Day of November, 2024

Katherine Kelly Vidal

Katherine Kelly Vidal
*Director of the United States Patent and Trademark Office*